(12) United States Patent
Ali et al.

(10) Patent No.: US 8,735,435 B2
(45) Date of Patent: *May 27, 2014

(54) CETP INHIBITORS

(75) Inventors: Amjad Ali, Freehold, NJ (US); Joann M. Napolitano, North Plainfield, NJ (US); Qiaolin Deng, Edison, NJ (US); Zhijian Lu, Clinton, NJ (US); Peter J. Sinclair, Doylestown, PA (US); Gayle E. Hallett, Smethwick (GB); Christopher F. Thompson, Arlington, MA (US); Nazia Quraishi, Bethesda, MD (US); Cameron J. Smith, Lawrenceville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 756 days.

This patent is subject to a terminal disclaimer.

(21) Appl. No.: 12/625,783

(22) Filed: Nov. 25, 2009

(65) Prior Publication Data

US 2010/0099716 A1  Apr. 22, 2010

Related U.S. Application Data

(63) Continuation of application No. 11/173,295, filed on Jul. 1, 2005, now Pat. No. 7,652,049.

(60) Provisional application No. 60/585,274, filed on Jul. 2, 2004, provisional application No. 60/646,103, filed on Jan. 21, 2005.

(51) Int. Cl.
*C07D 263/04* (2006.01)
*A61K 31/421* (2006.01)

(52) U.S. Cl.
CPC ............ *A61K 31/421* (2013.01); *C07D 263/04* (2013.01)
USPC .......................................... 514/376; 548/229

(58) Field of Classification Search
None
See application file for complete search history.

(56) References Cited

U.S. PATENT DOCUMENTS

| | | | |
|---|---|---|---|
| 4,179,442 A | 12/1979 | Kollensperger et al. | |
| 4,186,129 A | 1/1980 | Huth et al. | |
| 4,968,707 A | 11/1990 | Clark et al. | |
| 5,482,971 A | 1/1996 | Epstein et al. | |
| 5,817,826 A | 10/1998 | Ohtani et al. | |
| 5,846,990 A | 12/1998 | Murugesan et al. | |
| 6,057,352 A | 5/2000 | Brown et al. | |
| 6,242,637 B1 | 6/2001 | Emonds-Alt et al. | |
| 6,255,327 B1 | 7/2001 | Brenner et al. | |
| 6,310,095 B1 | 10/2001 | Sebti et al. | |
| 6,313,142 B1 | 11/2001 | Damon et al. | |
| 7,091,196 B2 | 8/2006 | Wang et al. | |
| 7,652,049 B2 * | 1/2010 | Ali et al. .......................... 514/376 | |
| 7,781,426 B2 * | 8/2010 | Ali et al. ......................... 514/217.1 | |
| 2003/0139406 A1 | 7/2003 | Liu et al. | |
| 2004/0220148 A1 | 11/2004 | Stilz et al. | |
| 2006/0040999 A1 | 2/2006 | Ali et al. | |
| 2008/0119476 A1 | 5/2008 | Ali et al. | |
| 2009/0042892 A1 | 2/2009 | Ali et al. | |
| 2009/0075979 A1 | 3/2009 | Ali et al. | |
| 2009/0137548 A1 | 5/2009 | Ali et al. | |

FOREIGN PATENT DOCUMENTS

| | | |
|---|---|---|
| EP | 0560407 | 9/1993 |
| EP | 0605729 | 7/1994 |
| EP | 1277743 | 1/2003 |
| WO | WO 96/38421 | 12/1996 |
| WO | WO 97/00612 | 1/1997 |
| WO | WO 98/23155 | 6/1998 |
| WO | WO 98/50029 | 11/1998 |
| WO | WO 98/50030 | 11/1998 |
| WO | WO 99/15487 | 4/1999 |
| WO | WO 99/37630 | 7/1999 |
| WO | WO 00/17165 | 3/2000 |
| WO | WO 01/19788 | 3/2001 |
| WO | WO 01/56996 | 8/2001 |
| WO | WO 03/022824 | 3/2003 |
| WO | WO 03/032981 A1 | 4/2003 |
| WO | WO 2004/082593 | 9/2004 |
| WO | WO 2005/095409 | 10/2005 |
| WO | WO2006/014357 | 2/2006 |
| WO | WO 2007/079186 | 7/2007 |
| WO | WO2006/014357 | 2/2009 |

OTHER PUBLICATIONS

U.S. Appl. No. 11/631,821, filed Jan. 3, 2007, Amjad Ali, et al.
Barter, et al.—Arterioscler Thromb Vasc, Biol., vol. 23(2), pp. 160-167, 2003.
Damon et al "Cleavage of N-Acyl Oxazolidones", Tetrahedron Letters, vol. 31, No. 20. pp. 2849-2852, 1990.
http://en.wikipedia.org/wiki/Cholesterylester_transfer_protein; p. 4, Sep. 11, 2008.

* cited by examiner

*Primary Examiner* — Zinna Northington Davis
(74) *Attorney, Agent, or Firm* — James L. McGinnis; Catherine D. Fitch

(57) ABSTRACT

Compounds having the structures of Formula I, including pharmaceutically acceptable salts of the compounds, are CETP inhibitors, and are useful for raising HDL-cholesterol, reducing LDL-cholesterol, and for treating or preventing atherosclerosis:

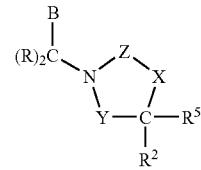

I

In the compounds of Formula I, B or $R^2$ is a phenyl group which has an ortho aryl, heterocyclic, benzoheterocyclic or benzocycloalkyl substituent, and one other position on the 5-membered ring has an aromatic, heterocyclic, cycloalkyl, benzoheterocyclic or benzocycloalkyl substituent connected directly to the ring or attached to the ring through a —$CH_2$—.

9 Claims, No Drawings

CETP INHIBITORS

CROSS REFERENCE TO RELATED APPLICATIONS

This application is a continuation under 35USC§120 of U.S. application Ser. No. 11/173,295, filed Jul. 1, 2005, now U.S. Pat. No. 7,652,049 which claims the benefit under 35 U.S.C. §119' (e) of U.S. Provisional Application No. 60/585,274, filed Jul. 2, 2004 and U.S. Provisional Application No. 60/646,103 filed Jan. 21, 2005.

FIELD OF THE INVENTION

This invention relates to a class of chemical compounds that inhibit cholesterol ester transfer protein (CETP) and therefore may have utility in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. New compounds are needed so that one or more pharmaceutical compounds can be found that are safe and effective. The novel compounds described herein are very potent CETP inhibitors. Some structurally similar compounds are found in WO2003/032981.

SUMMARY OF THE INVENTION

Compounds having Formula I, including pharmaceutically acceptable salts of the compounds, are CETP inhibitors, having the utilities described below:

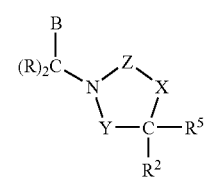

I

In the compounds of Formula I,

Y is selected from —C(=O)— and —(CRR$^1$)—;

X is selected from —O—, —NH—, —N(C$_1$-C$_5$alkyl)-, and —(CRR$^6$)—;

Z is selected from —C(=O)—, —S(O)$_2$—, and —C(=N—R$^9$)—, wherein R$^9$ is selected from the group consisting of H, —CN, and —C$_1$-C$_5$alkyl optionally substituted with 1-11 halogens;

Each R is independently selected from the group consisting of H, —C$_1$-C$_5$ alkyl, and halogen, wherein —C$_1$-C$_5$ alkyl is optionally substituted with 1-11 halogens;

B is selected from the group consisting of A$^1$ and A$^2$, wherein A$^1$ has the structure:

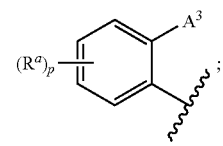

R$^1$ and R$^6$ are each independently selected from H, —C$_1$-C$_5$ alkyl, halogen, and —(C(R)$_2$)$_n$A$^2$, wherein —C$_1$-C$_5$ alkyl is optionally substituted with 1-11 halogens;

$R^2$ is selected from the group consisting of H, —$C_1$-$C_5$ alkyl, halogen, $A^1$, and —$(C(R)_2)_nA^2$, wherein —$C_1$-$C_5$ alkyl is optionally substituted with 1-11 halogens;

Wherein one of B and $R^2$ is $A^1$; and one of B, $R^1$, $R^2$, and $R^6$ is $A^2$ or —$(C(R)_2)_nA^2$; so that the compound of Formula I comprises one group $A^1$ and one group $A^2$;

$A^3$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group, wherein the point of attachment of $A^3$ to the phenyl ring to which $A^3$ is attached is a carbon atom; and
(d) a benzoheterocyclic ring comprising a phenyl ring fused to a 5-6-membered heterocyclic ring having 1-2 heteroatoms independently selected from O, N, and S, and optionally also having 1-2 double bonds (in addition to the double bond of the fused phenyl ring) wherein the point of attachment of $A^3$ to the phenyl ring to which $A^3$ is attached is a carbon atom;

$A^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group;
(d) a benzoheterocyclic ring comprising a phenyl ring fused to a 5-6-membered heterocyclic ring having 1-2 heteroatoms independently selected from O, N, and S, and optionally also having 1-2 double bonds (in addition to the double bond of the fused phenyl ring); and
(e) a —$C_3$-$C_8$ cycloalkyl ring optionally having 1-3 double bonds;

wherein $A^3$ and $A^2$ are each optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —OH, —$NR^3R^4$, —C(=O)$NR^3R^4$, —$NR^3$C(=O)$OC_1$-$C_6$ alkyl, —$NR^3$C(=O)$NR^3R^4$, —S(O)$_xC_1$-$C_6$ alkyl, —S(O)$_yNR^3R^4$, —$NR^3$S(O)$_yNR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$C_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)$SC_1$-$C_6$alkyl, —$NR^3$C(=O)$OC_1$-$C_6$ alkyl, and —S(O)$_xC_1$-$C_6$ alkyl, $R^a$ is optionally substituted with 1-15 halogens and is optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

with the proviso that when B is $A^1$, and X and Y are —$CH_2$—, and Z is —C(=O)—, and $R^2$ is phenyl which has a substituent $R^a$ in the 4-position, wherein $R^a$ is —$OC_1$-$C_6$alkyl which is optionally substituted as described above, then there are no other $R^a$ substitutents on $R^2$ in which $R^a$ is selected from —OH, —$OC_1$-$C_6$alkyl, —$OC_2$-$C_6$ alkenyl, —$OC_2$-$C_6$ alkynyl, and —$OC_3$-$C_8$ cycloalkyl optionally having 1-3 double bonds, all of which are optionally substituted as described above.

n is 0 or 1;

p is an integer from 0-4;

x is 0, 1, or 2;

y is 1 or 2;

$R^3$ and $R^4$ are each independently selected from H, —$C_1$-$C_5$ alkyl, —C(=O)$C_1$-$C_5$ alkyl and —S(O)$_yC_1$-$C_5$ alkyl, wherein —$C_1$-$C_5$ alkyl in all instances is optionally substituted with 1-11 halogens; and $R^5$ is selected from the group consisting of H, —OH, —$C_1$-$C_5$ alkyl, and halogen, wherein —$C_1$-$C_5$ alkyl is optionally substituted with 1-11 halogens.

In the compounds of Formula I and in subsequent compounds, alkyl, alkenyl, and alkynyl groups can be either linear or branched, unless otherwise stated.

DETAILED DESCRIPTION OF THE INVENTION

Many of compounds of this invention have a structure in accordance with Formula Ia, written below, or a pharmaceutically acceptable salt thereof:

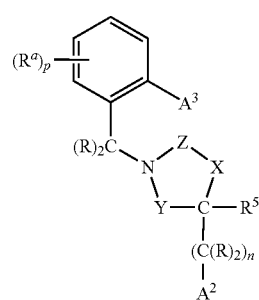

Ia

Many compounds of the invention have the structure of Formula Ib, or a pharmaceutically acceptable salt thereof:

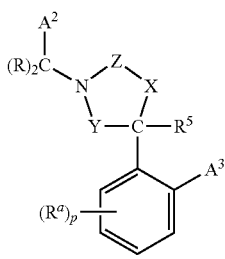

Many other compounds have the structure of Formula Ic or a pharmaceutically acceptable salt thereof:

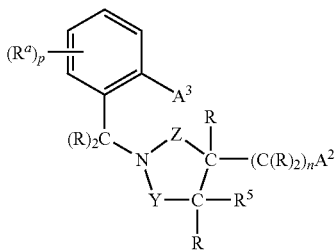

Still other compounds of the invention have a structure in accordance with Formula Id, or a pharmaceutically acceptable salt thereof:

Id

In a subset of the compounds of Formula I,

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(═O)$C_1$-$C_6$alkyl, —C(═O)$C_3$-$C_8$ cycloalkyl, —C(═O)H, —$CO_2$H, —$CO_2C_1$-$C_6$alkyl, —C(═O)S$C_1$-$C_6$alkyl, —$NR^3R^4$, —C(═O)$NR^3R^4$, —$NR^3$C(═O)O$C_1$-$C_6$ alkyl, —$NR^3$C(═O)$NR^3R^4$, —S(O)$_x$$C_1$-$C_6$ alkyl, —S(O)$_y$$NR^3R^4$, —$NR^3$S(O)$_y$$NR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the attached ring is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(═O)$C_1$-$C_6$alkyl, —C(═O)$C_3$-$C_8$ cycloalkyl, —$CO_2C_1$-$C_6$alkyl, —C(═O)S$C_1$-$C_6$alkyl, —$NR^3$C(═O)O$C_1$-$C_6$ alkyl, and —S(O)$_x$$C_1$-$C_6$ alkyl, then $R^a$ is optionally substituted with 1-15 halogens and is optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl, (f) —$OC_3$-$C_8$ cycloalkyl optionally having 1-3 double bonds and optionally substituted with 1-15 halogens, (g) —$CO_2$H, (h) —C(═O)$CH_3$, and (i) —$CO_2C_1$-$C_4$alkyl which is optionally substituted with 1-9 halogens;

with the proviso that when B is $A^1$, and X and Y are —$CH_2$—, and Z is —C(═O)—, and $R^2$ is phenyl which has a substituent $R^a$ in the 4-position, wherein $R^a$ is —$OC_1$-$C_6$alkyl which is optionally substituted with 1-11 halogens, then there are no other $R^a$ substitutents on $R^2$ in which $R^a$ is selected from —$OC_1$-$C_6$alkyl, —$OC_2$-$C_6$ alkenyl, —$OC_2$-$C_6$ alkynyl, and —$OC_3$-$C_8$ cycloalkyl optionally having 1-3 double bonds, all of which are optionally substituted as described above.

In many of the compounds of Formula I, Ia, Ib, Ic and Id, and pharmaceutically acceptable salts thereof, $A^3$ is phenyl, which is optionally substituted with 1-4 substituent groups $R^a$, wherein $R^a$ is independently selected from —$C_1$-$C_5$ alkyl, —$OC_1$-$C_3$alkyl, —$CO_2C_1$-$C_3$alkyl, —$CO_2$H, halogen, —$NR^3R^4$, —C(═O)$C_1$-$C_3$alkyl, —C(═O)H, —C(═O)$NR^3R^4$, —S$C_1$-$C_3$ alkyl, —$C_2$-$C_3$ alkenyl, —CN, —$NO_2$, and 1,2,4-oxadiazolyl, wherein —$C_1$-$C_3$ alkyl and —$C_1$-$C_5$ alkyl in all occurrences is optionally substituted with 1-6 substituents independently selected from 1-5 halogens and one —OH group; and —$C_2$-$C_3$ alkenyl is optionally substituted with 1-3 halogens.

In many of the compounds of Formula I, Ia, Ib, Ic, and Id, and pharmaceutically acceptable salts thereof, $A^2$ is selected from the group consisting of phenyl, cyclohexyl, and a heterocyclic 5-6 membered ring comprising 1-2 heteroatoms independently selected from O, N, S, and —N(O)— and optionally also comprising 1-3 double bonds, wherein $A^2$ is optionally substituted with 1-2 substituent groups independently selected from —$C_1$-$C_4$ alkyl, —$OC_1$-$C_3$ alkyl, —$NO_2$, —CN, —S(O)$_x$$C_1$-$C_3$ alkyl, —NHS(O)$_2$$C_1$-$C_3$ alkyl, —$NR^3R^4$, —$NR^3$C(═O)$R^4$, —$C_2$-$C_3$ alkenyl, —C(═O)$NR^3R^4$, halogen, and pyridyl, wherein $C_1$-$C_3$ alkyl, $C_1$-$C_4$ alkyl, and $C_2$-$C_3$alkenyl in all instances is optionally substituted with 1-3 halogens, with the proviso that for compounds of formula Ia, when B is $A^1$, and X and Y are —$CH_2$—, and Z is —C(═O)—, and $R^2$ is phenyl, then the number of $R^a$ groups on $R^2$ that are selected from —$OC_1$-$C_3$alkyl which are optionally substituted is 0 or 1.

In many of the compounds of Formula I, Ia, Ib, Ic, and Id, and pharmaceutically acceptable salts thereof, $R^3$ and $R^4$ are each independently selected from H and —$C_1$-$C_3$ alkyl.

In many of the compounds of Formula I, Ia, Ib, Ic, and Id, and pharmaceutically acceptable salts thereof, p is 0-2.

In subgroups of compounds of Formula I, including pharmaceutically acceptable salts thereof, $A^1$ is

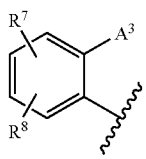

Wherein $R^7$ and $R^8$ are each independently selected from the group consisting of H, halogen, —$NR^3R^4$, —$C_1$-$C_3$ alkyl, —$OC_1$-$C_3$ alkyl, —CN, —$NO_2$, and pyridyl, wherein $C_1$-$C_3$ alkyl in all instances is optionally substituted with 1-3 halogens.

In sub-groups of the compounds of formula I, $A^2$ is selected from the group consisting of phenyl, pyridyl, and cyclohexyl, wherein $A^2$ is optionally substituted with 1-2 substituents independently selected from —$C_1$-$C_4$ alkyl, —$OC_1$-$C_4$ alkyl, —$NO_2$, —CN, and halogen, wherein $C_1$-$C_4$ alkyl in all uses is optionally substituted with 1-3 halogens, with the proviso that for compounds of formula I, when B is A1, and X and Y are $CH_2$, and Z is —(C=O)—, and $R^2$ is phenyl, then the number of $R^a$ groups on $R^2$ that are selected from —$OC_1$-$C_4$alkyl optionally substituted with 1-3 halogens is 0 or 1.

In other subgroups, $A^2$ is optionally substituted with 1-2 substituent groups independently selected from halogen, —$C_1$-$C_4$ alkyl, and —CN, wherein —$C_1$-$C_4$ alkyl is optionally substituted with 1-3 halogens.

In many embodiments of the invention, as described above, including pharmaceutically acceptable salts, $A^1$ is

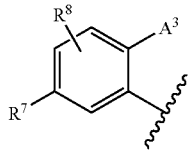

Wherein $R^7$ is selected from H, halogen, —$NR^3R^4$, —$C_1$-$C_3$ alkyl, —$OC_1$-$C_3$ alkyl, —CN, —$NO_2$, and pyridyl, wherein $C_1$-$C_3$ alkyl in all instances is optionally substituted with 1-3 halogens; and
$R^8$ is selected from the group consisting of H, halogen, —$CH_3$, —$CF_3$, —$OCH_3$, and —$OCF_3$.

In many preferred embodiments of this invention, $A^3$ is phenyl, which is substituted with 1-3 substituents independently selected from $C_1$-$C_4$alkyl, $OC_1$-$C_4$alkyl, —CN, Cl, F, —C(=O)$CH_3$, —CH=$CH_2$, —$CO_2$H, —$CO_2CH_3$, —S—$CH_3$, —S(O)$CH_3$, —S(O)$_2CH_3$, and —C(=O)$NR^3R^4$, wherein $C_1$-$C_4$alkyl and —$OC_1$-$C_4$alkyl are optionally substituted with 1-5 F substituents and optionally also substituted with one group —OH.

In other embodiments, A3 is phenyl which is optionally substituted with 1-3 substituents independently selected from the group consisting of Cl, F, —$C_1$-$C_4$ alkyl, and —$OC_1$-$C_4$ alkyl, wherein —$C_1$-$C_4$ alkyl and —$OC_1$-$C_4$ alkyl are optionally substituted with 1-5 F.

A preferred value of Y is —(CRR$^1$)—.

In some embodiments, R and $R^6$ are each independently selected from the group consisting of H and —$C_1$-$C_5$ alkyl, wherein —$C_1$-$C_5$ alkyl is optionally substituted with 1-11 halogens. In subsets of these embodiments, $R^1$ is selected from the group consisting of H, —$C_1$-$C_5$ alkyl, and —(C(R)$_2$)$_n$A$^2$, wherein —$C_1$-$C_5$ alkyl is optionally substituted with 1-11 halogens. In these, one of B and $R^2$ is $A^1$; and one of B, $R^1$, and $R^2$ is $A^2$ or —(C(R)$_2$)$_n$A$^2$; so that the compound of Formula I comprises one group $A^1$ and one group $A^2$.

In subgroups of compounds, $A^3$ is selected from the group consisting of:
(a) an aromatic ring selected from phenyl and naphthyl;
(b) a 5-6-membered heterocyclic ring having 1-4 heteroatoms independently selected from N, S, O, and —N(O)—, and optionally also comprising 1-3 double bonds and a carbonyl group, wherein the point of attachment of $A^3$ to the phenyl ring to which $A^3$ is attached is a carbon atom; and
(c) a benzoheterocyclic ring comprising a phenyl ring fused to a 5-6-membered heterocyclic ring having 1-2 heteroatoms independently selected from O, N, and —S(O)$_x$— and optionally 1-2 double bonds, wherein the point of attachment of $A^3$ to the phenyl ring to which $A^3$ is attached is a carbon atom.

In subgroups of compounds, $A^2$ is selected from the group consisting of:
(a) an aromatic ring selected from phenyl and naphthyl;
(b) a 5-6-membered heterocyclic ring having 1-4 heteroatoms independently selected from N, S, O, and —N(O)—, and optionally also comprising 1-3 double bonds and a carbonyl group;
(c) a benzoheterocyclic ring comprising a phenyl ring fused to a 5-6-membered heterocyclic ring having 1-2 heteroatoms independently selected from O, N, and S and optionally 1-2 double bonds; and
(d) a —$C_3$-$C_8$ cycloalkyl ring optionally having 1-3 double bonds;

In the subgroups of $A^3$ and $A^2$ above, $A^3$ and $A^2$ are each optionally substituted with 1-4 substituent groups independently selected from $R^a$.

A subgroup of $R^a$ comprises substituents that are independently selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —C(=O)H, —$CO_2$H, —$CO_2C_1$-$C_6$alkyl, —OH, —$NR^3R^4$, —$NR^3$C(=O)$OC_1$-$C_6$ alkyl, —S(O)$_xC_1$-$C_6$ alkyl, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;
wherein for compounds in which $R^a$ is selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —$CO_2C_1$-$C_6$alkyl, —$NR^3$C(=O)$OC_1$-$C_6$ alkyl, and —S(O)$_xC_1$-$C_6$ alkyl, $R^a$ is optionally substituted with 1-15 halogens and is optionally also substituted with one substituent group selected from (a) —OH, (b) —$NR^3R^4$, (c) —$OC_1$-$C_4$alkyl optionally substituted with 1-9 halogens and optionally also substituted with 1-2 substituent groups independently selected from —$OC_1$-$C_2$ alkyl and phenyl, and (d) phenyl which is optionally substituted with 1-3 groups independently selected from halogen, —$CH_3$, —$CF_3$, —$OCH_3$, and —$OCF_3$;
with the proviso that when B is $A^1$, and X and Y are —$CH_2$—, and Z is —C(=O)—, and $R^2$ is phenyl which has a substituent $R^a$ in the 4-position, wherein $R^a$ is —$OC_1$-$C_6$alkyl which is optionally substituted as described above, then there are no other $R^a$ substitutents on $R^2$ in which $R^a$ is —OH or —$OC_1$-$C_6$alkyl which is optionally substituted as described above.

In subgroups of compounds, n is an integer from 0-2. In other subgroups, n is 1 or 2.

In independent subgroups, $R^3$ and $R^4$ are each independently selected from H and —$C_1$-$C_5$ alkyl, wherein —$C_1$-$C_8$ alkyl in all instances is optionally substituted with 1-11 halogens. In other independent subgroups, $R^3$ and $R^4$ each independently selected from H and —$C_1$-$C_3$ alkyl, or from H and —$C_1$-$C_2$ alkyl.

In subgroups of Formula I, Z is selected from the group consisting of —C(=O)—, —S(O)$_2$—, and —C(=N—$R^9$)—, where $R^9$ is selected from the group consisting of H, —CN, and $CH_3$. A preferred value of Z is —C(=O)—.

In independent subgroups, $R^5$ is selected from the group consisting of H, —OH, and —$C_1$-$C_5$ alkyl, wherein —$C_1$-$C_5$ alkyl is optionally substituted with 1-11 halogens. In other subgroups, $R^5$ is selected from H and —$C_1$-$C_3$ alkyl, or from H and —$C_1$-$C_2$ alkyl.

In some subgroups, each R is independently selected from the group consisting of H and $C_1$-$C_3$ alkyl. In other groups, R is selected from H and $C_1$-$C_2$ alkyl. In other groups, R is H or $CH_3$ In some subgroups, $R^6$ is selected from the group consisting of H and —$C_1$-$C_3$ alkyl, wherein $C_1$-$C_3$ alkyl is optionally substituted with 1-5 halogens. In other subgroups, $R^6$ is selected from H and $C_1$-$C_2$ alkyl. In other groups, $R^6$ is H or $CH_3$, In some subgroups, $R^1$ is selected from the group consisting of H, —$C_1$-$C_3$ alkyl, and —$(C(R)_2)_nA^2$, wherein —$C_1$-$C_3$ alkyl is optionally substituted with 1-5 halogens; and $R^2$ is selected from the group consisting of H, —$C_1$-$C_3$ alkyl, $A^1$, and —$(C(R)_2)_nA^2$, wherein —$C_1$-$C_3$ alkyl is optionally substituted with 1-5 halogens, and $R^6$ is H or alkyl. In these subgroups, one of B and $R^2$ is $A^1$; and one of B, $R^1$, and $R^2$ is $A^2$ or —$(C(R)_2)_nA^2$; so that the compound of Formula I comprises one group $A^1$ and one group $A^2$.

In subgroups of compounds, $A^3$ is selected from the group consisting of:
(a) phenyl;
(b) a 5-6-membered aromatic heterocyclic ring having 1-2 heteroatoms independently selected from N, S, O, and —N(O)—, wherein the point of attachment of $A^3$ to the phenyl ring to which $A^3$ is attached is a carbon atom; and
(c) a benzoheterocyclic ring comprising a phenyl ring fused to a 5-membered aromatic heterocyclic ring having 1-2 heteroatoms independently selected from O, N, and —S(O)$_x$, wherein the point of attachment of $A^3$ to the phenyl ring to which $A^3$ is attached is a carbon atom.

In subgroups, $A^2$ is selected from:
(a) phenyl;
(b) a 5-6-membered heterocyclic ring having 1-4 heteroatoms independently selected from N, S, O, and —N(O)—, and optionally also comprising 1-3 double bonds;
(c) a benzoheterocyclic ring comprising a phenyl ring fused to a 5-membered heterocyclic ring having 1-2 heteroatoms independently selected from O, N, and S; and
(d) a —$C_5$-$C_6$ cycloalkyl ring.

In many compounds, $A^3$ and $A^2$ are each optionally substituted with 1-4 substituent groups independently selected from $R^a$. In various subgroups, $A^3$ is optionally substituted with 1-3 substituents $R^a$, or with 2-3 substituents $R^a$. In various subgroups, $A^2$ is optionally substituted with 1-3 substituents $R^a$, or with 1-2 substituents $R^a$. Often $A^2$ is substituted with 2 substituents $R^a$, or with 2-3 substituents $R^a$.

In many compounds, $A^3$ is selected from the group consisting of phenyl, thienyl, imidazolyl, pyrrolyl, pyrazolyl, pyridyl, N-oxido-pyridyl, thiazolyl, pyridazinyl, pyrimidinyl, pyrazinyl, benzothienyl, benzothienyl-5-oxide, and benzothienyl-5-dioxide.

In many compounds, $A^2$ is selected from the group consisting of phenyl, thienyl, imidazolyl, thiazolyl, pyrrolyl, pyrazolyl, 1,2,4-triazolyl, tetrazolyl, benzodioxolyl, pyridyl, N-oxido-pyridyl, pyridazinyl, pyrimidinyl, pyrazinyl, cyclopentyl, cyclohexyl, and tetrahydropyranyl.

In some subsets, $R^a$ is selected from the group consisting of —$C_1$-$C_4$ alkyl, —$C_2$-$C_4$ alkenyl, cyclopropyl, —$OC_1$-$C_2$alkyl, —C(=O)$C_1$-$C_2$alkyl, —C(=O)H, —$CO_2C_1$-$C_4$alkyl, —OH, —$NR^3R^4$, —$NR^3C$(=O)$OC_1$-$C_4$ alkyl, —S(O)$_xC_1$-$C_2$ alkyl, halogen, —CN, —$NO_2$, and a 5-6-membered heterocyclic ring having 1-2 heteroatoms independently selected from N, S, and O, wherein the point of attachment of said heterocyclic ring to the ring to which $R^a$ is attached ring is a carbon atom, wherein said heterocyclic ring is optionally substituted with 1-5 substituent groups independently selected from halogen;

wherein for compounds in which $R^a$ is selected from the group consisting of —$C_1$-$C_4$ alkyl, —$C_2$-$C_4$ alkenyl, —$OC_1$-$C_2$alkyl, —C(=O)$C_1$-$C_2$alkyl, —$CO_2C_1$-$C_4$alkyl, —$NR^3C$(=O)$OC_1$-$C_4$ alkyl, and —S(O)$_xC_1$-$C_2$ alkyl, the alkyl group of $R^a$ is optionally substituted with 1-5 halogens and is optionally also substituted with one substituent group selected from (a) —OH, (b) —$NR^3R^4$, (c) —$OCH_3$ optionally substituted with 1-3 fluorine atoms and optionally also substituted with one phenyl group, and (d) phenyl which is optionally substituted with 1-3 groups independently selected from halogen, —$CH_3$, —$CF_3$, —$OCH_3$, and —$OCF_3$;

with the proviso that when B is $A^1$, and X and Y are —$CH_2$—, and Z is —C(=O)—, and $R^2$ is phenyl which has a substituent $R^a$ in the 4-position, wherein $R^a$ is —$OC_1$-$C_2$alkyl which is optionally substituted as described above, then there are no other $R^a$ substitutents on $R^2$ in which $R^a$ is selected from —OH or —$OC_1$-$C_2$alkyl which is optionally substituted as described above.

In preferred subsets, X is selected from the group consisting of —O—, —NH—, and —N($C_1$-$C_3$alkyl)-. X may also be selected from the group consisting of —O—, —NH—, and —N($CH_3$). In highly preferred subsets, X is O.

In many subsets, Z is —C(=O)—.

A preferred subgroup of compounds has Formula Ie, including pharmaceutically acceptable salts thereof

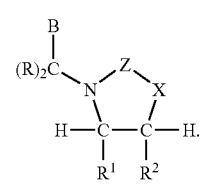

Ie

In compounds of formula Ie, X is selected from the group consisting of —O—, —NH—, —N($C_1$-$C_5$alkyl)- and —($CH_2$)—;

Z is selected from the group consisting of —C(=O)—, —S(O)$_2$—, and —C(=N—$R^9$)—, wherein $R^9$ is selected from the group consisting of H, —CN, and $C_1$-$C_5$alkyl optionally substituted with 1-11 halogens;

Each R is independently selected from the group consisting of H and —CH$_3$;

B is selected from the group consisting of A$^1$ and A$^2$, wherein A$^1$ has the structure:

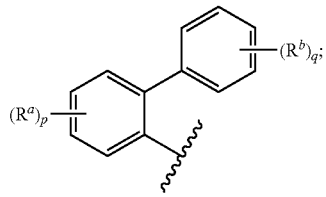

R$^1$ is selected from the group consisting of H, —C$_1$-C$_5$ alkyl, and —(C(R)$_2$)$_n$A$^2$, wherein —C$_1$-C$_5$ alkyl is optionally substituted with 1-11 halogens;

R$^2$ is selected from the group consisting of H, —C$_1$-C$_5$ alkyl, A$^1$, and —(C(R)$_2$)$_n$A$^2$, wherein —C$_1$-C$_5$ alkyl is optionally substituted with 1-11 halogens;

Wherein one of B and R$^2$ is A$^1$; and one of B, R$^1$, and R$^2$ is A$^2$ or —(C(R)$_2$)$_n$A$^2$; so that the compound of Formula Ie comprises one group A$^1$ and one group A$^2$;

A$^2$ is selected from the group consisting of phenyl, cyclohexyl, and pyridyl, wherein A$^2$ is optionally substituted with 1-2 substituent groups independently selected from halogen, —C$_1$-C$_4$ alkyl, and —CN, wherein —C$_1$-C$_4$ alkyl is optionally substituted with 1-3 halogens;

Each R$^a$ is independently selected from the group consisting of —C$_1$-C$_3$ alkyl and halogen, wherein —C$_1$-C$_3$ alkyl is optionally substituted with 1-3 halogens;

Each R$^b$ is independently selected from the group consisting of Cl, F, —C$_1$-C$_4$ alkyl, and —OC$_1$-C$_4$ alkyl, wherein —C$_1$-C$_4$ alkyl and —OC$_1$-C$_4$ alkyl are optionally substituted with 1-5 F;

n is 0 or 1;

p is an integer from 0-2; and q is an integer from 0-3.

Subsets of compounds having formula Ie include compounds of formula If, Ig, and Ih, and pharmaceutically acceptable salts thereof:

If

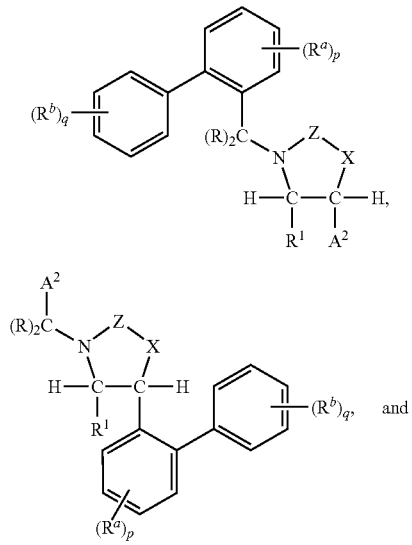

Ig and

Ih

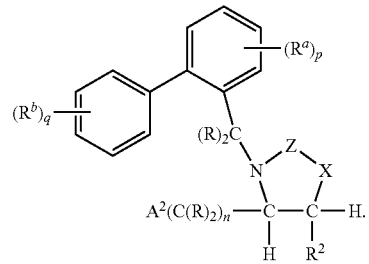

In the compounds of formula If, Ig, and Ih, R$^1$ and R$^2$ are each independently selected from H and —C$_1$-C$_5$ alkyl, wherein —C$_1$-C$_5$ alkyl is optionally substituted with 1-11 halogens. Other groups are as defined previously.

In subsets of the compounds described above, A$^2$ may be selected from the group consisting of phenyl, cyclohexyl, and pyridyl, wherein A$^2$ is optionally substituted with 1-2 substituent groups independently selected from halogen, —CH$_3$—CF$_3$, and —CN.

In subsets of the compounds described above, each R$^a$ independently is selected from the group consisting of —CF$_3$ and Cl.

In subsets of the compounds described above, each R$^b$ is independently selected from the group consisting of —C$_1$-C$_3$ alkyl, —OCH$_3$, and F.

In subsets of the compounds described above, R$^1$ and R$^2$ are each independently selected from the group consisting of H and —C$_1$-C$_2$ alkyl.

In subsets of the compounds described above, X is selected from —O—, —NH—, —N(CH$_3$)—, and —CH$_2$—.

In subsets of the compounds described above, Z is selected from the group consisting of —C(=O)—, —S(O)$_2$—, and —C(=N—CN)—.

In subsets of the compounds described above, p is 1.

In subsets of the compounds described above, q is 2 or 3.

A subset of compounds defined previously comprises compounds having formula II, and pharmaceutically acceptable salts thereof:

Ii

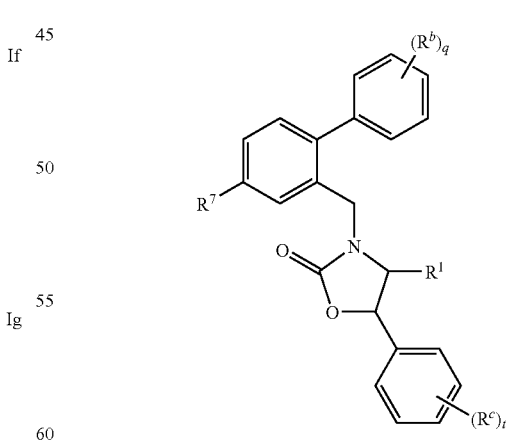

In formula Ii, R$^7$ is selected from the group consisting of Cl and —CF$_3$;

R$^c$ is selected from the group consisting of halogen, —CH$_3$—CF$_3$ and —CN; and t is an integer from 0-2. Other groups are as defined previously.

A subset of compounds defined previously comprises compounds having formula Ij, or a pharmaceutically acceptable salt thereof:

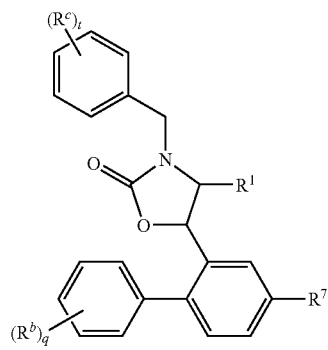

Ij

In formula Ii, $R^7$ is selected from the group consisting of Cl and —$CF_3$ $R^c$ is selected from the group consisting of halogen, —$CH_3$—$CF_3$, and —CN; and t is an integer from 0-2. Other groups are as defined previously.

Definitions

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, alkyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated (e.g., cycloalkyl may be defined as having one or more double bonds). The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"EDC" is 1-ethyl-3-(3-dimethylaminopropyl)carbodiimide.

"Heterocyclyl," "heterocycle," and "heterocyclic" means a fully or partially saturated or aromatic 5-6 membered ring containing 1-4 heteroatoms independently selected from N, S and O, unless otherwise stated.

"Benzoheterocycle" represents a phenyl ring fused to a 5-6-membered heterocyclic ring having 1-2 heteroatoms, each of which is O, N, or S, where the heterocyclic ring may be saturated or unsaturated. Examples include indole, benzofuran, 2,3-dihydrobenzofuran and quinoline.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"Weinreb amine" is N,O-dimethylhydroxylamine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to include all such isomeric forms of the compounds of Formula I and all mixtures of the compounds. When structures are shown with a stereochemical representation, other stereochemical structures are also included individually and collectively, such as enantiomers, diastereoisomers (where diastereomers are possible), and mixtures of the enantiomers and/or diastereomers, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are expected to be particularly effective in raising HDL-C and/or increasing the ratio of HDL-C to LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD-4522.

Finally compounds of this invention can be used with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and $β_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazem; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, aminone, milrinone, cilostamide, rolipram, and cilomilast; (26) phosphodiesterase-3B (PDE3B) inhibitors; (27) NE (norepinephrine) transport inhibitors, such as GW 320659, desipramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6, beta-Ala11, Phe13, Nle14]Bn(6-14) and [D-Phe6, Phe13]Bn(6-13) propylamide; (32) CNTF (Ciliary neurotrophic factors), such as GI-181771 (Glaxo-SmithKline), SR146131 (Sanofi Synthelabo), butabindide, PD170, 292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40)

ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining $IC_{50}$'s to identify compounds that are CETP inhibitors was performed based on a modification of the method described by Epps et al. employing BODIPY®-CE as the cholesteryl ester lipid donor. See Epps et al. (1995) *Method for measuring the activities of cholesteryl ester transfer protein (lipid transfer protein)*, Chem. Phys. Lipids. 77, 51-63.

Particles used in the assay were created from the following sources: Synthetic donor HDL particles containing DOPC (Dioleoyl Phosphatidyl Choline), BODIPY®-CE (Molecular Probes C-3927), triolein (a triglyceride), and apoHDL were essentially created by probe sonication as described by Epps et al, but with the addition of a non-diffusible quencher molecule, dabcyl dicetylamide, in order to reduce background fluorescence. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), and half the final concentration of acceptor particles was prepared, and 100 µL of the assay cocktail was added to each well of the plate. Test compounds in DMSO were added in a volume of 3 µL. The plate was mixed on a plate shaker and then incubated at 25° C. for 1 hour. A second assay cocktail containing donor particles, the remaining acceptor particles and 1×CETP buffer was prepared. 47 µL of the second assay cocktail was added to the reaction wells to start the assay. Assays were performed at 25° C. in a final volume of 150 L. Final concentrations of materials were: 5 ng/mL donor particles, 30 ng/µL acceptor particles (each expressed by protein content), 1×CETP buffer, 0.8 nM recombinant human CETP (expressed in CHO cells and partially purified), and up to 2% DMSO when testing compounds. The assay was followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well.

Data was evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate 1050.

EXAMPLES

The following schemes and examples are provided so that the invention will be more fully appreciated and understood. Starting materials are made using known procedures or as shown below.

The examples should not be construed as limiting the invention in any way. The scope of the invention is defined by the appended claims. Compounds of this invention have an $IC_{50}$ value as measured using the assay described above of less than or equal to 50 µM.

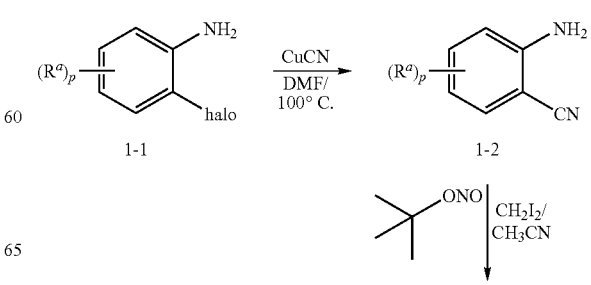

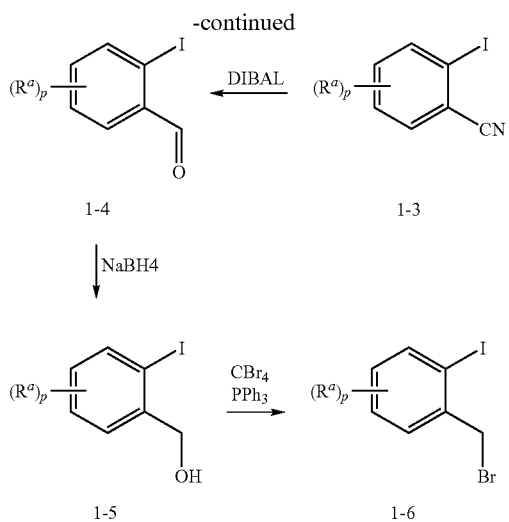

1-4      1-3

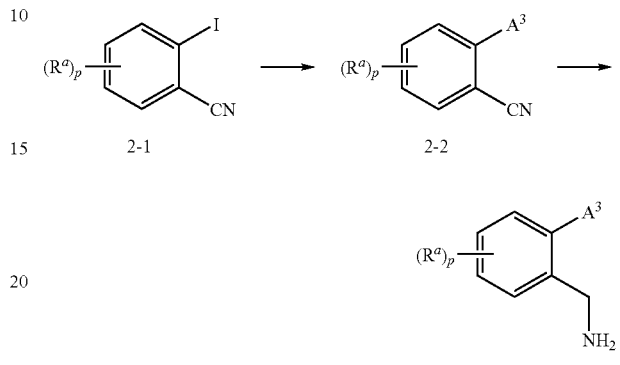

2-1      2-2      2-3 such as dichloromethane, dichloroethane or the like gives benzyl bromide 1-6 (See: Smith, M. B. and March, J. "March's Advanced Organic Chemistry", 5th Ed., John Wiley and Sons, New York, pp. 518-519 (2001) and references therein).

SCHEME 2

Intermediates 1-2, 1-3, 1-4, 1-5 and 1-6 utilized in the present invention can be purchased or prepared as shown in Scheme 1. An appropriately substituted 2-haloaniline 1-1 wherein $R^a$ and p are as defined in the claims and where the halogen is preferably iodo or bromo is treated with CuCN in DMF at elevated temperature to afford the corresponding 2-cyanoaniline. Alternatively, the nitrile can be prepared by treatment of 1-1 with KCN and CuI in the presence of a palladium (II) salt or in the presence of certain copper or nickel complexes (See: Smith, M. B. and March, J. "March's Advanced Organic Chemistry", 5th Ed., John Wiley and Sons, New York, pp. 867 (2001) and references therein). Iodides 1-3 are prepared by treatment of 1-2 with isoamylnitrite, n-pentylnitrite, t-butyl nitrite or the like in the presence of diiodomethane (see for example: Smith et al., J. Org. Chem. 55, 2543, (1990) and references cited therein) either neat or in a solvent such as THF or acetonitrile. Alternatively, the iodide can be prepared first by diazonium formation using isoamylnitrite, n-pentylnitrite, t-butyl nitrite, sodium nitrite, nitrous acid or the like followed by heating in the presence of iodine or an iodide salt such as copper iodide, sodium iodide, potassium iodide, tetrabutylammonium iodide or the like. Reduction of 1-3 with DIBAL in dichloromethane affords aldehyde 1-4. Reduction of aldehyde 1-4 with sodium borohydride or the like in methanol or ethanol or the like gives alcohol 1-5. Treatment of 1-5 with carbon tetrabromide and triphenylphosphine in solvents Intermediates 2-2 and 2-3 of the present invention wherein $R^a$, p, and $A^3$ are as defined in the claims can be prepared as shown in Scheme 2. 2-Cyanoiodobenzenes 2-1 can be purchased or prepared according to the procedures outlined in Scheme 1. Compounds 2-2 are prepared via a Suzuki or Stille reaction or variation thereof employing palladium catalyzed cross coupling of iodide 2-1 with an appropriately substituted aryl- or heteroaryl-boronic acid, -boronate ester or -trialkyl tin as described in Miyaua et al., Chem. Rev. 95, 2457 (1995) and references cited within and as described in Smith, M. B. and March, J. "March's Advanced Organic Chemistry", 5th Ed., John Wiley and Sons, New York, pp. 868-869 (2001) and references cited therein. Reduction of nitrile 2-2 is accomplished with lithium aluminum hydride in diethyl ether to afford 2-aminomethyl aniline 2-3. Alternatively, the nitrile can be reduced with palladium on carbon or Raney nickel under hydrogen atmosphere in methanol, ethanol or the like. Other methods for reduction of a nitrile to an aminomethyl group can be found in Smith, M. B. and March, J. "March's Advanced Organic Chemistry", 5th Ed., John Wiley and Sons, New York, pp. 1204 (2001) and references therein.

SCHEME 3

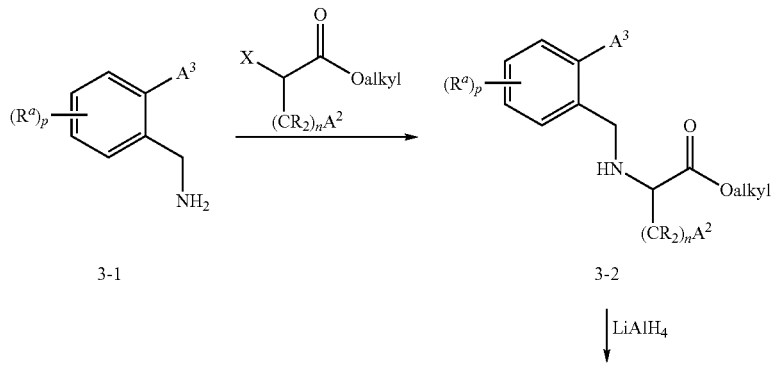

3-1      3-2

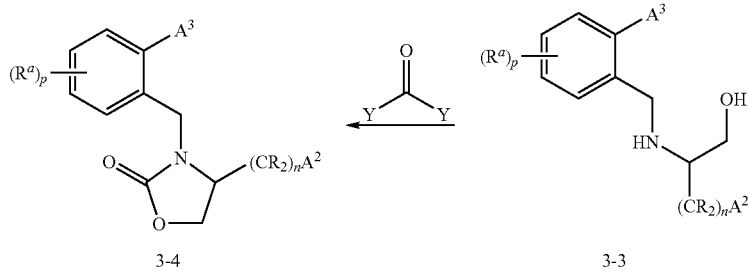

3-4

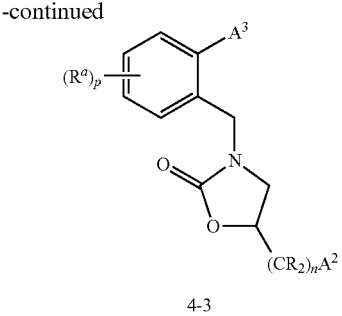

3-3

Compounds 3-4 of the present invention wherein R, $R^a$, p, $A^2$, $A^3$ and n are as defined in the claims can be prepared according to the procedure outlined in Scheme 3. Benzyl amines 3-1 can be purchased or prepared according to the procedure outlined in Scheme 2. Reaction of 3-1 with an appropriately substituted alkyl acetate bearing a leaving group at the 2-position affords secondary amine 3-2. Alkyl acetates can be purchased or prepared using known methods. The preferred leaving group is bromide or iodide, but may also be mesylate, tosylate or the like and the solvent may be dichloromethane, dichloroethane, tetrahydrofuran, dimethoxyethane, or the like. The reaction may be run with or without a base such as triethylamine, diisopropylethylamine, N-methylmorpholine, or the like. Reduction of the ester functionality of 3-2 affords amino alcohol 3-3. The preferred reducing reagent is $LiAlH_4$, in a solvent such as ether, tetrahydrofuran, dimethoxyethane, dioxane, or the like. Other methods for reduction of an ester can be found in "March's Advanced Organic Chemistry" $5^{th}$ Ed., John Wiley and Sons, New York, pp 1551. Amino alcohol 3-3 can be cyclised to oxazolidinone 3-4 using phosgene (Y=Cl) or a phosgene equivalent such as triphosgene (Y=$OCCl_3$) or carbonyl-diimidazole (Y=imidazole) or the like in a solvent such as dichloromethane, dichloroethane, tetrahydrofuran, dimethoxyethane, or the like and a base such as triethylamine, diisopropylethylamine, N-methylmorpholine, or the like. Enantiopure products may be obtained via chiral chromotography.

SCHEME 4

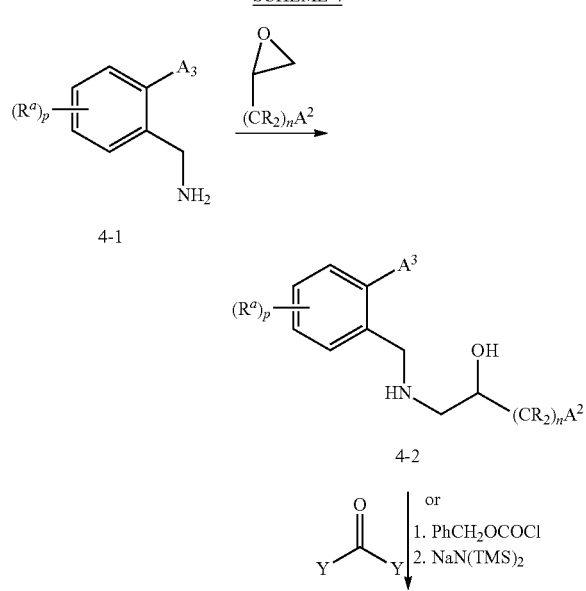

4-3

Compounds of the present invention 4-3 wherein R, $R^a$, p, $A^2$, $A^3$ and n are as defined in the claims can be prepared as shown in Scheme 4. An appropriately substituted benzylamine 4-1 can be reacted with an appropriately substituted oxirane to give amino alcohol 4-2. The oxiranes may be purchased or prepared from the corresponding aldehyde and a sulfur ylide as described in "March's Advanced Organic Chemistry" $5^{th}$ Ed., John Wiley and Sons, New York, pp 1247. Alternatively the epoxide may be made from epoxidation of an olefin, cyclization of a halohydrin or 1,2-diol, or other methods described in "March's Advanced Organic Chemistry" $5^{th}$ Ed., John Wiley and Sons, New York, pp 1051. The preferred solvent for this reaction is isopropanol. Alternatively, the epoxide opening may be carried out in a solvent such as acetonitrile or the like with the aid of a Lewis Acid catalyst such as $Yb(OTf)_3$ or the like. Amino alcohol 4-2 can be cyclised to oxazolidinone 4-3 using phosgene (Y=Cl) or a phosgene equivalent such as triphosgene (Y=$OCCl_3$) or carbonyl-diimidazole (Y=imidazole) or the like in a solvent such as dichloromethane, dichloroethane, tetrahydrofuran, dimethoxyethane, or the like and a base such as triethylamine, diisopropylethylamine, N-methylmorpholine, or the like. Alternatively, aminoalcohol 4-2 can be converted to an appropriate carbamate by treatment with reagents such as dibenzyl dicarbonate or benzyl chloroformate in the presence of bases such as triethylamine, diisopropylethylamine or the like in solvents such as dichloromethane, dichloroethane, tetrahydrofuran, dimethoxyethane or the like. The carbamates can then be converted into oxazolidinones 4-3 by treating with bases like lithium-, sodium- or potassium hexamethyldisilazide in solvents like tetrahydrofuran, dimethoxyethane or the like. Enantiopure products may be obtained via chiral chromotography.

SCHEME 5

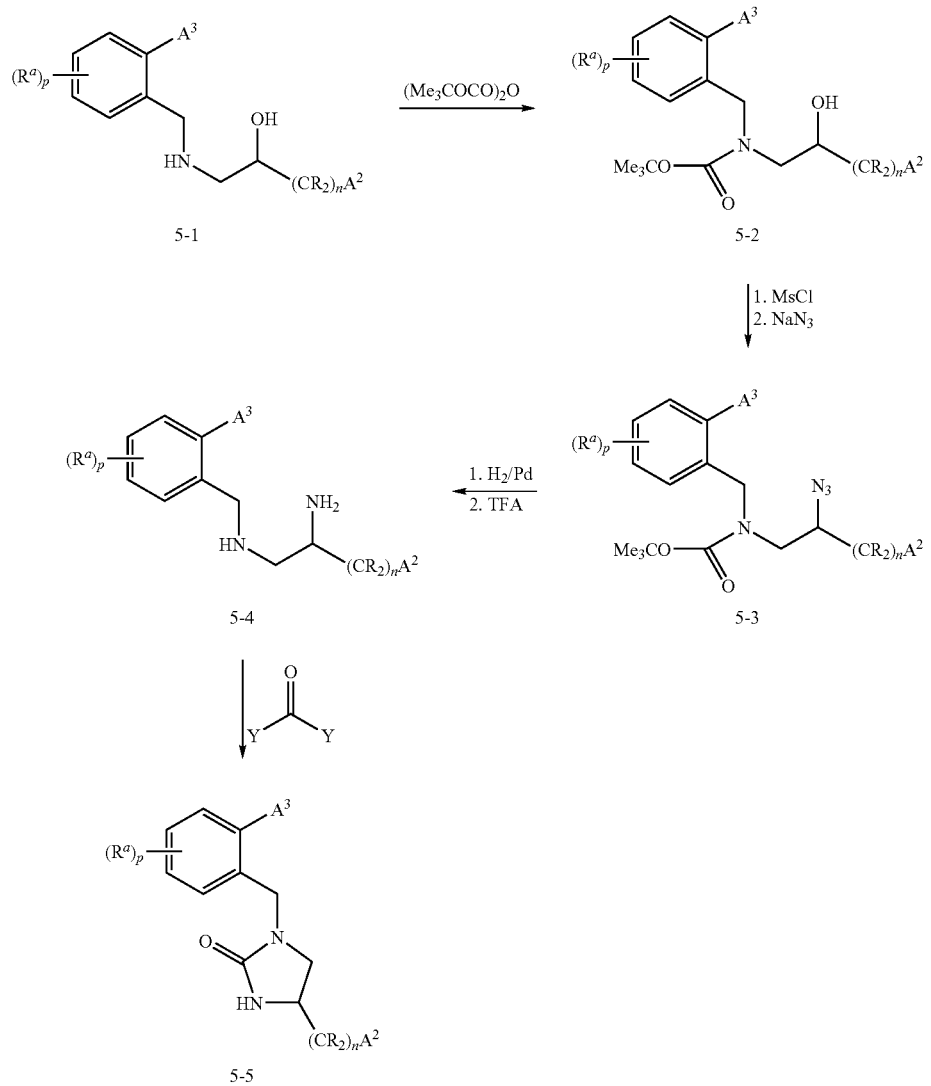

Compounds of the present invention 5-5 wherein R, $R^a$, p, $A^2$, $A^3$ and n are as defined in the claims can be prepared as shown in Scheme 5. Appropriately substituted aminoalcohol 5-1 can be prepared as shown in Scheme 4 and preferentially protected as a carbamate such as t-butyl carbamate (BOC) or benzyl carbamate (Cbz). Other carbamate and alternative protecting groups for nitrogen can be found in "Protective Groups in Organic Synthesis", $3^{rd}$ Ed. John Wiley and Sons, New York, pp 494. Protection of the nitrogen with a BOC or Cbz group can be carried out by reaction of 5-1 with di-t-butyldicarbonate or dibenzyldicarbonate in an appropriate solvent such as dichloromethane, dichloroethane, tetrahydrofuran, dimethoxyethane, or the like. Alcohol 5-2 can be converted to azide 5-3 by reaction with methanesulfonyl chloride in dichloromethane, dichloroethane, tetrahydrofuran, dimethoxyethane, or the like in the presence of an appropriate base such as triethylamine, diisopropylethylamine, N-methylmorpholine, or the like. Alternatively, the alcohol may be converted to an alternative leaving group, such as tosylate, iodide, bromide, or the like. The mesylate is then displaced by an azide source, such as $NaN_3$, $LiN_3$, $Bu_4NN_3$ or the like in an appropriate solvent, such as DMF, DMPU, or the like. Azide 5-3 can also be prepared by treatment of alcohol 5-2 with diphenylphosphoryl azide, diethylazodicarboxylate and triphenylphosphine in THF. Azide 5-3 can be reduced by hydrogenation over a metal catalyst such as $PtO_2$ or Pd/C or the like in an appropriate solvent, such as EtOAc, THF, EtOH, or the like. Following reduction and removal of the protecting group diamine 5-4 is obtained. For the BOC protecting group, $TFA/CH_2Cl_2$ is the preferred method of removal; for the CBZ protecting group, hydrogenation over a metal catalyst, such as $PtO_2$ or Pd/C or the like in an appropriate solvent, such as EtOAc, THF, EtOH, or the like is the preferred method of removal. Diamines 5-4 are cyclized to imidazolidinones 5-5 using phosgene (Y=Cl) or a phosgene equivalent such as triphosgene (Y=$OCCl_3$) or carbonyldiimidazole (Y=imidazole) or the like in a solvent such as dichloromethane, dichloroethane, tetrahydrofuran, dimethoxyethane, or the like and a base such as triethylamine, diisopropylethylamine, N-methylmorpholine, or the like. Enantiopure products may be obtained via chiral chromatography.

SCHEME 6

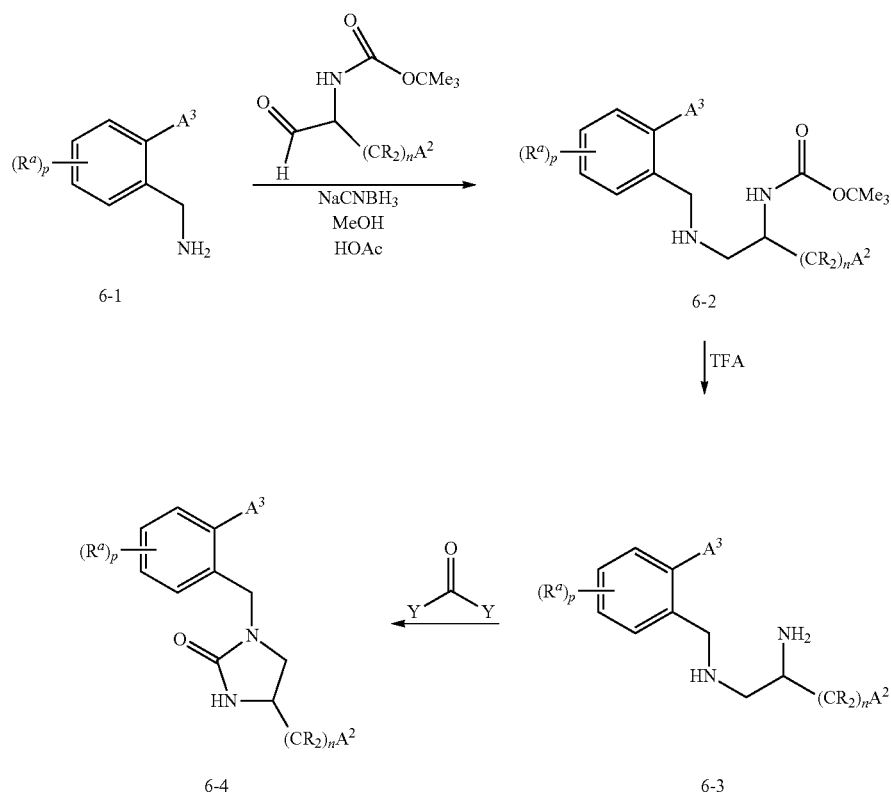

Compounds of the present invention 6-4 wherein R, $R^a$, p, $A^2$, $A^3$ and n are as defined in the claims can be prepared as shown in Scheme 6. Treatment of 6-1 with an appropriately substituted protected aminoaldehyde which can be purchased or prepared by known methods in the presence of a reducing agent such as sodium borohydride, sodium cyanoborohydride, sodium triacetoxyborohydride or the like in methanol, ethanol, dichloroethane, tetrahydrofuran or the like or according to methods described in Smith, M. B. and March, J. "March's Advanced Organic Chemistry", 5th Ed., John Wiley and Sons, New York, pp. 1187-1189 (2001) and references cited therein affords 6-2. Preferred conditions for this transformation are sodium cyanoborohydride in methanol with catalytic acetic acid. Deprotection of 6-2 affords 6-3. For the BOC protecting group, $TFA/CH_2Cl_2$ is the preferred method of deprotection. Diamines 6-3 are then cyclized to imidazolidinones 6-4 using phosgene (Y=Cl) or a phosgene equivalent such as triphosgene (Y=$OCCl_3$) or carbonyl-diimidazole (Y=imidazole) or the like in a solvent such as dichloromethane, dichloroethane, tetrahydrofuran, dimethoxyethane, or the like and a base such as triethylamine, diisopropylethylamine, N-methylmorpholine, or the like. Enantiopure products may be obtained using chiral chromatography.

SCHEME 7

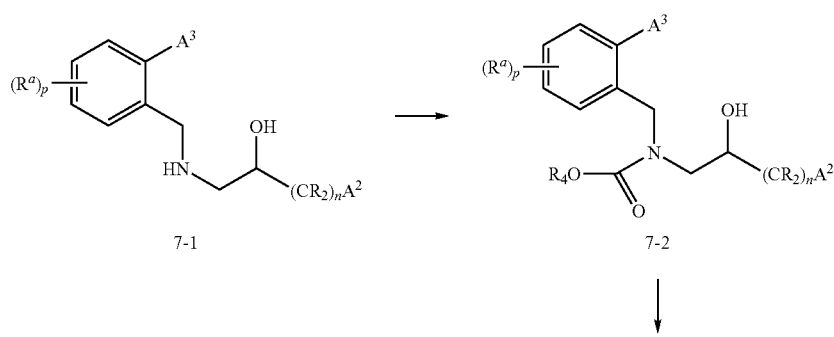

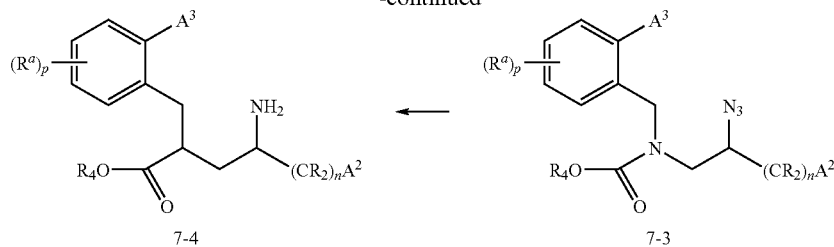

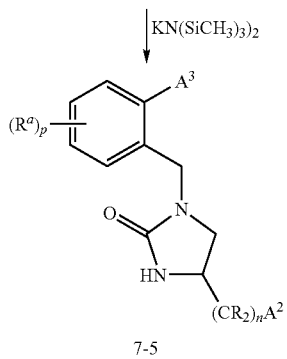

Compounds of the present invention 7-5 wherein R, $R^a$, p, $A^2$, $A^3$ and n are as defined in the claims can be prepared as shown in Scheme 7. Treatment of amine 7-1, prepared as described in Scheme 4 with an appropriate dicarbonate or chloroformate affords 7-2. 7-2 can be converted to azide 7-3 by reaction with methanesulfonyl chloride in dichloromethane, dichloroethane, tetrahydrofuran, dimethoxyethane, or the like in the presence of an appropriate base such as triethylamine, diisopropylethylamine, N-methylmorpholine, or the like. Alternatively, the alcohol may be converted to an alternative leaving group, such as tosylate, iodide, bromide, or the like. The mesylate is then displaced by an azide source, such as $NaN_3$, $LiN_3$, $Bu_4NN_3$ or the like in an appropriate solvent, such as DMF, DMPU, or the like. Azide 7-3 can also be prepared by treatment of alcohol 5-2 with diphenylphosphoryl azide, diethylazodicarboxylate and triphenylphosphine in THF. Azide 7-3 can be reduced to amine 7-4 with H2 over $PtO_2$ with THF as a solvent when $R_4$ is benzyl. Cyclization of 7-4 to imidazolidinones 7-5 is accomplished through the use of an appropriate base, such as lithium diisopropylamide or lithium-, sodium-, or potassium bis(trimethylsilyl)amide or the like in an appropriate solvent, such as THF, dimethoxyethane, DMF, DMA, or the like. Enantiopure products may be obtained via chiral chromatography.

-continued

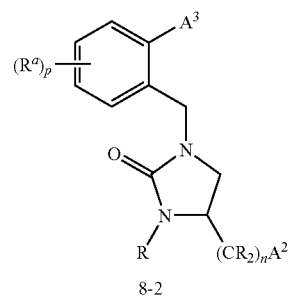

Compound 8-1 (prepared as described in Schemes 5, 6, and 7) wherein R, $R^a$, $A^2$, $A^3$, p, and n are as defined in the claims can be converted to 8-2 by treatment with an appropriate alkylating agent such as an alkyl halide, alkyl tosylate, alkyl mesylate, or the like (for example methyl iodide) in an appropriate solvent such as THF, dimethoxyethane, DMF, DMA, or the like, in the presence of an appropriate base, such as lithium diisopropylamide or lithium-, sodium-, or potassium bis(trimethylsilyl)amide or the like.

SCHEME 8

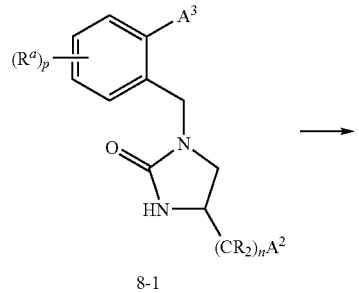

SCHEME 9

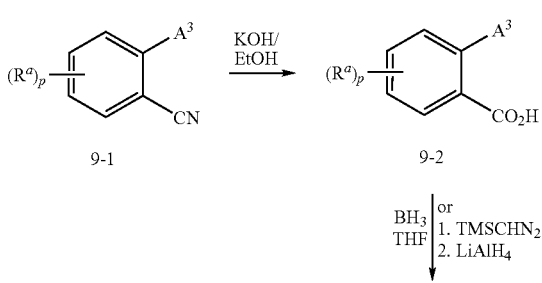

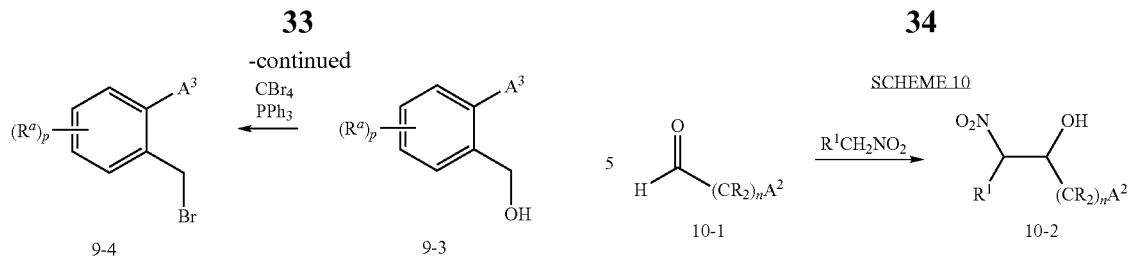

Intermediates 9-3 and 9-4 wherein $R^a$, p, and $A^3$ are as defined in the claims utilized in the present invention can be prepared as shown in Scheme 9. An appropriately substituted benzyl nitrile 9-1 prepared as shown in Scheme 2 can be heated with a base such as sodium hydroxide or potassium hydroxide or the like in an appropriate aqueous alcohol such as ethanol, propanol or the like to afford the appropriately substituted benzoic acid 9-2 (See: Smith, M. B. and March, J. "March's Advanced Organic Chemistry", $5^{th}$ Ed., John Wiley and Sons, New York, pp. 1179-1180 (2001) and references therein). Benzoic acids 9-2 can be reduced to benzyl alcohols 9-3 with reducing agents such as borane in solvents such as tetrahydrofuran or the like (See: Smith, M. B. and March, J. "March's Advanced Organic Chemistry", $5^{th}$ Ed., John Wiley and Sons, New York, pp. 1549 (2001) and references therein). Alternatively, 9-2 can be esterified by known methods including treatment with trimethylsilyldiazomethane and the resulting ester reduced to alcohol 9-3 with $LiAlH_4$ or the like. Intermediates 9-3 can be transformed into benzyl bromides 9-4 using reagents such as triphenylphosphine and carbon tetrabromide in solvents such as dichloromethane, dichloroethane or the like (See: Smith, M. B. and March, J. "March's Advanced Organic Chemistry", $5^{th}$ Ed., John Wiley and Sons, New York, pp. 518-519 (2001) and references therein).

Intermediates 10-4 of the present invention wherein R, $R^1$, $A^2$, p, and n are as defined in the claims can be prepared as shown in Scheme 10 from an appropriately substituted benzaldehyde 10-1 by condensation with a nitroalkane to afford the substituted nitroalcohol 10-2. This reaction may be catalyzed by aqueous bases such as sodium hydroxide or the like in solvents such as ethanol, methanol or the like. Nitroalcohols 10-2 can be reduced to aminoalcohols 10-3 with reductants such as Raney nickel, palladium on activated carbon or platinum oxide in the presence of hydrogen gas and aqueous acid in alcoholic solvents such as methanol, ethanol or the like (See: Langer, O., et al., *Bioorg. Med. Chem.*, 2001, 9, 677-694). Aminoalcohols 10-3 can be cyclised to oxazolidinones 10-4 using reagents such as phosgene (Y=Cl), triphosgene (Y=OCCl_3) or carbonyl diimidazole (Y=midazole) with bases such as triethylamine, diisopropylethylamine or the like in solvents like dichloromethane, dichloroethane, tetrahydrofuran, dimethoxyethane or the like.

Intermediates 11-4 of the present invention wherein R, R¹, A², p and n are as defined in the claims can be prepared as shown in scheme 11. Treatment of an N-carbamoyl-(N-methoxy-N-methyl)amide of an amino acid 11-1 which can be purchased or prepared by known methods with a Grignard or other organometallic reagent such as an organolithium affords the corresponding ketone 11-2. Reduction of the ketone with sodium borohydride or zinc borohydride in alcoholic solvents or THF or the like or with other reducing agents such as phenyldimethyl silane in THF affords alcohol 11-3 which can be cyclized to oxazolidinone 11-4 upon treatment with base such as KOH in solvents such as MeOH, EtOH or the like and THF, dioxane, dimethoxyethane or the like.

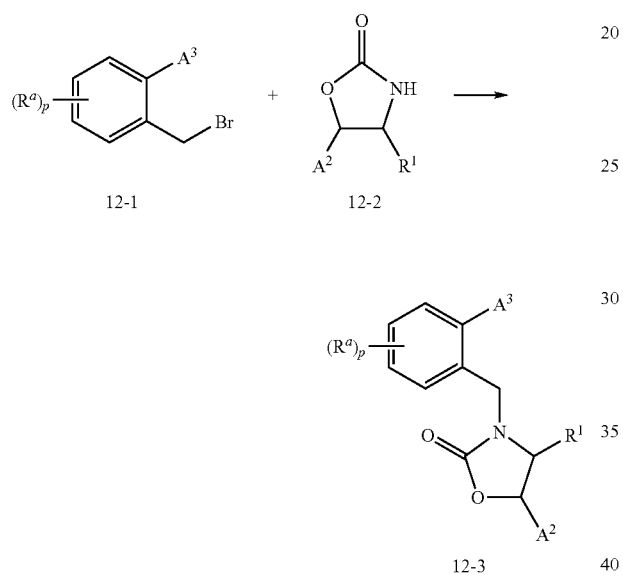

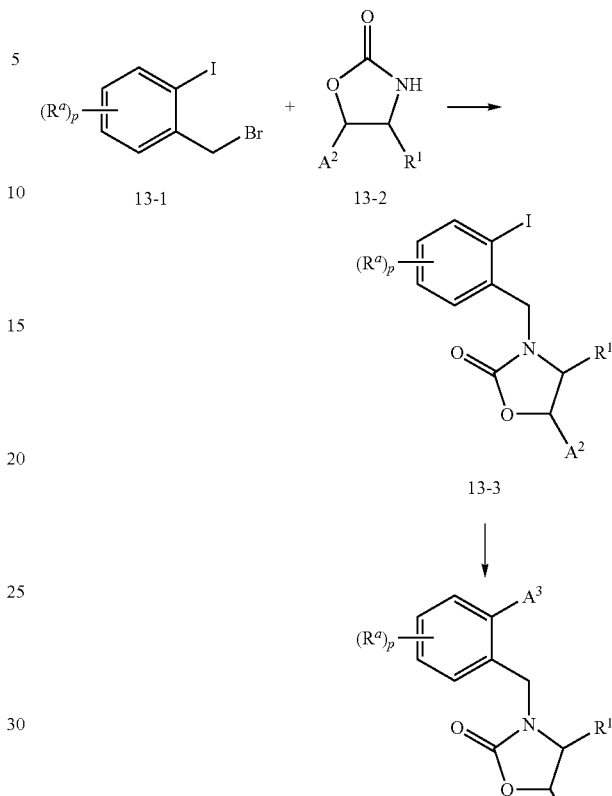

Compounds of the present invention 12-3 wherein R, R¹, R$^a$, A², A³, p and n are as defined in the claims can be prepared as shown in Scheme 12. Oxazolidinones 12-2, prepared as shown in Schemes 10 and 11 can be alkylated with benzyl bromides 12-1 which is prepared as shown in Scheme 9 using bases such as sodium hexamethyldisilazide or sodium hydride in solvents like tetrahydrofuran, dimethoxyethane, diethyl ether, dimethylformamide, dimethylacetamide, or the like to afford products 12-3.

Compounds of the present invention 13-4 wherein R, R¹, R$^a$, A², A³, p and n are as defined in the claims can be prepared as shown in Scheme 13. Oxazolidinones 13-2, prepared as shown in Schemes 10 and 11 can be alkylated with benzyl bromides 13-1 which can be prepared as shown in Scheme 1 using bases such as sodium hexamethyldisilazide or sodium hydride in solvents like tetrahydrofuran, dimethoxyethane, diethyl ether or the like to afford products 13-3. Compounds 13-4 are then prepared via a Suzuki or Stille reaction or variation thereof employing palladium catalyzed cross coupling of iodide 13-3 with an appropriately substituted aryl- or heteroaryl-boronic acid, -boronate ester or -trialkyl tin as described in Miyaua et al., *Chem. Rev.* 95, 2457 (1995) and references cited within and as described in Smith, M. B. and March, J. "March's Advanced Organic Chemistry", 5$^{th}$ Ed., John Wiley and Sons, New York, pp. 868-869 (2001) and references cited therein.

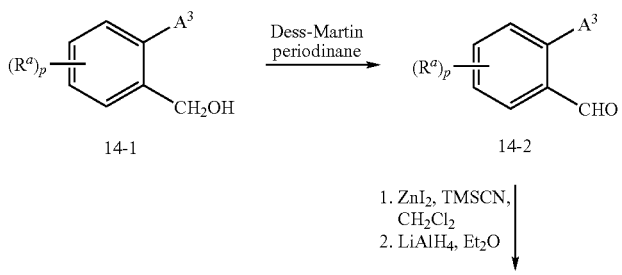

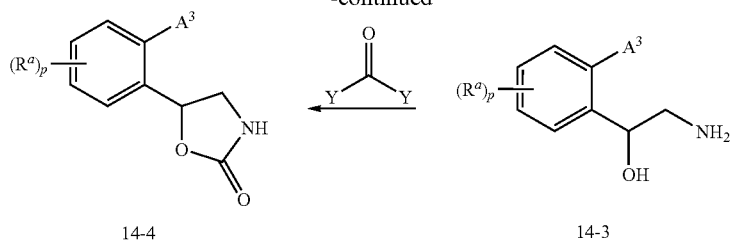

14-4    14-3

14-5

Compounds 14-5 of the present invention wherein R, $R^a$, $A^2$, $A^3$, p and n are as defined in the claims can be prepared as shown in Scheme 14. Benzyl alcohols 14-1 can be purchased or prepared according to the procedure outline in Scheme 9. Reaction of 14-1 with the Dess-Martin periodinane affords the corresponding benzylaldehydes 14-2. Other methods for oxidizing a primary hydroxyl group to an aldehyde can also be used, for example, Swern oxidation conditions, tetrapropylammonium perruthenate, pyridinium chlorochromate, sulfur trioxide-pyridine, or the like. 2-Amino-1-phenylethanols 14-3 can be prepared from 14-2 via the corresponding silylated cyanohydrin by treatment with trimethylsilyl cyanide and catalytic zinc iodide followed by reduction with lithium aluminum hydride or the like reducing agent. Alternatively, 2-amino-1-phenylethanols 14-3 can be prepared from 14-2 via the corresponding cyanohydrin by treatment with potassium cyanide followed by reduction. 2-Amino-1-phenylethanols 14-3 can be cyclized to oxazolidinones 14-4 using reagents such as phosgene (Y=Cl), triphosgene (Y=OCCl$_3$) or carbonyl diimidazole (Y=imidazole) with bases such as triethylamine, diisopropylethylamine or the like in solvents like dichloromethane, dichloroethane, tetrahydrofuran, dimethoxyethane or the like. Oxazolidinones 14-4 can be alkylated with alkyl, heteroalkyl, aryl, or heteroaryl bromides using bases such as sodium hexamethyldisilazide or sodium hydride in solvents like tetrahydrofuran, dimethoxyethane, diethyl ether or the like to afford products 14-5. Enantiopure products may be obtained via chiral chromatography.

SCHEME 15

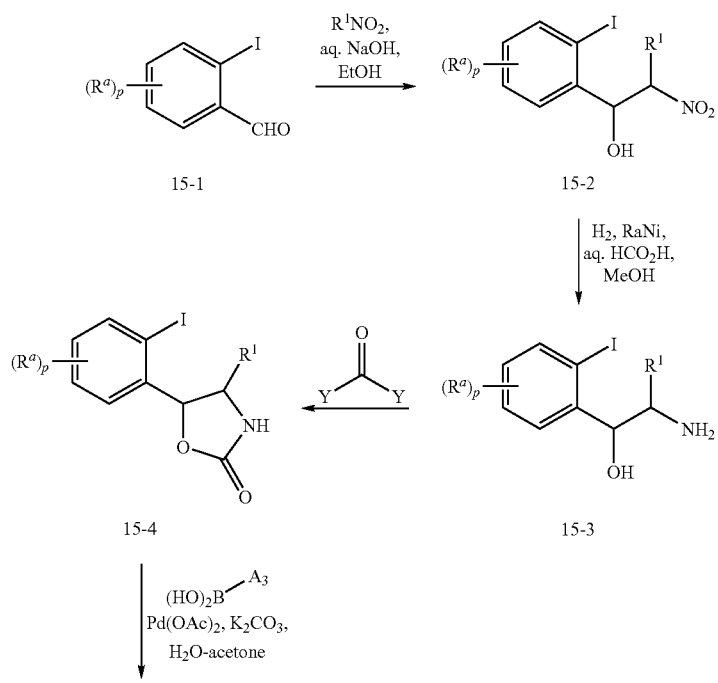

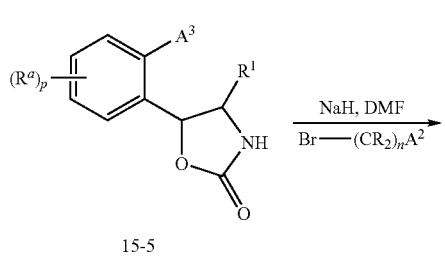 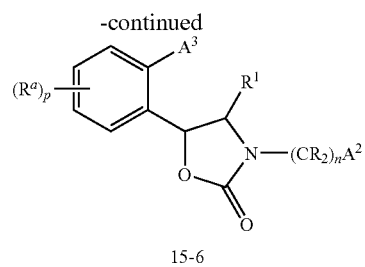

15-5 → 15-6

Compounds 15-6 of the present invention wherein R, R¹ Rᵃ, A², A³, p and n are as defined in the claims can be prepared as shown in Scheme 15. Aldehydes 15-1 can be purchased or prepared according to the procedure outline in Scheme 1. Condensation of 15-1 with a nitroalkane affords the substituted nitroalcohols 15-2. This reaction may be catalyzed by aqueous bases such as sodium hydroxide or the like in solvents such as ethanol, methanol, or the like. Nitroalcohols 15-2 can be reduced to aminoalcohols 15-3 with reductants such as Raney nickel, palladium on activated carbon, or platinum oxide in the presence of hydrogen gas and aqueous acid in alcoholic solvents such as methanol, ethanol or the like (See: Langer, O., et al., *Bioorg. Med. Chem.*, 2001, 9, 677-694). Aminoalcohols 15-3 can be cyclized to oxazolidinones 15-4 using reagents such as phosgene (Y=Cl), triphosgene (Y=OCCl₃) or carbonyl diimidazole (Y=imidazole) with bases such as triethylamine, diisopropylethylamine or the like in solvents like dichloromethane, dichloroethane, tetrahydrofuran, dimethoxyethane or the like. Oxazolidinones 15-5 are prepared via a Suzuki or Stille reaction or variation thereof employing palladium catalyzed cross coupling of iodides 15-4 with appropriately substituted aryl- or heteroaryl-boronic acids, -boronate esters or -trialkyl tin compounds, as described in Miyaura et al., *Chem. Rev.* 95, 2457 (1995) and references cited within, and as described in Smith, M. B. and March, J. "March's Advanced Organic Chemistry", 5th Ed., John Wiley and Sons, New York, pp. 868-869 (2001) and references cited therein. Oxazolidinones 15-5 can be alkylated with alkyl, heteroalkyl, aryl, or heteroaryl bromides using bases such as sodium hexamethyldisilazide or sodium hydride in solvents like tetrahydrofuran, dimethoxyethane, diethyl ether or the like to afford products 15-6. Enantiopure products may be obtained via chiral chromatography.

SCHEME 16

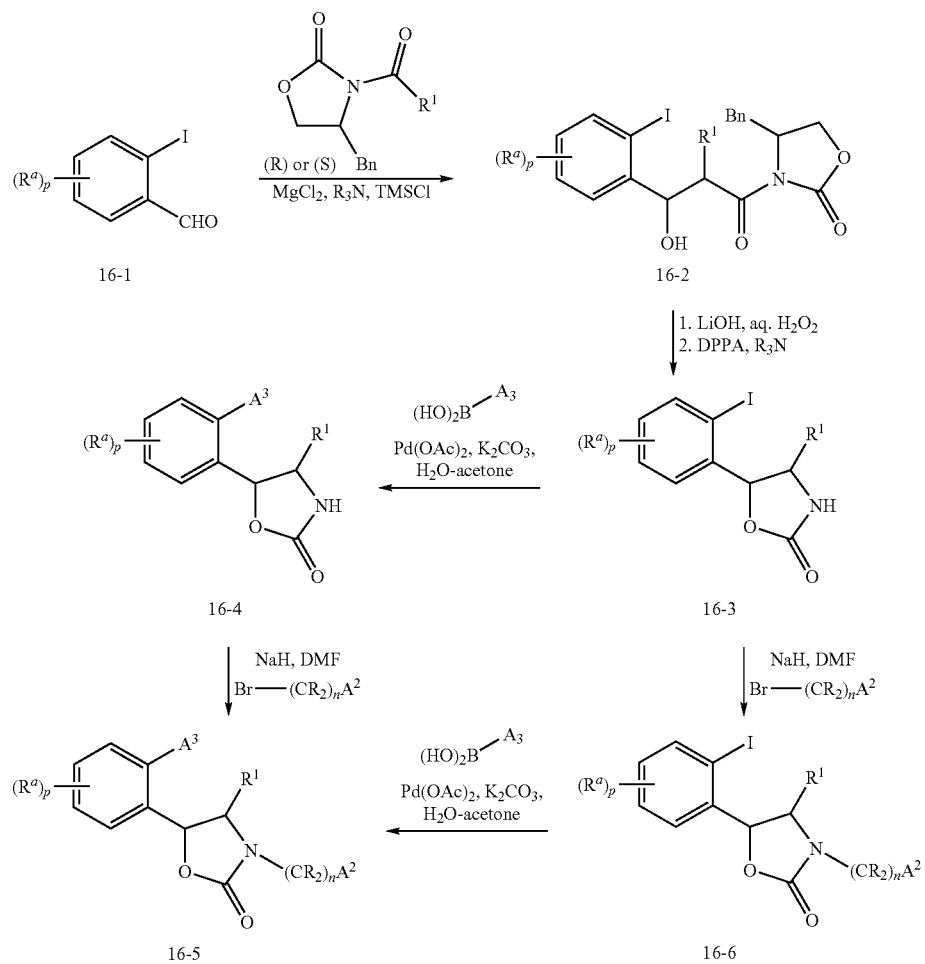

Compounds 16-5 of the present invention wherein R, $R^1$ $R^a$, $A^2$, $A^3$, p and n are as defined in the claims can be prepared as shown in Scheme 16. Aldehydes 16-1 can be purchased or prepared according to the procedure outline in Scheme 1. Condensation of 16-1 with chiral N-acyloxazolidinones affords the aldol adducts 16-2, as described in Evans, D. A. et al., *J. Am. Chem. Soc.,* 2002, 124, 392-3. The chiral N-acyloxazolidinones can be purchased or prepared as described in Ager, D. J.; Allen, D. A.; Schaad, D. R. *Synthesis* 1996, 1283-5. Compounds 16-2 can be hydrolyzed to the corresponding acids and then treated with diphenylphosphorazidate and a trialkylamine base to effect a Curtius rearrangement, affording chiral oxazolidinones 16-3. Oxazolidinones 16-4 are prepared via a Suzuki or Stille reaction or variation thereof employing palladium catalyzed cross coupling of iodides 16-3 with appropriately substituted aryl- or heteroaryl-boronic acids, -boronate esters or -trialkyl tin compounds, as described in Miyaura et al., *Chem. Rev.* 95, 2457 (1995) and references cited within, and as described in Smith, M. B. and March, J. "March's Advanced Organic Chemistry", 5th Ed., John Wiley and Sons, New York, pp. 868-869 (2001) and references cited therein. Oxazolidinones 16-4 can be alkylated with alkyl, heteroalkyl, aryl, or heteroaryl bromides using bases such as sodium hexamethyldisilazide or sodium hydride in solvents like tetrahydrofuran, dimethoxyethane, diethyl ether or the like to afford products 16-5. Alternatively, oxazolidinones 16-3 are alkylated with the appropriate bromides to afford compounds 16-6, which are subjected to a Suzuki or Stille reaction or variation thereof with appropriately substituted aryl- or heteroaryl-boronic acids, -boronate esters or -trialkyl tin compounds to afford products 16-5.

Example 1

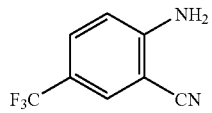

2-Amino-5-(trifluoromethyl)benzonitrile

A 2-liter flask was charged with 100 g (0.348 mol) of 4-amino-3-iodobenzotrifluoride, 40 g of CuCN and 750 mL of DMF. The mixture was heated to and then maintained at reflux for 1 hour. The reaction was cooled and poured into 3 L of water containing 300 mL of concentrated ammonium hydroxide. To the mixture was added 1 L $CH_2Cl_2$. The mixture was then filtered through celite. The layers were separated and the aqueous layer was back extracted with $CH_2Cl_2$. The organic extracts were combined and the solvent removed under reduced pressure. The residue was dissolved in 1.5 L of ether and the resulting solution was washed with 1N ammonium hydroxide, aqueous sodium bisulfate, 1N aqueous HCl and brine. The solution was dried over anhydrous $MgSO_4$ and filtered through a silica gel plug containing a layer of $MgSO_4$ on top. The plug was washed with 0.5 L ether. The ether solutions were combined and concentrated to 750 mL and let stand at room temperature. After 2 days the resulting solids were collected, washed with hexanes and dried under reduced pressure to afford 2-amino-5-(trifluoromethyl)benzonitrile $^1$H NMR (CDCl$_3$, 500 MHz) δ 7.68 (s, 1H), 7.58 (d, J=8.5 Hz, 1H), 6.81 (d, J=8.5 Hz, 1H), 4.80 (br s, 2H).

Example 2

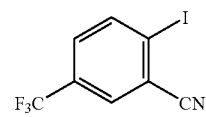

2-Iodo-5-(trifluoromethyl)benzonitrile

To a solution of 2-amino-5-(trifluoromethyl)benzonitrile (15.1 g) and diiodomethane (24 mL) in acetonitrile (150 mL) at 35° C. was added t-butyl nitrite (21 mL) dropwise. The reaction was maintained at 30-35° C. during the addition. The reaction was aged for 30 min and then was heated to 60° C. for 30 minutes. The reaction mixture was cooled, diluted with ether and washed 2× with water, 2× with aqueous sodium bisulfite, water and then brine. The solution was dried over anhydrous $MgSO_4$, filtered through a silica gel plug and then concentrated giving 100 g of a red oil. The product was purified by silica gel chromatography eluting sequentially with hexanes, 3:1 hexanes/$CH_2Cl_2$ and 1:1 hexanes/$CH_2Cl_2$ to afford 2-iodo-5-(trifluoromethyl)benzonitrile. $^1$H NMR (CDCl$_3$, 500 MHz) δ 8.10 (d, J=8.5 Hz, 1H), 7.85 (d, J=1.8 Hz, 1H), 7.52 (dd, J=8.5, 1.8 Hz, 1H).

Example 3

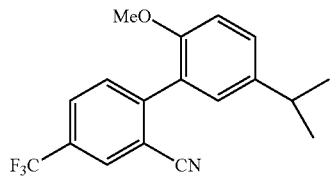 [SMILES: COc1ccc(C(C)C)cc1-c1ccc(C(F)(F)F)cc1C#N]

5'-Isopropyl-2'-methoxy-4-(trifluoromethyl)biphenyl-2-carbonitrile

To a solution of 2-iodo-5-(trifluoromethyl)benzonitrile (2.0 g, 6.7 mmol) and (5-isopropyl-2-methoxyphenyl)boronic acid (1.6 g, 8.4 mmol) in dimethyl ethylene glycol (30.4 mL) was added 2M $Na_2CO_3$ (6.8 mL), ethanol (9.6 mL), and water (10 mL). The solution was degassed with nitrogen for 2 minutes. Pd(PPh$_3$)$_4$ (774 mg, 0.67 mmol) was added and the solution was degassed with nitrogen again for 2 minutes. The solution was divided equally into two 40 mL microwave tubes. Each tube was degassed with nitrogen for 1 minute, sealed, and placed in a microwave reactor. The wattage was set for 200 W until the temperature reached 150° C. and then the temperature was held at 150° C. for ten minutes. The tubes were then cooled to room temperature, combined, poured into $H_2O$ (50 mL), and extracted with EtOAc (100 mL). The organic layer was washed with brine (50 mL), dried over $Na_2SO_4$, filtered, and concentrated. Purification by flash chromatography with 15% $CH_2Cl_2$/hexanes afforded 5'-isopropyl-2'-methoxy-4-(trifluoromethyl)biphenyl-2-carbonitrile as a light yellow oil. $R_f$=0.65 (25% EtOAc/hexanes). $^1$H NMR (CDCl$_3$, 500 MHz) δ 7.97 (s, 1H), 7.85 (d, J=8.0 Hz, 1H), 7.63 (d, J=8.0 Hz, 1H), 7.31 (dd, J=8.5, 2.0 Hz, 1H), 7.12 (d, J=2.0 Hz, 1H), 6.97 (d, J=8.5 Hz, 1H), 3.82 (s, 3H), 2.93 (m, 1H), 1.27 (d, J=7.0 Hz, 6H).

Example 4

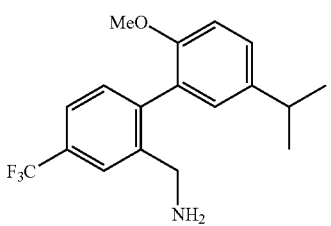 [SMILES: COc1ccc(C(C)C)cc1-c1ccc(C(F)(F)F)cc1CN]

1-[5'-Isopropyl-2'-methoxy-4-(trifluoromethyl)biphenyl-2-yl]methanamine

5'-Isopropyl-2'-methoxy-4-(trifluoromethyl)biphenyl-2-carbonitrile (996.2 mg, 3.12 mmol) was dissolved in Et$_2$O (33 mL) and cooled to 0° C. LAH (12.49 mL of a 1 M solution in Et$_2$O, 12.49 mmol) was added dropwise by syringe. After stirring at 0° C. for 10 minutes, the reaction was warmed to room temperature and stirred at room temperature for 6 hours. The reaction was then quenched by slow dropwise addition of 1.5 mL of H$_2$O (vigorous evolution of gas), followed by 1.5 mL of 30% NaOH, followed by 3.0 mL of H$_2$O. The resulting gelatinous precipitate was washed with 5×20 mL of CH$_2$Cl$_2$; the organic washes were dried over Na$_2$SO$_4$, filtered and concentrated. Purification of the residue by flash chromatography with 2% MeOH/CH$_2$Cl$_2$ containing 0.1% Et$_3$N afforded 1-[5'-isopropyl-2'-methoxy-4-(trifluoromethyl)biphenyl-2-yl]methanamine. R$_f$=0.30 (10% MeOH/CH$_2$Cl$_2$). LCMS=324.3 (M+1)$^+$. $^1$H NMR (CDCl$_3$, 500 MHz) δ 7.77 (s, 1H), 7.55 (d, J=6.8 Hz, 1H), 7.32 (d, J=7.8 Hz, 1H), 7.25 (dd, J=8.3, 2.1 Hz, 1H), 7.00 (d, J=2.1 Hz, 1H), 6.92 (d, J=8.4 Hz, 1H), 3.66-3.74 (m, 5H), 2.91 (m, 1H), 1.26 (d, J=6.9 Hz, 6H).

Example 5

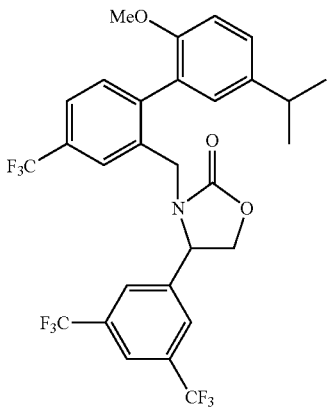 [SMILES: COc1ccc(C(C)C)cc1-c1ccc(C(F)(F)F)cc1CN1C(=O)OCC1c1cc(C(F)(F)F)cc(C(F)(F)F)c1]

4-[3,5-bis(trifluoromethyl)phenyl]-3-{[5'-isopropyl-2'-methoxy-4-(trifluoromethyl)biphenyl-2-yl]methyl}-1,3-oxazolidin-2-one

Step A: methyl [3,5-bis(trifluoromethyl)phenyl](hydroxy)acetate

To solution of [3,5-bis(trifluoromethyl)phenyl](hydroxy)acetic acid (510 mg, 1.77 mmol) in benzene (10 mL) was added MeOH (1.5 mL) followed by (trimethylsilyl)diazomethane (1.06 mL of a 2M solution in hexanes, 2.12 mmol). After 10 minutes, the reaction was quenched with several drops of HOAc (add until yellow color disappears). The reaction was concentrated and purified by flash chromatography with 10 to 80% EtOAc/hexanes to afford methyl [3,5-bis(trifluoromethyl)phenyl](hydroxy)acetate. $^1$H NMR (CDCl$_3$, 500 MHz) δ 7.94 (s, 2H), 7.85 (s, 1H), 5.32 (s, 1H), 3.83 (s, 3H), 3.68 (bs, 1H).

Step B: methyl [3,5-bis(trifluoromethyl)phenyl](bromo)acetate

Methyl [3,5-bis(trifluoromethyl)phenyl](hydroxy)acetate (300 mg, 0.993 mmol) was dissolved in CH$_2$Cl$_2$ (10 mL). The solution was cooled to 0° C. and CBr$_4$ (659 mg, 1.986 mmol) was added followed by PPh$_3$ (521 mg, 1.986 mmol). After 1 hour, the reaction was warmed to room temperature and stirred at room temperature for 1 hour. The reaction was filtered through a short plug of silica gel with CH$_2$Cl$_2$. The filtrate was concentrated and the residue was purified by flash chromatography with 5% EtOAc/hexanes to afford methyl [3,5-bis(trifluoromethyl)phenyl](bromo)acetate. R$_f$=0.24 (5% EtOAc/hexanes). $^1$H NMR (CDCl$_3$, 500 MHz) δ 8.02 (s, 2H), 7.87 (s, 1H), 5.41 (s, 1H), 3.83 (s, 3H).

Step C: methyl [3,5-bis(trifluoromethyl)phenyl]({[5'-isopropyl-2'-methoxy-4-(trifluoromethyl)biphenyl-2-yl]methyl}amino)acetate To a flask containing methyl [3,5-bis(trifluoromethyl)phenyl](bromo)acetate (237.7 mg, 0.651 mmol) was added 1-[5'-isopropyl-2'-methoxy-4-(trifluoromethyl)biphenyl-2-yl]methanamine (102.1 mg, 0.316 mmol) in CH$_2$Cl$_2$ (4 mL). The reaction was stirred at room temperature for 5 hours and then diluted with EtOAc (50 ml). The organic solution was washed with water and brine (15 mL each). The organic extract was dried over Na$_2$SO$_4$, filtered, and concentrated. Purification of the residue by flash chromatography (5 to 15% EtOAc/hexanes) afforded methyl[3,5-bis(trifluoromethyl)phenyl]({[5'-isopropyl-2'-methoxy-4-(trifluoromethyl)biphenyl-2-yl]methyl}amino)acetate. R$_f$=0.33 (15% EtOAc/hexanes). LCMS=608.4 (M+1)$^+$. $^1$H NMR (CDCl$_3$, 500 MHz) δ 7.76-7.79 (m, 3H), 7.62 (s, 1H), 7.56 (d, J=7.8 Hz, 1H), 7.31 (d, J=7.8 Hz, 1H), 7.23 (dd, J=8.2, 1.9 Hz, 1H), 6.96 (m, 1H), 6.89 (d, J=8.5 Hz, 1H), 4.30 (m, 1H), 3.54-3.70 (m, 8H), 2.87 (m, 1H), 1.21-1.23 (m, 6H).

Step D: 2-[3,5-bis(trifluoromethyl)phenyl]-2-({[5'-isopropyl-2'-methoxy-4-(trifluoromethyl)biphenyl-2-yl]-methyl}amino)ethanol A solution of methyl[3,5-bis(trifluoromethyl)phenyl]({[5'-isopropyl-2'-methoxy-4-(trifluoromethyl)biphenyl-2-yl]methyl}amino)acetate (13.2 mg, 0.0217 mmol) was dissolved in Et$_2$O (1.5 mL) and cooled to 0° C. LAH (108.5 μL of a 1 M solution in LAH, 0.1085 mmol) was added dropwise by syringe. The reaction was warmed to room temperature and stirred at room temperature for 1 hour. The reaction was then quenched by addition of H$_2$O (100 μL) followed by 1 N NaOH (100 μL), followed by H$_2$O (300 μL). The gelatinous precipitate was washed several times with CH$_2$Cl$_2$. The organic washes were filtered through a plug of silica gel with 2% MeOH/CH$_2$Cl$_2$ and the filtrate was concentrated. Purification of the residue by PTLC with 25% EtOAc/hexanes afforded 2-[3,5-bis(trifluoromethyl)phenyl]-2-({[5'-isopropyl-2'-methoxy-4-(trifluoromethyl)biphenyl-2-yl]methyl}amino)ethanol. R$_f$=0.27 (25% EtOAc/hexanes). LCMS=580.4 (M+1)$^+$. $^1$H NMR (CD$_2$Cl$_2$, 500 MHz) δ 7.79 (s, 1H), 7.75 (s, 2H), 7.63-7.68 (m, 1H), 7.55 (d, J=7.8 Hz, 1H), 7.31 (d, J=7.8 Hz, 1H), 7.23 (m, 1H), 6.94 (m, 1H), 6.89 (m, 1H), 3.43-3.76 (m, 9H), 2.86 (m, 1H), 1.90 (bs, 1H), 1.20 (d, J=6.8 Hz, 6H).

Step E: 4-[3,5-bis(trifluoromethyl)phenyl]-3-{[5'-isopropyl-2'-methoxy-4-(trifluoromethyl)biphenyl-2-yl]methyl}-1,3-oxazolidin-2-one To a solution of phosgene (21 μL of a 20% solution in toluene, ~0.0535 mmol) in CH$_2$Cl$_2$ (0.5 mL) was added 2-[3,5-bis(trifluoromethyl)phenyl]-2-({[5'-isopropyl-2'-methoxy-4-(trifluoromethyl)biphenyl-2-yl]methyl}amino)ethanol (3.1 mg, 0.00535 mmol) in CH$_2$Cl$_2$ (0.5 mL), followed by DIPEA (19 μL, 0.107 mmol). After stirring for 5 minutes, the reaction was poured into water (1 mL) and the mixture was extracted with EtOAc (20 mL). The organic extract was washed with H$_2$O, saturated NaHCO$_3$, and brine (5 mL each). The organic layer was then dried over Na$_2$SO$_4$, filtered, and concentrated. The residue was purified by PTLC to afford 4-[3,5-bis(trifluoromethyl)phenyl]-3-{[5'-isopropyl-2'-methoxy-4-(trifluoromethyl)biphenyl-2-yl]methyl}-1,3-oxazolidin-2-one. R$_f$=0.27 (25% EtOAc/hexanes). LCMS=606.3 (M+1)$^+$. $^1$H NMR (CD$_2$Cl$_2$, 500 MHz) (Doubling of some peaks observed; atropisomers present in 1:1 ratio) δ 7.84 (s, 1H), 7.19-7.60 (m, 6H), 6.80-6.87 (m, 2H), 3.84-4.68 (m, 5H), 3.68 & 3.64 (2 singlets, 3H), 2.82 (m, 1H), 1.17-1.21 (m, 6H).

Example 6

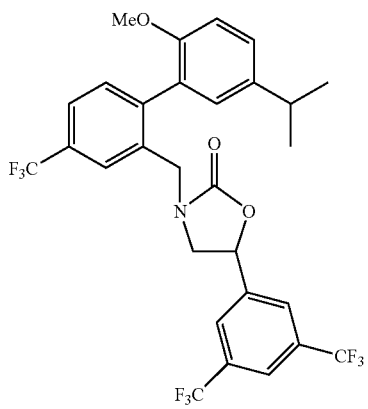 [SMILES: COc1ccc(C(C)C)cc1-c1ccc(C(F)(F)F)cc1CN1CC(c2cc(C(F)(F)F)cc(C(F)(F)F)c2)OC1=O]

5-[3,5-bis(trifluoromethyl)phenyl]-3-{[5'-isopropyl-2'-methoxy-4-(trifluoromethyl)biphenyl-2-yl]methyl}-1,3-oxazolidin-2-one Step A: 2-[3,5-bis(trifluoromethyl)phenyl]oxirane In a dry flask was placed NaH (1.09 g of 60% NaH, 27.27 mmol). DMSO (90 mL) was added followed by trimethylsulfoxonium iodide (7.0 g, 31.82 mmol). The reaction was stirred for 5 minutes and then 3,5-bis(trifluoromethyl)benzaldehyde (1.5 mL, 9.09 mmol) was added as a solution in DMSO (15 mL). The reaction was stirred at room temperature for 1 hour and then poured into ice/water (300 mL). The mixture was extracted with pentanes (3×150 mL). The pentane extracts were combined and filtered through a short plug of silica gel with 10% Et$_2$O/pentanes. The filtrate was concentrated and the residue was purified by flash chromatography with 10% Et$_2$O/pentanes to give 2-[3,5-bis(trifluoromethyl)phenyl]oxirane. R$_f$=0.42 (10% Et$_2$O/pentanes). $^1$H NMR (CDCl$_3$, 500 MHz) 7.82 (s, 1H), 7.74 (s, 2H), 3.99 (dd, J=3.9, 2.5 Hz, 1H), 3.23 (dd, J=5.2, 4.1 Hz, 1H), 2.79 (dd, J=5.5, 2.5 Hz, 1H).

Step B: 1-[3,5-bis(trifluoromethyl)phenyl]-2-({[5'-isopropyl-2'-methoxy-4-(trifluoromethyl)biphenyl-2-yl]methyl}amino)ethanol A solution of 1-[5'-isopropyl-2'-methoxy-4-(trifluoromethyl)biphenyl-2-yl]methenamine (300 mg, 0.929 mmol) and 2-[3,5-bis(trifluoromethyl)phenyl]oxirane (297 mg, 1.161 mmol) in 2-propanol (9 mL) was heated at reflux for 15 hours and then cooled to room temperature. The solution was concentrated, and purification of the residue by flash chromatography with 10 to 80% EtOAc/hexanes afforded 1-[3,5-bis(trifluoromethyl)phenyl]-2-({[5'-isopropyl-2'-methoxy-4-(trifluoromethyl)biphenyl-2-yl]methyl}amino)ethanol. R$_f$=0.24 (25% EtOAc/hexanes). LCMS=580.3 (M+1)$^+$. $^1$H NMR (CDCl$_3$, 500 MHz) δ 7.75-7.76 (m, 3H), 7.69 (s, 1H), 7.58 (d, J=7.8 Hz, 1H), 7.34 (d, J=7.7 Hz, 1H), 7.25 (m, 1H), 6.98 (bs, 1H), 6.92 (d, J=8.5 Hz, 1H), 4.62 (m, 1H), 3.65-3.82 (m, 5H), 2.89 (m, 1H), 2.79 (dd, J=12.4, 3.0 Hz, 1H), 2.48 (m, 1H), 1.23 (d, J=6.8 Hz, 6H).

Step C: 5-[3,5-bis(trifluoromethyl)phenyl]-3-{[5'-isopropyl-2'-methoxy-4-(trifluoromethyl)biphenyl-2-yl]methyl}-1,3-oxazolidin-2-one To a solution of 1-[3,5-bis(trifluoromethyl)phenyl]-2-({[5'-isopropyl-2'-methoxy-4-(trifluoromethyl)biphenyl-2-yl]methyl}amino)ethanol (31.9 mg, 0.0551 mmol) in CH$_2$Cl$_2$ (5 mL) at 0° C. was added DIPEA (67 μL, 0.386 mmol), followed by triphosgene (8.2 mg, 0.0276 mmol). The reaction was stirred at 0° C. for 30 minutes. The reaction was then poured into saturated NaHCO$_3$ (15 mL) and the mixture was extracted with EtOAc (50 mL). The organic layer was washed with brine (15 mL), dried over Na$_2$SO$_4$, filtered, and concentrated. Purification of the residue by flash chromatography (20% EtOAc/hexanes) afforded 5-[3,5-bis(trifluoromethyl)phenyl]-3-{[5'-isopropyl-2'-methoxy-4-(trifluoromethyl)biphenyl-2-yl]methyl}-1,3-oxazolidin-2-one. R$_f$=0.32 (25% EtOAc/hexanes). LCMS=606.3 (M+1)$^+$. $^1$H NMR (CD$_2$Cl$_2$, 500 MHz) (atropisomers present in 1:1 ratio, doubling of some peaks) δ 7.90 (s, 1H), 7.77 (s, 2H), 7.57-7.62 (m, 2H), 7.37 (d, J=8.0 Hz, 1H), 7.27 (m, 1H), 6.98 (s, 1H), 6.93 (dd, J=8.4, 3.2 Hz, 1H), 5.42-5.53 (m, 1H), 4.15-4.59 (m, 2H), 3.72 & 3.73 (2 singlets, 3H), 3.05-3.65 (m, 2H), 2.88 (m, 1H), 1.19-1.23 (m, 6H).

The 2 enantiomers could be separated by chiral HPLC using 15% IPA/heptanes and an AD chiral column.

Example 7

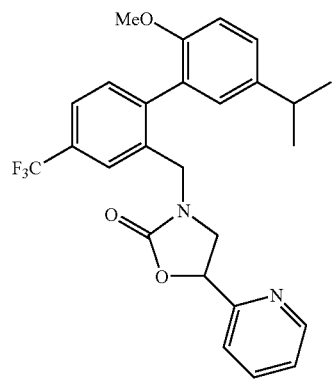 [SMILES: COc1ccc(C(C)C)cc1-c1ccc(C(F)(F)F)cc1CN1CC(c2ccccn2)OC1=O]

3-{[5'-Isopropyl-2'-methoxy-4-(trifluoromethyl)biphenyl-2-yl]methyl}-5-pyridin-2-yl-1,3-oxazolidin-2-one Step A: 2-({[5'-isopropyl-2'-methoxy-4-(trifluoromethyl)biphenyl-2-yl]methyl}amino)-1-pyridin-2-ylethanol A solution of 1-[5'-isopropyl-2'-methoxy-4-(trifluoromethyl)biphenyl-2-yl]methenamine (300 mg, 0.929 mmol) and 2-oxiran-2-ylpyridine (640 mg) [prepared by reaction of 2-pyridine carboxaldehyde with NaH and trimethylsulfoxonium iodide in DMSO] in 2-propanol (9 mL) was heated at reflux for 5 hours and then cooled to room temperature. The solution was concentrated, and the residue was purified by flash chromatography with 50 to 100% EtOAc/hexanes containing 0.5% Et$_3$N to afford 2-({[5'-isopropyl-2'-methoxy-4-(trifluoromethyl)biphenyl-2-yl]methyl}amino)-1-pyridin-2-ylethanol. Analysis by LCMS showed the desired product contaminated with several minor impurities. This material was used in the next reaction without further purification or analysis.

Step B: Benzyl (2-hydroxy-2-pyridin-2-ylethyl){[5'-isopropyl-2'-methoxy-4-(trifluoromethyl)biphenyl-2-yl]methyl}carbamate A solution of (PhCH$_2$OCO)$_2$O (103 mg, 0.360 mmol) in dry CH$_2$Cl$_2$ (2 mL) was added by cannula to a stirred solution of 2-({[5'-isopropyl-2'-methoxy-4-(trifluoromethyl)biphenyl-2-yl]methyl}amino)-1-pyridin-2-ylethanol (160 mg, 0.360 mmol) in dry CH$_2$Cl$_2$ (10 mL) at room temperature under N$_2$. The reaction was stirred for 2 h at room temperature and concentrated in vacuo to give the crude product. This was purified by flash chromatography (Si, 25×160 mm, 0-50% EtOAc in hexanes gradient) to afford benzyl (2-hydroxy-2-pyridin-2-ylethyl) {[5'-isopropyl-2'-methoxy-4-(trifluoromethyl)biphenyl-2-yl]methyl}carbamate. R$_f$=0.63 (50% EtOAc/hexanes). LCMS calc.=579.25; found=579.2 (M+1)$^+$.

Step C: 3-{[5'-Isopropyl-2'-methoxy-4-(trifluoromethyl)biphenyl-2-yl]methyl}-5-pyridin-2-yl-1,3-oxazolidin-2-one A solution of potassium bis(trimethylsilyl)amide (464 μL of a 0.5M solution in toluene, 0.232 mmol) was added dropwise to a stirred solution of benzyl (2-hydroxy-2-pyridin-2-ylethyl){[5'-isopropyl-2'-methoxy-4-(trifluoromethyl)biphenyl-2-yl]methyl}carbamate (134.3 mg, 0.232 mmol) in dry THF (10 mL) at room temperature under N$_2$. After stirring at room temperature for 1 h, the reaction was quenched with saturated NH$_4$Cl (10 mL) and extracted with EtOAc (3×20 mL). The combined extracts were dried (Na$_2$SO$_4$) and concentrated in vacuo to give the crude product. This was purified by flash chromatography (Si, 25×160 mm, 0-70% EtOAc in hexanes gradient) to afford 3-{[5'-isopropyl-2'-methoxy-4-(trifluoromethyl)biphenyl-2-yl]methyl}-5-pyridin-2-yl-1,3-oxazolidin-2-one. R$_f$=0.58 (50% EtOAc/hexanes). LCMS calc.=471.19; found=471.2 (M+1)$^+$.

Example 8

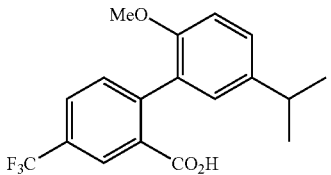 [SMILES: COc1ccc(C(C)C)cc1-c1ccc(C(F)(F)F)cc1C(=O)O]

5'-Isopropyl-2'-methoxy-4-(trifluoromethyl)biphenyl-2-carboxylic acid

A solution of 5'-isopropyl-2'-methoxy-4-(trifluoromethyl) biphenyl-2-carbonitrile (727 mg, 2.28 mmol) and KOH (767 mg, 13.7 mmol) in H$_2$O (7.70 mL) and i-PrOH (11.55 mL) was subjected to microwave irradiation (300 W 130° C., 4 h) in a sealed tube. The reaction mixture was concentrated in vacuo to remove the i-PrOH. The aqueous slurry obtained was diluted with water (50 mL) and extracted with EtOAc (50 mL). The organic extract was dried (Na$_2$SO$_4$) and concentrated in vacuo to afford 5'-isopropyl-2'-methoxy-4-(trifluoromethyl)biphenyl-2-carboxamide. The aqueous layer was acidified with concentrated HCl and extracted with EtOAc (3×50 mL). The combined organic extracts were dried (Na$_2$SO$_4$) and concentrated in vacuo to give 5'-isopropyl-2'-methoxy-4-(trifluoromethyl)biphenyl-2-carboxylic acid as a colorless solid. $^1$H NMR (CDCl$_3$, 500 MHz) δ 8.01 (s, 1H), 7.71 (d, J=7.8 Hz, 1H), 7.41 (d, J=7.8 Hz, 1H), 7.14 (d, J=8.1 Hz, 1H), 7.04 (s, 1H), 6.77 (d, J=8.1, 1H), 3.68 (s, 3H), 2.84 (septet, J=6.7 Hz, 1H), 1.19 (d, J=6.7 Hz, 6H).

Example 9

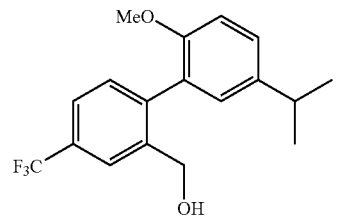

[5'-Isopropyl-2'-methoxy-4-(trifluoromethyl)biphenyl-2-yl]methanol

A solution of borane in THF (1 M, 859 μL, 0.859 mmol) was added dropwise to a stirred solution of 5'-isopropyl-2'-methoxy-4-(trifluoromethyl)biphenyl-2-carboxylic acid and 5'-isopropyl-2'-methoxy-4-(trifluoromethyl)biphenyl-2-carboxamide (3:1, 96.8 mg, 0.286 mmol) in dry THF at room temperature under N$_2$. The reaction was stirred at room temperature for 3 h and carefully quenched with water (10 mL). The mixture was extracted with EtOAc (3×20 mL) and the combined extracts were washed with brine, dried (Na$_2$SO$_4$) and concentrated in vacuo to give the crude product. This was purified by flash chromatography (Si, 125×160 mm, 0-30% EtOAc in hexanes gradient) to afford [5'-isopropyl-2'-methoxy-4-(trifluoromethyl)biphenyl-2-yl]methanol as a colorless oil. R$_f$=0.27 (10% EtOAc/hexanes). $^1$H NMR (CDCl$_3$, 500 MHz) δ 7.89 (br s, 1H), 7.62 (dd, J=8.0, 1.3 Hz, 1H), 7.36 (d, J=8.0 Hz, 1H), 7.29 (dd, J=8.5, 2.3 Hz, 1H), 7.03 (d, J=2.3 Hz, 1H), 6.96 (d, J=8.5, 1H), 4.51 (m, 2H), 3.74 (s, 3H), 2.93 (septet, J=7.0 Hz, 1H), 2.51 (s, 1H), 1.29 (d, J=7.0 Hz, 6H).

Example 10

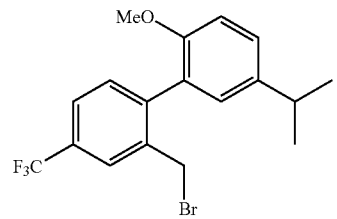

2-(Bromomethyl)-5'-isopropyl-2'-methoxy-4-(trifluoromethyl)biphenyl

CBr$_4$ (112 mg, 0.211 mmol) and Ph$_3$P (55 mg, 0.211 mmol) were added successively to a stirred solution of [5'-isopropyl-2'-methoxy-4-(trifluoromethyl)biphenyl-2-yl]

methanol (57.1 mg, 0.176 mmol) in dry CH$_2$Cl$_2$ (1 mL) at 0° C. under N$_2$. The solution was stirred at room temperature for 1 h and the reaction mixture was concentrated in vacuo to afford the crude product. This was purified by flash chromatography (Si, 12×160 mm, 0-20% EtOAc in hexanes gradient) to give 2-(bromomethyl)-5'-isopropyl-2'-methoxy-4-(trifluoromethyl)biphenyl as a colorless oil. R$_f$=0.95 (20% EtOAc/hexanes). LCMS calc.=387.05; found=387.0 (M+1)$^+$. $^1$H NMR (CDCl$_3$, 500 MHz) δ 7.83 (br s, 1H), 7.60 (dd, J=8.0, 1.3 Hz, 1H), 7.37 (d, J=8.0 Hz, 1H), 7.29 (dd, J=8.5, 2.3 Hz, 1H), 7.14 (d, J=2.3 Hz, 1H), 6.95 (d, J=8.5, 1H), 4.45 (d, J=10.6 Hz, 1H), 4.33 (d, J=10.6 Hz, 1H), 3.76 (s, 3H), 2.94 (septet, J=6.9 Hz, 1H), 1.29 (d, J=6.9 Hz, 6H).

Example 11

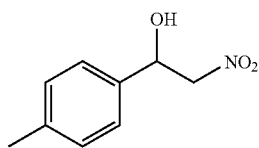

1-(4-Methylphenyl)-2-nitroethanol

A stirred solution of 4-methylbenzaldehyde (325 mg, 319 μL, 2.71 mmol) and nitromethane (531 μL, 9.89 mmol) in absolute EtOH (20 mL) at 0° C. was treated with 10% aq. NaOH (m/v) (1.14 mL, 2.84 mmol), stirred for 1 h and treated with 2% aq. acetic acid (m/v) (8.54 mL, 2.84 mmol). The reaction was stirred for 1 h at room temperature then partitioned between water (50 mL) and EtOAc (50 mL). The aqueous layer was extracted with EtOAc (2×50 mL) and the combined organic extracts were washed with saturated NaHCO$_3$ (50 mL) and brine (50 mL), dried (Na$_2$SO$_4$) and concentrated in vacuo to afford 1-(4-methylphenyl)-2-nitroethanol as a colorless oil. $^1$H NMR (CDCl$_3$, 500 MHz) δ 7.28 (d, J=8.1 Hz, 2H), 7.21 (d, J=8.1 Hz, 2H), 5.42 (dt, J=9.6, 3.3 Hz, 1H), 4.60 (dd, J=13.3, 9.7 Hz, 1H), 4.49 (dd, J=13.3, 3.1 Hz, 1H), 2.79 (d, J=3.7, 1H), 2.36 (s, 3H).

Example 12

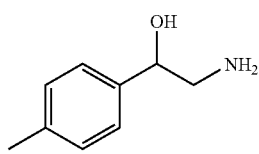

2-Amino-1-(4-methylphenyl)ethanol

A suspension of 10% Pd/C (24 mg) in a solution of 1-(4-methylphenyl)-2-nitroethanol (50 mg, 0.276 mmol) in absolute EtOH (1 mL) was stirred overnight at room temperature under 15 psi of H2. The reaction mixture was filtered through a pad of Celite and the filtrate was concentrated in vacuo to afford 2-amino-1-(4-methylphenyl)ethanol as an oil. LCMS calc.=152.10; found=152 (M+1)$^+$. $^1$H NMR (CDCl$_3$, 500 MHz) δ 7.20 (d, J=8.0 Hz, 2H), 7.13 (d, J=8.0 Hz, 2H), 4.57 (dd, J=7.9, 3.9 Hz, 1H), 2.86 (dd, J=12.7, 3.9 Hz, 1H), 2.76 (dd, J=12.7, 7.9 Hz, 1H), 2.33 (s, 3H).

Example 13

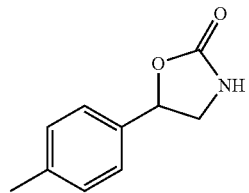

5-(4-Methylphenyl)-1,3-oxazolidin-2-one

Diisopropylethylamine (181 mg, 244 μL, 1.40 mmol) and triphosgene (138 mg, 0.466 mmol) were added successively to a stirred solution of 2-amino-1-(4-methylphenyl)ethanol (35.2 mg, 0.233 mmol) in dry CH$_2$Cl$_2$ (22 mL) at 0° C. under N$_2$. The reaction was stirred at 0° C. for 1 h then concentrated in vacuo to a volume of about 5 mL. The mixture was diluted with water (50 mL) and extracted with EtOAc (3×50 mL). The combined organic extracts were dried (Na$_2$SO$_4$) and concentrated in vacuo to give the crude product. This was purified by flash chromatography (Si, 12×160 mm, 0-80% EtOAc in hexanes gradient) to afford 5-(4-methylphenyl)-1,3-oxazolidin-2-one. R$_f$=0.41 (50% EtOAc/hexanes). LCMS calc.=178.08; found=178.1 (M+1)$^+$. $^1$H NMR (CDCl$_3$, 500 MHz) δ 7.25 (d, J=7.4 Hz, 2H), 7.19 (d, J=7.4 Hz, 2H), 6.69 (br s, 1H), 5.55 (t, J=7.8 Hz, 1H), 3.93 (t, J=8.6 Hz, 1H), 3.52 (t, J=8.1 Hz, 1H), 2.35 (s, 3H).

Example 14

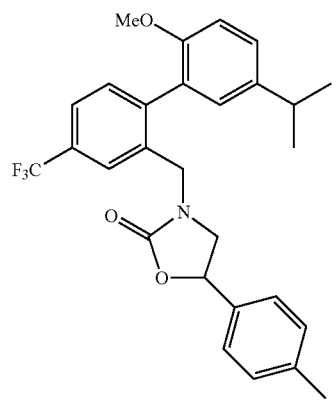 [SMILES: COc1ccc(C(C)C)cc1-c1ccc(C(F)(F)F)cc1CN1CC(c2ccc(C)cc2)OC1=O]

3-{[5'-Isopropyl-2'-methoxy-4-(trifluoromethyl)biphenyl-2-yl]methyl}-5-(4-methylphenyl)-1,3-oxazolidin-2-one Sodium hydride (6.4 mg of a 60% dispersion in mineral oil, 0.161 mmol) was added to a stirred solution of 5-(4-methylphenyl)-1,3-oxazolidin-2-one (37.7 mg, 0.0973 mmol) in dry THF (1 mL) at room temperature under N$_2$. The reaction was stirred for 30 min and a solution of 2-(bromomethyl)-5'-isopropyl-2'-methoxy-4-(trifluoromethyl)biphenyl (19.0 mg, 0.107 mmol) in dry THF (2 mL) was added by cannula. The reaction was stirred at room temperature for 3 days. The reaction was quenched with saturated NH$_4$Cl (10 mL) and extracted with EtOAc (3×20 mL). The combined organic extracts were washed with brine (10 mL), dried (Na$_2$SO$_4$) and concentrated in vacuo to give the crude product. This was purified by flash chromatography (Si, 12×160 mm, 0-80% EtOAc in hexanes gradient) to afford 3-{[5'-isopropyl-2'-methoxy-4-(trifluoromethyl)biphenyl-2-yl]methyl}-5-(4-methylphenyl)-1,3-oxazolidin-2-one as a colorless oil. $R_f$=0.37 (20% EtOAc/hexanes). LCMS calc.=484.21; found=484.2 (M+1)$^+$. $^1$H NMR (benzene-d$_6$, 500 MHz, 1:1 mixture of atropisomers) δ 7.76 (s, 0.5H), 7.65 (s, 0.5H), 7.31 (d, J=7.7 Hz, 1H), 7.08 (dd, J=8.4, 2.4 Hz, 1H), 7.05 (br d, J=7.8 Hz, 1H), 6.95-6.86 (m, 5H), 6.58 (t, J=7.7 Hz, 1H), 4.74 (t, J=8.0 Hz, 0.5H), 4.70 (t, J=8.0 Hz, 0.5H), 4.50 (d, J=15.7 Hz, 0.5H), 4.42 (d, J=15.7 Hz, 0.5H), 4.25 (d, J=15.7 Hz, 0.5H), 4.11 (d, J=15.7 Hz, 0.5H), 3.26 (s, 1.5H), 3.21 (s, 1.5H), 2.81 (t, J=8.6 Hz, 0.5H), 2.76 (septet, J=7.0 Hz, 1H), 2.68 (t, J=8.6 Hz, 0.5H), 2.55 (t, J=8.6 Hz, 0.5H), 2.53 (t, J=8.6 Hz, 0.5H), 2.04 (s, 3H), 1.20 (t, J=7.0 Hz, 3H), 1.19 (t, J=7.0 Hz, 3H).

Example 15

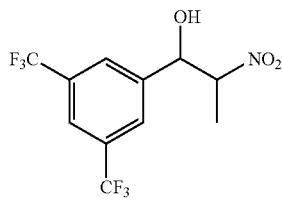 [SMILES: CC(C(O)c1cc(C(F)(F)F)cc(C(F)(F)F)c1)[N+](=O)[O-]]

1-[3,5-Bis(trifluoromethyl)phenyl]-2-nitropropan-1-ol

A stirred solution of 3,5-bis(trifluoromethyl)benzaldehyde (1.00 g, 4.13 mmol) and nitroethane (1.13 g, 1.08 mL, 15.1 mmol) in absolute EtOH (20 mL) at 0° C. was treated with 10% aq. NaOH (m/v) (1.73 mL, 4.34 mmol), stirred for 1 h and treated with 2% aq. acetic acid (m/v) (13.0 mL, 4.32 mmol). The reaction was stirred for 1 h at room temperature then partitioned between water (50 mL) and EtOAc (50 mL). The aqueous layer was extracted with EtOAc (2×50 mL) and the combined organic extracts were washed with saturated NaHCO$_3$ (50 mL) and brine (50 mL), dried (Na$_2$SO$_4$) and concentrated in vacuo to afford a 1.5:1 mixture of threo- and erythro-1-[3,5-bis(trifluoromethyl)phenyl]-2-nitropropan-1-ol as a colorless oil. $^1$H NMR (CDCl$_3$, 500 MHz) threo-diastereoisomer: δ 7.88 (br s, 1H), 7.86 (br s, 2H), 5.22 (d, J=8.4 Hz, 1H), 4.77 (dq, J=8.4, 6.9 Hz, 1H), 3.03 (br s 1H), 1.42 (d, J=6.9 Hz, 3H), erythro-diastereoisomer: δ 7.90 (br s, 1H), 7.86 (br s, 2H), 5.59 (d, J=3.2 Hz, 1H), 4.72 (dq, J=3.2, 6.9 Hz, 1H), 3.03 (br s 1H), 1.50 (d, J=6.9 Hz, 3H).

Example 16

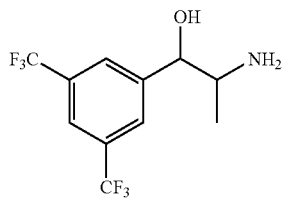

2-Amino-1-[3,5-bis(trifluoromethyl)phenyl]propan-1-ol

A suspension of Raney Nickel (50 mg) in a solution of a 1.5:1 mixture of threo- and erythro-1-[3,5-bis(trifluoromethyl)phenyl]-2-nitropropan-1-ol (50 mg, 0.158 mmol) in 30% (v/v) aqueous HCO$_2$H (0.75 mL) and MeOH (10 mL) was stirred overnight at room temperature under 15 psi of H$_2$. The reaction mixture was filtered through a pad of Celite and the filtrate was concentrated in vacuo to remove the MeOH. The aqueous slurry was adjusted to pH 9-10 with 28% aq NH$_4$OH, diluted with water (20 mL) and extracted with EtOAc (3×20 mL). The combined extracts were washed with brine (10 mL), dried (Na$_2$SO$_4$) and concentrated in vacuo to afford a mixture of threo- and erythro-2-amino-[3,5-bis(trifluoromethyl)phenyl]propan-1-ol as colorless solid. LCMS calc.=288.08; found=288.1 (M+1)$^+$. $^1$H NMR (CDCl$_3$, 500 MHz) threo-diastereoisomer: δ 7.79 (br s, 3H), 4.35 (br s, 1H), 3.25 (br s, 1H), 2.59 (br s, 3H), 0.86 (d, J=6.1 Hz, 3H), erythro-diastereoisomer: δ 7.79 (br s, 3H), 4.71 (br s, 1H), 3.00 (br s, 1H), 2.59 (br s, 3H), 1.06 (d, J=5.0 Hz, 3H).

Example 17

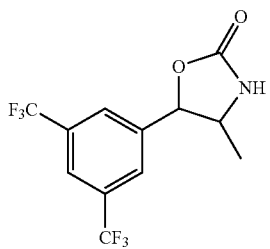 [SMILES: CC1NC(=O)OC1c1cc(C(F)(F)F)cc(C(F)(F)F)c1]

5-[3,5-Bis(trifluoromethyl)phenyl]-4-methyl-1,3-oxazolidin-2-one

Diisopropylethylamine (106 mg, 142 μL, 0.817 mmol) and triphosgene (20.2 mg, 0.068 mmol) were added successively to a stirred solution of 2-Amino-1-[3,5-bis(trifluoromethyl)phenyl]propan-1-ol (39.1 mg, 0.136 mmol) in dry CH$_2$Cl$_2$ (10 mL) at 0° C. under N$_2$. The reaction was stirred at 0° C. for 1 h then concentrated in vacuo to a volume of about 5 mL. The mixture was diluted with water (50 mL) and extracted with EtOAc (3×50 mL). The combined organic extracts were dried (Na$_2$SO$_4$) and concentrated in vacuo to give the crude product. This was purified by flash chromatography (Si, 12×160 mm, 0-70% EtOAc in hexanes gradient) to afford threo-5-[3,5-bis(trifluoromethyl)phenyl]-4-methyl-1,3-oxazolidin-2-one (17.5 mg) and erythro-5-[3,5-bis(trifluoromethyl)phenyl]-4-methyl-1,3-oxazolidin-2-one (14.4 mg) as colorless solids. threo-diastereoisomer: $R_f$=0.63 (50% EtOAc/hexanes). LCMS calc.=314.06; found=314.1 (M+1)$^+$. $^1$H NMR (CDCl$_3$, 600 MHz) δ 7.90 (br s, 1H), 7.83 (br s, 2H), 6.71 (br s, 1H), 5.17 (d, J=7.0 Hz, 1H), 3.86 (br pentet, J=6.2 Hz, 1H), 1.48 (d, J=6.2 Hz, 1H). This compound was separated into its enantiomers (4R,5R)-5-[3,5-bis(trifluoromethyl)phenyl]-4-methyl-1,3-oxazolidin-2-one and (4S,5S)-5-[3,5-bis(trifluoromethyl)phenyl]-4-methyl-1,3-oxazolidin-2-one using chiral HPLC (AS column, 20×250 mm, 20% i-PrOH in heptane). erythro-diastereoisomer: $R_f$=0.38 (50% EtOAc/hexanes). LCMS calc.=314.06; found=314.1 (M+1)$^+$. NMR (CDCl$_3$, 600 MHz) δ 7.90 (br s, 1H), 7.79 (br s, 2H), 5.83 (d, J=8.0 Hz, 1H), 5.34 (br s, 1H), 4.31 (br pentet, J=7.0 Hz, 1H), 0.84 (d, J=6.6 Hz, 1H). This compound was separated into its two enantiomers (4S,5R)-5-[3,5-bis(trifluoromethyl)phenyl]-4-methyl-1,3-oxazolidin-2-one and (4R,5S)-5-[3,5-bis(trifluoromethyl)phenyl]-4-methyl-1,3-oxazolidin-2-one using chiral HPLC (AS column, 20×250 mm, 15% i-PrOH in heptane).

Chiral Synthesis of (4S,5R)-5-[3,5-Bis(trifluoromethyl)phenyl]-4-methyl-1,3-oxazolidin-2-one This intermediate can be made directly from the chiral starting material CBZ-L-alanine by the 3-step route shown below. The compound (4R,5S)-5-[3,5-bis(trifluoromethyl) phenyl]-4-methyl-1,3-oxazolidin-2-one can be made by an analogous route starting from CBZ-D-alanine.

Step 1

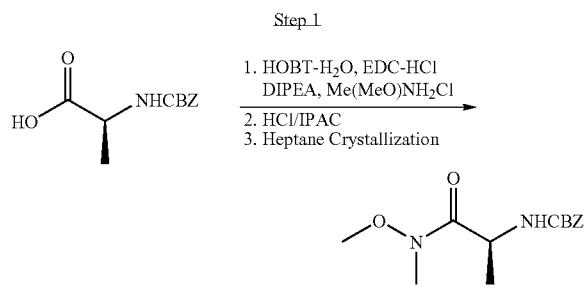

CBZ-L-Alanine (6.5 kg, 28.5 mol), HOBT-hydrate (4.8 kg, 34.8 mol), Weinreb amine-HCl salt (3.4 kg, 36.2 mol) and THF (32 L) are charged to a clean flask under nitrogen. The mixture is cooled to 0-10° C. and then DIPEA (12.4 L) is slowly added at a temperature less than 25° C. EDC-HCl (7 Kg, 36.2 mol) is then added slowly with cooling at 15°-25° C. The slurry is aged overnight at 20°-25° C. The mixture is then cooled to 0°-10° C. and 3 N HCl (12 L) is added slowly. Then IPAC (32 L) is added and the layers are separated. The organic layer is washed once with HCl (13 L) and twice with 8% NaHCO₃ (13 L) (CAUTION: FOAMING). The organic layer is then concentrated under vacuum to about 15 L at 50° C. The clear solution is cooled slowly to room temperature, allowing the product to crystallize. Heptane (~70 L) is then added slowly. The slurry is filtered, washed with heptane (18 L), and dried at room temperature on the filter pot. Product is obtained with >99.9% ee measured by chiral HPLC.

Step 2

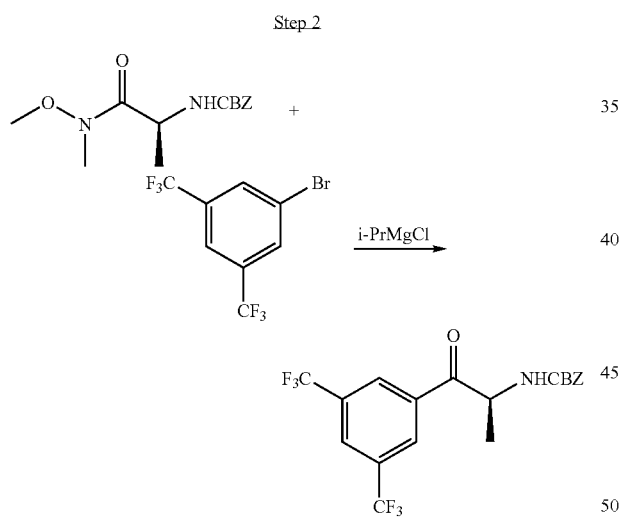

The Weinreb amide from Step 1 (6 kg, 22.5 mol) and 3,5-bis(trifluoromethyl)bromobenzene (4.85 L, 28.1 mol) are dissolved in anhydrous THF (24 L). The solution is purged with nitrogen to remove oxygen. The water content should be <500 ppm at this point. Atmospheric distillation can be carried out to azeotropically remove water if necessary. The solution is cooled to −10° C. and iso-PrMgCl in THF (56.4 mol) is slowly added (2 hours) to the reaction via addition funnel, maintaining a reaction temperature ≤−5° C. The solution is allowed to warm to 20° C. and aged overnight at 20° C., until the amide is <0.5 LCAP. The reaction is then cooled to −10° C. under nitrogen and is quenched slowly over 2 hours into 5N HCl (14 L) that is maintained at 0-5° C. MTBE (12 L) is added and the biphasic mixture is agitated for 5 min. After warming to 20°-25° C., it is allowed to settle for 30 min, and then the layers are separated. The organic layer is washed with water twice (12 L).

The organic layer is vacuum transferred through a 1-micron in-line PTFE filter into a distillation flask and is then concentrated to ~12 L under vacuum (internal temperature <40° C.) to a minimum agitated volume. The solution is then azeotropically dried with toluene and taken to a minimum agitated volume again. The solution is used directly in the next step.

If a solid product is desired, heptane is added to the organic layer after it has been concentrated to a minimum agitated volume. The distillation is continued under vacuum at 40°-55° C. until the final volume is 40 L. The solution is cooled to 35°-37° C., seeded (~0.5%, 30 gms) and then aged for 30 min to allow for a full seed bed to grow. The slurry is cooled to 10° C. over 2-3 hrs. The slurry is then filtered, washed with 5° C. heptane (18 L), and allowed to dry fully on the filter pot using a vacuum/nitrogen sweep overnight. The dried solid is obtained with >99.9 ee %. The amide can be recrystallized from straight heptane if the optical purity is not sufficient.

Step 3

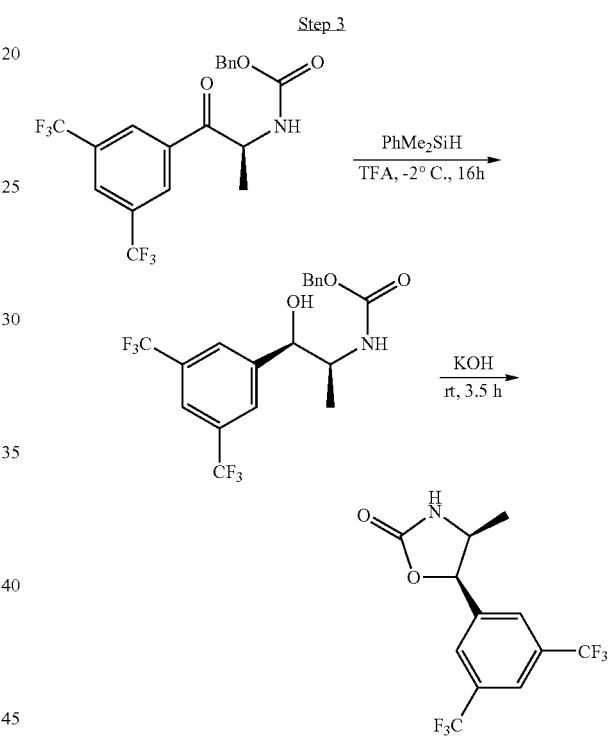

TFA (9 L) is added to a 100 L Buchi reactor under an inert atmosphere and is cooled to −5° C. The ketone product from Step 2 (5.50 kg, 13.1 mol) is added as a solid followed by a TFA rinse (2 L). The solution is cooled to −5° C. and is stirred until all the solid dissolves. The silane (2.18 kg, 15.7 mol) is added slowly over ~1 h (in two portions) while keeping the temperature at <0° C. The reaction is aged at −2 to −6° C. for 15-20 h, at which time LC reveals <2% of the ketone remains. A 50 w/w % KOH solution is prepared by adding 13.6 kg of KOH pellets (87 w %) slowly to 10 L water while keeping the highly exothermic dissolution at <30° C. The solution is stored in a refrigerator.

The reaction is quenched with ~2 L of the 50 w/w % KOH solution with vigorous stirring and cooling, keeping temp at ~20° C. Cold THF (16.5 L, previously stored in freezer) is added, followed by slow addition of the remainder of the KOH solution (~13.7 L), followed by a 2 L water rinse while keeping temp <20° C. After complete addition of KOH, the reaction is aged at room temperature. The reaction is quenched after 3 h with 27.5 L IPAC and 20 L 20% w/v aq NaCl.

The aqueous and organic layers are separated. The organic layer is washed with 26 L of 20% w/v aq NaCl, then with 36 L water, then with 31 L 0.5 N HCl, and finally with 32 L of water. The organic layer is concentrated to ~10 L. Heptane (20 L) is added, yielding crystals. The organic layer is concentrated to ~10 L. Heptane (20 L) is added again, and the organic layer is concentrated to ~10 L. Heptane (22 L) is added and the slurry is aged at rt. The solid is filtered and washed with 24 L heptane. A solid product is obtained (98.8% purity, >99.95% ee, by LC). The solid is then re-dissolved in 12.5 L MeOH (endothermic). At rt, 3 L water is added, and the mixture is aged to initiate crystallization. Water (9.5 L) is added over ~60 min at rt. After aging for 60 min, the slurry is filtered and the solid is washed with 5 L MeOH/water (1/1.5), 5 L MeOH/water (1/4) and then 4 L water. The solid product is dried at 50° C. under vacuum (99.9% pure by LC, >99.95% ee).

The reaction in Step 3 can also be carried out using Al(O-i-Pr)$_3$ as the reducing agent. For example, the ketone (6 kg) is heated at 50° C. with 0.3 eq of Al(O-i-Pr)$_3$ (790 g) in 12 L IPA and 18 L of toluene for 15.5 hours. The solution is cooled to ambient temperature, and solid KOH pellets (1.35 kg) are added slowly with vigorous stirring, while keeping the temperature at <25° C. After about 2 hours, when HPLC shows >99.5% cyclization, 33 L of 1N HCl solution is added to quench the reaction, which is kept at <25° C. If a rag layer of solids forms, it should be filtered off to upgrade the enantiomeric excess. The organic layer is then washed first with 36 L of 0.5N HCl, then with 6 L IPA combined with 45 L water, and finally with 6 L IPA combined with 36 L water. The organic layer is transferred via an inline filter. The solvent is switched to heptane (target volume is ~42 L) at ~40° C. until <2 v % toluene is left. Aging at rt for 2 h gives the solid product.

HPLC Method for assays used in Step 3:
Ace-C$_8$ column 250×4.6 mm A: MeCN; B: 0.1% H$_3$PO$_4$ in H$_2$O;
Gradient: 5A:95B at 0 min to 95A:5B at 9 min; hold 95A:5B until 13 min; return to 5A:95B 13-15 min.
Conditions: 35° C., 1.5 mL/min, 210 nm

Example 18

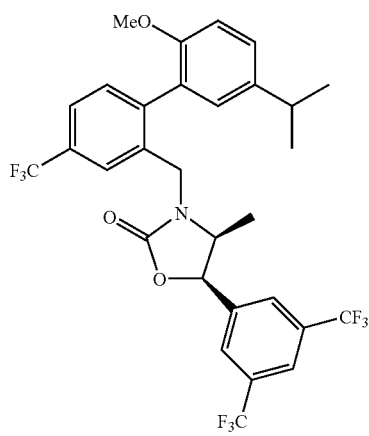 [SMILES: COc1ccc(C(C)C)cc1-c1ccc(C(F)(F)F)cc1CN1C(=O)O[C@H](c2cc(C(F)(F)F)cc(C(F)(F)F)c2)[C@@H]1C]

erythro-5-[3,5-Bis(trifluoromethyl)phenyl]-3-{[5'-isopropyl-2'-methoxy-4-(trifluoromethyl)biphenyl-2-yl]methyl}-4-methyl-1,3-oxazolidin-2-one Sodium bis(trimethylsilyl)amide (172 µL of a 1M solution in THF, 0.172 mmol) was added to a stirred solution of erythro-5-[3,5-bis(trifluoromethyl)phenyl]-4-methyl-1,3-oxazolidin-2-one (50 mg, 0.129 mmol) in dry THF (1 mL) at room temperature under N$_2$. The reaction was stirred for 15 min and a solution of 2-(bromomethyl)-5'-isopropyl-2'-methoxy-4-(trifluoromethyl)biphenyl (27.0 mg, 0.0861 mmol) in dry THF (2 mL) was added by cannula. The reaction was stirred at room temperature for 3 days. The reaction was quenched with saturated NH$_4$Cl (10 mL) and extracted with EtOAc (3×20 mL). The combined organic extracts were washed with brine (10 mL), dried (Na$_2$SO$_4$) and concentrated in vacuo to give the crude product. This was purified by flash chromatography (Si, 12×160 mm, 0-40% EtOAc in hexanes gradient) to afford erythro-5-[3,5-bis(trifluoromethyl)phenyl]-3-{[5'-isopropyl-2'-methoxy-4-(trifluoromethyl)biphenyl-2-yl]methyl}-4-methyl-1,3-oxazolidin-2-one as a colorless oil. R$_f$=0.64 (20% EtOAc/hexanes). LCMS calc.=620.18; found=620.2 (M+1)$^+$. $^1$H NMR (benzene-d$_6$, 600 MHz, 1:1 mixture of atropisomers) δ 7.94 (s, 0.5H), 7.72 (s, 0.5H), 7.64 (s, 0.5H), 7.63 (s, 0.5H), 7.39-7.34 (m, 3H), 7.12-7.04 (m, 2H), 6.95 (d, J=2.1 Hz, 0.5H), 6.86 (d, J=1.7 Hz, 0.5H), 6.64 (d, J=8.5 Hz, 0.5H), 6.56 (d, J=8.5 Hz, 0.5H), 4.99 (d, J=15.9 Hz, 0.5H), 4.93 (d, J=15.9 Hz, 0.5H), 4.73 (d, J=7.9 Hz, 0.5H), 4.61 (d, J=7.9 Hz, 0.5H), 3.88 (d, J=15.9 Hz, 0.5H), 3.82 (d, J=15.9 Hz, 0.5H), 3.35 (s, 1.5H), 3.24 (s, 1.5H), 3.05 (septet, J=6.9 Hz, 0.5H), 3.01 (septet, J=6.9 Hz, 0.5H), 2.75 (m, 1H), 1.19 (dd, J=6.9, 2.7 Hz, 3H), 1.17 (dd, J=10.9, 6.9 Hz, 3H), -0.18 (d, J=6.4 Hz, 1.5H), -0.33 (t, J=6.4 Hz, 1.5H). This compound was separated into its two enantiomers (4R,5S)-5-[3,5-bis(trifluoromethyl)phenyl]-3-{[5'-isopropyl-2'-methoxy-4-(trifluoromethyl)biphenyl-2-yl]methyl}-4-methyl-1,3-oxazolidin-2-one and (4S,5R)-5-[3,5-bis(trifluoromethyl)phenyl]-3-{[5'-isopropyl-2'-methoxy-4-(trifluoromethyl)biphenyl-2-yl]methyl}-4-methyl-1,3-oxazolidin-2-one using chiral HPLC (AD column, 20×250 mm, 3% i-PrOH in heptane).

Example 19

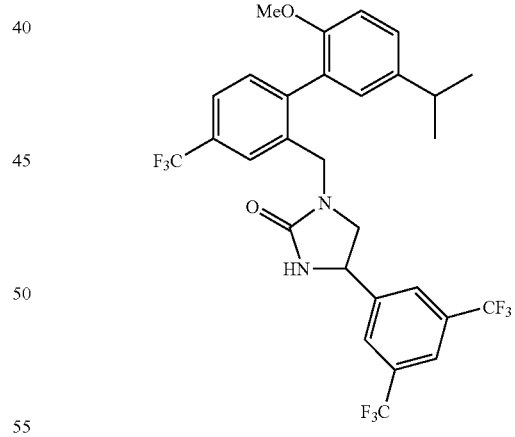

4-[3,5-bis(trifluoromethyl)phenyl]-1-{[5'-isopropyl-2'-methoxy-4-(trifluoromethyl)biphenyl-2-yl]methyl}imidazolidin-2-one Step A: tert-butyl{2-[3,5-bis(trifluoromethyl)phenyl]-2-hydroxyethyl}{[5'-isopropyl-2'-methoxy-4-(trifluoromethyl)biphenyl-2-yl]-methyl}carbamate To a solution of 1-[3,5-bis(trifluoromethyl)phenyl]-2-({[5'-isopropyl-2'-methoxy-4-(trifluoromethyl)biphenyl-2- yl]methyl}amino)ethanol (Example 6 Step B, 325.0 mg, 0.561 mmol) in CH$_2$Cl$_2$ (15 mL) was added BOC$_2$O (122 mg, 0.561 mmol) and DIPEA (98 μL, 0.561 mmol). The reaction was stirred at room temperature. After 5 hours, additional BOC$_2$O (50 mg, 0.229 mmol) and DIPEA (50 μL, 0.287 mmol) were added. The reaction was stirred at room temperature for 48 hours. The reaction was then concentrated to ~2 mL, diluted with hexanes (8 mL) and purified by flash chromatography with 10 to 20% EtOAc/hexanes to afford tert-butyl{2-[3,5-bis(trifluoromethyl)phenyl]-2-hydroxyethyl}{[5'-isopropyl-2'-methoxy-4-(trifluoromethyl)biphenyl-2-yl]methyl}carbamate. R$_f$=0.38 (25% EtOAc/hexanes). LCMS=580.3 (M+1−BOC)$^+$. $^1$H NMR (CD$_2$Cl$_2$, 500 MHz) δ 7.78 (s, 1H), 7.54-7.67 (m, 4H), 7.23-7.33 (m, 2H), 6.90-6.95 (m, 2H), 3.15-4.82 (m, 9H), 2.87 (m, 1H), 1.19-1.43 (m, 15 H).

Step B: 1-[3,5-bis(trifluoromethyl)phenyl]-2-((tert-butoxycarbonyl){[5'-isopropyl-2'-methoxy-4-(trifluoromethyl)biphenyl-2-yl]methyl}amino)ethyl methanesulfonate To a solution of tert-butyl{2-[3,5-bis(trifluoromethyl)phenyl]-2-hydroxyethyl}{[5'-isopropyl-2'-methoxy-4-(trifluoromethyl)biphenyl-2-yl]methyl}carbamate (350.1 mg, 0.516 mmol) in CH$_2$Cl$_2$ (15 mL) was added DIPEA (450 μL, 2.58 mmol). The solution was cooled to 0° C. and MsCl (100 μL, 1.29 mmol) was added. After 45 minutes of stirring at 0° C., the reaction was diluted with EtOAc (100 mL) and washed with saturated NaHCO$_3$ (25 mL), brine (25 mL), 1N HCl (25 mL), and brine (2×25 mL). The organic layer was dried over Na$_2$SO$_4$, filtered, and concentrated. The residue was put through a short plug of silica gel with 25% EtOAc/hexanes and concentrated. The product, 1-[3,5-bis(trifluoromethyl)phenyl]-2-((tert-butoxycarbonyl){[5'-isopropyl-2'-methoxy-4-(trifluoromethyl)biphenyl-2-yl]methyl}amino)ethyl methanesulfonate, was used immediately in the next reaction without further characterization. R$_f$=0.33 (25% EtOAc/hexanes).

Step C: tert-butyl {2-azido-2-[3,5-bis(trifluoromethyl)phenyl]ethyl}{[5'-isopropyl-2'-methoxy-4-(trifluoromethyl)biphenyl-2-yl]methyl}carbamate The 1-[3,5-bis(trifluoromethyl)phenyl]-2-((tert-butoxycarbonyl){[5'-isopropyl-2'-methoxy-4-(trifluoromethyl)biphenyl-2-yl]methyl}amino)ethyl methanesulfonate from the previous reaction was dissolved in DMPU (15 mL) and treated with NaN$_3$ (140 mg, 2.15 mmol). The reaction was stirred at room temperature for 15 hours and then diluted with EtOAc (75 ml). The solution was washed with H$_2$O (5×40 mL) and brine (40 mL). The organic layer was dried over Na$_2$SO$_4$, filtered, and concentrated. The residue was purified with 20% EtOAc/hexanes to afford tert-butyl{2-azido-2-[3,5-bis(trifluoromethyl)phenyl]ethyl}{[5'-isopropyl-2'-methoxy-4-(trifluoromethyl)biphenyl-2-yl]methyl}carbamate. R$_f$=0.52 (15% EtOAc/hexanes). LCMS=605.3 (M+1−BOC)$^+$. $^1$H NMR (C$_6$D$_6$, 500 MHz, 70° C.) δ 7.80 (s, 1H), 7.67 (s, 1H), 7.48 (s, 2H), 7.36 (d, J=7.8 Hz, 1H), 7.01-7.11 (m, 2H), 6.89 (m, 1H), 6.64 (d, J=8.6 Hz, 1H), 4.22-4.69 (m, 3H), 3.28 (s, 3H), 2.61-3.16 (m, 3H), 1.34 (s, 9H), 1.13-1.18 (m, 6H).

Step D: mixture of tert-butyl {2-amino-2-[3,5-bis(trifluoromethyl)phenyl]ethyl}{[5'-isopropyl-2'-methoxy-4-(trifluoromethyl)biphenyl-2-yl]methyl}carbamate and tert-butyl [1-[3,5-bis(trifluoromethyl)phenyl]-2-({[5'-isopropyl-2'-methoxy-4-(trifluoromethyl)biphenyl-2-yl]methyl}amino)ethyl]carbamate To a solution of tert-butyl{2-azido-2-[3,5-bis(trifluoromethyl)phenyl]ethyl}{[5'-isopropyl-2'-methoxy-4-(trifluoromethyl)biphenyl-2-yl]methyl}carbamate (300 mg, 0.426 mmol) in EtOAc (15 mL) was added 10% Pd on C (100 mg). The reaction was placed under H$_2$ and stirred at room temperature for 5 hours. At this time the reaction was complete to give a mixture of two products, tert-butyl {2-amino-2-[3,5-bis(trifluoromethyl)phenyl]ethyl}{[5'-isopropyl-2'-methoxy-4-(trifluoromethyl)biphenyl-2-yl]methyl}carbamate and tert-butyl [1-[3,5-bis(trifluoromethyl)phenyl]-2-({[5'-isopropyl-2'-methoxy-4-(trifluoromethyl)biphenyl-2-yl]methyl}amino)ethyl]carbamate. The catalyst was filtered off and the filtrate was concentrated to afford the product mixture. LCMS=679.3 (M+1)$^+$. The products were used in the next reaction without further purification or characterization.

Step E: 1-[3,5-bis(trifluoromethyl)phenyl]-N$^2$-{[5'-isopropyl-2'-methoxy-4-(trifluoromethyl)biphenyl-2-yl]-methyl}ethane-1,2-diamine To a solution of 283.5 mg (0.418 mmol) of the mixture of tert-butyl {2-amino-2-[3,5-bis(trifluoromethyl)phenyl]ethyl}{[5'-isopropyl-2'-methoxy-4-(trifluoromethyl)biphenyl-2-yl]methyl}carbamate and tert-butyl [1-[3,5-bis(trifluoromethyl)phenyl]-2-({[5'-isopropyl-2'-methoxy-4-(trifluoromethyl)biphenyl-2-yl]methyl}amino)ethyl]carbamate in CH$_2$Cl$_2$ (15 mL) was added TFA (1.5 mL). The reaction was stirred at room temperature for 5 hours and then poured into 1 N NaOH (50 mL). The mixture was extracted with CH$_2$Cl$_2$ (3×50 mL) and the organic extracts were combined, dried over Na$_2$SO$_4$, filtered, and concentrated. Purification of the residue by flash chromatography with 5 to 10% MeOH/CH$_2$Cl$_2$ gave 1-[3,5-bis(trifluoromethyl)phenyl]-N$^2$-{[5'-isopropyl-2'-methoxy-4-(trifluoromethyl)biphenyl-2-yl]methyl}ethane-1,2-diamine. R$_f$=0.46 (10% MeOH/CH$_2$Cl$_2$). LCMS=579.2 (M+1)$^+$. $^1$H NMR (CD$_2$Cl$_2$, 500 MHz) δ 7.83 (s, 2H), 7.77 (s, 2H), 7.55 (d, J=7.8 Hz, 1H), 7.31 (d, J=8.1 Hz, 1H), 7.24 (dd, J=8.4, 2.3 Hz, 1H), 6.99 (d, J=2.0 Hz, 1H), 6.92 (d, J=8.5 Hz, 1H), 4.06 (m, 1H), 3.59-3.76 (m, 2H), 3.69 (s, 3H), 2.88 (m, 1H), 2.67 (dd, J=11.9, 4.3 Hz, 1H), 2.51 (m, 1H), 1.22 (d, J=6.9 Hz, 6H).

Step F: 4-[3,5-bis(trifluoromethyl)phenyl]-1-{[5'-isopropyl-2'-methoxy-4-(trifluoromethyl)biphenyl-2-yl]methyl}imidazolidin-2-one A solution of 1-[3,5-bis(trifluoromethyl)phenyl]-N$^2$-{[5'-isopropyl-2'-methoxy-4-(trifluoromethyl)biphenyl-2-yl]methyl}ethane-1,2-diamine (125.2 mg, 0.217 mmol) in CH$_2$Cl$_2$ (30 mL) was cooled to 0° C. and DIPEA (227 μL, 1.30 mmol) was added. Next, triphosgene (32.2 mg, 0.109 mmol) was added. The reaction was stirred at 0° C. for 45 minutes and then poured into saturated NaHCO$_3$ (20 mL). The mixture was extracted with EtOAc (100 mL) and the organic layer was washed with brine (25 mL), dried over Na$_2$SO$_4$, filtered and concentrated. The residue was purified by flash chromatography with 40% EtOAc/hexanes to afford 4-[3,5-bis(trifluoromethyl)phenyl]-1-{[5'-isopropyl-2'-methoxy-4-(trifluoromethyl)biphenyl-2-yl]methyl}imidazolidin-2-one. $R_f$=0.22 (40% EtOAc/hexane). LCMS=605.2 (M+1)$^+$. $^1$H NMR (CDCl$_3$, 500 MHz) (atropisomers present in 1:1 ratio; doubling of some peaks observed) δ 7.83 (s, 1H), 7.78 (s, 2H), 7.55-7.62 (m, 2H), 7.32 (d, J=7.8 Hz, 1H), 7.22 (m, 1H), 6.94 (s, 1H), 6.88 (d, J=8.3 Hz, 1H), 5.33 & 5.24 (2 singlets, 1H), 4.80-4.88 (m, 1H), 4.00-4.61 (m, 2H), 3.72 & 3.70 (2 singlets, 3H), 3.55-3.59 (m, 1H), 2.83-2.93 (m, 2H), 1.17-1.23 (m, 6H).

The two enantiomers of this compound could be separated using an AD chiral column with 5% IPA/heptanes.

Example 20

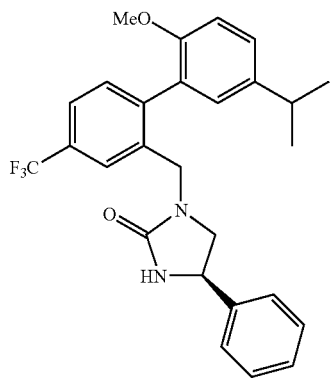 [SMILES: COc1ccc(C(C)C)cc1-c1ccc(C(F)(F)F)cc1CN1C[C@@H](c2ccccc2)NC1=O]

(4R)-1-{[5'-isopropyl-2'-methoxy-4-(trifluoromethyl)biphenyl-2-yl]methyl}-4-phenylimidazolidin-2-one Step A: tert-butyl [(1R)-2-hydroxy-1-phenylethyl]carbamate To a solution of (2R)-2-amino-2-phenylethanol (400 mg, 2.91 mmol) in CH$_2$Cl$_2$ (15 mL) was added BOC$_2$O (636 mg, 2.91 mmol) and DIPEA (507 µL, 2.91 mmol). The reaction was stirred at room temperature for 18 hours, diluted with EtOAc (75 mL) and washed with H$_2$O, brine, 1N HCl, brine, saturated NaHCO$_3$, and brine (25 mL each). The organic layer was dried over Na$_2$SO$_4$, filtered, and concentrated. Purification of the residue by flash chromatography with 50% EtOAc/hexanes afforded tert-butyl [(1R)-2-hydroxy-1-phenylethyl]carbamate. $R_f$=0.23 (40% EtOAc/hexane). $^1$H NMR (CDCl$_3$, 600 MHz) δ 7.27-7.37 (m, 5H), 5.27 (bs, 1H), 4.78 (bs, 1H), 3.83 (bs, 2H), 2.46 (bs, 1H), 1.44 (bs, 9H).

Step B: tert-butyl [(1R)-2-oxo-1-phenylethyl]carbamate

To a solution of tert-butyl [(1R)-2-hydroxy-1-phenylethyl] carbamate (200 mg, 0.844 mmol) in CH$_2$Cl$_2$ (20 mL) at 0° C. was added Dess-Martin periodinane (447 mg, 1.05 mmol). The reaction was stirred at 0° C. for 15 minutes and then at room temperature for 30 minutes. The reaction was then diluted with EtOAc (75 mL) and washed rapidly with 10% K$_2$CO$_3$ (2×30 mL). The organic layer was dried over Na$_2$SO$_4$, filtered, and concentrated. Purification of the residue on a short column of silica gel with 50% EtOAc/hexanes gave tert-butyl [(1R)-2-oxo-1-phenylethyl]carbamate. $^1$H NMR (CDCl$_3$, 600 MHz) (a major and a minor conformer observed). Data for major conformer given) δ 9.53 (s, 1H), 7.29-740 (m, 5H), 5.80 (bs, 1H), 5.31 (m, 1H), 1.42 (s, 91-1). This material was used immediately in the following reaction.

Step C: tert-butyl[(1R)-2-({[5'-isopropyl-2'-methoxy-4-(trifluoromethyl)biphenyl-2-yl] methyl}amino)-1-phenylethyl]carbamate To a solution of tert-butyl[(1R)-2-oxo-1-phenylethyl]carbamate (113.8 mg, 0.484 mmol) in MeOH (7 mL) was added 1-[5'-isopropyl-2'-methoxy-4-(trifluoromethyl)biphenyl-2-yl]methenamine (98 mg, 0.303 mmol), followed by NaCNBH$_3$ (30 mg, 0.477 mmol) and HOAc (2 drops). The reaction was stirred overnight at room temperature, diluted with EtOAc (75 mL), and washed with 1 N NaOH (25 mL) and brine (25 mL). The organic layer was dried over Na$_2$SO$_4$, filtered, and concentrated. Purification of the residue by flash chromatography with 5 to 25% EtOAc/hexanes gave tert-butyl[(1R)-2-({[5'-isopropyl-2'-methoxy-4-(trifluoromethyl)biphenyl-2-yl]methyl}amino)-1-phenylethyl]carbamate. $R_f$=0.30 (25% EtOAc/hexane). LCMS=543.4 (M+1)$^+$.

Step D: (1R)—N$^2$-{[5'-isopropyl-2'-methoxy-4-(trifluoromethyl)biphenyl-2-yl]methyl}-1-phenylethane-1,2-diamine To a solution of tert-butyl[(1R)-2-({[5'-isopropyl-2'-methoxy-4-(trifluoromethyl)biphenyl-2-yl]methyl}amino)-1-phenylethyl]carbamate (150 mg, 0.277 mmol) containing minor impurities in CH$_2$Cl$_2$ (10 mL) was added TFA (1 mL). The reaction was stirred at room temperature for 2 hours and then poured into 1 N NaOH (25 mL). The mixture was extracted with CH$_2$Cl$_2$ (3×25 mL). The combined organic extracts were dried over Na$_2$SO$_4$, filtered, and concentrated. Purification of the resulting residue by flash chromatography with 0 to 10% MeOH/CH$_2$Cl$_2$ afforded (1R)—N$^2$-{[5'-isopropyl-2'-methoxy-4-(trifluoromethyl)biphenyl-2-yl]methyl}-1-phenylethane-1,2-diamine. $R_f$=0.27 (10% MeOH/CH$_2$Cl$_2$). LCMS=443.4 (M+1)$^+$.

Step E: (4R)-1-{[5'-isopropyl-2'-methoxy-4-(trifluoromethyl)biphenyl-2-yl]methyl}-4-phenylimidazolidin-2-one A solution of (1R)—N$^2$-{[5'-isopropyl-2'-methoxy-4-(trifluoromethyl)biphenyl-2-yl]methyl}-1-phenylethane-1,2-diamine (96.0 mg, 0.22 mmol) in CH$_2$Cl$_2$ (15 mL) was cooled to 0° C. and DIPEA (230 µL, 1.32 mmol) was added followed by triphosgene (32.6 mg, 0.11 mmol). After 45 minutes, the reaction was poured into saturated NaHCO$_3$ (25 mL). The mixture was extracted with EtOAc (75 mL). The organic layer was washed with brine, dried over Na$_2$SO$_4$, filtered, and concentrated. Purification of the residue by flash chromatography with 10 to 60% EtOAc/hexanes afforded (4R)-1-{[5'-isopropyl-2'-methoxy-4-(trifluoromethyl)biphenyl-2-yl]methyl}-4-phenylimidazolidin-2-one. The minor enantiomer was removed by chiral HPLC using an AD chiral column and 15% IPA/heptanes to afford enantiomerically pure product. $R_f$=0.16 (40% EtOAc/hexanes). LCMS=469.3 (M+1)$^+$. $^1$H NMR (CDCl$_3$, 500 MHz) (atropisomers present in 1:1 ratio, doubling of some peaks observed) δ 7.65 (m, 1H), 7.54 (d, J=7.7 Hz, 1H), 7.21-7.36 (m, 71-1), 6.87-6.94 (m, 2H), 4.65-4.77 (m, 21-1), 4.10-4.49 (m, 2H), 3.71 & 3.72 (2 singlets, 3H), 3.49-3.53 (m, 1H), 2.94-2.97 (m, 1H), 2.87 (m, 1H), 1.19-1.24 (m, 6H).

Example 21

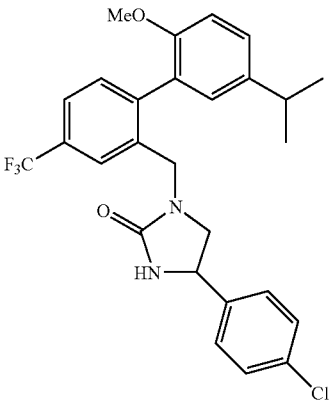 [SMILES: COc1ccc(C(C)C)cc1-c1ccc(C(F)(F)F)cc1CN1CC(c2ccc(Cl)cc2)NC1=O]

4-(4-chlorophenyl)-1-{[5'-isopropyl-2'-methoxy-4-(trifluoromethyl)biphenyl-2-yl]methyl}imidazolidin-2-one

Step A: 1-(4-chlorophenyl)-2-({[5'-isopropyl-2'-methoxy-4-(trifluoromethyl)biphenyl-2-yl]methyl}amino)ethanol A solution of 1-[5'-isopropyl-2'-methoxy-5-(trifluoromethyl)biphenyl-2-yl]methanamine (300 mg, 1.1 mmol) and 2-(4-chlorophenyl)oxirane (143 µL, 1.2 mmol) in isopropyl alcohol (10.5 mL) was heated to reflux for 24 hours. The reaction was concentrated and purified by flash chromatography with 5% to 80% EtOAc/hexanes to afford 1-(4-chlorophenyl)-2-({[5'-isopropyl-2'-methoxy-4-(trifluoromethyl)biphenyl-2-yl]methyl}amino)ethanol. $R_f$=0.37 (50% EtOAc/hexanes). LCMS=478.1 (M+1)$^+$. $^1$H NMR (CDCl$_3$, 500 MHz) δ 7.70 (s, 1H), 7.55 (d, J=7.5 Hz, 1H), 7.33-7.19 (m, 6H), 6.97 (s, 1H), 6.90 (d, J=8.5 Hz, 1H), 4.52 (m, 1H), 3.77-3.62 (m, 5H), 2.89 (m, 1H), 2.71 (m, 1H), 2.51 (m, 1H), 1.24 (d, J=7.0 Hz, 6H).

Step B: benzyl [2-(4-chlorophenyl)-2-hydroxyethyl]{[5'-isopropyl-2'-methoxy-4-(trifluoromethyl)biphenyl-2-yl]methyl}carbamate To a solution of 1-(4-chlorophenyl)-2-({[5'-isopropyl-2'-methoxy-4-(trifluoromethyl)biphenyl-2-yl]methyl}amino)ethanol (40 mg, 0.08 mmol) in CH$_2$Cl$_2$ (2 mL) was added dibenzyl dicarbonate (24 mg, 0.08 mmol). The reaction was stirred at room temperature for 24 hours and then poured into H$_2$O (15 mL). The resultant mixture was extracted with EtOAc (50 mL) and the organic layer was washed with brine (15 mL), dried over Na$_2$SO$_4$, filtered, and concentrated. Purification of the residue by flash chromatography with 5% to 60% EtOAc/hexanes afforded benzyl [2-(4-chlorophenyl)-2-hydroxyethyl]{[5'-isopropyl-2'-methoxy-4-(trifluoromethyl)biphenyl-2-yl]methyl}carbamate. $R_f$=0.20 (25% EtOAc/hexanes). LCMS=612.2 (M+1)$^+$. $^1$H NMR(C$_6$D$_6$, 600 MHz, peaks broadened and/or doubled; rotamers and/or atropisomers present) δ 7.98-6.45 (m, 15 H), 5.00-3.46 (m, 6H), 3.20-2.96 (m, 5H), 2.72 (m, 1H), 1.20-1.15 (m, 6H).

Step C: benzyl [2-azido-2-(4-chlorophenyl)ethyl]{[5'-isopropyl-2'-methoxy-4-(trifluoromethyl)biphenyl-2-yl]methyl}carbamate A solution of benzyl [2-(4-chlorophenyl)-2-hydroxyethyl]{[5'-isopropyl-2'-methoxy-4-(trifluoromethyl)biphenyl-2-yl]methyl}carbamate. (44 mg, 0.07 mmol) in CH$_2$Cl$_2$ (6 mL) was cooled to 0° C. and N,N diisopropylethylamine (63 lit, 0.36 mmol) was added followed by methanesulfonyl chloride (14 µL, 0.18 mmol). The reaction was stirred at 0° C. for 30 minutes and then poured into saturated NaHCO$_3$ (15 mL). The resultant mixture was extracted with EtOAc (50 mL) and the organic layer was washed with brine (15 mL), dried over Na$_2$SO$_4$, filtered through a short plug of silica gel, and concentrated. The residue was redissolved in DMPU (6 mL) and sodium azide (12 mg, 0.18 mmol) was added. The reaction was stirred at room temperature for 24 hours and then poured into H$_2$O (15 mL). The resultant mixture was extracted with EtOAc (50 mL) and the organic layer was washed with H$_2$O (2×15 mL) and brine (15 mL), dried over Na$_2$SO$_4$, filtered, and concentrated. Purification of the residue by flash chromatography with 25% EtOAc/hexanes afforded benzyl [2-azido-2-(4-chlorophenyl)ethyl]{[5'-isopropyl-2'-methoxy-4-(trifluoromethyl)biphenyl-2-yl]methyl}carbamate. $R_f$=0.66 (25% EtOAc/hexanes). LCMS=637.3 (M+1)$^+$. $^1$H NMR (C$_6$D$_6$, 600 MHz, peaks doubled; rotamers and/or atropisomers present) δ 8.03-6.52 (m, 15 H), 5.00-5.08 (m, 2H), 4.76-4.12 (m, 3H), 3.28-2.86 (m, 5H), 2.77 (m, 1H), 1.23-1.18 (m, 6H).

Step D: benzyl [2-amino-2-(4-chlorophenyl)ethyl]{[5'-isopropyl-2'-methoxy-4-(trifluoromethyl)biphenyl-2-yl]methyl}carbamate To a solution of benzyl [2-azido-2-(4-chlorophenyl)ethyl]{[5'-isopropyl-2'-methoxy-4-(trifluoromethyl)biphenyl-2-yl]methyl}carbamate (30 mg, 0.05 mmol) in THF (1 mL) was added PtO$_2$ (8 mg) and the reaction was stirred at room temperature under hydrogen for 1 hour. The catalyst was removed by filtration through a plug of Celite with 100% EtOAc and the filtrate was concentrated to afford crude benzyl [2-amino-2-(4-chlorophenyl)ethyl]{[5'-isopropyl-2'-methoxy-4-(trifluoromethyl)biphenyl-2-yl]methyl}carbamate. $R_f$=0.66 (25% EtOAc/hexanes). LCMS=611.3 (M+1)$^+$.

Step E: 4-(4-chlorophenyl)-1-{[5'-isopropyl-2'-methoxy-4-(trifluoromethyl)biphenyl-2-yl]methyl}imidazolidin-2-one To a solution of benzyl [2-amino-2-(4-chlorophenyl)ethyl]{[5'-isopropyl-2'-methoxy-4-(trifluoromethyl)biphenyl-2-yl]methyl}carbamate (30 mg, 0.05 mmol) in THF (2 mL) was added potassium bis(trimethylsilyl)amide (295 µL of a 0.5M solution in toluene, 0.147 mmol) The reaction was stirred at room temperature for 30 minutes and then quenched with saturated NH$_4$Cl (15 mL). The resultant mixture was extracted with EtOAc (25 mL) and the organic layer was washed with H$_2$O (15 mL) and brine (15 mL), dried over Na$_2$SO$_4$, filtered, and concentrated. Purification of the residue by flash chromatography with 5% to 60% EtOAc/hexanes afforded 4-(4-chlorophenyl)-1-{[5'-isopropyl-2'-methoxy-4-(trifluoromethyl)biphenyl-2-yl]methyl}imidazolidin-2-one. $R_f$=0.46 (5% MeOH/CH$_2$Cl$_2$). LCMS=503.1 (M+1)$^+$. $^1$H NMR (C$_6$D$_6$, 600 MHz, atropisomers observed; doubling of peaks.) δ 7.90-7.03 (m, 6H), 6.89-6.20 (m, 4H), 4.69-3.88 (m, 3H), 3.16 (s, 3H), 2.88-2.30 (m, 3H), 1.18-1.13 (m, 6H).

Example 22

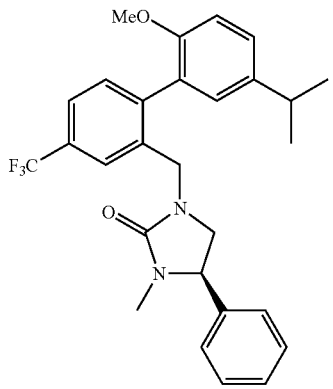 [SMILES: COc1ccc(C(C)C)cc1-c1ccc(C(F)(F)F)cc1CN1C[C@@H](c2ccccc2)N(C)C1=O]

(4R)-1-{[5'-isopropyl-2'-methoxy-4-(trifluoromethyl)biphenyl-2-yl]methyl}-3-methyl-4-phenylimidazolidin-2-one To a solution of (4R)-1-{[5'-isopropyl-2'-methoxy-4-(trifluoromethyl)biphenyl-2-yl]methyl}-4-phenylimidazolidin-2-one (12.6 mg, 0.0269 mmol) in THF (1.5 mL) was added MeI (10 µL, 0.162 mmol), followed by KHMDS (162 µL of a 0.5 M solution in toluene, 0.081 mmol). The reaction was stirred at room temperature for 10 minutes, and then poured into water (10 mL). The mixture was extracted with EtOAc (30 mL) and the organic layer was washed with brine (10 mL), dried over $Na_2SO_4$, filtered, and concentrated. Purification of the residue by flash chromatography with 50% EtOAc/hexanes afforded (4R)-1-{[5'-isopropyl-2'-methoxy-4-(trifluoromethyl)biphenyl-2-yl]methyl}-3-methyl-4-phenylimidazolidin-2-one. $R_f$=0.26 (40% EtOAc/hexanes). LCMS=483.2 $(M+1)^+$. $^1H$ NMR ($CDCl_3$, 500 MHz, atropisomers observed; doubling of peaks.) δ 7.68-7.53 (m, 2H), 7.21-7.36 (m, 7H), 6.87-6.94 (m, 2H), 4.08-4.56 (m, 3H), 3.72 & 3.71 (2 singlets, 3H), 3.34-3.38 (m, 1H), 2.77-2.89 (m, 2H), 2.67 & 2.63 (2 singlets, 3H), 1.18-1.26 (m, 6H).

Following the procedures outlined in EXAMPLES 1-22 the compounds listed in Table 1 were prepared:

TABLE 1

| Example | R | LCMS (M + 1)+ |
|---|---|---|
| 23 | | 618.1 |
| 24 | | 470.2 |
| 25 | | 470.4 |
| 26 | | 538.2 |
| 27 | | 504.1 |
| 28 | | 538.2 |
| 29 | | 471.2 |
| 30 | | 538.2 |

TABLE 1-continued
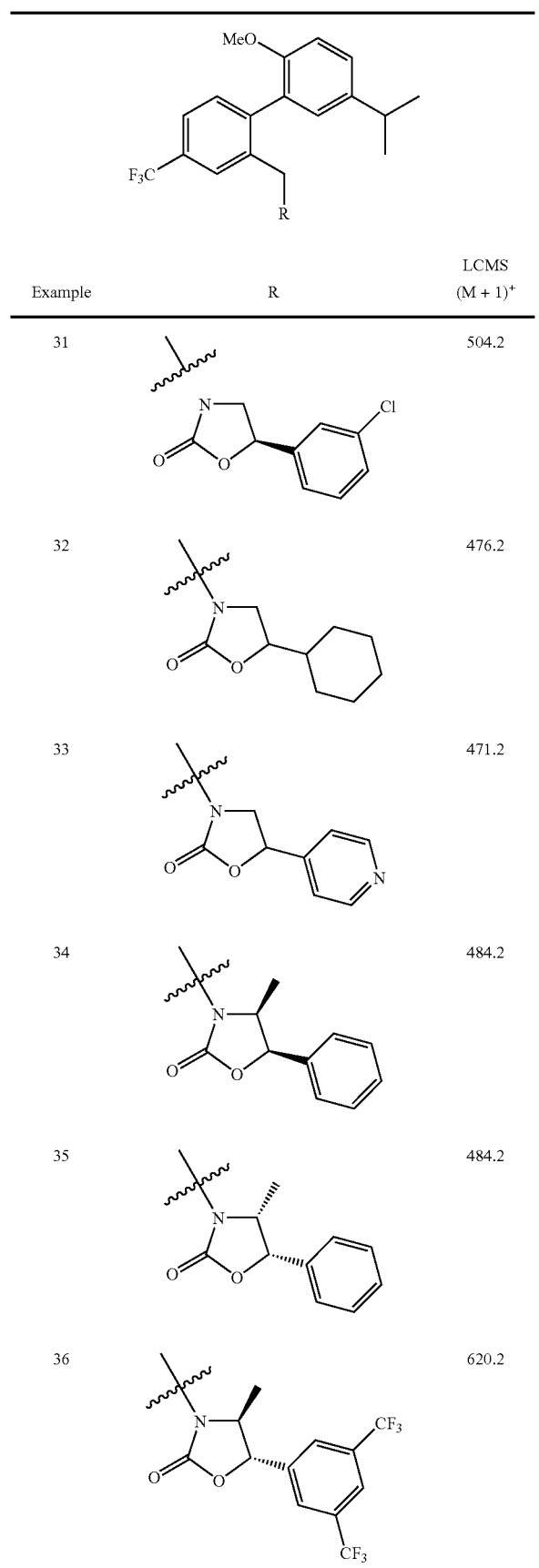
| Example | R | LCMS (M + 1)+ |
|---|---|---|
| 31 | | 504.2 |
| 32 | | 476.2 |
| 33 | | 471.2 |
| 34 | | 484.2 |
| 35 | | 484.2 |
| 36 | | 620.2 |
TABLE 1-continued
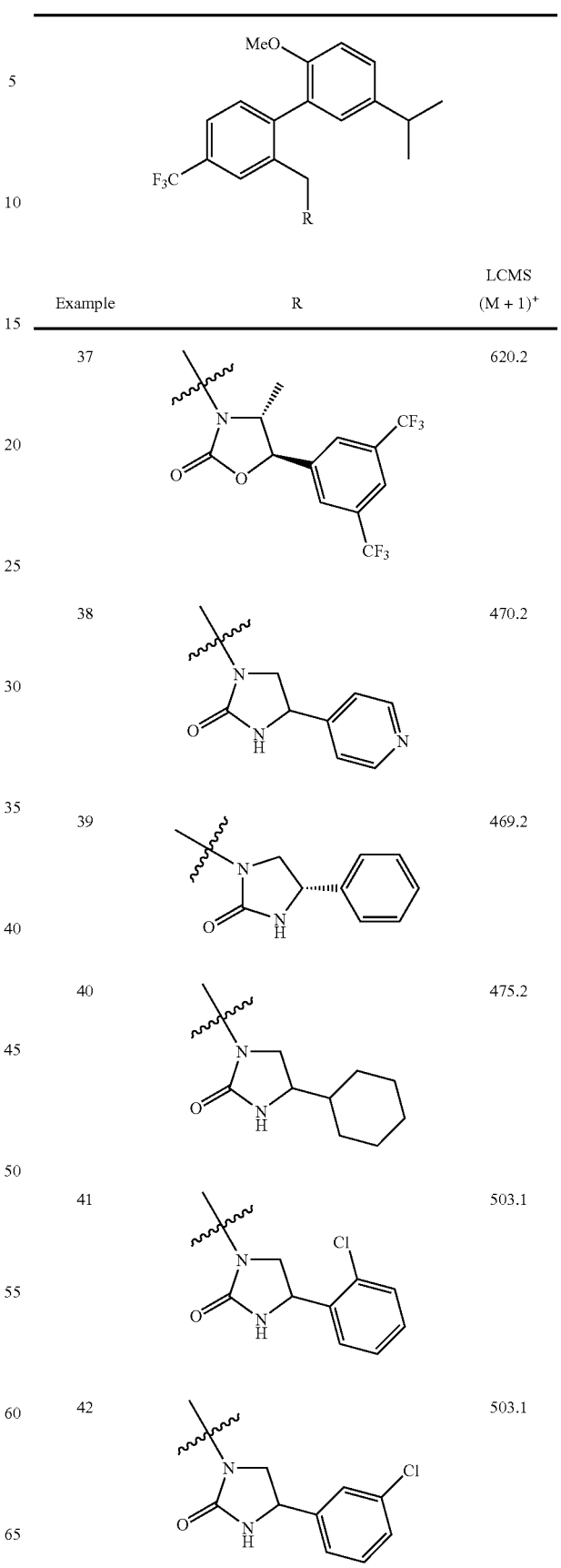
| Example | R | LCMS (M + 1)+ |
|---|---|---|
| 37 | | 620.2 |
| 38 | | 470.2 |
| 39 | | 469.2 |
| 40 | | 475.2 |
| 41 | | 503.1 |
| 42 | | 503.1 |

TABLE 1-continued

| Example | R | LCMS (M + 1)+ |
|---|---|---|
| 43 | [4-(trifluoromethyl)phenyl imidazolidinone] | 537.2 |
| 44 | [3-(trifluoromethyl)phenyl imidazolidinone] | 537.2 |
| 45 | [2-pyridyl imidazolidinone] | 470.2 |
| 46 | [3-pyridyl imidazolidinone] | 470.2 |
| 47 | [3,5-bis(trifluoromethyl)phenyl N-methyl imidazolidinone] | 619.2 |
| 48 | [3,5-bis(trifluoromethyl)phenyl ethyl oxazolidinone, racemic] | 634.1 |

TABLE 1-continued

| Example | R | LCMS (M + 1)+ |
|---|---|---|
| 49 | [3,5-bis(trifluoromethyl)phenyl ethyl oxazolidinone, racemic] | 634.1 |

Example 50

4-[3,5-bis(trifluoromethyl)phenyl]-2-{[5'-isopropyl-2'-methoxy-4-(trifluoromethyl)biphenyl-2-yl]methyl}-1,2,5-thiadiazolidine 1,1-dioxide A solution of 1-[3,5-bis(trifluoromethyl)phenyl]-N²-{[5'-isopropyl-2'-methoxy-4-(trifluoromethyl)biphenyl-2-yl]methyl}ethane-1,2-diamine (8.0 mg, 0.014 mmol) and sulfamide (2.0 mg, 0.021 mmol) in pyridine (300 μL) was heated to 120° C. in a sealed tube. After 3 hours, the reaction was cooled to room temperature and diluted with 25 mL of EtOAc. The organic solution was washed with 1 N HCl (2×5 mL) and brine (1×5 mL), dried over $Na_2SO_4$, filtered, and concentrated. Purification of the residue by PTLC with 25% EtOAc/hexanes afforded 4-[3,5-bis(trifluoromethyl)phenyl]-2-{[5'-isopropyl-2'-methoxy-4-(trifluoromethyl)biphenyl-2-yl]methyl}-1,2,5-thiadiazolidine 1,1-dioxide. $R_f$=0.29 (25% EtOAc/hexanes). LCMS=641.1 (M+1)+. ¹H NMR ($CDCl_3$, 500 MHz; atropisomers present) δ 7.58-7.85 (m, 5H), 7.35-

6.86 (m, 4H), 4.82-4.94 (m, 2H), 3.54-4.42 (m, 6H), 2.71-2.91 (m, 2H), 1.11-1.26 (m, 6H).

Example 51

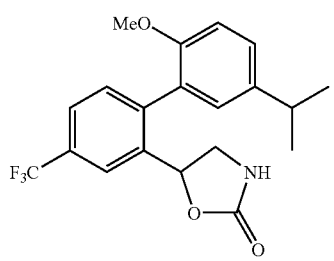 [SMILES: COc1ccc(C(C)C)cc1-c1ccc(C(F)(F)F)cc1C1CNC(=O)O1]

5-[5'-isopropyl-2'-methoxy-4-(trifluoromethyl)biphenyl-2-yl]-1,3-oxazolidin-2-one Step A: [5'-isopropyl-2'-methoxy-4-(trifluoromethyl)biphenyl-2-yl]methanol To a solution of 1.08 g of 5'-isopropyl-2'-methoxy-4-(trifluoromethyl)biphenyl-2-carbonitrile (EXAMPLE 3) in 25 mL of n-PrOH, was added 0.97 g of KOH. The mixture was heated to reflux and stirred at this temperature for 36 h, then cooled and concentrated to a clear oil. This oil was partitioned between 15 mL of water and 10 mL of $Et_2O$. The aqueous phase was extracted with 10 mL of $Et_2O$. The combined organics were washed with brine (15 mL), dried over $Na_2SO_4$, and concentrated. The residue was purified by flash chromatography on a Biotage Horizon 40S column, eluting with 1 CV of 95% hexanes-5% of a mixture of 5% formic acid in acetone, followed by a linear gradient of the acetone mixture in hexanes from 5 to 100% over 10 CV. The resulting white solid was dissolved in 10 mL of 9:1 benzene-MeOH and excess $TMSCH_2N_2$ was added. The mixture was stirred for 10 min at room temperature, then quenched with trifluoroacetic acid and concentrated. The residue was dissolved in 15 mL of $Et_2O$ and cooled to 0° C. A 1-M solution of $LiAlH_4$ in $Et_2O$ (5.4 mL) was added dropwise via addition funnel. The cooling bath was removed once the addition was complete, and the mixture was stirred 2 h at room temperature, then recooled to 0° C. and quenched by dropwise addition of 0.2 mL of water, 0.2 mL of 15% aqueous NaOH, and 0.5 mL of water. The cooling bath was removed once the addition was complete, and the mixture was stirred 30 min at room temperature, filtered (washing the solids liberally with $Et_2O$), and concentrated. Flash chromatography on a Biotage Horizon, 40S column, eluting with 1 CV of 4% EtOAc in hexanes, followed by a linear gradient of EtOAc in hexanes from 4 to 100% over 10 CV provided the title compound. Mass spectrum (ESI) 307.2 (M−17). $^1$H NMR (500 MHz, $CDCl_3$): δ 7.85 (s, 1H), 7.60 (d, J=8 Hz, 1H), 7.33 (d, J=8 Hz, 1H), 7.25 (dd, J=2 Hz, 9 Hz, 1H), 6.99 (d, J=2.5 Hz, 1H), 6.93 (d, J=8.5 Hz, 1H), 4.49 (m, 2H), 3.74 (s, 3H), 2.90 (septet, J=7 Hz, 1H), 1.25 (d, J=7 Hz, 6H).

Step B: 5'-isopropyl-2'-methoxy-4-(trifluoromethyl)biphenyl-2-carbaldehyde

To a solution of 0.725 g of [5'-isopropyl-2'-methoxy-4-(trifluoromethyl)biphenyl-2-yl]methanol in 10 mL of $CH_2Cl_2$ was added 1.14 g of Dess-Martin periodinane. The mixture was stirred at room temperature for 30 min, then filtered and concentrated. The residue was purified by flash chromatography on a Biotage Horizon, 40S column, eluting with 1 CV of 1% EtOAc in hexanes, followed by a linear gradient of EtOAc in hexanes from 1 to 100% over 10 CV to provide the title compound. Mass spectrum (ESI) 323.2 (M+1). $^1$H NMR (500 MHz, $CDCl_3$): δ 9.81 (s, 1H), 8.28 (s, 1H), 7.88 (dd, J=1.5 Hz, 8 Hz, 1H), 7.54 (d, J=8 Hz, 1H), 7.33 (dd, J=2 Hz, 8 Hz, 1H), 7.16 (d, J=2.5 Hz, 1H), 6.95 (d, J=8.5 Hz, 1H), 3.74 (s, 3H), 2.95 (septet, J=7 Hz, 1H), 1.29 (d, J=7 Hz, 6H).

Step C: 2-amino-1-[5'-isopropyl-2'-methoxy-4-(trifluoromethyl)biphenyl-2-yl]ethanol To a solution of 0.679 g of 5'-isopropyl-2'-methoxy-4-(trifluoromethyl)biphenyl-2-carbaldehyde in 1.5 mL of $CH_2Cl_2$ was added ca. 5 mg of $ZnI_2$, then 0.23 g of trimethylsilyl cyanide. The mixture was stirred at room temperature for 3 h, and then partitioned between 15 mL of water and 10 mL of $Et_2O$. The aqueous phase was extracted with 2×10 mL of $Et_2O$. The combined organics were dried over $Na_2SO_4$ and concentrated. The residue was dissolved in 15 mL of $Et_2O$ and cooled to 0° C. A 1-M solution of $LiAlH_4$ in $Et_2O$ (4.2 mL) was added dropwise via addition funnel. The cooling bath was removed once the addition was complete, and the mixture was stirred overnight at room temperature, then recooled to 0° C. and quenched by dropwise addition of 0.15 mL of water, 0.15 mL of 15% aqueous NaOH, and 0.4 mL of water. The cooling bath was removed once the addition was complete, and the mixture was stirred 30 min at room temperature, filtered (washing the solids liberally with $Et_2O$), and concentrated to provide the title compound, which was used without further purification. Mass spectrum (ESI) 354.2 (M+1). Some $^1$H NMR signals are doubled because of atropoisomerism. $^1$H NMR (500 MHz, $CDCl_3$): δ 7.88 (s, 1H), 7.55 (app t, J=7.5 Hz, 1H), 7.22-7.28 (m, 2H), 6.99, 6.95 (d, J=2.5 Hz, 1H), 6.92, 6.90 (sm 1H), 4.52 (m, 1H), 3.70 (s, 3H), 2.90 (septet, J=7 Hz, 1H), 2.81 (m, 1H), 2.60-2.70 (m, 2H), 1.23-1.28 (m, 6H).

Step D: 5-[5'-isopropyl-2'-methoxy-4-(trifluoromethyl)biphenyl-2-yl]-1,3-oxazolidin-2-one To a 0° C. solution of 0.44 g of 2-amino-1-[5'-isopropyl-2'-methoxy-4-(trifluoromethyl)biphenyl-2-yl]ethanol in 15 mL of $CH_2Cl_2$ was added 0.241 g of diisopropylethylamine, then 0.185 g of triphosgene. The mixture was stirred at 0° C. for 30 min, and then diluted with 30 mL of EtOAc and 20 mL of saturated $NaHCO_3$. The phases were separated and the organic phase was washed with 20 mL of brine, dried ($Na_2SO_4$), and concentrated. The residue was purified by flash chromatography on a Biotage Horizon, 40S column, eluting with 1 CV of 5% EtOAc in hexanes, followed by a linear gradient of EtOAc in hexanes from 5 to 100% over 10 CV to provide the title compound. Mass spectrum (ESI) 380.2 (M+1). $^1$H NMR signals are doubled because of atropoisomerism $^1$H NMR (500 MHz, $CDCl_3$): δ 7.90, 7.86 (s, 1H), 7.66 (d, J=8 Hz, 1H), 7.35 (d, J=8 Hz, 1H), 7.27 (dd, J=2.5 Hz, 8.5 Hz 1H), 7.03 (d, J=2.5 Hz, 0.5H), 6.87-6.93 (m, 1.5H), 5.65, 5.50 (t, J=8 Hz, 1H), 5.23, 5.09 (s, 1H), 3.75 (s, 1.5H), 3.69 (s, 1.5H), 3.68, 3.51 (t, J=9 Hz, 0.5H), 3.31, 3.19 (t, J=8.5 Hz, 0.5H), 2.90 (septet, J=7 Hz, 1H), 1.25, 1.24 (d, J=7 Hz, 6H).

Further purification by HPLC on Chiralpak AD 2×25 cm, eluting with 10% isopropanol in heptane at 9 mL/min, provided two enantiomers: enantiomer A, $t_R$=15.1 min; enantiomer B, $t_R$=17.4 min.

Example 52

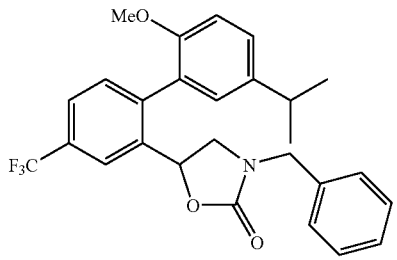 [SMILES: COc1ccc(C(C)C)cc1-c1ccc(C(F)(F)F)cc1C1CN(Cc2ccccc2)C(=O)O1]

3-Benzyl-5-[5'-isopropyl-2'-methoxy-4-(trifluoromethyl)biphenyl-2-yl]-1,3-oxazolidin-2-one To a 0° C. solution of 44 mg of 5-[5'-isopropyl-2'-methoxy-4-(trifluoromethyl)biphenyl-2-yl]-1,3-oxazolidin-2-one in 1 mL of DMF was added 10 mg of sodium hydride. The mixture was stirred 10 min at room temperature, and then 24 mg of benzyl bromide was added. The mixture was stirred overnight at room temperature, then diluted with 15 mL of EtOAc and 5 mL of water. The phases were separated and the organic phase was washed with 5 mL each of water and brine, dried (Na$_2$SO$_4$), and concentrated. The residue was purified by flash chromatography on a Biotage Horizon, 25S column, eluting with 1 CV of hexanes, followed by a linear gradient of EtOAc in hexanes from 0 to 50% over 10 CV to provide the title compound. Mass spectrum (ESI) 470.1 (M+1). $^1$H NMR (500 MHz, CDCl$_3$): δ 7.86, 7.76 (s, 1H), 7.62 (d, J=8 Hz, 1H), 7.14-7.40 (m, 7H), 7.01, 6.77 (d, J=2.5 Hz, 1H), 6.87, 6.83 (d, J=8.5 Hz, 1H), 5.45, 5.53 (m, 1H), 4.30-4.53 (m, 2H), 3.73, 3.55 (s, 3H), 3.48, 3.30 (m, 1H), 3.10, 2.96 (t, J=8.5 Hz, 1H), 2.89, 2.82 (septet, J=7 Hz, 1H), 1.24, 1.16 (m, 6H).

Example 53

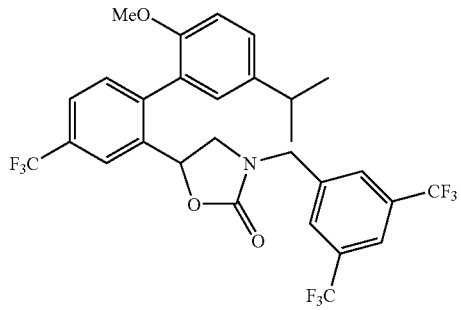 [SMILES: COc1ccc(C(C)C)cc1-c1ccc(C(F)(F)F)cc1C1CN(Cc2cc(C(F)(F)F)cc(C(F)(F)F)c2)C(=O)O1]

3-[3,5-bis(trifluoromethyl)benzyl]-5-[5'-isopropyl-2'-methoxy-4-(trifluoromethyl)biphenyl-2-yl]-1,3-oxazolidin-2-one (racemic)

Following the procedure described in EXAMPLE 50, 43 mg of 5-[5'-isopropyl-2'-methoxy-4-(trifluoromethyl)biphenyl-2-yl]-1,3-oxazolidin-2-one and 43 mg of 3,5-bis(trifluoromethyl)benzyl bromide gave the title compound. Mass spectrum (ESI) 606.1 (M+1). $^1$H NMR signals are doubled because of atropoisomerism. $^1$H NMR (500 MHz, CDCl$_3$): δ 7.58-7.88 (m, 5H), 7.34 (d, J=8 Hz, 1H), 7.23 (m, 1H), 7.02, 6.79 (d, J=2 Hz, 1H), 6.88, 6.85 (d, J=8.5 Hz, 1H), 5.45, 5.42 (m, 1H), 4.52-4.64 (m, 1.5H), 4.36 (d, J=15.5 Hz, 0.5 H), 3.74, 3.57 (s, 3H), 3.49, 3.34 (m, 1H), 3.09, 2.99 (t, J~8.5 Hz, 1H), 2.89, 2.81 (septet, J=7 Hz, 1H), 1.24, 1.12 (m, 6H).

Example 54

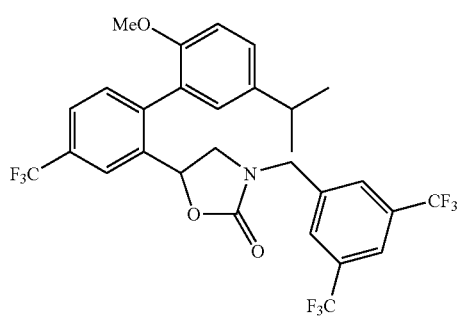 [SMILES: COc1ccc(C(C)C)cc1-c1ccc(C(F)(F)F)cc1C1CN(Cc2cc(C(F)(F)F)cc(C(F)(F)F)c2)C(=O)O1]

3-[3,5-bis(trifluoromethyl)benzyl]-5-[5'-isopropyl-2'-methoxy-4-(trifluoromethyl)biphenyl-2-yl]-1,3-oxazolidin-2-one (enantiomer A)

Following the procedure described in EXAMPLE 50, 43 mg of 5-[5'-isopropyl-2'-methoxy-4-(trifluoromethyl)biphenyl-2-yl]-1,3-oxazolidin-2-one, enantiomer A, and 43 mg of 3,5-bis(trifluoromethyl)benzyl bromide gave the title compound. Analytical HPLC on Chiralpak AS 4.6×250 mm, eluting with 5% isopropanol in heptane at 0.5 mL/min: $t_R$=9.9 min Example 55

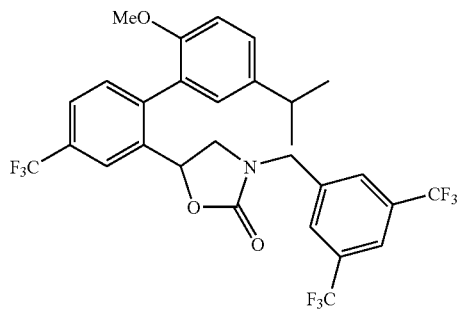 [SMILES: COc1ccc(C(C)C)cc1-c1ccc(C(F)(F)F)cc1C1CN(Cc2cc(C(F)(F)F)cc(C(F)(F)F)c2)C(=O)O1]

3-[3,5-bis(trifluoromethyl)benzyl]-5-[5'-isopropyl-2'-methoxy-4-(trifluoromethyl)biphenyl-2-yl]-1,3-oxazolidin-2-one (enantiomer B)

Following the procedure described in EXAMPLE 50, 44 mg of 5-[5'-isopropyl-2'-methoxy-4-(trifluoromethyl)biphenyl-2-yl]-1,3-oxazolidin-2-one, enantiomer B, and 43 mg of 3,5-bis(trifluoromethyl)benzyl bromide gave the title com-

Example 56

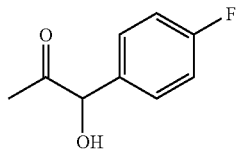

1-(4-Fluorophenyl)-1-hydroxyacetone

A suspension of ground LaCl$_3$ (26 mg, 0.104 mmol) in dry THF (7.8 mL) under N$_2$ was cooled to −78° C. and stirred for 15 min. A solution of n-BuLi (1.6 M in hexanes, 195 µL, 0.312 mmol) was added and stirring was continued for 15 min. The reaction was warmed to 0° C. and stirred for 30 min. Trimethylsilyl cyanide (31 mg, 42 µL, 0.312 mmol) was added and the reaction was stirred for 30 min at 0° C. and warmed to room temperature over 30 min. A solution of acetyltrimethylsilane (Cunico, R. F., Kuan, C.-P., *J. Org. Chem.*, 1985, 50, 5410-5413) (121 mg, 1.04 mmol) and 4-fluorobenzaldehyde (142 mg, 1.14 mmol) in dry THF (19 mL) was added by cannula and the reaction was stirred at room temperature for 2 h. After this time 1N HCl (24 mL) was added and the reaction was stirred for 1 h. Et$_2$O (25 mL) was added and the organic layer was separated and washed with H$_2$O (2×25 mL). The combined aqueous layers were extracted with Et$_2$O (3×50 mL). The combined organic extracts were dried (MgSO$_4$) and concentrated in vacuo to give the crude product. This was purified by flash chromatography (Si, 25×160 mm, 0-50% EtOAc in hexanes gradient) to give 1-(4-fluorophenyl)-1-hydroxyacetone as a colorless solid. R$_f$=0.31 (20% EtOAc/hexanes). $^1$H NMR (CDCl$_3$, 500 MHz) δ 7.29 (m, 2H), 7.08-7.04 (m, 2H), 5.06 (d, J=3.6 Hz, 1H), 4.35 (t, J=6.5 Hz, 1H), 2.05 (s, 3H).

Example 57

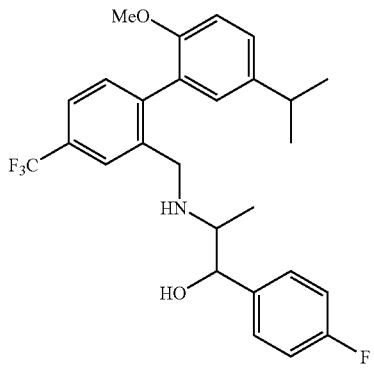 [SMILES: COc1ccc(C(C)C)cc1-c1ccc(C(F)(F)F)cc1CNC(C)C(O)c1ccc(F)cc1]

erythro- and threo-1-(4-Fluorophenyl)-2-({[5'-isopropyl-2'-methoxy-4-(trifluoromethyl)biphenyl-2-yl]methyl}amino)propan-1-ol NaCNBH$_3$ (19 mg, 0.306 mmol) was added to a solution of {[5'-isopropyl-2'-methoxy-4-(trifluoromethyl)biphenyl-2-yl]methyl}amine (67 mg, 0.204 mmol) and 1-(3,5-dichlorophenyl)-1-hydroxyacetone (45 mg, 0.204 mmol) in MeOH at room temperature followed by acetic acid (2 drops). The reaction was stirred for 5 h at room temperature. The reaction mixture was diluted with EtOAc (20 mL), H$_2$O (20 mL and brine (5 mL). The aqueous layer was extracted with EtOAc (2×20 mL). The combined organic extracts were dried (Na$_2$SO$_4$) and concentrated in vacuo to give the crude product. This was purified by flash chromatography (Si, 12×160 mm, 0-50% EtOAc in hexanes gradient) to give the two possible diastereoisomers, erythro-1-(4-fluorophenyl)-2-({[5'-isopropyl-2'-methoxy-4-(trifluoromethyl)biphenyl-2-yl]methyl}amino)propan-1-ol (68.4 mg) and threo-1-(4-fluorophenyl)-2-({[5'-isopropyl-2'-methoxy-4-(trifluoromethyl)biphenyl-2-yl]methyl}amino)propan-1-ol (48.9 mg) as colorless oils. erythro-diastereoisomer: R$_f$=0.40 (20% EtOAc/hexanes). LCMS calc.=476.22; found=476.2 (M+1)$^+$. $^1$H NMR (500 MHz, CDCl$_3$) δ 7.72 (s, 1H), 7.60 (d, J=7.8 Hz, 1H), 7.36 (m, 1H), 7.27 (dd, J=8.5, 2.3 Hz, 1H), 7.19 (m, 2H), 7.04-6.92 (m, 4H), 4.63-4.56 (m, 1H), 3.85-3.65 (m, 7H), 2.92 (m, 1H), 2.72 (m, 1H), 1.26 (t, J=8.0 Hz, 6H), 0.64 (t, J=5.4 Hz, 3H). threo-diastereoisomer: R$_f$=0.20 (20% EtOAc/hexanes). LCMS calc.=476.22; found=476.2 (M+1)$^+$. $^1$H NMR (500 MHz, CDCl$_3$) δ 7.73 (d, J=9.0 Hz, 1H), 7.58 (d, J=7.9 Hz, 1H), 7.32 (m, 1H), 7.24 (m, 3H), 7.07-6.97 (m, 3H), 6.92 (d, J=8.5 Hz, 1H), 4.05 (d, J=7.9 Hz, 1H), 3.82-3.70 (m, 5H), 3.59 (d, J=13 Hz, 1H), 3.51 (d, J=13 Hz, 1H), 2.90 (m, 1H), 2.51 (m, 1H), 1.25 (m, 6 H), 0.73 (d, J=6.4 Hz, 3H).

Example 58

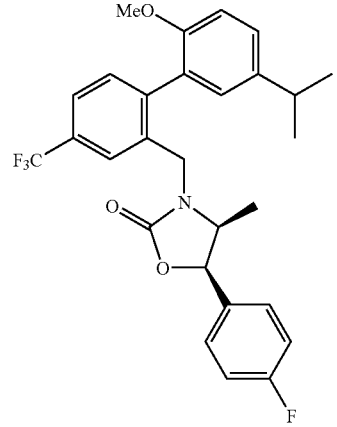 [SMILES: COc1ccc(C(C)C)cc1-c1ccc(C(F)(F)F)cc1CN1C(=O)O[C@H](c2ccc(F)cc2)[C@@H]1C]

erythro-5-(4-Fluorophenyl)-3-{[5'-isopropyl-2'-methoxy-4-(trifluoromethyl)biphenyl-2-yl]methyl}-4-methyl-1,3-oxazolidin-2-one As for EXAMPLE 7 Step 3. R$_f$=0.38 (20% EtOAc/hexanes). LCMS calc.=502.20; found=502.2 (M+1)$^+$. $^1$H NMR (500 MHz, benzene-d$_6$, 1:1 mixture of atropisomers) δ 7.96 (s, 0.5H), 7.75 (s, 0.5H), 7.35 (d, J=7.7 Hz, 1H), 7.10-7.06 (m, 2H), 6.94 (d, J=2.1 Hz, 0.5H), 6.88 (d, J=2.1 Hz, 0.5H), 6.69-6.62 (m, 4.5H), 6.55 (d, J=8.4 Hz, 0.5H), 4.95 (d, J=15.9 Hz, 0.5H), 4.86 (d, J=15.8 Hz, 0.5H), 4.80 (d, J=7.9 Hz, 0.5H), 4.70 (d, J=7.8 Hz, 0.5H), 4.04 (d, J=15.8 Hz, 0.5H), 3.93 (d, J=15.9 Hz, 0.5H), 3.36 (s, 1.5H), 3.22 (s, 1.5H), 3.14

(m, 0.5H), 3.05 (m, 0.5H), 2.79-2.71 (m, 1H), 1.18 (m, 6H), 0.02 (d, J=6.5 Hz, 1.5H), −0.04 (d, J=6.5 Hz, 1.5H). This compound was separated into its two enantiomers (4R,5S)-5-(4-Fluorophenyl)-3-{[5'-isopropyl-2'-methoxy-4-(trifluoromethyl)biphenyl-2-yl]methyl}-4-methyl-1,3-oxazolidin-2-one and (4S,5R)-5-(4-Fluorophenyl)-3-{[5'-isopropyl-2'-methoxy-4-(trifluoromethyl)biphenyl-2-yl]methyl}-4-methyl-1,3-oxazolidin-2-one using chiral HPLC (AD column, 20×250 mm, 3% EtOH in heptane).

Following the procedures outlined in EXAMPLE 58 the compounds listed in Table 2 were prepared:

TABLE 2

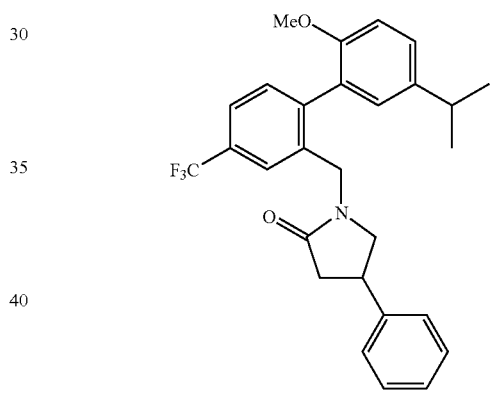

Example 64

1-{[5'-Isopropyl-2'-methoxy-4-(trifluoromethyl)biphenyl-2-yl]methyl}-4-phenylpyrrolidin-2-one Sodium bis(trimethylsilyl)amide (114 μL of a 1M solution in THF, 0.114 mmol) was added to a stirred solution of 4-phenylpyrrolidin-2-one (Winans, C. F., Adkins, H., *J. Am. Chem. Soc.*, 1933, 55, 4167-4176) (17 mg, 0.103 mmol) in dry THF (1 mL) at room temperature under $N_2$. The reaction was stirred for 5 min and a solution of 2-(bromomethyl)-5'-isopropyl-2'-methoxy-4-(trifluoromethyl)biphenyl (20 mg, 0.0516 mmol) in dry THF (2 mL) was added by cannula. The reaction was stirred at room temperature for 3 days. The reaction was quenched with saturated $NH_4Cl$ (10 mL) and extracted with EtOAc (3×20 mL). The combined organic extracts were washed with brine (10 mL), dried ($Na_2SO_4$) and concentrated in vacuo to give the crude product. This was purified by flash chromatography (Si, 12×160 mm, 0-90% EtOAc in hexanes gradient) to afford 1-{[5'-isopropyl-2'-methoxy-4-(trifluoromethyl)biphenyl-2-yl]methyl}-4-phenylpyrrolidin-2-one as a colorless oil. $R_f$=0.11 (20% EtOAc/hexanes). LCMS calc.=468.22; found=468.2 $(M+1)^+$. $^1H$ NMR (600 MHz, benzene-d$_6$, 1:1 mixture of atropisomers) δ 7.79 (s, 0.5H), 7.73 (s, 0.5H), 7.33 (d, J=7.7 Hz, 1H), 7.08-7.04 (m, 4H), 6.99 (m, 1H), 6.92 (s, 0.5H), 6.88 (s, 0.5H), 6.76 (dd, J=16.0, 7.4 Hz, 2H), 6.60 (dd, J=8.5, 3.1 Hz, 1H), 4.58 (d, J=15.4 Hz, 1H), 4.38 (t, J=13.9 Hz, 1H), 3.29 (s, 1.5H), 3.26 (s, 1.5H), 2.85-2.73 (m, 3H), 2.63-2.57 (m, 1H), 2.38-2.28 (m, 1H), 2.21-2.11 (m, 1H), 1.20-1.16 (m, 6H).

Example 65

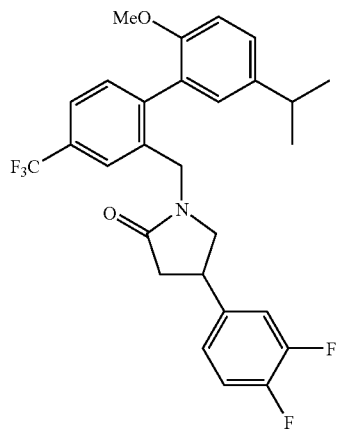 [SMILES: COc1ccc(C(C)C)cc1-c1ccc(C(F)(F)F)cc1CN1CC(c2ccc(F)c(F)c2)CC1=O]

4-(3,4-Difluorophenyl)-1-{[5'-isopropyl-2'-methoxy-4-(trifluoromethyl)biphenyl-2-yl]methyl}pyrrolidin-2-one Prepared by a similar method as EXAMPLE 64 starting with 4-(3,4-difluorophenyl)pyrrolidin-2-one (prepared by a similar method as in Marivet, M. C., Bourguignon, J.-J.; Lugnier, C., Mann, A., Stoclet, J.-C., Wermuth, C.-G. *J. Med. Chem.*, 1989, 32, 1450-1457). LCMS calc.=504.20; found=504.2 (M+1)$^+$.

Example 66

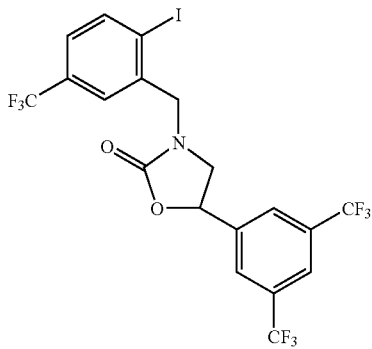 [SMILES: O=C1OC(c2cc(C(F)(F)F)cc(C(F)(F)F)c2)CN1Cc1cc(C(F)(F)F)ccc1I]

5-[3,5-bis(trifluoromethyl)phenyl]-3-[2-iodo-5-(trifluoromethyl)benzyl]1,3-oxazolidin-2-one A stirred suspension of sodium hydride (60% in oil, 167 mg, 4.18 mmol) in THF (5 mL) was treated at 0° C. with 5-[3,5-bis(trifluoromethyl)phenyl]-1,3-oxazolidin-2-one (500 mg, 1.67 mmol) dissolved in THF (1 mL), under an atmosphere of N$_2$. The reaction was stirred for 20 min and a solution of 2-(bromomethyl)-1-iodo-4-(trifluoromethyl)benzene (610 mg, 1.67 mmol) in THF (1 mL) was added dropwise. The reaction was stirred at room temperature for 18 h. The reaction was quenched with H$_2$O (1 mL) and partitioned between EtOAc (80 mL) and H$_2$O (25 mL). The aqueous phase was re-extracted with EtOAc (2×20 mL) and the combined organic extracts were washed with brine (30 mL), dried (MgSO$_4$) and concentrated in vacuo to give the crude product. This was purified by flash silica-gel chromatography (0-30% EtOAc in hexanes gradient) to afford 5-[3,5-bis(trifluoromethyl)phenyl]-3-[2-iodo-5-(trifluoromethyl)benzyl]1,3-oxazolidin-2-one. R$_f$=0.55 (515% EtOAc/hexanes). LCMS 584 (M+1)$^+$. $^1$H NMR (CDCl$_3$, 500 MHz) δ 8.05 (d, J=8.2 Hz, 1H), 7.95 (br s, 1H), 7.85 (br s, 2H), 7.51 (br s, 1H), 7.32 (m, 1H), 5.72 (t, J=8.0 Hz, 1H), 4.74 (d, J=15.5 Hz, 1H), 4.64 (d, J=15.3 Hz), 4.14 (t, J=7.1 Hz, 1H), 3.47 (dd, J=7.1, 1.6 Hz).

Example 67

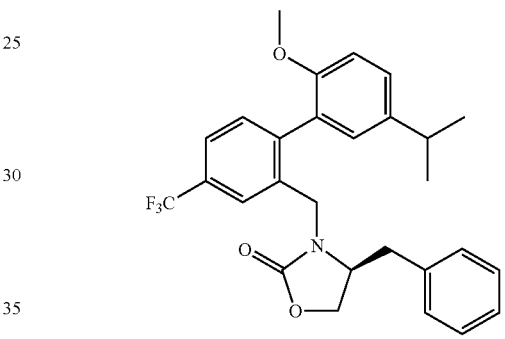

(4S)-4-benzyl-3-{[5'-isopropyl-2'-methoxy-4-(trifluoromethyl)biphenyl-2-yl]-methyl}-1,3-oxazolidin-2-one Step A: (4S)-4-benzyl-3-[2-iodo-5-(trifluoromethyl)benzyl]1,3-oxazolidin-2-one A stirred suspension of sodium hydride (60% in oil, 27 mg, 0.68 mmol) in THF (3 mL) was treated at 0° C. with (S)-4-benzyl-2-oxazolidinone (49 mg, 0.27 mmol) dissolved in THF (1 mL), under an atmosphere of N$_2$. The reaction was stirred for 20 min and a solution of 2-(bromomethyl)-1-iodo-4-(trifluoromethyl)benzene (100 mg, 0.27 mmol) in THF (1 mL) was added dropwise. The reaction was stirred at room temperature for 18 h. The reaction was quenched with H$_2$O (1 mL) and partitioned between EtOAc (80 mL) and H$_2$O (25 mL). The aqueous phase was re-extracted with EtOAc (2×20 mL) and the combined organic extracts were washed with brine (30 mL), dried (MgSO$_4$) and concentrated in vacuo to give the crude product. This was purified by flash silica-gel chromatography (0-30% EtOAc in hexanes gradient) to afford (4S)-4-benzyl-3-[2-iodo-5-(trifluoromethyl)benzyl]1,3-oxazolidin-2-one. R$_f$=0.45 (15% EtOAc/hexanes). LCMS 462 (M+1)$^+$. $^1$H NMR (CDCl$_3$, 500 MHz) δ 8.04 (d, J=8.2 Hz, 1H), 7.54 (br s, 1H), 7.33-7.27 (m, 5H), 7.11-7.10 (m, 2H), 7.32 (m, 1H), 4.80 (d, J=16.0 Hz, 1H), 4.49 (d, J=16.1 Hz), 4.28 (t, J=8.7 Hz, 1H), 4.25 (t, J=9.1, 4.8 Hz, 1H), 3.94 (m, 1H), 3.16 (dd, J=13.5, 4.8 Hz, 1H), 2.73 (dd, J=9.1, 4.4 Hz, 1H).

Step B: (4S)-4-benzyl-3-{[5'-isopropyl-2'-methoxy-4-(trifluoromethyl)biphenyl-2-yl]methyl}-1,3-oxazolidin-2-one A stirred suspension of (4S)-4-benzyl-3-[2-iodo-5-(trifluoromethyl)benzyl]1,3-oxazolidin-2-one (63 mg, 0.137 mmol), 2-methoxy-5-isopropylphenyl boronic acid (52 mg, 0.274 mmol), $K_2CO_3$ (47 mg, 0.34 mmol) and $Pd(OAc)_2$ (9.2 mg, 0.0137 mmol) in acetone:$H_2O$ (5:1) (6 mL) was heated at reflux for 1 h. The reaction mixture was concentrated in vacuo, diluted with $H_2O$ (15 mL) and extracted with EtOAC (3×30 mL). The combined organic extracts were washed with brine (30 mL), dried ($MgSO_4$), filtered and concentrated. The crude product was purified by silica-gel flash chromatography (0-20% EtOAc in hexanes gradient) to (4S)-4-benzyl-3-{[5'-isopropyl-2'-methoxy-4-(trifluoromethyl)biphenyl-2-yl]methyl}-1,3-oxazolidin-2-one. $R_f$=0.35 (15% EtOAc/hexanes). LCMS 484 (M+1)$^+$. $^1$H NMR (CDCl$_3$, 500 MHz) (atropisomers present; doubling of some peaks observed in $^1$H NMR) δ 7.72 (br s 1H), 7.65 (br s, 1H), 7.42 (m, 1H), 7.32-7.22 (m, 3H), 7.08 (d, J=2.3 Hz, 1H), 6.90-6.84 (m, 3H), 4.80 (d, J=15.8 Hz, 1H), 4.35 (d, J=15.8 Hz), 4.28 (t, J=8.7 Hz, 1H), 3.96-3.92 (m, 3H), 3.78 (s, 3H), 3.62-3.52 (m, 1H), 2.94-2.86 (m, 1H), 2.82 (dd, J=9.4, 3.9 Hz, 1H), 2.42 (dd, J=9.6, 3.9 Hz), 1.26 (s, 3H), 1.10 (s, 3H).

Example 68

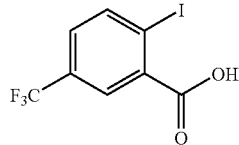 [SMILES: O=C(O)c1cc(C(F)(F)F)ccc1I]

2-Iodo-5-(trifluoromethyl)benzoic acid

Potassium hydroxide (3.78 g; 0.0673 mol) was added to a stirred solution of 2-iodo-5-(trifluoromethyl)benzonitrile (EXAMPLE 2; 4 g; 0.0135 mol) in a 1:1 isopropanol:$H_2O$ solution (60 mL). The reaction was heated at reflux for 14 h and then partitioned between $H_2O$ (50 mL) and EtOAc (50 mL). The aqueous layer was extracted with EtOAc (50 mL) and acidified to pH 5 with 6N HCl. The aqueous layer was further extracted with EtOAc (4×50 mL) and the combined extracts were washed with brine (50 mL), dried over $MgSO_4$, filtered, and concentrated in vacuo to afford 2-iodo-5-(trifluoromethyl)benzoic acid as a yellow solid. LCMS=317.0 (M+1)$^+$. $^1$H NMR (CDCl$_3$, 500 MHz): δ 8.27 (d, J=1.6 Hz, 1 H), 8.25 (d, J=8.2 Hz, 1 H), 7.47 (dd, J=8.2, 1.8 Hz, 1 H).

Example 69

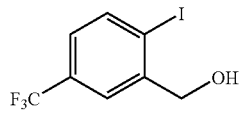

[2-Iodo-5-(trifluoromethyl)phenyl]methanol

Borane-THF (1.0M solution in THF; 94 mL; 94 mmol) was added to a stirred solution of 2-iodo-5-(trifluoromethyl)benzoic acid (2.97 g; 9.4 mmol) in THF (300 mL) at 0° C. under $N_2$. The reaction was heated at reflux for 90 min and then carefully quenched with 6N HCl until no further gas evolution. The reaction was diluted with $H_2O$ (250 mL) and extracted with EtOAc (3×250 mL). The combined extracts were washed with brine (300 mL), dried over $MgSO_4$, filtered, and concentrated in vacuo. The crude material was purified by flash chromatography (0-25% EtOAc/hexanes gradient) to afford [2-iodo-5-(trifluoromethyl)phenyl]methanol as a white solid. LCMS=285.0 (M−17)$^+$. $^1$H NMR (CDCl$_3$, 500 MHz): δ 7.97 (d, J=8.3 Hz, 1 H), 7.79 (s, 1 H), 7.28 (d, J=8.4 Hz, 1 H), 4.75 (s, 2 H). An alternative procedure is as follows: To a solution of 2-Iodo-5-(trifluoromethyl)benzaldehyde (EXAMPLE 80, Step A, 9 g) in THF (100 mL) and water (10 mL) at 0° C. was added $NaBH_4$ (0.5 g). The reaction was stirred 30 minutes. To the reaction mixture was added dilute aqueous HCl (cautiously). The mixture was extracted with ether and the ether layer was washed with water, then brine. The ether layer was then dried over anhydrous $MgSO_4$, filtered and concentrated. The material is chromatographed on $SiO_2$ using a step gradient of 1:3 $CH_2Cl_2$/hexanes, then 1:1 $CH_2Cl_2$/hexanes, then 100% $CH_2Cl_2$ to afford [2-iodo-5-(trifluoromethyl)phenyl]methanol as a white solid.

Example 70

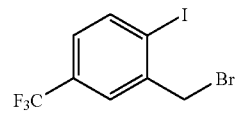

2-(Bromoethyl)-1-iodo-4-(trifluoromethyl)benzene

Carbon tetrabromide (1.86 g; 5.6 mmol) and triphenylphosphine (1.47 g; 5.6 mmol) were added successively to a stirred solution of [2-iodo-5-(trifluoromethyl)phenyl]methanol (1.13 g; 3.74 mmol) in $CH_2Cl_2$ (25 mL) at 0° C. under $N_2$. The reaction was stirred at room temperature for 48 h. A second equivalent of carbon tetrabromide (1.2 g; 3.74 mmol) and triphenylphosphine (0.98 g; 3.74 mmol) was added and the reaction was stirred an additional 14 h. The solvent was removed in vacuo and the residue was purified by flash chromatography (0-25% EtOAc/hexanes gradient) to afford 2-(bromoethyl)-1-iodo-4-(trifluoromethyl)benzene as a clear oil. $^1$H NMR (CDCl$_3$, 500 MHz): δ 8.02 (d, J=8.2 Hz, 1 H), 7.73 (d, J=1.8 Hz, 1 H), 7.26 (dd, J=8.3, 1.8 Hz, 1 H), 4.64 (s, 2 H).

Example 71

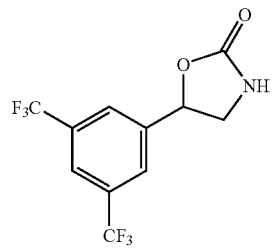 [SMILES: O=C1NCC(c2cc(C(F)(F)F)cc(C(F)(F)F)c2)O1]

5-[3,5-bis(trifluoromethyl)phenyl]-1,3-oxazolidin-2-one

Following the procedure described in EXAMPLE 13, 5.46 g of 2-amino-1-[3,5-bis(trifluoromethyl)phenyl]ethanol yielded 5-[3,5-bis(trifluoromethyl)phenyl]-1,3-oxazolidin-2-one as an off-white solid. LCMS=300.1 (M+1)$^+$. $^1$H NMR (CDCl$_3$, 500 MHz): δ 7.94 (s, 1 H), 7.89 (s, 2 H), 5.81-5.77 (m, 1 H), 5.29 (s, 1 H), 4.17-4.12 (m, 1 H), 3.59-3.55 (m, 1 H).

Example 72

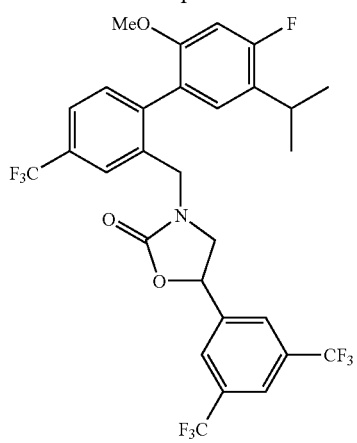

5-[3,5-bis(trifluoromethyl)phenyl]-3-{[4'-fluoro-5'isopropyl-2'-methoxy-4-(trifluoromethyl)biphenyl-2-yl]methyl}-1,3-oxazolidin-2-one A mixture of 5-[3,5-bis(trifluoromethyl)phenyl]-3-[2-iodo-5-(trifluoromethyl)benzyl]-1,3-oxazolidin-2-one (60 mg; 0.103 mmol), (4-fluoro-5-isopropyl-2-methoxyphenyl)boronic acid (27 mg; 0.129 mmol), palladium acetate (7 mg; 0.0103 mmol), and potassium carbonate (36 mg; 0.257 mmol) in 5:1 acetone/water (6 mL) was heated at reflux for 1 h. Acetone was removed in vacuo and the residue was diluted with $H_2O$ (10 mL) and extracted with $CH_2Cl_2$ (3×10 mL). The combined extracts were washed with brine (10 mL), dried over $Na_2SO_4$, filtered, and concentrated in vacuo. The residue was purified by flash chromatography (0-25% EtOAc/hexanes gradient) to afford 5-[3,5-bis(trifluoromethyl)phenyl]-3-{[4'-fluoro-5'-isopropyl-2'-methoxy-4-(trifluoromethyl)biphenyl-2-yl]methyl}-1,3-oxazolidin-2-one as a clear glass. LCMS=624.2 (M+1)$^+$. $^1$H NMR (benzene-$d_6$, 500 MHz, 1:1 mixture of atropisomers): δ 7.60 (s, 1.5 H), 7.45 (s, 0.5 H), 7.31-7.25 (m, 3 H), 6.98-6.94 (m, 1 H), 6.87-6.82 (m, 1 H), 6.43-6.37 (m, 1 H), 4.54 (d, J=15.6 Hz, 0.5 H), 4.40-4.36 (m, 1 H), 4.47 (d, J=15.6 Hz, 0.5 H), 3.96 (d, J=15.5 Hz, 0.5 H), 3.80 (d, J=15.8 Hz, 0.5 H), 3.24-3.15 (m, 1 H), 3.02 (s, 3H), 2.62-2.58 (m, 0.5 H), 2.53-2.48 (m, 0.5 H), 2.12-2.07 (m, 0.5 H), 2.04-2.00 (m, 0.5 H) 1.22-1.11 (m, 6 H).

The racemic material was separated by chiral HPLC using 15% IPA/heptane and an OD column into its two enantiomers.

(5R)-5-[3,5-bis(trifluoromethyl)phenyl]-3-{[4'-fluoro-5'isopropyl-2'-methoxy-4-(trifluoromethyl)biphenyl-2-yl]methyl}-1,3-oxazolidin-2-one: LCMS=624.2 (M+1)$^+$. $^1$H NMR (benzene-$d_6$, 500 MHz, 1:1 mixture of atropisomers): δ 7.62 (s, 1.5 H), 7.47 (s, 0.5 H), 7.34-7.27 (m, 3H), 6.99-6.95 (m, 1 H), 6.88-6.83 (m, 1 H), 6.44-6.39 (m, 1 H), 4.54 (d, J=15.5 Hz, 0.5 H), 4.47-4.41 (m, 1 H), 4.33 (d, J=15.6 Hz, 0.5 H), 3.98 (d, J=15.7 Hz, 0.5 H), 3.82 (d, J=15.8 Hz, 0.5 H), 3.24-3.15 (m, 1 H), 3.05 (s, 3 H), 2.67-2.62 (m, 0.5 H), 2.57-2.52 (m, 0.5 H), 2.16-2.11 (m, 0.5 H), 2.09-2.04 (m, 0.5 H) 1.22-1.11 (m, 6 H).

(5S)-5-[3,5-bis(trifluoromethyl)phenyl]-3-{[4'-fluoro-5'isopropyl-2'-methoxy-4-(trifluoromethyl)biphenyl-2-yl]methyl}-1,3-oxazolidin-2-one: LCMS=624.2 (M+1)$^+$. $^1$H NMR (benzene-$d_6$, 500 MHz, 1:1 mixture of atropisomers): δ 7.63 (s, 1.5 H), 7.48 (s, 0.5 H), 7.35-7.27 (m, 3H), 7.00-6.95 (m, 1 H), 6.88-6.83 (m, 1 H), 6.44-6.38 (m, 1 H), 4.54 (d, J=15.8 Hz, 0.5 H), 4.48-4.42 (m, 1 H), 4.34 (d, J=15.8 Hz, 0.5 H), 3.99 (d, J=15.8 Hz, 0.5 H), 3.83 (d, J=15.8 Hz, 0.5 H), 3.25-3.15 (m, 1 H), 3.05 (s, 3 H), 2.68-2.63 (m, 0.5 H), 2.58-2.53 (m, 0.5 H), 2.18-2.12 (m, 0.5 H), 2.10-2.05 (m, 0.5 H) 1.23-1.11 (m, 6 H).

Example 73

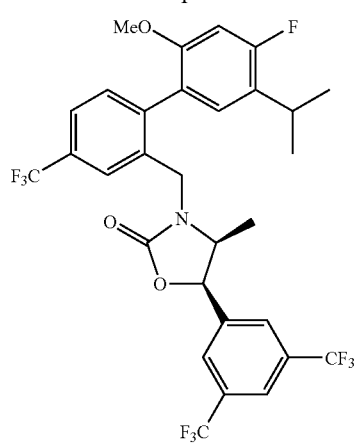

Step 1: (4S,5R)-5-[3,5-bis(trifluoromethyl)phenyl]-3-[2-iodo-5-(trifluoromethyl)benzyl]-4-methyl-1,3-oxazolidin-2-one To a stirred suspension of sodium hydride (60% dispersion in mineral oil; 1.3 g; 0.0325 mol) in THF (60 mL) at 0° C. under $N_2$ was added dropwise a solution of (4S,5R)-5-[3,5-bis(trifluoromethyl)phenyl]-4-methyl-1,3-oxazolidin-2-one (Example 17) (4.077 g; 0.013 mol) in THF (50 mL). Gas evolution was observed. The resultant mixture stirred at 0° C. for 30 min prior to addition of a solution of 2-(bromomethyl)-1-iodo-4-(trifluoromethyl)benzene (4.754 g; 0.013 mol) in THF (20 mL). The reaction was allowed to warm to room temperature and stirred for 14 h. The reaction was carefully quenched with $H_2O$ (15 mL) and partitioned between EtOAc (250 mL) and $H_2O$ (75 mL). The aqueous layer was extracted with EtOAc (3×100 mL). Combined organic layers were washed with brine (100 mL), dried ($MgSO_4$), filtered and concentrated in vacuo. The residue was purified by flash chromatography (0-20% EtOAc/hexanes gradient) to afford 6.4 g (82.5%) of (4S,5R)-5-[3,5-bis(trifluoromethyl)phenyl]-3-[2-iodo-5-(trifluoromethyl)benzyl]-4-methyl-1,3-oxazolidin-2-one as a white solid. LCMS=598.1 (M+1)$^+$. $^1$H NMR (CDCl$_3$, 500 MHz): δ 8.03 (d, J=8.2 Hz, 1 H), 7.90 (s, 1 H), 7.79 (s, 2 H), 7.58 (s, 1 H), 7.30 (dd, J=8.2 Hz, J=2.0 Hz, 1 H), 5.76 (d, J=8 Hz, 1 H), 4.88 (d, J=15.8 Hz, 1 H), 4.37 (d, J=15.8 Hz, 1 H), 4.09-4.02 (m, 1 H), 0.8 (d, J=6.6 Hz, 3 H).

Step 2: (4S,5R)-5-[3,5-bis(trifluoromethyl)phenyl]-3-{[4'-fluoro-5'-isopropyl-2'-methoxy-4-(trifluoromethyl)biphenyl-2-yl]-methyl}-4-methyl-1,3-oxazolidin-2-one A stirred mixture of (4S,5R)-5-[3,5-bis(trifluoromethyl)phenyl]-3-[2-iodo-5-(trifluoromethyl)benzyl]-4-methyl-1,3-oxazolidin-2-one (4.29 g; 7.19 mmol), (4-fluoro-5-isopropyl-2-methoxyphenyl)boronic acid (Example 78) (4.57 g; 21.57 mmol), tetrakis(triphenylphosphine)palladium (0) (1.0 g; 0.86 mmol), and sodium carbonate (6.35 g) in $C_6H_6$/EtOH/$H_2O$ (120 mL/17 mL/51 mL) was heated at reflux (100° C.) under $N_2$ for 14 h. The reaction was partitioned between EtOAc (200 mL) and $H_2O$ (100 mL). The aqueous phase was extracted with EtOAc (3×200 mL). The combined organic phases were washed with brine (100 mL), dried ($MgSO_4$), filtered and concentrated in vacuo. The residue was purified by silica-gel flash chromatography (0-25% EtOAc/hexanes gradient) to afford (4S,5R)-5-[3,5-bis(trifluoromethyl)phenyl]-3-{[4'-fluoro-5'-isopropyl-2'-methoxy-4-(trifluoromethyl)biphenyl-2-yl]methyl}-4-methyl-1,3-oxazolidin-2-one as a yellow solid. To remove the yellow impurity, 2.7 g were dissolved in 165 mL EtOH and 275 mg decolorizing charcoal was added (activated carbon, Darco, G-60, 100 mesh powder, Aldrich). The mixture was stirred at room temperature for 40 min, filtered, and concentrated in vacuo. Trituration with ca. 25 mL hexanes afforded 2.46 g of the title compound as a white solid. ¹H NMR indicated trace impurities which were removed by silica gel flash chromatography (0-15% EtOAc/hexanes gradient). Residual solvent was removed by lyophilization from acetonitrile. LCMS=638.3 (M+1)⁺. ¹H NMR (benzene-d₆, 500 MHz, 1:1 mixture of atropisomers): δ 7.82 (s, 0.5H), 7.60 (s, 0.5 H), 7.57 (s, 1 H), 7.33 (d, J=8 Hz, 1 H), 7.27 (d, J=9.9 Hz, 2 H), 7.02-6.98 (m, 1H), 6.89 (d, J=8.5 Hz, 0.5 H), 6.82 (d, J=8.5 Hz, 0.5 H), 6.45 (d, J=12.1 Hz, 0.5 H), 6.35 (d, J=11.9 Hz, 0.5 H), 4.94 (d, J=16.0 Hz, 0.5 H), 4.87 (d, J=15.8 Hz, 0.5 H), 4.54 (d, J=8.0 Hz, 0.5 H), 4.50 (d, J=7.8 Hz, 0.5 H), 3.74-3.66 (m, 1 H), 3.23-3.15 (m, 1 H), 3.12 (s, 1.5 H), 2.99 (s, 1.5 H), 2.97-2.92 (m, 0.5H), 2.89-2.84 (m, 0.5 H), 1.21-1.09 (m, 6 H), −0.27 (d, J=6.7 Hz, 1.5 H), −0.40 (d, J=6.7 Hz, 1.5 H).

Alternate procedure for making (4S,5R)-5-[3,5-bis(trifluoromethyl)phenyl]-3-{[4'-fluoro-5'isopropyl-2'-methoxy-4-(trifluoromethyl)biphenyl-2-yl]methyl}-4-methyl-1,3-oxazolidin-2-one A mixture of (4S,5R)-5-[3,5-bis(trifluoromethyl)phenyl]-3-[2-iodo-5-(trifluoromethyl)benzyl]-4-methyl-1,3-oxazolidin-2-one (50 mg; 0.084 mmol), (4-fluoro-5-isopropyl-2-methoxyphenyl)boronic acid (EXAMPLE 78, 22 mg; 0.105 mmol), palladium acetate (6 mg; 0.0103 mmol), and potassium carbonate (29 mg; 0.257 mmol) in 5:1 acetone/water (6 mL) was heated at reflux for 1 h. Acetone was removed in vacuo and the residue was diluted with H₂O (10 mL) and extracted with CH₂Cl₂ (3×10 mL). The combined extracts were washed with brine (10 mL), dried over Na₂SO₄, filtered, and concentrated in vacuo. The residue was purified by flash chromatography (0-25% EtOAc/hexanes gradient) to afford (4S,5R)-5-[3,5-bis(trifluoromethyl)phenyl]-3-{[4'-fluoro-5'isopropyl-2'-methoxy-4-(trifluoromethyl)biphenyl-2-yl]methyl}-4-methyl-1,3-oxazolidin-2-one as a clear glass. This product can also be made by the method provided in Example 372.

Example 74

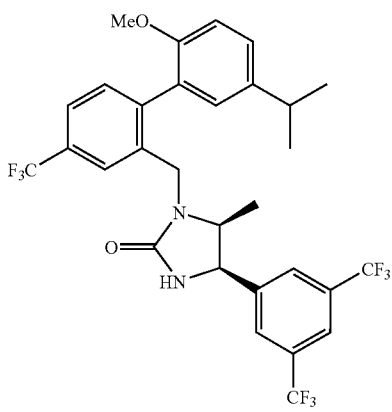 [SMILES: COc1ccc(C(C)C)cc1-c1ccc(C(F)(F)F)cc1CN1C(=O)N[C@H](c2cc(C(F)(F)F)cc(C(F)(F)F)c2)[C@@H]1C]

(4R,5S)-4-[3,5-bis(trifluoromethyl)phenyl]-1-{[5'-isopropyl-2'-methoxy-4-(trifluoromethyl)biphenyl-2-yl]methyl}-5-methylimidazolidin-2-one Step A: (4S,5S)-5-[3,5-bis(trifluoromethyl)phenyl]-3-{[5'-isopropyl-2'-methoxy-4-(trifluoromethyl)biphenyl-2-yl]methyl}-4-methyl-1,3-oxazolidin-2-one ((4S,5S)-5-[3,5-bis(trifluoromethyl)phenyl]-4-methyl-1,3-oxazolidin-2-one) (46.2 mg, 0.148 mmol) was placed in a dry flask and DMA (3 mL) was added. NaHMDS (296 µL of a 1M solution in THF, 0.296 mmol) was added and the reaction was stirred for 5 min. At this time, 2'-(bromomethyl)-5-isopropyl-4'-(trifluoromethyl)biphenyl-2-yl methyl ether (80.0 mg, 0.207 mmol) was added by cannula in DMA (2 mL). After 30 min, the reaction was quenched with saturated NH₄Cl (2 mL). The mixture was diluted with EtOAc (40 mL). The organic layer was washed with water (15 mL), and brine (15 mL), dried over Na₂SO₄, filtered, and concentrated. Purification of the residue by flash chromatography with 25% EtOAc/hexanes afforded (4S,5S)-5-[3,5-bis(trifluoromethyl)phenyl]-3-{[5'-isopropyl-2'-methoxy-4-(trifluoromethyl)biphenyl-2-yl]methyl}-4-methyl-1,3-oxazolidin-2-one. R_f=0.27 (25% EtOAc/hexanes). LCMS=620.2 (M+1)⁺. ¹H NMR (CDCl₃, 500 MHz; atropisomers present) δ 6.90-7.88 (m, 9H), 4.04-5.05 (m, 3H), 3.25-3.74 (m, 4H), 2.88 (m, 1H), 1.19-1.24 (m, 6H), 0.99-1.07 (m, 3H).

Step B: (1S,2S)-1-[3,5-bis(trifluoromethyl)phenyl]-2-({[5'-isopropyl-2'-methoxy-4-(trifluoromethyl)biphenyl-2-yl]methyl}amino)propan-1-ol To a solution of (4S,5S)-5-[3,5-bis(trifluoromethyl)phenyl]-3-{[5'-isopropyl-2'-methoxy-4-(trifluoromethyl)biphenyl-2-yl]methyl}-4-methyl-1,3-oxazolidin-2-one (147.7 mg, 0.239 mmol) in EtOH (7.5 mL) was added H₂O (1.5 mL) and KOH (150 mg, 2.67 mmol). The solution was heated to 75° C. for 30 h and then cooled to room temperature. EtOAc (75 mL) was added and the organic layer was washed with H₂O (15 mL) and brine (2×15 mL). The organic layer was dried over Na₂SO₄, filtered, and concentrated. The residue was purified by flash chromatography to afford (1S,2S)-1-[3,5-bis(trifluoromethyl)phenyl]-2-({[5'-isopropyl-2'-methoxy-4-(trifluoromethyl)biphenyl-2-yl]methyl}amino)propan-1-ol. R_f=0.44 (40% EtOAc/hexanes). LCMS=594.2 (M+1)⁺. ¹H NMR (CDCl₃, 500 MHz) δ 6.93-7.78 (m, 9H), 3.51-4.20 (m, 6H), 2.91 (m, 1H), 2.49 (m, 1H), 1.22-1.26 (m, 6H), 0.79-0.81 (m, 3H).

Step C: tert-butyl{(1S,2S)-2-[3,5-bis(trifluoromethyl)phenyl]-2-hydroxy-1-methylethyl}{[5'-isopropyl-2'-methoxy-4-(trifluoromethyl)biphenyl-2-yl]methyl}carbamate To a solution of (1S,2S)-1-[3,5-bis(trifluoromethyl)phenyl]-2-({[5'-isopropyl-2'-methoxy-4-(trifluoromethyl)biphenyl-2-yl]methyl}amino)propan-1-ol (135.5 mg, 0.228 mmol) in CH₂Cl₂ (5 mL) was added BOC₂O (49.7 mg, 0.228 mmol). The reaction was stirred at room temperature for 2 days; during this time, 2 additional portions of BOC₂O (25 mg each) were added. After 2 days, the reaction was concentrated, and the residue was purified by flash chromatography with 20% EtOAc/hexanes to afford tert-butyl{(1S,2S)-2-[3,5-bis(trifluoromethyl)phenyl]-2-hydroxy-1-methylethyl}{[5'-isopropyl-2'-methoxy-4-(trifluoromethyl)biphenyl-2-yl]methyl}carbamate. R_f=0.41 (40% EtOAc/hexanes). LCMS=594.2 (M+1−BOC)⁺.

Step D: tert-butyl{(1S,2R)-2-azido-2-[3,5-bis(trifluoromethyl)phenyl]-1-methylethyl}{[5'-isopropyl-2'-methoxy-4-(trifluoromethyl)biphenyl-2-yl]methyl}carbamate A dry flask was charged with THF (1 mL) diethyl azodicarboxylate (DEAD) (11 µL, 0.0698 mmol) and diphenylphosphoryl azide (DPPA) (15 µL, 0.0698 mmol). tert-butyl{(1S,2S)-2-[3,5-bis(trifluoromethyl)phenyl]-2-hydroxy-1-methylethyl}{[5'-isopropyl-2'-methoxy-4-

(trifluoromethyl)biphenyl-2-yl]methyl}carbamate (20.7 mg, 0.0698 mmol) was added by cannula in THF (1 mL). Next Ph₃P (18.3 mg, 0.0698 mmol) was added. The reaction was stirred at room temperature for 30 min, and then additional DEAD (11 µL, 0.0698 mmol), DPPA (15 µL, 0.0698 mmol), and Ph₃P (18.3 mg, 0.0698 mmol) were added. After an additional 30 min, the reaction was diluted with EtOAc (40 mL) and washed with water and brine (15 mL each). The organic layer was dried over Na₂SO₄, filtered, and concentrated. Purification of the residue by flash chromatography with 15% EtOAc/hexanes afforded tert-butyl{(1S,2R)-2-azido-2-[3,5-bis(trifluoromethyl)phenyl]-1-methylethyl}{[5'-isopropyl-2'-methoxy-4-(trifluoromethyl)biphenyl-2-yl]methyl}carbamate. R$_f$=0.60 (25% EtOAc/hexanes). LCMS=619.3 (M+1−BOC)⁺.

Step E: (1R,2S)-1-azido-1-[3,5-bis(trifluoromethyl) phenyl]-N-{[5'-isopropyl-2'-methoxy-4-(trifluoromethyl)biphenyl-2-yl]methyl}propan-2-amine To a solution of tert-butyl{(1S,2R)-2-azido-2-[3,5-bis(trifluoromethyl)phenyl]-1-methylethyl}{[5'-isopropyl-2'-methoxy-4-(trifluoromethyl)biphenyl-2-yl] methyl}carbamate (21.7 mg, 0.030 mmol) in CH₂Cl₂ (2 mL) was added TFA (200 mL). The reaction was stirred at room temperature for 1 hour and then diluted with CH₂Cl₂ (25 mL). The CH₂Cl₂ solution was washed with 1 N NaOH (15 mL) and the aqueous phase was re-extracted with CH₂Cl₂ (25 mL). The organic extracts were combined, washed with brine (20 mL), dried over Na₂SO₄, filtered, and concentrated. Purification of the residue by flash chromatography with 15% EtOAc/hexanes afforded (1R,2S)-1-azido-1-[3,5-bis(trifluoromethyl)phenyl]-N-{[5'-isopropyl-2'-methoxy-4-(trifluoromethyl)biphenyl-2-yl]methyl}propan-2-amine. R$_f$=0.45 (15% EtOAc/hexanes). LCMS=619.2 (M+1)⁺.

Step F: (1R,2S)-1-[3,5-bis(trifluoromethyl)phenyl]-N²-{[5'-isopropyl-2'-methoxy-4-(trifluoromethyl) biphenyl-2-yl]-methyl}propane-1,2-diamine To a solution of (1R,2S)-1-azido-1-[3,5-bis(trifluoromethyl)phenyl]-N-{[5'-isopropyl-2'-methoxy-4-(trifluoromethyl)biphenyl-2-yl]methyl}propan-2-amine (17.8 mg, 0.0288 mmol) in THF (3 mL) was added PtO₂ (12 mg, 0.053 mmol). The reaction was placed under hydrogen balloon atmosphere and stirred at room temperature for 3 h. The catalyst was removed by filtration and the filtrate was concentrated. The residue was put through a short plug of silica gel with 0-10% MeOH/CH₂Cl₂ to give (1R,2S)-1-[3,5-bis (trifluoromethyl)phenyl]-N²-{[5'-isopropyl-2'-methoxy-4-(trifluoromethyl)biphenyl-2-yl]methyl}propane-1,2-diamine. LCMS=619.2 (M+1)⁺.

Step G: (4R,5S)-4-[3,5-bis(trifluoromethyl)phenyl]-1-{[5'-isopropyl-2'-methoxy-4-(trifluoromethyl)biphenyl-2-yl]methyl}-5-methylimidazolidin-2-one A solution of (1R,2S)-1-[3,5-bis(trifluoromethyl)phenyl]-N²-{[5'-isopropyl-2'-methoxy-4-(trifluoromethyl)biphenyl-2-yl]methyl}propane-1,2-diamine (8.0 mg, 0.0135 mmol) in CH₂Cl₂ (2 mL) was cooled to 0° C. and DIPEA (14 µL, 0.081 mmol) was added followed by triphosgene (2 mg, 0.00657 mmol). The reaction was stirred at 0° C. for 30 min and then diluted with EtOAc (30 mL). The reaction was washed with saturated NaHCO₃ (10 mL) and brine (10 mL). The organic layer was dried over Na₂SO₄, filtered, and concentrated. Purification of the residue by flash chromatography with 40% EtOAc/hexanes afforded (4R,5S)-4-[3,5-bis(trifluoromethyl)phenyl]-1-{[5'-isopropyl-2'-methoxy-4-(trifluoromethyl)biphenyl-2-yl]methyl}-5-methylimidazolidin-2-one. R$_f$=0.24 (40% EtOAc/hexanes). LCMS=619.2 (M+1)⁺. ¹H NMR (CD₂Cl₂, 600 MHz; atropisomers present) δ 6.91-7.84 (m, 9H), 3.84-4.94 (m, 4H), 3.64-3.80 (m, 4H), 2.88 (m, 1H), 1.18-1.26 (m, 6H), 0.27-0.42 (m, 3H).

Example 75

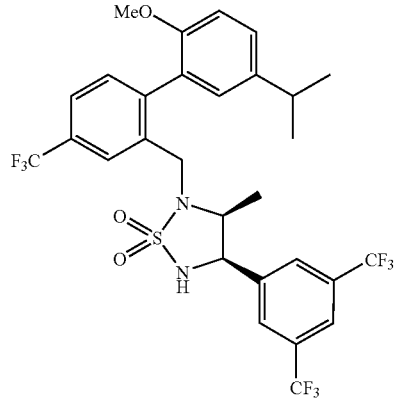 [SMILES: COc1ccc(C(C)C)cc1-c1ccc(C(F)(F)F)cc1CN1[C@@H](C)[C@@H](c2cc(C(F)(F)F)cc(C(F)(F)F)c2)NS1(=O)=O]

(3S,4R)-4-[3,5-bis(trifluoromethyl)phenyl]-2-{[5'-isopropyl-2'-methoxy-4-(trifluoromethyl)biphenyl-2-yl]methyl}-3-methyl-1,2,5-thiadiazolidine 1,1-dioxide A glass reaction tube was charged with (1R,2S)-1-[3,5-bis (trifluoromethyl)phenyl]-N²-{[5'-isopropyl-2'-methoxy-4-(trifluoromethyl)biphenyl-2-yl]methyl}propane-1,2-diamine (15.9 mg, 0.0269 mmol), sulfamide (4 mg, 0.0403 mmol), and pyridine (600 µL). The tube was flushed with N₂, sealed, and heated at 120° C. for 2 h. The reaction was then cooled to room temperature, diluted with EtOAc (40 mL) and washed with H₂O, 1N HCl, and brine (10 mL each). The organic layer was dried over Na₂SO₄, filtered, and concentrated. Purification of the residue by flash chromatography with 25% EtOAc/hexanes afforded (3S,4R)-4-[3,5-bis(trifluoromethyl)phenyl]-2-{[5'-isopropyl-2'-methoxy-4-(trifluoromethyl)biphenyl-2-yl]methyl}-3-methyl-1,2,5-thiadiazolidine 1,1-dioxide. R$_f$=0.27 (25% EtOAc/hexanes). LCMS=655.2 (M+1)⁺. ¹H NMR (C₆D₆, 500 MHz; atropisomers present) δ 6.51-8.19 (m, 9H), 3.64-4.53 (m, 4H), 3.00-3.18 (m, 4H), 2.73 (m, 1H), 1.13-1.20 (m, 6H), −0.03-0.09 (m, 3H).

Example 76

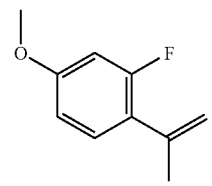

2-fluoro-1-isopropenyl-4-methoxybenzene

Step A: 2-(2-fluoro-4-methoxyphenyl)propan-2-ol

To a solution of 2'-fluoro-4'-methoxyacetophenone (4.45 g, 26.5 mmol) in THF (50 ml) at 0° C., a solution of 2.4 M MeMgBr (11.6 mmol, 27.8 mmol) was added. The mixture was stirred at 0° C. and then room temperature for 4 h. The reaction was quenched with saturated ammonium chloride solution. The organic was extracted with ethyl acetate (3×50 ml). The combined ethyl acetate layers were washed with brine and dried over sodium sulfate. The resulting alcohol was obtained as an oil after flash column using EtOAc:hexane=2:8 as the elute.

Step B: 2-fluoro-1-isopropenyl-4-methoxybenzene

To a solution of 2-(2-fluoro-4-methoxyphenyl)propan-2-ol from Step A (3.89 g, 21.14 mmol) in methylene chloride (50 ml) at 0° C., MsCl (1.95 ml, 25.4 mmol) and triethylamine (6.52 ml, 46.5 mmol) were added. The solution was stirred at 0° C. and then room temperature for 2 h. The solution was diluted with methylene chloride (100 ml), washed with water, and dried over sodium sulfate. The title compound was obtained as an oil after flash column using EtOAc:hexane=1:9 as the elute. $^1$H NMR (CDCl$_3$, 500 MHz) δ 7.25 (t, J=9.0 Hz, 1H), 6.68 (dd, J=8.5, 2.5 Hz, 1H), 6.63 (dd, J=13, 2.5 Hz, 1H), 5.20 (d, J=17.0 Hz, 2H), 3.82 (s, 3H), 2.18 (s, 3H).

Alternate route to make
2-fluoro-1-isopropenyl-4-methoxybenzene

A solution of sodium bis(trimethylsilyl)-amide, 1.0M in tetrahydrofuran (714 ml, 0.714 m) was added to a suspension of methyltriphenylphosphonium bromide (255 g, 0.714 m) in THF (2.50 L) cooled with an ice bath. The resultant yellow colored suspension was stirred for 30 minutes at ice bath temperature and then cooled to −78° C. A total of 2-fluoro-4-methoxyacetophenone (100 g, 0.595 m) in THF (200 ml) was added dropwise and stirred at −78° C. for 1.5 hours. Reaction mixture was allowed to warm to room temperature for one hour, quenched with acetic acid (~80 ml) where color change was observed from yellow to off white and stirred for 30 minutes (pH~7)(slight exotherm noted). The mixture was concentrated to a slush, diluted with 7:2 hexane:ethyl acetate, and was allowed to sit overnight. Solids were removed by filtration and the filtrate was concentrated to yellow oil. The title compound was obtained after flash column using 9:1 hexane:ethyl as the eluant.

Example 77

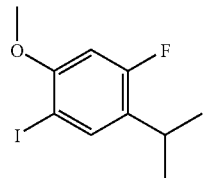

1-fluoro-4-iodo-2-isopropyl-5-methoxybenzene

A solution of the 2-fluoro-1-isopropenyl-4-methoxybenzene (Example 76, 1.96 g, 11.81 mmol) in MeOH (30 ml) was charged with hydrogen at 1 atm with catalytic amount of Pd/C. The mixture was stirred at room temperature for 1 h. The mixture was filtered through Celite. The filtrate was then added to a mixture of silver sulfate (3.68 g, 11.81 mmol) and Iodine (3.00 g, 11.81 mmol) in MeOH (10 ml). The mixture was stirred at room temperature for 3 h until the color of solution became light yellow. The mixture was filtered and the filtrate was concentrated. The title compound was obtained after flash column using EtOAc:hexane 5:95 as the elute. $^1$H NMR (CDCl$_3$, 500 MHz) δ 7.61 (d, J=8.0 Hz, 1H), 6.56 (d, J=12.5 Hz, 1H), 3.90 (s, 3H), 118 (m, 1H), 1.28 (m, 6H).

Example 78

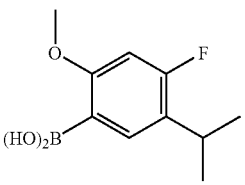

(4-fluoro-5-isopropyl-2-methoxyphenyl)boronic acid

To a solution of 1-fluoro-4-iodo-2-isopropyl-5-methoxybenzene (Example 77, 2.61 g, 8.88 mmol) in THF at −78° C., n-BuLi (4.26 ml, 10.65 mmol, 2.5 M) was added dropwise. The solution was stirred at −78° C. for 30 min. Trimethyl borate (2.98 ml, 26.6 mmol) was added. The solution was then stirred at −78° C. for 3 h. The reaction was quenched at −78° C. with saturated ammonium chloride and the mixture was warmed to room temperature. The organic was extracted with ethyl acetate (3×50 ml). The combined ethyl acetate layers were washed with brine and dried over sodium sulfate. The title compound was obtained as a solid pure enough for next step. Further purification with silica gel caused decomposition of product. $^1$H NMR (CDCl$_3$, 500 MHz) δ 7.74 (d, J=10.0 Hz, 1H), 6.62 (d, J=12.5 Hz, 1H), 5.65 (br s, 2H), 3.92 (s, 3H), 3.20 (m, 1H), 1.22 (m, 6H).

The boronic acid intermediate can also be made by the following 4-step process:

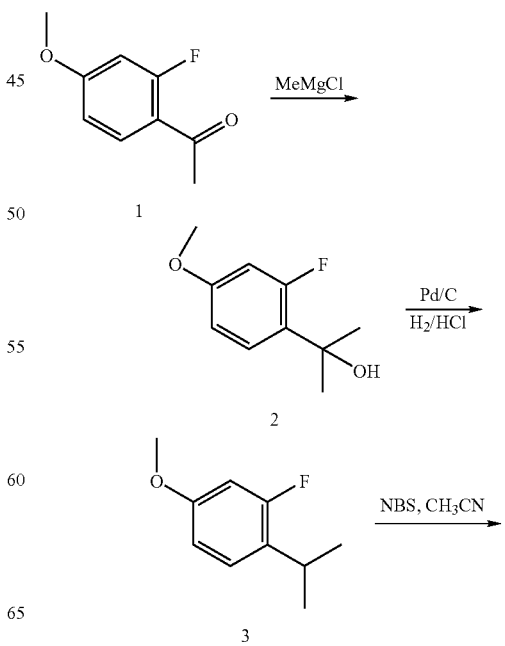

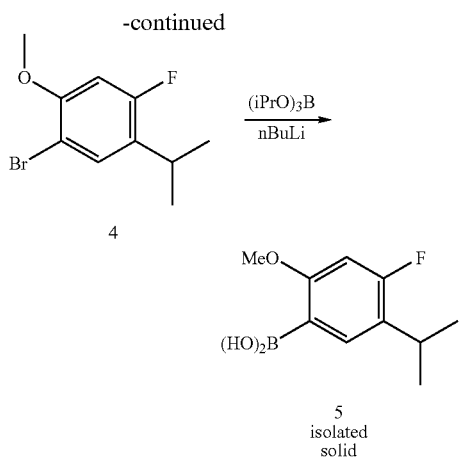

Conversion of 1 to 2:

THF (24 L) was added to a 100 L cylindrical vessel at room temperature. To this was added 2.75 kg of CeCl₃. The resultant slurry was aged at room temperature for 1.5 hours. A sample was then examined under a microscope to confirm that the desired form change had occurred. The slurry was cooled to 9° C. and MeMgCl was added. The rate of addition was adjusted to maintain internal temperature below 19° C. The mixture was cooled to −11° C., and a solution of acetophenone 1 (4.0 kg diluted to 10 L with THF) was added dropwise, maintaining the internal temperature below 0° C. The reaction mixture was then aged at a temperature below 0° C. for an hour. The reaction was quenched with 5.7 L of 3N HCl in a dropwise fashion, maintaining the internal temperature below 15° C. The quenched reaction mixture was then aged at 5-10° C. for 1.5 hours and was filtered through a plug of Solka Floc.

Hydrogenation of 2 to 3:

The THF solution of 2 was solvent switched into ethanol (~18 L volume), and 1.9 L HCl was added, followed by 190 gm of 10% Pd/C (50% water). The mixture was placed under 15 psi hydrogen at 40° C. until the reaction was complete based on HPLC analysis. The mixture was cooled to room temperature. The catalyst was removed by filtration using Solka-Flok as a filter aid. The anisole product in ethanol was then solvent switched into acetonitrile for the next step.

Bromination of 3 to 4:

Anisole 3 is diluted in acetonitrile (1.72 L, 4 mL MeCN/mMol 3). This mixture is warmed to 35° C., and NBS (1.1 eq, 84 g) is added in a single solid addition. The reaction is complete in 2-4 hours. The solution is concentrated to 400 mL total volume and diluted with 1 L of toluene. The solution is then washed with sodium thiosulfate and water to remove the succinimide by-product. The organic layer is then concentrated and solvent switched to toluene.

Conversion of Aryl Bromide 4 to Boronic Acid 5:

A 75 L glass reaction vessel was charged with 1.87 kg of aryl bromide 4 (7.6 Mol), which was added as 6.4 kg of a 29.1 wt % solution of 4 in toluene. This solution was diluted with 5.6 L of THF. The vessel was flushed with nitrogen, and tri-isopropylborate (1.35 eq, 2.35 L, 10.3 Mol) was added. The mixture was cooled to <−70° C. Then 5.9 L of 1.6 M n-BuLi in hexanes (9.5 Mol) was added slowly over 4 hours, maintaining a temperature of <−55° C. Thirty minutes after completion of the n-BuLi addition, the reaction was complete by LC analysis. The reaction was warmed to −35° C. and quenched into 3.0 M H₂SO₄ solution (5.6 L). The aqueous phase after the quench should be acidic (pH~2). MTBE (7.5 L) was added to the mixture to dilute the organic layer. The mixture was stirred (15 min) and the aqueous layer was cut away. The organic layer was washed with another 5.6 L of a 3.0 M H₂SO₄ solution (15 min). After separating layers again, the organic MTBE/Toluene layer was extracted twice with 1 M KOH (15.1 L first and then 7.6 L). The two KOH extractions were combined, diluted with 2-propanol (6.4 L), and cooled to 15° C. Then the solution was slowly acidified to pH ~2 using 3.0 M sulphuric acid (~7.6 L) while maintaining temperature at 15-20° C. The resulting slurry was stirred for 1 h and then filtered. The filter cake was washed with water (2×6 L) and dried under an air flow for 1 day. The filtered solid was placed in an oven under vacuum at 50° C. for 2-3 days to decompose a diaryl impurity and to dry the solid. The off-white crystalline solid was isolated to yield 1.59 kg of boronic acid 5.

Example 79

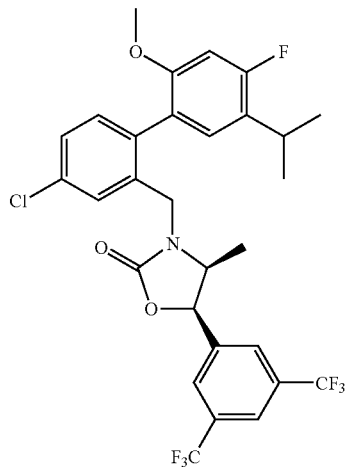 [SMILES: COc1cc(F)c(C(C)C)cc1-c1ccc(Cl)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-[(4-chloro-4'-fluoro-5'-isopropyl-2'-methoxybiphenyl-2-yl)methyl]-4-methyl-1,3-oxazolidin-2-one Step A: 1-bromo-2-(bromomethyl)-4-chlorobenzene A mixture of 2-bromo-5-chloro-toluene (2.00 g, 9.75 mmol), NBS (2.08 g, 11.7 mmol) and catalytic amount of AIBN in carbon tetrachloride (50 ml) was stirred under refluxing conditions for 4 h. TLC (EtOAc:hexane=5:95) showed no starting material. The mixture was filtered and the filtrate was concentrated. The title compound was obtained as a white solid after flash column using EtOAc:hexane=5:95 as the elute. ¹H NMR (CDCl₃, 500 MHz) δ 7.53 (d, J=9.0 Hz, 1H), 7.47 (d, J=2.5 Hz, 1H), 7.18 (dd, J=8.5, 2.5 Hz, 1H), 4.60 (s, 2H).

Step B. (4S,5R)-5-[3,5-bis(trifluoromethyl)phenyl]-3-(2-bromo-5-chlorobenzyl)-4-methyl-1,3-oxazolidin-2-one To a solution of (4S,5R)-5-[3,5-bis(trifluoromethyl)phenyl]-4-methyl-1,3-oxazolidin-2-one (0.050 g, 0.16 mmol) in THF (1 ml) at 0° C., NaH (7.6 mg, 0.19 mmol, 60%) was added. The mixture was stirred at 0° C. for 30 min. The title compound from Step A (0.059 g, 0.21 mmol) was added. The whole mixture was stirred at 0° C. for 1 h and warmed to room temperature for 4 h. The reaction was quenched with saturated ammonium chloride. The organic was extracted with ethyl acetate (3×15 ml). The combined ethyl acetate layers were washed with brine and dried over sodium sulfate. The title compound was obtained after preparative TLC purification using EtOAc:hexane=2:8 as the elute. $^1$H NMR (CDCl$_3$, 500 MHz) δ 7.92 (s, 1H), 7.82 (s, 2H), 7.55 (d, J=8.5 Hz, 1H), 7.43 (d, J=2.5 Hz, 1H), 7.23 (dd, J=8.5, 2.5 Hz, 1H), 5.77 (d, J=8.0 Hz, 1H), 4.86 (d, J=16.0 Hz, 1H), 4.36 (d, J=16.0 Hz, 1H), 4.11 (m, 1H), 0.82 (d, J=6.5 Hz, 3H).

Step C. (4S,5R)-5-[3,5-bis(trifluoromethyl)phenyl]-3-[(4-chloro-4'-fluoro-5'-isopropyl-2'-methoxybiphenyl-2-yl)methyl]-4-methyl-1,3-oxazolidin-2-one A mixture of (4S,5R)-5-[3,5-bis(trifluoromethyl)phenyl]-3-(2-bromo-5-chlorobenzyl)-4-methyl-1,3-oxazolidin-2-one (44 mg, 0.085 mmol), (4-fluoro-5-isopropyl-2-methoxyphenyl)boronic acid (Example 78, 23 mg, 0.11 mmol), potassium carbonate (25 mg, 0.18 mmol) and catalytic amount of PdOAc in a 4:1 mixture of acetone/water was heated to reflux for 1 h. Acetone was removed and water was added. The organic was extracted with methylene chloride (3×15 ml). The combined methylene chloride layers were washed with brine and dried over sodium sulfate. The title compound was obtained as a solid after preparative reverse phase HPLC. $^1$H NMR (CDCl$_3$, 500 MHz) δ 1:1 mixture of rotamer δ 7.90 (s, 1H), 7.73 (s, 2H), 7.49 (m, 1H), 7.40 (m, 1H), 7.20 (m, 1H), 7.00 (m, 1H), 6.68 (dd, J=12.0, 3.0 Hz, 1H), 5.63 (d, J=8.0 Hz, ½ H), 5.44 (d, J=8.0 Hz, ½ H), 4.85 (d, J=10.0 Hz, ½ H), 4.82 (d, J=10.0 Hz, ½ H), 4.03 (d, J=16.0 Hz, ½ H), 3.84 (m, 1½ H), 3.80 (s, 3H), 3.20 (m, 1H), 1.20 (m, 6H), 0.56 (d, J=6.5 Hz, 3/2 H), 0.38 (d, J=6.5H, 3/2 H). LC-MS (M+1): 604.3, 4.61 min.

Example 80

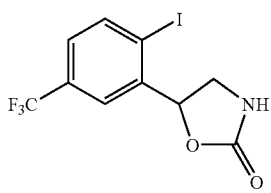

5-[2-iodo-5-(trifluoromethyl)phenyl]-1,3-oxazolidin-2-one

Step A: 2-iodo-5-(trifluoromethyl)benzaldehyde

To a solution of 2-iodo-5-(trifluoromethyl)benzonitrile (EXAMPLE 2, 42 g) in CH$_2$Cl$_2$ (300 mL) at −78° C. was added a solution of DIBAL in CH$_2$Cl$_2$ (175 mL, 1M) over 30 minutes. A precipitate formed. The reaction was warmed to 0° C. An additional 25 mL of the DIBAL solution was added dropwise over 30 minutes. The reaction was poured into 200 mL 2N aqueous HCl, diluted with ether and stirred 1 hour. TLC analysis indicates imine still present and an additional 100 mL 2N aqueous was added and the reaction stirred overnight. Imine was still present by TLC analysis and 200 mL 2N aqueous HCl was added and the mixture stirred 2 hours. The layers were separated and the aqueous layer back extracted with ether. The ether extracts were combined, washed with brine, dried over anhydrous MgSO$_4$, filtered and concentrated. The product was purified by silica gel chromatography eluting with 95:5 hexanes/EtOAc to give 2-Iodo-5-(trifluoromethyl)benzaldehyde as a white solid. $^1$H NMR (500 MHz, CDCl$_3$): δ 10.00 (s, 1H), 8.12 (s, 1H), 8.11 (d, J=8 Hz, 1H), 7.53 (dd, J=2 Hz, 8 Hz, 1H).

Step B: 5-[2-iodo-5-(trifluoromethyl)phenyl]-1,3-oxazolidin-2-one

To a 0° C. solution of 0.2 g of 2-iodo-5-(trifluoromethyl)benzaldehyde in 3 mL of EtOH was added 0.13 mL of nitromethane, then 0.28 mL of a 2.5 N solution of NaOH. The mixture was stirred at 0° C. for 3 h, and then neutralized by addition of 2.1 mL of a 0.33 N aqueous solution of AcOH. The mixture was partitioned between 10 mL of water and 10 mL of EtOAc. The aqueous phase was extracted with 2×5 mL of EtOAc. The combined organics were washed with 10 mL of brine, dried over Na$_2$SO$_4$, and concentrated. The residue was dissolved in 4 mL of MeOH and 0.5 mL of 88% aqueous formic acid was added. Approximately 200 mg of a Raney nickel slurry was added and the mixture was flushed with H2, and stirred under an H2 balloon for 4 h. The mixture was filtered through a pad of Celite, washing with MeOH, and the filtrate was concentrated. The residue was partitioned between 10 mL of 10% aqueous NH$_4$OH and 20 mL of EtOAc. The aqueous phase was extracted with 2×10 mL of EtOAc. The combined organics were washed with 10 mL of brine, dried over Na$_2$SO$_4$, and concentrated. The residue was dissolved in 2 mL of CH$_2$Cl$_2$. To the solution was added 0.114 mL of diisopropylethylamine, then 0.065 g of triphosgene. The mixture was stirred at 0° C. for 30 min, then diluted with 10 mL of EtOAc and 10 mL of saturated NaHCO$_3$. The aqueous phase was extracted with 2×10 mL, of EtOAc. The combined organics were washed with 10 mL of brine, dried over Na$_2$SO$_4$, and concentrated. The residue was purified by flash chromatography on a Biotage Horizon, 25S column, eluting with 1 CV of 4% EtOAc in hexanes, followed by a linear gradient of EtOAc in hexanes from 4 to 100% over 10 CV to provide the title compound. Mass spectrum (ESI) 350.0 (M+1). $^1$H NMR (500 MHz, CDCl$_3$): δ 8.00 (d, J=8 Hz, 1H), 7.74 (br s, 1H), 7.33 (br d, J=8 Hz, 1H), 5.80 (dd, J=7 Hz, 9 Hz 1H), 5.05-5.50 (br, 1H), 4.28 (t, J=9 Hz, 1.5H), 3.36 (dd, J=7 Hz, 9 Hz, 1H).

Example 81

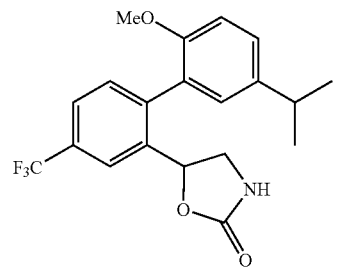 [SMILES: COc1ccc(C(C)C)cc1-c1ccc(C(F)(F)F)cc1C1CNC(=O)O1]

5-[5'-isopropyl-2'-methoxy-4-(trifluoromethyl)biphenyl-2-yl]-1,3-oxazolidin-2-one To a solution of 65 mg of 5-[5'-isopropyl-2'-methoxy-4-(trifluoromethyl)biphenyl-2-yl]-1,3-oxazolidin-2-one, 45 mg of (5-isopropyl-2-methoxyphenyl)boronic acid, and 66 mg of potassium carbonate in 6 mL of acetone and 1.5 mL of water was added ca. 5 mg of palladium acetate. The mixture was heated to reflux and stirred at this temperature for 1.5 h. Acetone was removed by rotary evaporation and the residue was diluted with 10 mL of EtOAc and 10 mL of water. The aqueous phase was extracted with 10 mL of EtOAc. The combined organics were washed with 10 mL of brine, dried over Na$_2$SO$_4$, and concentrated. The residue was purified by flash chromatography on a Biotage Horizon, 25S column, eluting with 1 CV of 10% EtOAc in hexanes, followed by a linear gradient of EtOAc in hexanes from 10 to 100% over 10 CV to provide the title compound. Spectral data are provided in EXAMPLE 49.

Following the procedures outlined in EXAMPLE 52 the compounds listed in Table 2 were prepared:

TABLE 3

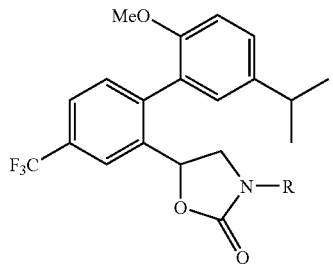

| EXAMPLE | R | LC/MS Data (M + 1) |
|---|---|---|
| 82 | 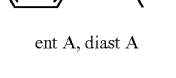 ent A | 488.1 |
| 83 | 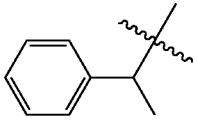 ent A | 504.1 |
| 84 | 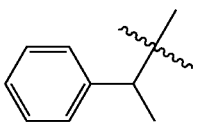 ent A | 495.1 |
| 85 | 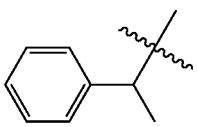 ent A | 476.2 |

TABLE 3-continued

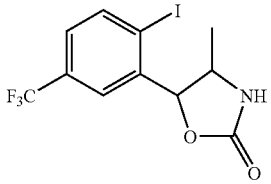 [SMILES: CC1NC(=O)OC1c1cc(C(F)(F)F)ccc1I]

| EXAMPLE | R | LC/MS Data (M + 1) |
|---|---|---|
| 86 | ent A, diast A | 484.2 |
| 87 | ent A, diast B | 484.2 |
| 88 | ent B, diast A | 484.2 |
| 89 | ent B, diast B | 484.2 |

Example 90

5-[2-iodo-5-(trifluoromethyl)phenyl]-4-methyl-1,3-oxazolidin-2-one

Following the procedure described in EXAMPLE 80 and using nitroethane, 0.2 g of 2-iodo-5-(trifluoromethyl)benzaldehyde provided 0.102 g of the desired product, which was separated into the cis and trans diastereomers by flash chromatography Biotage Horizon, 25S column, eluting with 1 CV of 10% EtOAc in hexanes, followed by a linear gradient of EtOAc in hexanes from 10 to 100% over 10 CV.

trans-5-[2-iodo-5-(trifluoromethyl)phenyl]-4-methyl-1,3-oxazolidin-2-one: Mass spectrum (ESI) 372.1 (M+1). $^1$H NMR (500 MHz, CDCl$_3$): δ 8.02 (d, J=8 Hz, 1H), 7.61 (d, J=1.5 Hz, 1H), 7.32 (dd, J=2 Hz, 8 Hz, 1H), 6.16 (s, 1H), 5.39

(d, J=4 Hz, 1H), 3.76 (dq, J=6 Hz, 4.5 Hz, 1H), 1.62 (d, J=6 Hz, 3H).

cis-5-[2-iodo-5-(trifluoromethyl)phenyl]-4-methyl-1,3-oxazolidin-2-one: Mass spectrum (ESI) 372.1 (M+1). $^1$H NMR (500 MHz, CDCl$_3$): δ 7.98 (d, J=8 Hz, 1H), 7.60 (br s, 1H), 7.33 (dd, J=1.5 Hz, 8 Hz, 1H), 6.25 (s, 1H), 5.85 (d, J=8 Hz, 1H), 3.76 (dq, J=8 Hz, 7 Hz, 1H), 0.81 (d, J=7 Hz, 3H).

Example 91

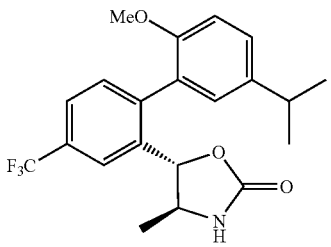 [SMILES: COc1ccc(C(C)C)cc1-c1ccc(C(F)(F)F)cc1[C@@H]1OC(=O)N[C@H]1C]

trans-5-[5'-isopropyl-2'-methoxy-4-(trifluoromethyl)biphenyl-2-yl]-4-methyl-1,3-oxazolidin-2-one (racemic)

To a solution of 0.036 g of trans-5-[2-iodo-5-(trifluoromethyl)phenyl]-4-methyl-1,3-oxazolidin-2-one, 0.024 g of (5-isopropyl-2-methoxyphenyl)boronic acid, and 0.04 g of potassium carbonate in 2 mL of acetone and 0.5 mL of water was added ca. 2 mg of palladium acetate. The mixture was heated to reflux and stirred at this temperature for 1.5 h. Acetone was removed by rotary evaporation and the residue was diluted with 10 mL of EtOAc and 10 mL of water. The aqueous phase was extracted with 10 mL of EtOAc. The combined organics were washed with 10 mL of brine, dried over Na$_2$SO$_4$, and concentrated. The residue was purified by flash chromatography on a Biotage Horizon, 25S column, eluting with 1 CV of 10% EtOAc in hexanes, followed by a linear gradient of EtOAc in hexanes from 10 to 100% over 10 CV to provide the title compound. Mass spectrum (ESI) 394.2 (M+1). $^1$H NMR signals are doubled because of atropoisomerism. $^1$H NMR (500 MHz, CDCl$_3$): δ 7.80, 7.78 (s, 1H), 7.64, 7.63 (d, J~8 Hz, 1H), 7.35 (d, J=7.5 Hz, 1H), 7.27, 7.26 (d, J~8 Hz 1H), 7.00, 6.95 (d, J=2.5 Hz, 1H), 6.93, 6.92 (d, J~8 Hz, 1H), 5.87, 5.81 (s, 1H), 5.16, 5.10 (d, J~5 Hz, 1H), 3.70-3.78 (m, 3.5H), 3.49 (m, 0.5H), 2.89 (m, 1H), 1.24 (m, 6H), 0.90, 0.70 (d, J=6.5 Hz, 3H).

Example 92

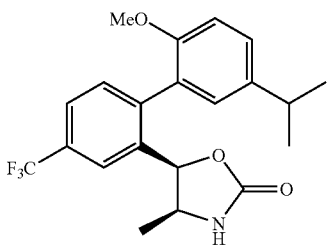 [SMILES: COc1ccc(C(C)C)cc1-c1ccc(C(F)(F)F)cc1[C@H]1OC(=O)N[C@H]1C]

cis-5-[5'-isopropyl-2'-methoxy-4-(trifluoromethyl)biphenyl-2-yl]-4-methyl-1,3-oxazolidin-2-one (racemic)

Following the procedure described in EXAMPLE 91, 0.046 g of cis-5-[2-iodo-5-(trifluoromethyl)phenyl]-4-methyl-1,3-oxazolidin-2-one provided the desired product. Mass spectrum (ESI) 394.2 (M+1). $^1$H NMR signals are doubled because of atropoisomerism. $^1$H NMR (500 MHz, CDCl$_3$): δ 7.89, 7.88 (s, 1H), 7.65, 7.64 (d, J~7.5 Hz, 1H), 7.34, 7.32 (d, J~8 Hz, 1H), 7.26 (d, J=8.5 Hz, 1H), 6.98, 6.86 (d, J=2.5 Hz, 1H), 6.91, 6.89 (d, J~8 Hz, 1H), 5.83, 5.75 (s, 1H), 5.69, 5.61 (d, J~8 Hz, 1H), 3.75 (s, 1.8H), 3.58-3.70 (m, 2H), 3.32 (m, 0.6H), 2.88 (m, 1H), 1.23 (m, 6H), 0.89, 0.71 (d, J=6.5 Hz, 3H).

Example 93

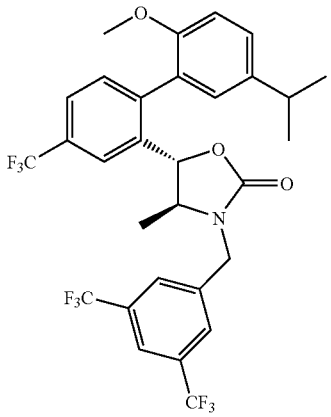 [SMILES: COc1ccc(C(C)C)cc1-c1ccc(C(F)(F)F)cc1[C@@H]1OC(=O)N(Cc2cc(C(F)(F)F)cc(C(F)(F)F)c2)[C@H]1C]

trans-3-[3,5-bis(trifluoromethyl)benzyl]-5-[5'-isopropyl-2'-methoxy-4-(trifluoromethyl)biphenyl-2-yl]-4-methyl-1,3-oxazolidin-2-one (racemic)

To a 0° C. solution of 30 mg of trans-5-[5'-isopropyl-2'-methoxy-4-(trifluoromethyl)biphenyl-2-yl]-4-methyl-1,3-oxazolidin-2-one in 1 mL of DMF was added 8 mg of sodium hydride. The mixture was stirred 10 min at room temperature, and then 32 mg of 3,5-bis(trifluoromethyl)benzyl bromide was added. The mixture was stirred overnight at room temperature, then diluted with 10 mL of EtOAc and 10 mL of water. The phases were separated and the aqueous phase was extracted with 5 mL of EtOAC. The combined organics were washed with 5 mL of brine, dried (Na$_2$SO$_4$), and concentrated. The residue was purified by flash chromatography on a Biotage Horizon, 25S column, eluting with 1 CV of 4% EtOAc in hexanes, followed by a linear gradient of EtOAc in hexanes from 4 to 100% over 10 CV to provide the title compound. Mass spectrum (ESI) 620.2 (M+1). $^1$H NMR signals are doubled because of atropoisomerism. $^1$H NMR (500 MHz, CDCl$_3$): δ 7.53-7.80 (m, 5H), 7.33 (d, J=8 Hz, 1H), 7.21-7.29 (m, 1H), 7.00, 6.76 (d, J=2.5 Hz, 1H), 6.91, 6.86 (d, J=8.5 Hz, 0.4H), 5.15, 5.10 (d, J=4.5 Hz, 1H), 4.80, 4.74 (d, J=16 Hz, 1H), 4.25, 4.21 (d, 16 Hz, 1H), 3.76 (s, 2H), 3.49 (s, 1H), 3.43 (m, 0.4H), 3.18 (m, 0.5H), 2.77-2.98 (m, 1H), 1.24 (m, 3H), 1.16 (m, 3H), 0.78, 0.61 (d, J=6.5 Hz, 3H).

Example 94

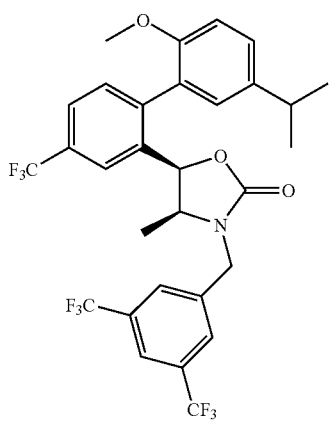 [SMILES: COc1ccc(C(C)C)cc1-c1ccc(C(F)(F)F)cc1[C@H]1OC(=O)N(Cc2cc(C(F)(F)F)cc(C(F)(F)F)c2)[C@H]1C]

cis-3-[3,5-bis(trifluoromethyl)benzyl]-5-[5'-isopropyl-2'-methoxy-4-(trifluoromethyl)biphenyl-2-yl]-4-methyl-1,3-oxazolidin-2-one (racemic)

Following the procedure described in EXAMPLE 93, 40 mg of cis-5-[5'-isopropyl-2'-methoxy-4-(trifluoromethyl)biphenyl-2-yl]-4-methyl-1,3-oxazolidin-2-one and 42 mg of 3,5-bis(trifluoromethyl)benzyl bromide gave the title compound. Mass spectrum (ESI) 620.2 (M+1). $^1$H NMR signals are doubled because of atropoisomerism. $^1$H NMR (500 MHz, CDCl$_3$): δ 7.82-7.94 (m, 2H), 7.62-7.74 (m, 3H), 7.39, 7.37 (d, J=8 Hz, 1H), 7.25, 7.17 (br d, J=8.5 Hz, 1H), 7.00, 6.78 (s, 1H), 6.87, 6.84 (d, J=8.5 Hz, 1H), 5.59, 5.56 (d, J=4.5 Hz, 1H), 4.96 (d, J=16 Hz, 1H), 4.22, 4.11 (d, J=16 Hz, 1H), 3.76 (s, 2H), 3.58 (s, 1H), 3.40 (m, 0.4H), 2.85-3.00 (m, 1H), 2.78 (m, 0.5H), 1.23 (d, J=7 Hz, 3H), 1.06 (m, 3H), 0.88, 0.69 (d, J=6.5 Hz, 3H).

Example 95

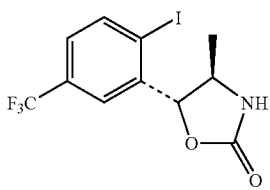

(4R,5R)-5-[2-iodo-5-(trifluoromethyl)phenyl]-4-methyl-1,3-oxazolidin-2-one

Step A: (4S)-4-benzyl-3-{(2R,3S)-3-hydroxy-3-[2-iodo-5-(trifluoromethyl)phenyl]-2-methylpropanoyl}-1,3-oxazolidin-2-one

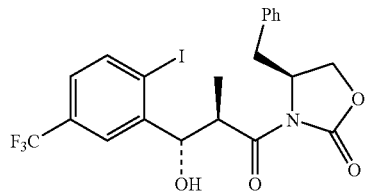 [SMILES: C[C@@H](C(=O)N1C(=O)OC[C@@H]1Cc1ccccc1)[C@H](O)c1cc(C(F)(F)F)ccc1I]

A mixture of 1.8 g of 5'-isopropyl-2'-methoxy-4-(trifluoromethyl)biphenyl-2-carbaldehyde (EXAMPLE 80, Step A), 1.16 g of (4S)-4-benzyl-3-propionyl-1,3-oxazolidin-2-one, 0.048 g of magnesium chloride, 1.40 mL of triethylamine, and 0.91 mL of chlorotrimethylsilane in 10 mL of EtOAc was stirred at r.t. for 24 h, then filtered through a 10×10 cm plug of silica gel, eluting with 400 mL of Et$_2$O. The filtrate was concentrated, and 10 mL of MeOH was added along with 2 drops of trifluoroacetic acid. This solution was stirred at r.t. for 30 min and concentrated to a pale yellow oil. The residue was purified by flash chromatography on a Biotage Horizon, 65 i column, eluting with 15 CV of 10% acetone in hexanes to provide the title compound. Mass spectrum (ESI) 516.2 (M–OH). $^1$H NMR (500 MHz, CDCl$_3$): δ 8.00 (d, J=8.5 Hz, 1H), 7.76 (d, J=2 Hz, 1H), 7.22-7.32 (m, 4H), 7.07 (br d, J=6.5 Hz, 2H), 5.18 (dd, J=6.5 Hz, 7.5 Hz, 1H), 4.67 (m, 1H), 4.46 (dq, J=6.5 Hz, 7.5 Hz, 1H), 4.17 (t, J=9 Hz, 1H), 4.11 (dd, J=3 Hz, 9 Hz, 1H), 3.97 (d, J=8 Hz, 1H), 3.19 (dd, J=7 Hz, 13.5 Hz, 1H), 2.57 (dd, J=9.5 Hz, 13.5 Hz, 1H), 1.34 (d, J=7.5 Hz, 3H).

Step B: (4R,5R)-5-[2-iodo-5-(trifluoromethyl)phenyl]-4-methyl-1,3-oxazolidin-2-one To a 0° C. solution of 0.65 g of (4S)-4-benzyl-3-{(2R,3S)-3-hydroxy-3-[2-iodo-5-(trifluoromethyl)phenyl]-2-methylpropanoyl}-1,3-oxazolidin-2-one in 6 mL of 3:1 tetrahydrofuran-water was added 0.102 g of lithium hydroxide in 1.5 mL of water, then 0.554 mL of a 30% aqueous solution of hydrogen peroxide. The solution was stirred 1 h at 0° C., at which point LC/MS analysis showed no starting material. A 1.5 M solution of sodium sulfite (3.7 mL) was added to the cold solution, which was then poured into a separatory funnel and extracted with 2×10 mL of CH$_2$Cl$_2$. The combined CH$_2$Cl$_2$ extracts were back-extracted with 20 mL of 3:1 water-saturated aqueous NaHCO$_3$. The combined aqueous layers were acidified (pH<1) with 6 N HCl and extracted with 4×10 mL of EtOAc. The combined EtOAc extracts were washed with 10 mL of brine, dried over Na$_2$SO$_4$, and concentrated. The residue was dissolved in 10 mL of toluene. Diphenylphosphoryl azide (0.315 mL) and 0.24 mL of triethylamine were added and the mixture was stirred overnight at 100° C., then cooled and concentrated. The residue was purified by flash chromatography on a Biotage Horizon, 40S column, eluting with 1 CV of 5% EtOAc in hexanes, followed by a linear gradient of EtOAc in hexanes from 5 to 100% over 10 CV to provide the title compound. Mass spectrum (ESI) 372.1 (M+1). $^1$H NMR (500 MHz, CDCl$_3$): δ 8.02 (d, J=8 Hz, 1H), 7.61 (d, J=1.5 Hz, 1H), 7.32 (dd, J=2 Hz, 8 Hz, 1H), 6.16 (s, 1H), 5.39 (d, J=4 Hz, 1H), 3.76 (dq, J=6 Hz, 4.5 Hz, 1H), 1.62 (d, J=6 Hz, 3H). Analytical HPLC on Chiralpak AD 4.6×250 mm, eluting with 4% ethanol in heptane at 0.75 mL/min (t$_R$=21.56 min for R,R; t$_R$=18.00 min for S,S) showed 98% e.e.

Example 96

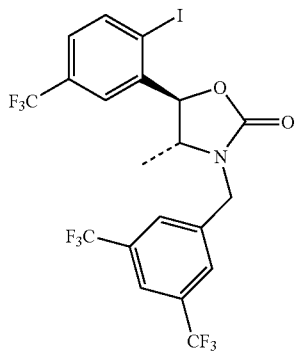 [SMILES: C[C@@H]1[C@@H](c2cc(C(F)(F)F)ccc2I)OC(=O)N1Cc1cc(C(F)(F)F)cc(C(F)(F)F)c1]

(4R,5R)-3-[3,5-bis(trifluoromethyl)benzyl]-5-[2-iodo-5-(trifluoromethyl)phenyl]-4-methyl-1,3-oxazolidin-2-one To a 0° C. solution of 95 mg of (4R,5R)-5-[2-iodo-5-(trifluoromethyl)phenyl]-4-methyl-1,3-oxazolidin-2-one in 1 mL of DMF was added 20 mg of sodium hydride. The mixture was stirred 10 min at 0° C.; then 94 mg of 3,5-bis(trifluoromethyl)benzyl bromide was added. The mixture was stirred 10 min at 0° C., then diluted with 10 mL of EtOAc and 10 mL of water. The phases were separated and the aqueous phase was extracted with 10 mL of EtOAc. The combined organic phases were washed with 10 mL of brine, dried over Na$_2$SO$_4$, and concentrated. The residue was purified by flash chromatography on a Biotage Horizon, 25M column, eluting with 1 CV of 2% EtOAc in hexanes, followed by a linear gradient of EtOAc in hexanes from 2 to 100% over 10 CV to provide the title compound. Mass spectrum (ESI) 598.1 (M+1). $^1$H NMR (500 MHz, CDCl$_3$): δ 8.00 (d, J=8.5 Hz, 1H), 7.77 (s, 1H), 7.58 (br s, 3H), 7.34 (dd, J=1.5 Hz, 8 Hz, 1H), 5.36 (d, J=4 Hz, 1H), 4.89 (d, J=16 Hz, 1H), 4.31 (d, J=16 Hz, 1H), 4.48 (dq, J=6 Hz, 4 Hz, 1H), 1.55 (d, J=6.5 Hz, 3H).

Example 97

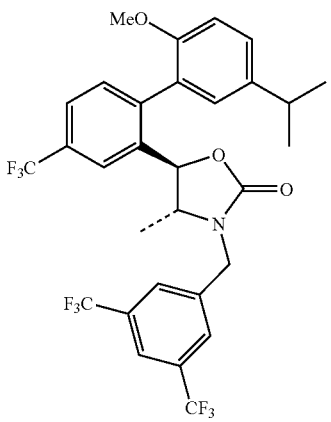 [SMILES: COc1ccc(C(C)C)cc1-c1ccc(C(F)(F)F)cc1[C@H]1OC(=O)N(Cc2cc(C(F)(F)F)cc(C(F)(F)F)c2)[C@@H]1C]

(4R,5R)-3-[3,5-bis(trifluoromethyl)benzyl]-5-[5'-isopropyl-2'-methoxy-4-(trifluoromethyl)biphenyl-2-yl]-4-methyl-1,3-oxazolidin-2-one Following the procedure described in EXAMPLE 81, 41 mg of (4R,5R)-3-[3,5-bis(trifluoromethyl)benzyl]-5-[2-iodo-5-(trifluoromethyl)phenyl]-4-methyl-1,3-oxazolidin-2-one and 17 mg of (5-isopropyl-2-methoxyphenyl)boronic acid gave title compound. Mass spectrum (ESI) 620.4 (M+1). $^1$H NMR signals are doubled because of atropoisomerism. $^1$H NMR (500 MHz, CDCl$_3$): δ 7.53-7.80 (m, 5H), 7.33 (d, J=8 Hz, 1H), 7.21-7.29 (m, 1H), 7.00, 6.76 (d, J=2.5 Hz, 1H), 6.91, 6.86 (d, J=8.5 Hz, 0.4H), 5.15, 5.10 (d, J=4.5 Hz, 1H), 4.80, 4.74 (d, J=16 Hz, 1H), 4.25, 4.21 (d, 16 Hz, 1H), 3.76 (s, 2H), 3.49 (s, 1H), 3.43 (m, 0.4H), 3.18 (m, 0.5H), 2.77-2.98 (m, 1H), 1.24 (m, 3H), 1.16 (m, 3H), 0.78, 0.61 (d, J=6.5 Hz, 3 Hz).

Example 98

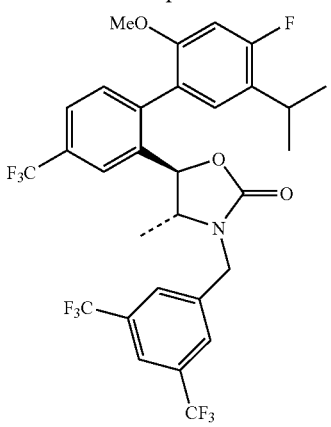

(4R,5R)-3-[3,5-bis(trifluoromethyl)benzyl]-5-[4'-fluoro-5'-isopropyl-2'-methoxy-4-(trifluoromethyl)biphenyl-2-yl]-4-methyl-1,3-oxazolidin-2-one Following the procedure described in EXAMPLE 81, 38.5 mg of (4R,5R)-3-[3,5-bis(trifluoromethyl)benzyl]-5-[2-iodo-5-(trifluoromethyl)phenyl]-4-methyl-1,3-oxazolidin-2-one and 18 mg of (4-fluoro-5-isopropyl-2-methoxyphenyl)boronic acid (EXAMPLE 78) gave the title compound. Mass spectrum (ESI) 638.3 (M+1). $^1$H NMR signals are doubled because of atropoisomerism. $^1$H NMR (500 MHz, CDCl$_3$): δ 7.55-7.80 (m, 5H), 7.29 (d, J=8 Hz, 1H), 7.00, 6.77 (d, J=8.5 Hz, 1H), 6.68, 6.63 (d, J~12 Hz, 1H), 5.08, 5.04 (d, J~5 Hz, 1H), 4.81, 4.75 (d, J=16 Hz, 1H), 4.26, 4.23 (d, 15.5 Hz, 1H), 3.75 (s, 2H), 3.50 (s, 1H), 3.43 (m, 0.5H), 3.12-3.24 (m, 1.5H), 1.24, 1.22 (d, J~5 Hz, 3H), 1.17, 1.06 (d, J=7 Hz, 3H), 0.84, 0.70 (d, J=6 Hz, 3H).

Example 99

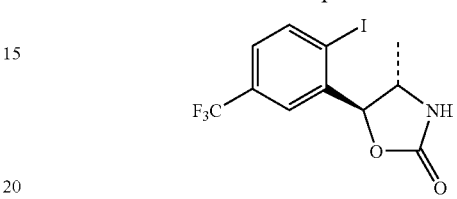

(4S,5S)-5-[2-iodo-5-(trifluoromethyl)phenyl]-4-methyl-1,3-oxazolidin-2-one

Step A: (4R)-4-benzyl-3-{(2S,3R)-3-hydroxy-3-[2-iodo-5-(trifluoromethyl)phenyl]-2-methylpropanoyl}-1,3-oxazolidin-2-one

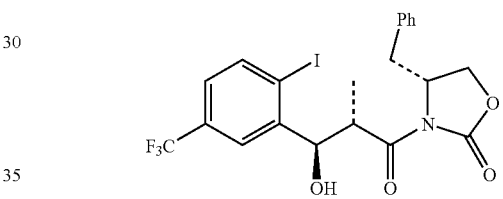

Following the procedure described in EXAMPLE 95, Step A, 0.72 g of 5'-isopropyl-2'-methoxy-4-(trifluoromethyl)biphenyl-2-carbaldehyde (EXAMPLE 80, Step A), 0.466 g of (4R)-4-benzyl-3-propionyl-1,3-oxazolidin-2-one, 0.02 g of magnesium chloride, 0.56 mL of triethylamine, and 0.38 mL of chlorotrimethylsilane provided the title compound. Mass spectrum (ESI) 516.2 (M−OH). $^1$H NMR (500 MHz, CDCl$_3$): δ 8.00 (d, J=8.5 Hz, 1H), 7.76 (d, J=2 Hz, 1H), 7.22-7.32 (m, 4H), 7.07 (br d, J=6.5 Hz, 2H), 5.18 (dd, J=6.5 Hz, 7.5 Hz, 1H), 4.67 (m, 1H), 4.46 (dq, J=6.5 Hz, 7.5 Hz, 1H), 4.17 (t, J=9 Hz, 1H), 4.11 (dd, J=3 Hz, 9 Hz, 1H), 3.97 (d, J=8 Hz, 1H), 3.19 (dd, J=7 Hz, 13.5 Hz, 1H), 2.57 (dd, J=9.5 Hz, 13.5 Hz, 1H), 1.34 (d, J=7.5 Hz, 3H).

Step B: (4S,5S)-5-[2-iodo-5-(trifluoromethyl)phenyl]-4-methyl-1,3-oxazolidin-2-one Following the procedure described in EXAMPLE 95, Step B, 0.214 g of (4R)-4-benzyl-3-{(2S,3R)-3-hydroxy-3-[2-iodo-5-(trifluoromethyl)phenyl]-2-methylpropanoyl}-1,3-oxazolidin-2-one, 0.034 g of lithium hydroxide, 0.16 mL of a 30% aqueous solution of hydrogen peroxide, 0.1 mL of diphenylphosphoryl azide, and 0.072 mL of triethylamine provide the title compound. Mass spectrum (ESI) 372.1 (M+1). $^1$H NMR (500 MHz, CDCl$_3$): δ 8.02 (d, J=8 Hz, 1H), 7.61 (d, J=1.5 Hz, 1H), 7.32 (dd, J=2 Hz, 8 Hz, 1H), 6.16 (s, 1H), 5.39 (d, J=4 Hz, 1H), 3.76 (dq, J=6 Hz, 4.5 Hz, 1H), 1.62 (d, J=6 Hz, 3H). Analytical HPLC on Chiralpak AD 4.6×250 mm, eluting with 4% ethanol in heptane at 0.75 mL/min ($t_R$=21.56 min for R,R; $t_R$=18.00 min for S,S) showed 99% e.e.

Example 100

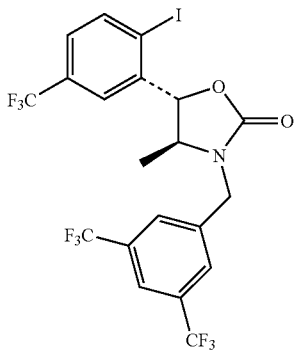

(4S,5S)-3-[3,5-bis(trifluoromethyl)benzyl]-5-[2-iodo-5-(trifluoromethyl)phenyl]-4-methyl-1,3-oxazolidin-2-one Following the procedure described in EXAMPLE 96, 0.108 g of (4S,5S)-5-[2-iodo-5-(trifluoromethyl)phenyl]-4-methyl-1,3-oxazolidin-2-one, 23 mg of sodium hydride, and 107 mg of 3,5-bis(trifluoromethyl)benzyl bromide provided the title compound. Mass spectrum (ESI) 598.1 (M+1). $^1$H NMR (500 MHz, CDCl$_3$): δ 8.00 (d, J=8.5 Hz, 1H), 7.77 (s, 1H), 7.58 (br s, 3H), 7.34 (dd, J=1.5 Hz, 8 Hz, 1H), 5.36 (d, J=4 Hz, 1H), 4.89 (d, J=16 Hz, 1H), 4.31 (d, J=16 Hz, 1H), 4.48 (dq, J=6 Hz, 4 Hz, 1H), 1.55 (d, J=6.5 Hz, 3H).

Example 101

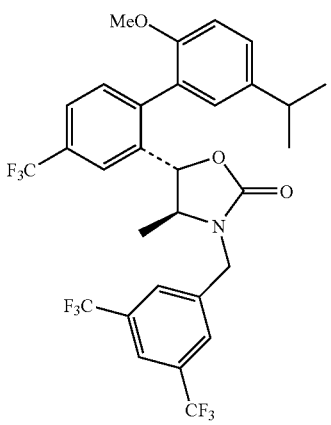

(4S,5S)-3-[3,5-bis(trifluoromethyl)benzyl]-5-[5'-isopropyl-2'-methoxy-4-(trifluoromethyl)biphenyl-2-yl]-4-methyl-1,3-oxazolidin-2-one Following the procedure described in EXAMPLE 81, 40 mg of (4S,5S)-3-[3,5-bis(trifluoromethyl)benzyl]-5-[2-iodo-5-(trifluoromethyl)phenyl]-4-methyl-1,3-oxazolidin-2-one and 17 mg of (5-isopropyl-2-methoxyphenyl)boronic acid gave the title compound. Mass spectrum (ESI) 620.4 (M+1). $^1$H NMR signals are doubled because of atropoisomerism. $^1$H NMR (500 MHz, CDCl$_3$): δ 7.53-7.80 (m, 5H), 7.33 (d, J=8 Hz, 1H), 7.21-7.29 (m, 1H), 7.00, 6.76 (d, J=2.5 Hz, 1H), 6.91, 6.86 (d, J=8.5 Hz, 0.4H), 5.15, 5.10 (d, J=4.5 Hz, 1H), 4.80, 4.74 (d, J=16 Hz, 1H), 4.25, 4.21 (d, 16 Hz, 1H), 3.76 (s, 2H), 3.49 (s, 1H), 3.43 (m, 0.4H), 3.18 (m, 0.5H), 2.77-2.98 (m, 1H), 1.24 (m, 3H), 1.16 (m, 3H), 0.78, 0.61 (d, J=6.5 Hz, 3 Hz).

Example 102

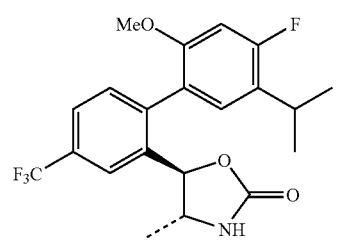 [SMILES: COc1cc(F)c(C(C)C)cc1-c1ccc(C(F)(F)F)cc1[C@H]1OC(=O)N[C@@H]1C]

(4R,5R)-5-[4'-fluoro-5'-isopropyl-2'-methoxy-4-(trifluoromethyl)biphenyl-2-yl]-4-methyl-1,3-oxazolidin-2-one Following the procedure described in EXAMPLE 81, 240 mg of (4R,5R)-5-[2-iodo-5-(trifluoromethyl)phenyl]-4-methyl-1,3-oxazolidin-2-one and 171 mg of (4-fluoro-5-isopropyl-2-methoxyphenyl)boronic acid (EXAMPLE 78) gave the title compound. Mass spectrum (ESI) 412.3 (M+1). $^1$H NMR signals are doubled because of atropoisomerism. $^1$H NMR (500 MHz, CDCl$_3$): δ 7.79, 7.77 (s, 1H), 7.64, 7.62 (dd, J~2.5 Hz, 8 Hz, 1H), 7.32, 7.31 (d, J~8 Hz, 1H), 7.00, 6.95 (d, J=8.5 Hz, 1H), 6.70, 6.67 (d, J=12 Hz, 1H), 6.47, 6.43 (s, 1H), 5.08, 5.04 (d, J=5 Hz, 0.1H), 3.68-3.80 (m, 3.5H), 3.53 (m, 0.5H), 3.21 (m, 1H), 1.19-1.30 (m, 6H), 0.95, 0.77 (d, J=6 Hz, 3H).

Following the procedures outlined in EXAMPLE 96 the compounds listed in Table 4 were prepared from (4R,5R)-5-[4'-fluoro-5'-isopropyl-2'-methoxy-4-(trifluoromethyl)biphenyl-2-yl]-4-methyl-1,3-oxazolidin-2-one:

TABLE 4

| EXAMPLE | R | LC/MS Data (M + 1) |
|---|---|---|
| 103 | ![2-fluorobenzyl] | 520.3 |

TABLE 4-continued

| EXAMPLE | R | LC/MS Data (M + 1) |
|---|---|---|
| 104 | 3-fluorobenzyl | 520.3 |
| 105 | 4-fluorobenzyl | 520.3 |
| 106 | 3,4-difluorobenzyl | 538.4 |
| 107 | 1-phenylethyl (diastereomer A) | 516.4 |
| 108 | 1-phenylethyl (diastereomer B) | 516.4 |
| 109 | pyridin-4-ylmethyl | 503.3 |
| 110 | (2,6-dichloropyridin-4-yl)methyl | 571.4 |

Example 111

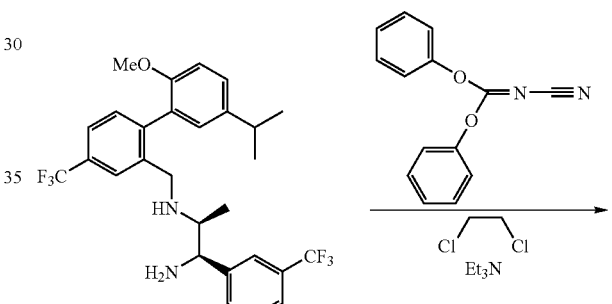

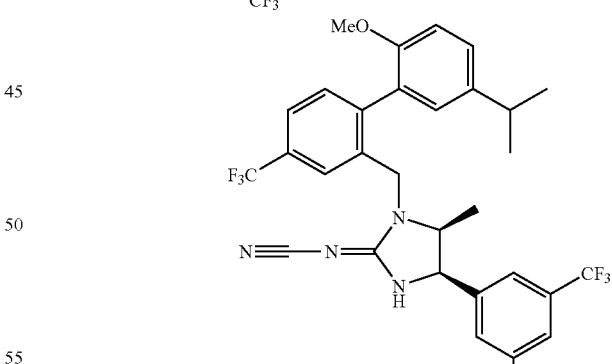

((4R,5S)-4-[3,5-bis(trifluoromethyl)phenyl]-1-{[5'-isopropyl-2'-methoxy-4-(trifluoromethyl)biphenyl-2-yl]methyl}-5-methylimidazolidin-2-ylidene)cyanamide To a solution of (1R,2S)-1-[3,5-bis(trifluoromethyl)phenyl]-N²-{[5'-isopropyl-2'-methoxy-4-(trifluoromethyl)biphenyl-2-yl]methyl}propane-1,2-diamine (25.1 mg, 0.0424 mmol) in dichloroethane (1.5 mL) was added triethylamine (15 µL, 0.105 mmol) and diphenyl cyanocarbonimidate (13 mg, 0.053 mmol). The reaction was heated at 60° C. overnight, cooled to room temperature, filtered, and loaded directly onto a silica gel column for purification by flash chromatography with 10 to 40% EtOAc/hexanes to afford ((4R,5S)-4-[3,5-bis(trifluoromethyl)phenyl]-1-{[5'-isopropyl-2'-methoxy-4-(trifluoromethyl)biphenyl-2-yl]methyl}-5-methylimidazolidin-2-ylidene)cyanamide. $R_f$=0.20 (25% EtOAc/hexanes). LCMS=643.3 (M+1)$^+$. $^1$H NMR ($C_6D_6$, 500 MHz; atropisomers present, doubling of some peaks) δ 6.53-8.83 (m, 10H), 3.61-4.91 (m, 3H), 3.28-2.70 (m, 5H), 1.14-1.25 (m, 6H), −0.39-0.26 (m, 3H).

Following the general procedures outlined above, the compounds in Table 5 were prepared:

TABLE 5

| Compound | A$^3$ | A$^2$ | Z | LCMS (M + 1) |
|---|---|---|---|---|
| 112 | 2-Cl, 5-Cl phenyl | 3,5-diF phenyl | CO | 515.1 |
| 113 | 2-OMe, 4-F, 5-iPr phenyl | 3,5-diF phenyl | CO | 537.3 |
| 114 | 2-Cl, 5-Cl phenyl | 3,5-di(CF$_3$) phenyl | CO | 615.3 |
| 115 | 2-OMe, 4-F, 5-iPr phenyl | 3,5-diCl phenyl | CO | 569.3 |
| 116 | 2-OMe, 4-F, 5-iPr phenyl | 3,5-di(CF$_3$) phenyl | CO | 637.3 |

TABLE 5-continued

| Compound | A³ | A² | Z | LCMS (M + 1) |
|---|---|---|---|---|
| 117 | methoxy, fluoro, isopropyl-substituted phenyl | 3,5-bis(trifluoromethyl)phenyl | SO₂ | 673.3 |

---

INTERMEDIATE 1

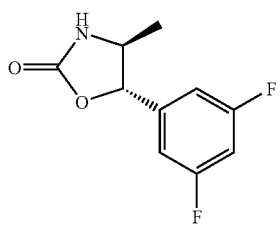

(4S,5R)-5-(3,5-difluorophenyl)-4-methyl-1,3-oxazolidin-2-one

Step A: benzyl [(1S)-2-(3,5-difluorophenyl)-1-methyl-2-oxoethyl]carbamate

To a –15° C. solution of benzyl {(1S)-2-[methoxy(methyl)amino]-1-methyl-2-oxoethyl}carbamate (1.96 g, 7.36 mmol) in THF (9.4 mL) was added i-propyl magnesium chloride (3.6 mL of a 2M solution in Et₂O, 7.2 mmol). The reaction was stirred at –15° C. for 15 minutes and then 3,5-difluorophenylmagnesium bromide (29.44 mL of a 0.5 M solution in THF, 14.72 mmol) was added. The reaction was warmed to room temperature and stirred for 24 hours. The reaction was then poured into saturated NH₄Cl (100 mL) and extracted with EtOAc (3×100 mL). The organic extracts were washed with water and brine (100 mL each), dried over Na₂SO₄, filtered, and concentrated. Purification of the residue by flash chromatography on silica gel (15% EtOAc/hexanes) afforded benzyl [(1S)-2-(3,5-difluorophenyl)-1-methyl-2-oxoethyl]carbamate. R$_f$=0.34 (15% EtOAc/hexanes). LCMS=342.3 (M+Na)⁺.

Step B: benzyl [(1S,2S)-2-(3,5-difluorophenyl)-2-hydroxy-1-methylethyl]carbamate To a –78° C. solution of benzyl [(1S)-2-(3,5-difluorophenyl)-1-methyl-2-oxoethyl]carbamate (1.35 g, 4.23 mmol) in THF (75 mL) was added L-Selectride (6.35 mL of a 1M solution in THF, 6.35 mmol). After stirring at –78° C. for 1 hour, the reaction was poured into 1N HCl (50 mL). The mixture was extracted with EtOAc (2×100 mL). The organic extracts were washed with water and brine (50 mL each), dried over Na₂SO₄, filtered, and concentrated. Purification of the residue by flash chromatography on silica gel (5 to 40% EtOAc/hexanes) afforded benzyl [(1S,2S)-2-(3,5-difluorophenyl)-2-hydroxy-1-methylethyl]carbamate (major product). LCMS=322.3 (M+1)⁺.

Step C: (4S,5R)-5-(3,5-difluorophenyl)-4-methyl-1,3-oxazolidin-2-one

To a solution of [(1S,2S)-2-(3,5-difluorophenyl)-2-hydroxy-1-methylethyl]carbamate (900 mg, 2.80 mmol) in THF (28.6 mL) was added MeOH (14.3 mL) and 7.5 N KOH (7.2 mL). The reaction was stirred at room temperature for 4 hours and then extracted with EtOAc (2×75 mL). The organic extracts were washed with water and brine (50 mL each), dried over Na₂SO₄, filtered, and concentrated. Purification of the residue by flash chromatography on silica gel (10 to 75% EtOAc/hexanes) afforded (4S,5S)-5-(3,5-difluorophenyl)-4-methyl-1,3-oxazolidin-2-one. R$_f$=0.07 (25% EtOAc/hexanes). LCMS=214.3 (M+1)⁺. ¹H NMR (CDCl₃, 500 MHz) δ 6.89-6.93 (m, 2H), 6.82 (m, 1H), 6.24 (bs, 1H), 5.01 (d, J=6.8 Hz, 1H), 3.79 (m, 1H), 1.42 (d, J=6.2 Hz, 3H).

INTERMEDIATE 2

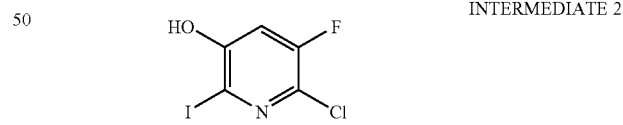

6-chloro-5-fluoro-2-iodopyridin-3-ol

To a solution of 6-chloro-5-fluoropyridin-3-ol (307.8 mg, 2.08 mmol) in water (11 mL) was added Na₂CO₃ (441 mg, 4.16 mmol) and I₂ (549 mg, 2.08 mmol). After 2 hours, the reaction mixture was acidified with 1 N HCl to pH 3, diluted with EtOAc (100 mL), and washed with aq. NaHSO₃ and brine (50 mL each). The organic layer was dried over Na₂SO₄, filtered and concentrated to afford 6-chloro-5-fluoro-2-iodopyridin-3-ol. LCMS=273.9 (M+1)⁺. ¹H NMR (CDCl₃, 500 MHz) δ 7.11 (d, J=8.5 Hz, 1H), 5.47 (d, J=1.4 Hz, 1H).

INTERMEDIATE 3

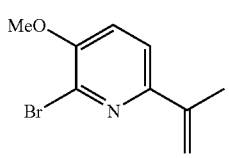

2-bromo-6-isopropenyl-3-methoxypyridine

In a tube were placed 2-bromo-6-iodo-3-methoxypyridine (700 mg, 2.236 mmol), isopropenylboronic acid (212 mg, 2.460 mmol), DME (7.5 mL), EtOH (2.8 mL), and 1M aq. $Na_2CO_3$ (5.6 mL). The mixture was degassed with $N_2$. Next, $Pd(PPh_3)_4$ (206 mg, 0.179 mmol) was added and the mixture was degassed again with $N_2$. The tube was sealed and heated at 80° C. for 16 hours. The reaction was then cooled to room temperature, diluted with EtOAc (100 mL), and washed with saturated $NaHCO_3$ and brine (50 mL each). The organic layer was dried over $Na_2SO_4$, filtered, and concentrated. Purification of the residue by flash chromatography on silica gel (0 to 15% EtOAc/hexanes) afforded 2-bromo-6-isopropenyl-3-methoxypyridine. $R_f$=0.38 (25% EtOAc/hexanes). LCMS=230.0 (M+1)$^+$. $^1$H NMR (CDCl$_3$, 500 MHz) δ 7.36 (d, J=8.5 Hz, 1H), 7.07 (d, J=9.4 Hz, 1H), 5.81 (s, 1H), 5.21 (s, 1H), 3.92 (s, 3H), 2.16 (s, 3H).

INTERMEDIATE 4

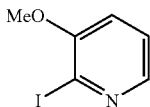

2-iodo-3-methoxypyridine

To a solution of 2-iodopyridin-3-ol (45.3 mg, 0.205 mmol) in DMF (3 mL) was added $Cs_2CO_3$ (334 mg, 1.030 mmol) and MeI (25 µL, 0.410 mmol). After 1 hour, the reaction was poured into water (10 mL), diluted with EtOAc (20 mL), washed with water (3×10 mL) and brine (10 mL). The organic layer was dried over $Na_2SO_4$, filtered, and concentrated to afford 2-iodo-3-methoxypyridine. LCMS=236.1 (M+1)$^+$. $^1$H NMR (CDCl$_3$, 500 MHz) δ 8.00 (dd, J=1.4, 4.6 Hz, 1H), 7.20 (dd, J=4.6, 8.0 Hz, 1H), 7.00 (dd, 1.4, 8.3 Hz, 1H), 3.90 (s, 3H).

INTERMEDIATE 5

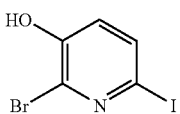

2-bromo-6-iodopyridin-3-ol

To a solution of 2-bromopyridin-3-ol (1.00 g, 5.80 mmol) in water (30 mL) was added $Na_2CO_3$ (1.23 g, 11.60 mmol) and $I_2$ (1.53 g, 5.80 mmol). After 1 hour, the reaction was quenched with 1 N HCl (20 mL), extracted with EtOAc (2×100 mL), and washed with aq. $NaHSO_3$ and brine (50 mL each). The organic layer was dried over $Na_2SO_4$, filtered and concentrated. Purification of the residue by flash chromatography on silica gel (20 to 40% EtOAc/hexanes) afforded 2-bromo-6-iodopyridin-3-ol. $R_f$=0.44 (25% EtOAc/hexanes). LCMS=301.9 (M+1)$^+$. $^1$H NMR (CDCl$_3$, 500 MHz) δ 7.56 (d, J=8.3 Hz, 1H), 6.99 (d, J=8.3 Hz, 1H), 5.65 (s, 1H).

INTERMEDIATE 6

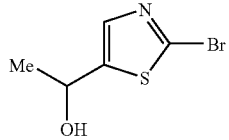

1-(2-bromo-1,3-thiazol-5-yl)ethanol

To a 0° C. solution of 2-bromo-5-formylthiazole (100.6 mg, 0.524 mmol) in THF (5 mL) was added MeMgBr (175 µL of a 3M solution in $Et_2O$, 0.524 mmol). After 30 minutes, additional MeMgBr (50 µL of a 3M solution in $Et_2O$, 0.150 mmol) was added. After 30 more minutes, the reaction was quenched by pouring into saturated $NH_4Cl$ (20 mL). The mixture was extracted with EtOAc (50 mL) and the organic layer was washed with water and brine (25 mL each). The organic layer was dried over $Na_2SO_4$, filtered, and concentrated. Purification of the residue by flash chromatography (0 to 80% EtOAc/hexanes) afforded 1-(2-bromo-1,3-thiazol-5-yl)ethanol. $R_f$=0.13 (25% EtOAc/hexanes). LCMS=210.0 (M+1)$^+$. $^1$H NMR (CDCl$_3$, 500 MHz) δ 7.40 (s, 1H), 5.12 (q, J=6.4 Hz, 1H), 1.59 (d, J=6.4 Hz, 3H).

INTERMEDIATE 7

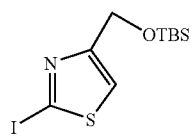

4-({[tert-butyl(dimethyl)silyl]oxy}methyl)-2-iodo-1,3-thiazole

Step A: 4-({[tert-butyl(dimethyl)silyl]oxy}methyl)-1,3-thiazole

To a solution of 1,3-thiazol-4-ylmethanol (311.4 mg, 2.7 mmol) in $CH_2Cl_2$ (15 mL) was added $Et_3N$ (1.9 mL, 13.6 mmol). The solution was cooled to −78° C. and TBSOTf (776 µL, 3.38 mmol) was added. The reaction was warmed to room temperature and stirred for 1 hour. Next, the reaction was diluted with EtOAc (75 mL) and washed with saturated $NaHCO_3$, brine, 1N HCl, and brine (20 mL each). The organic layer was dried over $Na_2SO_4$, filtered, and concentrated. The residue was purified by flash chromatography on silica gel (0 to 15% EtOAc/hexanes) to afford 4-({[tert-butyl (dimethyl)silyl]oxy}methyl)-1,3-thiazole. $R_f$=0.28 (15% EtOAc/hexanes). LCMS=230.1 (M+1)$^+$. $^1$H NMR (CDCl$_3$, 600 MHz) δ 8.77 (d, J=2.0 Hz, 1H), 7.25 (m, 1H), 4.93 (d, J=1.1 Hz, 2H), 0.95 (s, 9H), 0.12 (s, 6H).

Step B: 4-({[tert-butyl(dimethyl)silyl]oxy}methyl)-2-iodo-1,3-thiazole

To a −78° C. solution of 4-({[tert-butyl(dimethyl)silyl]oxy}methyl)-1,3-thiazole (106.4 mg, 0.465 mmol) in THF (5 mL) was added dropwise a solution of n-BuLi (465 µL of a 1.6M solution in hexanes, 0.744 mmol). The reaction was stirred at −78° C. for 30 minutes, and then a solution of iodine (295 mg, 1.16 mmol) in THF (5 mL) was added by cannula. The reaction was warmed to room temperature for 15 minutes and then quenched by pouring into aq. $NaHSO_3$ (20 mL). The mixture was extracted with EtOAc (60 mL) and the organic layer was washed with brine, saturated $NaHCO_3$, and brine (20 mL each). The organic layer was dried over $Na_2SO_4$, filtered, and concentrated. Purification of the residue by flash chromatography (15% EtOAc/hexanes) afforded 4-({[tert-butyl(dimethyl)silyl]oxy}methyl)-2-iodo-1,3-thiazole. $R_f$=0.55 (15% EtOAc/hexanes). LCMS=356.0 (M+1)$^+$. $^1$H NMR (CDCl$_3$, 600 MHz) δ 7.16 (s, 1H), 4.86 (s, 2H), 0.93 (s, 9H), 0.10 (s, 6H).

INTERMEDIATE 8

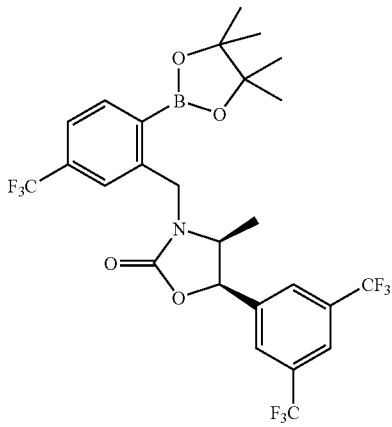

(4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one To a solution of (4S,5R)-5-[3,5-bis(trifluoromethyl)phenyl]-3-[2-iodo-5-(trifluoromethyl)benzyl]-4-methyl-1,3-oxazolidin-2-one (975 mg, 1.633 mmol) in DMSO (16 mL) were added bis(pinacolato)diboron (1.24 g, 4.899 mmol), [1,1'-Bis(diphenylphosphino)-ferrocene]dichloropalladium (II) complex with dichloromethane (1:1) (133 mg, 0.1633 mmol), and KOAc (320 mg, 3.266 mmol). The mixture was degassed with $N_2$, and then heated at 80° C. for 16 hours. The reaction was then cooled to room temperature, diluted with EtOAc (200 mL), and washed with saturated $NaHCO_3$ and brine (80 mL each). The organic layer was dried over $Na_2SO_4$, filtered through a plug of silica, and concentrated. Purification of the residue by reverse-phase chromatography (C-18, 10 to 95% MeCN/water with 0.1% TFAA) afforded (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one. LCMS=598.1 $(M+1)^+$. $^1H$ NMR ($CDCl_3$, 500 MHz) δ 7.98 (d, J=7.8 Hz, 1H), 7.88 (s, 1H), 7.78 (s, 2H), 7.67 (s, 1H), 7.57 (d, J=7.8 Hz, 1H), 5.68 (d, J=7.5 Hz, 1H), 5.01 (d, J=15.6 Hz, 1H), 4.76 (d, J=15.5 Hz, 1H), 3.98-3.93 (m, 1H), 1.35 (d, J=6.9 Hz, 12H), 0.77 (d, J=6.7 Hz, 3 H).

Example 118

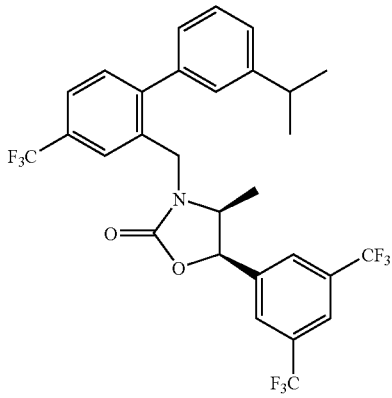 [SMILES: CC(C)c1cccc(-c2ccc(C(F)(F)F)cc2CN2C(=O)O[C@H](c3cc(C(F)(F)F)cc(C(F)(F)F)c3)[C@@H]2C)c1]

(4S,5R)-5-[3,5-bis(trifluoromethyl)phenyl]-3-{[3'-isopropyl-4-(trifluoromethyl)biphenyl-2-yl]methyl}-4-methyl-1,3-oxazolidin-2-one In a tube were placed (4S,5R)-5-[3,5-bis(trifluoromethyl)phenyl]-3-[2-iodo-5-(trifluoromethyl)benzyl]-4-methyl-1,3-oxazolidin-2-one (52.5 mg, 0.0879 mmol), 3-isopropylbenzeneboronic acid (17.3 mg, 0.106 mmol), DME (370 μL), EtOH (120 μL), and 1M aqueous $Na_2CO_3$ (264 μL, 0.264 mmol). The mixture was degassed with $N_2$. Next, $Pd(PPh_3)_4$ (10.2 mg, $8.8 \times 10^{-3}$ mmol) was added and the mixture was degassed again with $N_2$. The tube was sealed and heated at 100° C. for two hours. The reaction was then cooled to room temperature, diluted with EtOAc (50 mL), and washed with water and brine (15 mL each). The organic layer was dried over $Na_2SO_4$, filtered, and concentrated. Purification of the residue by flash chromatography on silica gel (0 to 15% EtOAc/hexanes) afforded (4S,5R)-5-[3,5-bis(trifluoromethyl)phenyl]-3-{[3'-isopropyl-4-(trifluoromethyl)biphenyl-2-yl]methyl}-4-methyl-1,3-oxazolidin-2-one. $R_f$=0.29 (15% EtOAc/hexanes). LCMS=590.1 $(M+1)^+$. $^1H$ NMR ($CDCl_3$, 500 MHz) δ 7.85 (s, 1H), 7.72 (s, 1H), 7.68 (s, 2H), 7.64 (d, J=8.0 Hz, 1H), 7.44 (d, J=8.0 Hz, 1H), 7.39 (t, J=7.6 Hz, 1H), 7.29 (d, J=7.8 Hz, 1H), 7.15 (bs, 1H), 7.11 (bd, J=7.5 Hz, 1H), 5.46 (d, J=8.0 Hz, 1H), 4.91 (d, J=15.7 Hz, 1H), 4.21 (d, J=15.8 Hz, 1H), 3.69 (m, 1H), 2.96 (m, 1H), 1.26-1.28 (m, 6H), 0.38 (d, J=6.4 Hz, 3H).

Example 119

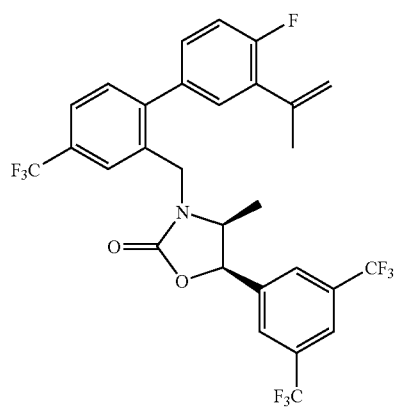 [SMILES: C=C(C)c1cc(-c2ccc(C(F)(F)F)cc2CN2C(=O)O[C@H](c3cc(C(F)(F)F)cc(C(F)(F)F)c3)[C@@H]2C)ccc1F]

(4S,5R)-5-[3,5-bis(trifluoromethyl)phenyl]-3-{[4'-fluoro-3'-isopropenyl-4-(trifluoromethyl)biphenyl-2-yl]methyl}-4-methyl-1,3-oxazolidin-2-one In a tube was placed (4S,5R)-5-[3,5-bis(trifluoromethyl)phenyl]-3-{[3'-chloro-4'-fluoro-4-(trifluoromethyl)biphenyl-2-yl]methyl}-4-methyl-1,3-oxazolidin-2-one (Example 146) (30.2 mg, 0.0504 mmol), isopropenylboronic acid (27 mg, 0.31 mmol), 1,1-bis(di-t-butylphosphino)ferrocene palladium chloride (5.5 mg, $8.4 \times 10^{-3}$ mmol), THF (350 μL) and 1 M aq. $K_2CO_3$ (350 mL). The tube was degassed with nitrogen, sealed, and heated at 100° C. for 5 hours. The reaction was then cooled to room temperature, diluted with EtOAc (50 mL) and washed with water and brine (15 mL each). The organic layer was dried over $Na_2SO_4$, filtered, and concentrated. Purification of the residue by flash chromatography on silica gel (0 to 15% EtOAc/hexanes) afforded (4S,5R)-5-[3,5-bis(trifluoromethyl)phenyl]-3-{[4'-fluoro-3'-isopropenyl-4-(trifluoromethyl)biphenyl-2-yl]methyl}-4-methyl-1,3-oxazolidin-2-one. $R_f$=0.29 (15% EtOAc/hexanes). LCMS=606.2 $(M+1)^+$. $^1H$ NMR ($CDCl_3$, 500 MHz) δ 7.86 (s, 1H), 7.70 (s, 3H), 7.64 (d, J=8.0 Hz, 1H), 7.42 (d, J=8.0 Hz, 1H), 7.23 (dd, J=7.8, 2.0 Hz, 1H), 7.12-7.17 (m, 2H), 5.54 (d, J=8.0 Hz, 1H), 5.28 (s, 1H), 5.26 (s, 1H), 4.90 (d, J=15.8 Hz, 1H), 4.18 (d, J=15.8 Hz, 1H), 3.78 (m, 1H), 2.16 (s, 3H), 0.47 (d, J=6.7 Hz, 3H).

Example 120

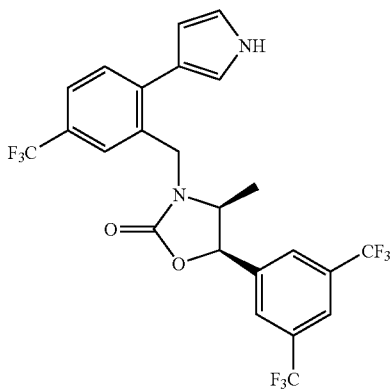 [SMILES: C[C@H]1[C@@H](c2cc(C(F)(F)F)cc(C(F)(F)F)c2)OC(=O)N1Cc1cc(C(F)(F)F)ccc1-c1cc[nH]c1]

(4S,5R)-5-[3,5-bis(trifluoromethyl)phenyl]-4-methyl-3-[2-(1H-pyrrol-3-yl)-5-(trifluoromethyl)benzyl]-1,3-oxazolidin-2-one To a 0° C. solution of (4S,5R)-5-[3,5-bis(trifluoromethyl)phenyl]-4-methyl-3-{5-(trifluoromethyl)-2-[1-(triisopropylsilyl)-1H-pyrrol-3-yl]benzyl}-1,3-oxazolidin-2-one (Example 149) (22.6 mg, 0.0326 mmol) in THF (2 mL) was added TBAF (65 µL of a 1M solution in THF, 0.065 mmol). After 30 minutes, the reaction was quenched with saturated NH$_4$Cl (5 mL). The mixture was extracted with EtOAc (35 mL) and the organic layer was washed with water and brine (15 mL each). The organic layer was dried over Na$_2$SO$_4$, filtered, and concentrated. Purification of the residue by flash chromatography on silica gel (25 to 60% EtOAc/hexanes) afforded (4S,5R)-5-[3,5-bis(trifluoromethyl)phenyl]-4-methyl-3-[2-(1H-pyrrol-3-yl)-5-(trifluoromethyl)benzyl]-1,3-oxazolidin-2-one. R$_f$=0.11 (25% EtOAc/hexanes). LCMS=537.1 (M+1)$^+$. $^1$H NMR (CDCl$_3$, 600 MHz) δ 8.49 (s, 1H), 7.85 (s, 1H), 7.71 (s, 2H), 7.64 (s, 1H), 7.58 (d, J=8.1 Hz, 1H), 7.51 (d, J=8.0 Hz, 1H), 6.88-6.91 (m, 2H), 6.33 (d, J=1.6 Hz, 1H), 5.53 (d, J=8.0 Hz, 1H), 5.02 (d, J=15.7 Hz, 1H), 4.46 (d, J=15.6 Hz, 1H), 3.80 (m, 1H), 0.49 (d, J=6.6 Hz, 3H).

Example 121

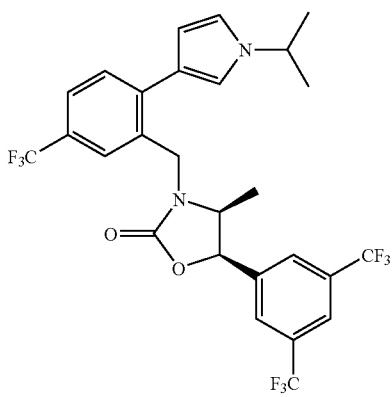 [SMILES: CC(C)n1ccc(-c2ccc(C(F)(F)F)cc2CN2C(=O)O[C@H](c3cc(C(F)(F)F)cc(C(F)(F)F)c3)[C@@H]2C)c1]

(4S,5R)-5-[3,5-bis(trifluoromethyl)phenyl]-3-[2-(1-isopropyl-1H-pyrrol-3-yl)-5-(trifluoromethyl)benzyl]-4-methyl-1,3-oxazolidin-2-one To a solution of (4S,5R)-5-[3,5-bis(trifluoromethyl)phenyl]-4-methyl-3-[2-(1H-pyrrol-3-yl)-5-(trifluoromethyl)benzyl]-1,3-oxazolidin-2-one (6.8 mg, 0.0127 mmol) (Example 120) in DMSO (300 µL) was added powdered KOH (3.6 mg, 0.0643 mmol). After stirring for 15 minutes, 2-iodopropane (3.2 µL, 0.032 mmol) was added. After 1.5 hours of stirring at room temperature, water (5 mL) was added, and the mixture was extracted, first with CH$_2$Cl$_2$ (2×15 mL) and then with EtOAc (2×15 mL). The combined organics were dried over Na$_2$SO$_4$, filtered, and concentrated. Purification of the residue by PTLC (25% EtOAc/hexanes) afforded (4S,5R)-5-[3,5-bis(trifluoromethyl)phenyl]-3-[2-(1-isopropyl-1H-pyrrol-3-yl)-5-(trifluoromethyl)benzyl]-4-methyl-1,3-oxazolidin-2-one. R$_f$=0.33 (25% EtOAc/hexanes). LCMS=579.2 (M+1)$^+$. $^1$H NMR (CDCl$_3$, 500 MHz) δ 7.85 (s, 1H), 7.71 (s, 2H), 7.61 (s, 1H), 7.56 (d, J=8.0 Hz, 1H), 7.50 (d, J=8.0 Hz, 1H), 6.83 (t, J=2.1 Hz, 1H), 6.79 (t, J=2.5 Hz, 1H), 6.24 (t, J=2.3 Hz, 1H), 5.49 (d, J=8.0 Hz, 1H), 5.04 (d, J=15.5 Hz, 1H), 4.48 (d, J=15.6 Hz, 1H), 4.27 (m, 1H), 3.76 (m, 1H), 1.48 (d, J=6.6 Hz, 6H), 0.49 (d, J=6.6 Hz, 3H).

Example 122

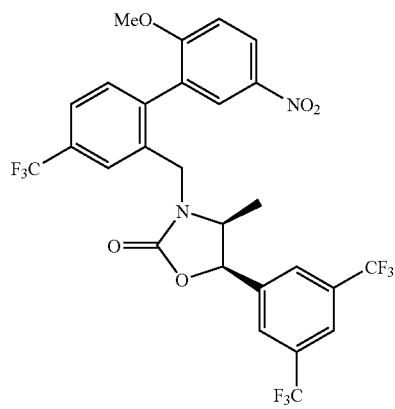 [SMILES: COc1ccc([N+](=O)[O-])cc1-c1ccc(C(F)(F)F)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-{[2'-methoxy-5'-nitro-4-(trifluoromethyl)biphenyl-2-yl]methyl}-4-methyl-1,3-oxazolidin-2-one To a solution of (4S,5R)-5-[3,5-bis(trifluoromethyl)phenyl]-3-{[2'-methoxy-4-(trifluoromethyl)biphenyl-2-yl]methyl}-4-methyl-1,3-oxazolidin-2-one (example 143) (159.4 mg, 0.276 mmol) in HOAc (5 mL) was added HNO$_3$ (1.5 mL). After 45 minutes, additional HNO$_3$ (1.5 mL) was added. 45 minutes later, the reaction was quenched by pouring into ice water (30 mL). The mixture was extracted with EtOAc (75 mL), and the organic layer was washed with 1 N NaOH, saturated NaHCO$_3$, and brine (25 mL each). The organic layer was dried over Na$_2$SO$_4$, filtered, and concentrated. Purification of the residue by flash chromatography on silica gel (8 to 40% EtOAc/hexanes) afforded (4S,5R)-5-[3,5-bis(trifluoromethyl)phenyl]-3-{[2'-methoxy-5'-nitro-4-(trifluoromethyl)biphenyl-2-yl]methyl}-4-methyl-1,3-oxazolidin-2-one. R$_f$=0.11 (25% EtOAc/hexanes). LCMS=623.1 (M+1)$^+$. $^1$H NMR (CDCl$_3$, 500 MHz, rotamers present) δ 8.34 (m, 1H), 8.10 (m, 1H), 7.85 (d, J=6.9 Hz, 1H), 7.61-7.71 (m, 4H), 7.40 (m, 1H), 7.11 (m, 1H), 5.66 (d, J=8.0 Hz), 5.28 (d, J=8.2 Hz), 4.89-4.94 (m, 1H), 3.74-4.09 (m, 5H), 0.61 (d, J=6.6 Hz), 0.47 (d, J=6.5 Hz).

Example 123

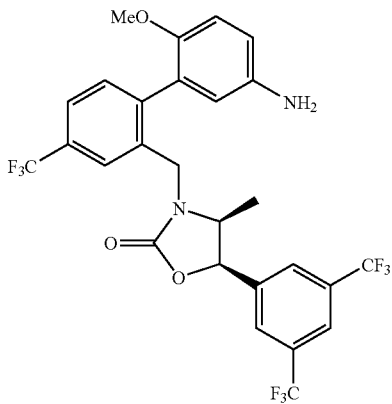 [SMILES: COc1ccc(N)cc1-c1ccc(C(F)(F)F)cc1CN1C(=O)O[C@H](c2cc(C(F)(F)F)cc(C(F)(F)F)c2)[C@@H]1C]

(4S,5R)-3-{[5'-amino-2'-methoxy-4-(trifluoromethyl)biphenyl-2-yl]methyl}-5-[3,5-bis(trifluoromethyl)phenyl]-4-methyl-1,3-oxazolidin-2-one To a solution of (4S,5R)-5-[3,5-bis(trifluoromethyl)phenyl]-3-{[2'-methoxy-5'-nitro-4-(trifluoromethyl)biphenyl-2-yl]methyl}-4-methyl-1,3-oxazolidin-2-one (example 122) (48.2 mg, 0.077 mmol) in EtOAc (4 mL) was added PtO$_2$ (12 mg) and the reaction was placed under an atmosphere of hydrogen (balloon) and stirred vigorously. After 45 minutes, the catalyst was removed by filtration through a plug of silica gel with 100% EtOAc. The filtrate was concentrated to afford (4S,5R)-3-{[5'-amino-2'-methoxy-4-(trifluoromethyl)biphenyl-2-yl]methyl}-5-[3,5-bis(trifluoromethyl)phenyl]-4-methyl-1,3-oxazolidin-2-one. R$_f$=0.20 (40% EtOAc/hexanes). LCMS=593.2 (M+1)$^+$. $^1$H NMR (CDCl$_3$, 500 MHz, rotamers present) δ 7.85 (s, 1H), 7.60-7.70 (m, 4H), 7.36 (d, J=7.8 Hz, 1H), 6.74-6.84 (m, 2H), 6.56 (s, 1H), 5.45-5.54 (m, 1H), 4.82-4.87 (m, 1H), 3.64-4.17 (m, 2H), 3.70 (s, 3H), 0.43-0.53 (m, 3H).

Example 124

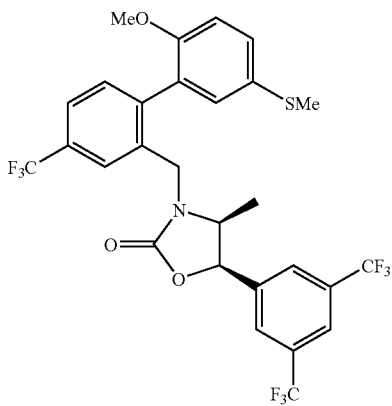 [SMILES: COc1ccc(SC)cc1-c1ccc(C(F)(F)F)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-{[2'-methoxy-5'-(methylthio)-4-(trifluoromethyl)biphenyl-2-yl]methyl}-4-methyl-1,3-oxazolidin-2-one To a solution of (4S,5R)-3-{[5'-amino-2'-methoxy-4-(trifluoromethyl)biphenyl-2-yl]methyl}-5-[3,5-bis(trifluoromethyl)phenyl]-4-methyl-1,3-oxazolidin-2-one (Example 123) (40 mg, 0.0676 mmol) in CHCl$_3$ (1 mL) that had been degassed with N$_2$ was added methyl disulfide (10 μL, 0.101 mmol) and t-butyl nitrite (16 μL, 0.135 mmol). The reaction was stirred at room temperature for 30 minutes and then heated to reflux for 2 hours. The reaction was then cooled to room temperature and diluted with hexanes (3 mL). The solution was loaded directly onto a silica gel column and eluted with 25% EtOAc/hexanes. Fractions containing the desired product were combined and repurified by silica gel chromatography with 5 to 25% EtOAc/hexanes to afford (4S,5R)-5-[3,5-bis(trifluoromethyl)phenyl]-3-{[2'-methoxy-5'-(methylthio)-4-(trifluoromethyl)biphenyl-2-yl]methyl}-4-methyl-1,3-oxazolidin-2-one. R$_f$=0.52 (40% EtOAc/hexanes). LCMS=624.1 (M+1)$^+$. $^1$H NMR (CDCl$_3$, 600 MHz, rotamers present) δ 6.94-7.85 (m, 9H), 5.58 (d, J=8.1 Hz) 5.25 (d, J=7.8 Hz), 4.94 (d, J=15.8 Hz), 4.85 (d, J=15.7 Hz), 3.65-4.12 (m, 5H), 2.47 (s), 2.44 (s), 0.54 (d, J=6.6 Hz), 0.40 (d, J=6.6 Hz).

Example 125

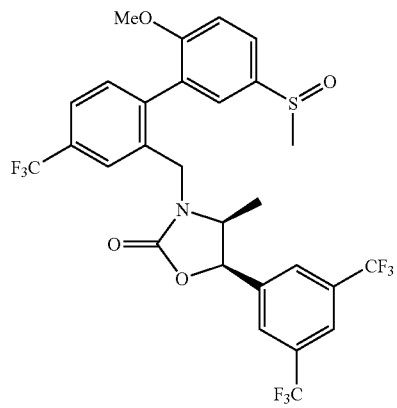

(4S,5R)-5-[3,5-bis(trifluoromethyl)phenyl]-3-{[2'-methoxy-5'-(methylsulfinyl)-4-(trifluoromethyl)biphenyl-2-yl]methyl}-4-methyl-1,3-oxazolidin-2-one To a −60° C. solution of (4S,5R)-5-[3,5-bis(trifluoromethyl)phenyl]-3-{[2'-methoxy-5'-(methylthio)-4-(trifluoromethyl)biphenyl-2-yl]methyl}-4-methyl-1,3-oxazolidin-2-one (example 124) (32.5 mg, 0.0522 mmol) in CH$_2$Cl$_2$ (5 mL) was added m-CPBA (14.6 mg, 77% purity, 0.0652 mmol). The reaction was warmed slowly to −20° C. and then diluted with EtOAc (35 mL), washed with aq. NaHSO$_3$, brine, saturated NaHCO$_3$, and brine (15 mL each). The organic layer was dried over Na$_2$SO$_4$, filtered, and concentrated. Purification of the residue by flash chromatography on silica gel (20 to 100% EtOAc/hexanes) afforded (4S,5R)-5-[3,5-bis(trifluoromethyl)phenyl]-3-{[2'-methoxy-5'-(methylsulfinyl)-4-(trifluoromethyl)biphenyl-2-yl]methyl}-4-methyl-1,3-oxazolidin-2-one. R$_f$=0.10 (75% EtOAc/hexanes). LCMS=640.1 (M+1)$^+$. $^1$H NMR (CDCl$_3$, 600 MHz) δ 7.10-7.86 (m, 9H), 4.87-5.59 (m, 2H), 3.56-4.14 (m, 5H), 2.79 (s), 2.75 (s), 2.73 (s), 0.61 (d, J=6.5 Hz), 0.57 (d, J=6.4 Hz), 0.46 (d, J=6.4 Hz), 0.43 (d, J=6.5 Hz).

Example 126

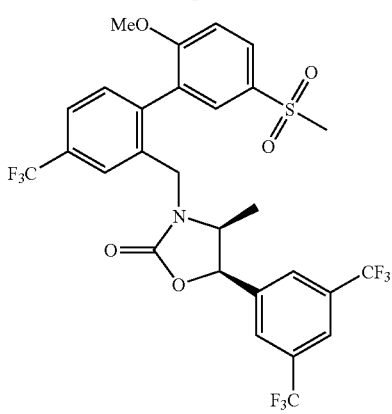 [SMILES: COc1ccc(S(C)(=O)=O)cc1-c1ccc(C(F)(F)F)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-{[2'-methoxy-5'-(methylsulfonyl)-4-(trifluoromethyl)biphenyl-2-yl]methyl}-4-methyl-1,3-oxazolidin-2-one To a 0° C. solution of (4S,5R)-5-[3,5-bis(trifluoromethyl)phenyl]-3-{[2'-methoxy-5'-(methylthio)-4-(trifluoromethyl)biphenyl-2-yl]methyl}-4-methyl-1,3-oxazolidin-2-one (example 124) (7.8 mg, 0.013 mmol) in CH$_2$Cl$_2$ (1 mL) was added m-CPBA (14 mg, 77% purity, 0.063 mmol). The reaction was stirred at room temperature for 30 minutes and then diluted with EtOAc (35 mL), washed with aq. NaHSO$_3$, brine, saturated NaHCO$_3$, and brine (15 mL each). The organic layer was dried over Na$_2$SO$_4$, filtered, and concentrated. Purification of the residue by PTLC (50% EtOAc/hexanes) afforded (4S,5R)-5-[3,5-bis(trifluoromethyl)phenyl]-3-{[2'-methoxy-5'-(methylsulfonyl)-4-(trifluoromethyl)biphenyl-2-yl]methyl}-4-methyl-1,3-oxazolidin-2-one. R$_f$=0.11 (40% EtOAc/hexanes). LCMS=656.2 (M+1)$^+$. $^1$H NMR (CDCl$_3$, 600 MHz, rotamers present) δ 7.99-8.02 (m, 1H), 7.84-7.86 (m, 1H), 7.75-7.78 (m, 1H), 7.58-7.72 (m, 4H), 7.38-7.42 (m, 1H), 7.15-7.18 (m, 1H), 5.55 (d, J=8.0 Hz), 5.26 (d, J=8.1 Hz), 4.91-4.97 (m, 1H), 3.63-4.03 (m, 5H), 3.12 (s), 3.10 (s), 0.62 (d, J=6.6 Hz), 0.48 (d, J=6.6 Hz).

Example 127

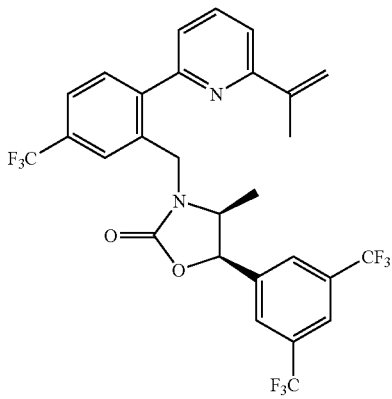 [SMILES: C=C(C)c1cccc(-c2ccc(C(F)(F)F)cc2CN2C(=O)O[C@H](c3cc(C(F)(F)F)cc(C(F)(F)F)c3)[C@@H]2C)n1]

(4S,5R)-5-[3,5-bis(trifluoromethyl)phenyl]-3-[2-(6-isopropenylpyridine-2-yl)-5-(trifluoromethyl)benzyl]-4-methyl-1,3-oxazolidin-2-one

Step A: 2-bromo-6-isopropenylpyridine

In a tube were placed 2,6-dibromopyridine (100 mg, 0.422 mmol), isopropenylboronic acid (40 mg, 0.464 mmol), DME (1.5 mL), EtOH (500 µL), and 1M aqueous Na$_2$CO$_3$ (1 mL, 1.0 mmol). The mixture was degassed with N$_2$. Next, Pd(PPh$_3$)$_4$ (37 mg, 0.032 mmol) was added and the mixture was degassed again with N$_2$. The tube was sealed and heated at 100° C. for 1 hour. The reaction was then cooled to room temperature, diluted with EtOAc (50 mL), and washed with water and brine (15 mL each). The organic layer was dried over Na$_2$SO$_4$, filtered, and concentrated. Purification of the residue by flash chromatography on silica gel (5% EtOAc/hexanes) afforded 2-bromo-6-isopropenylpyridine. R$_f$=0.45 (15% EtOAc/hexanes). LCMS=200.0 (M+1)$^+$. $^1$H NMR (CDCl$_3$, 500 MHz) δ 7.49 (t, J=7.8 Hz, 1H), 7.39 (d, J=7.8 Hz, 1H), 7.34 (d, J=8.0 Hz, 1H), 5.93 (s, 1H), 5.32 (m, 1H), 2.17 (s, 3H).

Step B: (4S,5R)-5-[3,5-bis(trifluoromethyl)phenyl]-3-[2-(6-isopropenylpyridine-2-yl)-5-(trifluoromethyl)benzyl]-4-methyl-1,3-oxazolidin-2-one In a tube were placed 2-bromo-6-isopropenylpyridine (17.5 mg, 0.0878 mmol), (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (26.2 mg, 0.0439 mmol), DME (190 µL), EtOH (62 µL), and 1M aqueous Na$_2$CO$_3$ (100 µL, 0.1 mmol). The mixture was degassed with N$_2$. Next, Pd(PPh$_3$)$_4$ (9 mg, 7.8×10$^{-3}$ mmol) was added and the mixture was degassed again with N$_2$. The tube was sealed and heated at 100° C. for 2 hours. The reaction was then cooled to room temperature, diluted with EtOAc (50 mL), and washed with water and brine (15 mL each). The organic layer was dried over Na$_2$SO$_4$, filtered, and concentrated. Purification of the residue by flash chromatography on silica gel (5 to 25% EtOAc/hexanes) afforded (4S,5R)-5-[3,5-bis(trifluoromethyl)phenyl]-3-[2-(6-isopropenylpyridine-2-yl)-5-(trifluoromethyl)benzyl]-4-methyl-1,3-oxazolidin-2-one. R$_f$=0.15 (15% EtOAc/hexanes). LCMS=589.1 (M+1)$^+$. $^1$H NMR (CDCl$_3$, 500 MHz) δ 7.81-7.85 (m, 2H), 7.74 (s, 1H), 7.69-7.69 (m, 3H), 7.58 (d, J=8.0 Hz, 1H), 7.53 (d, J=7.7 Hz, 1H), 7.34 (d, J=7.6 Hz, 1H), 5.94 (s, 1H), 5.48 (d, J=7.7 Hz, 1H), 5.36 (s, 1H), 5.06 (d, J=16.0 Hz, 1H), 4.47 (d, J=16.1 Hz, 1H), 3.91 (m, 1H), 2.23 (s, 3H), 0.50 (d, J=6.6 Hz, 3H).

Example 128

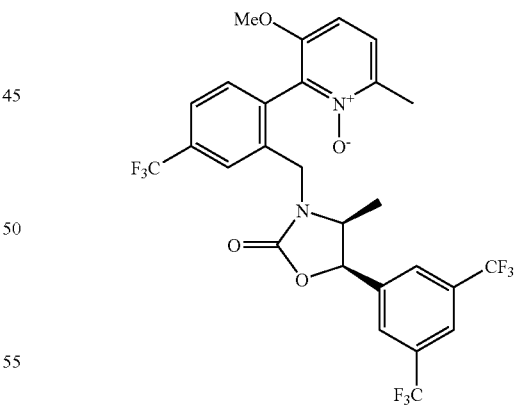

(4S,5R)-5-[3,5-bis(trifluoromethyl)phenyl]-3-[2-(3-methoxy-6-methyl-1-oxidopyridin-2-yl)-5-(trifluoromethyl)benzyl]-4-methyl-1,3-oxazolidin-2-one To a 0° C. solution of (4S,5R)-5-[3,5-bis(trifluoromethyl)phenyl]-3-[2-(3-methoxy-6-methylpyridin-2-yl)-5-(trifluoromethyl)benzyl]-4-methyl-1,3-oxazolidin-2-one (Example 174) (7.6 mg, 0.0128 mmol) in CH$_2$Cl$_2$ (1.3 mL) was added m-CPBA (5.8 mg, 77% purity, 0.0256 mmol). The reaction was stirred at room temperature for 1 hour and then diluted with CH$_2$Cl$_2$ (10 mL), washed with aq. NaHSO$_3$, saturated K$_2$CO$_3$, and brine (5 mL each). The organic layer was dried over Na$_2$SO$_4$, filtered, and concentrated. Purification of the residue by PTLC (50% Et$_2$O/CH$_2$Cl$_2$) afforded the title compound. R$_f$=0.23 (50% Et$_2$O/CH$_2$Cl$_2$). LCMS=609.2 (M+1)$^+$. $^1$H NMR (CDCl$_3$, 500 MHz) δ 7.85 (s, 1H), 7.78 (d, J=7.7 Hz, 1H), 7.70 (s, 2H), 7.62 (s, 1H), 7.53 (d, J=7.8 Hz, 1H), 7.32 (d, J=8.9 Hz, 1H), 7.04 (d, J=9.2 Hz, 1H), 5.74 (d, J=8.3 Hz, 1H), 4.88 (d, J=14.8 Hz, 1H), 4.11-3.96 (m, 1H), 3.88 (d, J=14.9 Hz, 1H), 3.86 (s, 3H), 2.49 (s, 3H), 0.65 (d, J=6.6 Hz, 3H).

Example 129

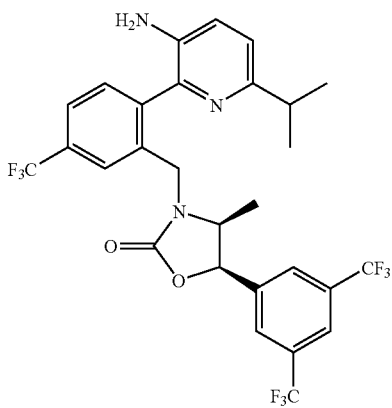 [SMILES: CC(C)c1ccc(N)c(-c2ccc(C(F)(F)F)cc2CN2C(=O)O[C@H](c3cc(C(F)(F)F)cc(C(F)(F)F)c3)[C@@H]2C)n1]

(4S,5R)-3-[2-(3-amino-6-isopropylpyridine-2-yl)-5-(trifluoromethyl)benzyl]-5-[3,5-bis(trifluoromethyl)phenyl]-4-methyl-1,3-oxazolidin-2-one To a solution of (4S,5R)-5-[3,5-bis(trifluoromethyl)phenyl]-3-[2-(6-isopropenyl-3-nitropyridin-2-yl)-5-(trifluoromethyl)benzyl]-4-methyl-1,3-oxazolidin-2-one (example 177) (19.3 mg, 0.0305 mmol) in EtOH (300 µL) was added 10% Pd/C (5 mg). The reaction was placed under a H$_2$ atmosphere (balloon) and stirred vigorously. After 90 minutes, the mixture was loaded on to a PTLC plate and purified (30% EtOAc/hexanes, developed twice), affording (4S,5R)-3-[2-(3-amino-6-isopropylpyridine-2-yl)-5-(trifluoromethyl)benzyl]-5-[3,5-bis(trifluoromethyl)phenyl]-4-methyl-1,3-oxazolidin-2-one. R$_f$=0.63 (30% EtOAc/hexanes, developed twice). LCMS=606.2 (M+1)$^+$. $^1$H NMR (CDCl$_3$, 500 MHz) δ 7.84 (s, 1H), 7.78 (s, 1H), 7.72 (d, J=8.0 Hz, 1H), 7.69 (s, 2H), 7.55 (d, J=8.0 Hz, 1H), 7.09-7.05 (m, 2H), 5.53-5.52 (m, 1H), 4.92 (d, J=5.5 Hz, 1H), 4.15-4.10 (m, 1H), 3.89-3.78 (m, 1H), 3.48 (s, 2H), 3.00-2.95 (m, 1H), 1.26-1.23 (m, 6H), 0.44 (d, J=5.1 Hz, 3H).

Example 130

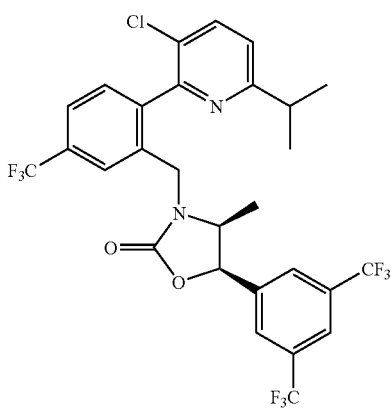 [SMILES: CC(C)c1ccc(Cl)c(-c2ccc(C(F)(F)F)cc2CN2C(=O)O[C@H](c3cc(C(F)(F)F)cc(C(F)(F)F)c3)[C@@H]2C)n1]

(4S,5R)-5-[3,5-bis(trifluoromethyl)phenyl]-3-[2-(3-chloro-6-isopropylpyridine-2-yl)-5-(trifluoromethyl)benzyl]-4-methyl-1,3-oxazolidin-2-one To a solution of CuCl$_2$ (9.3 mg) and t-butyl nitrite (6.6 µL, 0.0559 mmol) in MeCN (300 µL) was added (4S,5R)-3-[2-(3-amino-6-isopropylpyridine-2-yl)-5-(trifluoromethyl)benzyl]-5-[3,5-bis(trifluoromethyl)phenyl]-4-methyl-1,3-oxazolidin-2-one (Example 129) (16.9 mg, 0.0279 mmol) in MeCN (300 µL) via cannula. The reaction was heated at 60° C. for 1 hour and then cooled to room temperature, diluted with EtOAc (20 mL) and washed with water and brine (8 mL each). The organic layer was dried over Na$_2$SO$_4$, filtered, and concentrated. Purification of the residue by PTLC (30% EtOAc/hexanes) afforded (4S,5R)-5-[3,5-bis(trifluoromethyl)phenyl]-3-[2-(3-chloro-6-isopropylpyridine-2-yl)-5-(trifluoromethyl)benzyl]-4-methyl-1,3-oxazolidin-2-one. R$_f$=0.56 (30% EtOAc/hexanes). LCMS=625.1 (M+1)$^+$. $^1$H NMR (CDCl$_3$, 500 MHz) δ 7.85 (s, 1H), 7.78 (d, J=8.3 Hz, 1H), 7.73-7.71 (m, 2H), 7.68 (s, 2H), 7.53 (d, J=7.8 Hz, 1H), 7.24 (d, J=8.2 Hz, 1H), 5.55 (d, J=7.7 Hz, 1H), 5.05 (d, J=15.4 Hz, 1H), 3.97 (d, J=15.4 Hz, 1H), 3.88-3.82 (m, 1H), 3.17-3.08 (m, 1H), 1.30-1.32 (m, 6H), 0.53 (d, J=6.7 Hz, 3H).

Example 131

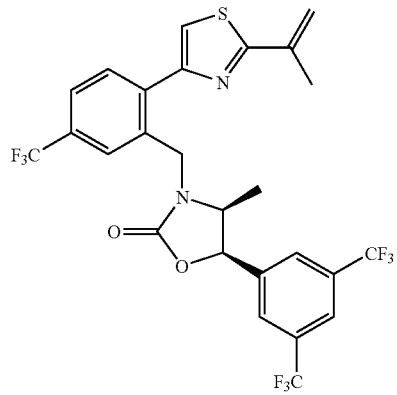 [SMILES: C=C(C)c1nc(-c2ccc(C(F)(F)F)cc2CN2C(=O)O[C@H](c3cc(C(F)(F)F)cc(C(F)(F)F)c3)[C@@H]2C)cs1]

(4S,5R)-5-[3,5-bis(trifluoromethyl)phenyl]-3-[2-(2-isopropenyl-1,3-thiazol-4-yl)-5-(trifluoromethyl)benzyl]-4-methyl-1,3-oxazolidin-2-one Step A: 4-bromo-2-isopropenyl-1,3-thiazole In a tube were placed 2,4-dibromothiazole (100 mg, 0.411 mmol), isopropenylboronic acid (39 mg, 0.452 mmol), DME (1.625 mL), EtOH (563 µL), and 1M aqueous Na$_2$CO$_3$ (1.03 mL, 1.03 mmol). The mixture was degassed with N$_2$. Next, Pd(PPh$_3$)$_4$ (24 mg, 0.0206 mmol) was added and the mixture was degassed again with N$_2$. The tube was sealed and heated at 100° C. for 2 hours. The reaction was then cooled to room temperature, diluted with EtOAc (50 mL), and washed with water and brine (15 mL each). The organic layer was dried over Na$_2$SO$_4$, filtered, and concentrated. Purification of the residue by flash chromatography on silica gel (0 to 15% EtOAc/hexanes) afforded 4-bromo-2-isopropenyl-1,3-thiazole; NMR showed an impurity present that was not removed. R$_f$=0.53 (15% EtOAc/hexanes). LCMS=206.0 (M+1)$^+$. $^1$H NMR (CDCl$_3$, 500 MHz) δ 7.13 (s, 1H), 5.87 (s, 1H), 5.33 (d, J=1.3 Hz, 1H), 2.21 (s, 3H).

Step B: (4S,5R)-5-[3,5-bis(trifluoromethyl)phenyl]-3-[2-(2-isopropenyl-1,3-thiazol-4-yl)-5-(trifluoromethyl)benzyl]-4-methyl-1,3-oxazolidin-2-one In a tube were placed 4-bromo-2-isopropenyl-1,3-thiazole (20 mg, 0.097 mmol), (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (29.4 mg, 0.0492 mmol), THF (340 µL), 1M aqueous K$_2$CO$_3$ (340 µL), and 1,1-bis(di-t-butylphosphino)ferrocene palladium chloride (3.2 mg, 4.9×10$^{-3}$ mmol). The mixture was degassed with N$_2$. The tube was sealed and heated at 100° C. for 1.5 hours. The reaction was then cooled to room temperature, diluted with EtOAc (50 mL), and washed with water and brine (15 mL each). The organic layer was dried over Na$_2$SO$_4$, filtered, and concentrated. Purification of the residue by flash chromatography on silica gel (5 to 25% EtOAc/ hexanes) and then by PTLC (90% CH₂Cl₂/hexanes) afforded (4S,5R)-5-[3,5-bis(trifluoromethyl)phenyl]-3-[2-(2-isopropenyl-1,3-thiazol-4-yl)-5-(trifluoromethyl)benzyl]-4-methyl-1,3-oxazolidin-2-one. $R_f$=0.16 (15% EtOAc/hexanes). LCMS=595.1 (M+1)⁺. ¹H NMR (CD₂Cl₂, 500 MHz) δ 7.90 (s, 1H), 7.64-7.76 (m, 5H), 7.38 (s, 1H), 5.89 (s, 1H), 5.60 (d, J=8.1 Hz, 1H), 5.37 (d, J=1.2 Hz, 1H), 4.99 (d, J=16.0 Hz, 1H), 4.66 (d, J=16.0 Hz, 1H), 3.94 (m, 1H), 2.25 (s, 3H), 0.59 (d, J=6.4 Hz, 3H).

Example 132

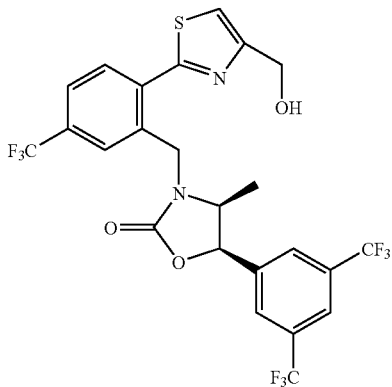 [SMILES: C[C@H]1[C@@H](c2cc(C(F)(F)F)cc(C(F)(F)F)c2)OC(=O)N1Cc1cc(C(F)(F)F)ccc1-c1nc(CO)cs1]

(4S,5R)-5-[3,5-bis(trifluoromethyl)phenyl]-3-[2-[4-(hydroxymethyl)-1,3-thiazol-2-yl]-5-(trifluoromethyl)benzyl]-4-methyl-1,3-oxazolidin-2-one To a 0° C. solution of (4S,5R)-5-[3,5-bis(trifluoromethyl)phenyl]-3-[2-[4-({[tert-butyl(dimethyl)silyl]oxy}methyl)-1,3-thiazol-2-yl]-5-(trifluoromethyl)benzyl]-4-methyl-1,3-oxazolidin-2-one (Example 178) (54.0 mg, 0.0774 mmol) in THF (10 mL) was added TBAF (194 μL of a 1M solution in THF, 0.194 mmol). The reaction was stirred at 0° C. for 30 minutes and then quenched by pouring into saturated NH₄Cl (15 mL). The mixture was extracted with EtOAc (60 mL) and the organic layer was washed with water and brine (15 mL each). The organic layer was dried over Na₂SO₄, filtered, and concentrated. Purification of the residue by flash chromatography on silica gel (60% EtOAc/hexanes) afforded (4S,5R)-[3,5-bis(trifluoromethyl)phenyl]-3-[2-[4-(hydroxymethyl)-1,3-thiazol-2-yl]-5-(trifluoromethyl)benzyl]-4-methyl-1,3-oxazolidin-2-one. $R_f$=0.11 (40% EtOAc/hexanes). LCMS=585.1 (M+1)⁺. ¹H NMR (CDCl₃, 500 MHz) δ 7.85 (s, 1H), 7.81 (d, J=8.0 Hz, 1H), 7.70-7.73 (m, 4H), 7.36 (s, 1H), 5.52 (d, J=8.0 Hz, 1H), 5.39 (d, J=15.3 Hz, 1H), 4.81 (s, 2H), 4.55 (d, J=15.3 Hz, 1H), 3.87 (m, 1H), 0.69 (d, J=6.7 Hz, 3H).

Example 133

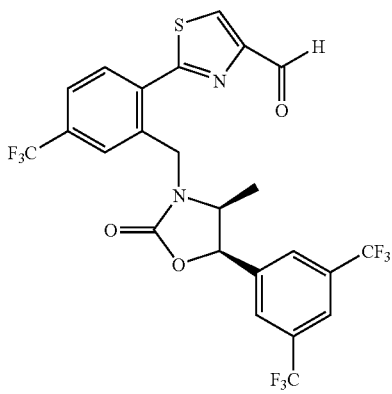 [SMILES: C[C@H]1[C@@H](c2cc(C(F)(F)F)cc(C(F)(F)F)c2)OC(=O)N1Cc1cc(C(F)(F)F)ccc1-c1nc(C=O)cs1]

2-[2-({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazole-4-carbaldehyde To a 0° C. solution of (4S,5R)-5-[3,5-bis(trifluoromethyl)phenyl]-3-[2-[4-(hydroxymethyl)-1,3-thiazol-2-yl]-5-(trifluoromethyl)benzyl]-4-methyl-1,3-oxazolidin-2-one (Example 132) (40.9 mg, 0.070 mmol) in CH₂Cl₂ (5 mL) was added DMP (59.4 mg, 0.140 mmol). The reaction was warmed to room temperature and stirred for 45 minutes. Next the reaction was diluted with EtOAc (40 mL) and washed with 1N NaOH (2×15 mL) and brine (2×15 mL). The organic layer was dried over Na₂SO₄, filtered, and concentrated. Purification of the residue by flash chromatography on silica gel (50% EtOAc/hexanes) afforded 2-[2-({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazole-4-carbaldehyde. $R_f$=0.24 (40% EtOAc/hexanes). LCMS=583.1 (M+1)⁺. ¹H NMR (CDCl₃, 500 MHz) δ 10.09 (s, 1H), 8.33 (s, 1H), 7.87 (s, 2H), 7.82 (d, J=8.2 Hz, 1H), 7.79 (s, 2H), 7.72, (d, J=8.1 Hz, 1H), 5.70 (d, J=8.0 Hz, 1H), 5.13 (d, J=16.0 Hz, 1H), 4.83 (d, J=16.0 Hz, 1H), 4.23 (m, 1H), 0.75 (d, J=6.6 Hz, 3H).

Example 134

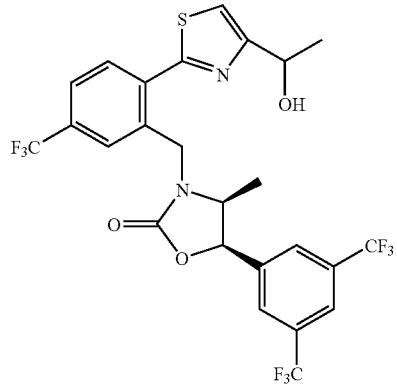 [SMILES: CC(O)c1csc(-c2ccc(C(F)(F)F)cc2CN2C(=O)O[C@H](c3cc(C(F)(F)F)cc(C(F)(F)F)c3)[C@@H]2C)n1]

(4S,5R)-5-[3,5-bis(trifluoromethyl)phenyl]-3-[2-[4-(1-hydroxyethyl)-1,3-thiazol-2-yl]-5-(trifluoromethyl)benzyl]-4-methyl-1,3-oxazolidin-2-one To a −40° C. solution of 2-[2-({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazole-4-carbaldehyde (Example 133) (43.9 mg, 0.075 mmol) in Et₂O (7.5 mL) was added MeMgBr (30 μL of a 3M solution in Et₂O, 0.10 mmol). The reaction was monitored closely by TLC and additional MeMgBr was added dropwise until nearly all starting aldehyde was consumed. At this point, the reaction was quenched by pouring it into saturated NH₄Cl (15 mL). The mixture was extracted with EtOAc (50 mL) and the organic layer was washed with water and brine (15 mL each). The organic layer was dried over Na₂SO₄, filtered, and concentrated. Purification of the residue by flash chromatography on silica gel (5 to 50% EtOAc/hexanes) afforded (4S,5R)-5-[3,5-bis(trifluoromethyl)phenyl]-3-[2-[4-(1-hydroxyethyl)-1,3-thiazol-2-yl]-5-(trifluoromethyl)benzyl]-4-methyl-1,3-oxazolidin-2-one. $R_f$=0.17 (40% EtOAc/hexanes). LCMS=599.1 (M+1)⁺. ¹H NMR (CDCl₃, 500 MHz) δ 7.70-7.86 (m, 6H), 7.31-7.32 (m, 1H), 5.53-5.55 (m, 1H), 5.35-5.41 (m, 1H), 5.06 (m, 1H), 4.57-4.62 (m, 1H), 3.88 (m, 1H), 1.61-1.63 (m, 3H), 0.69 (d, J=6.7 Hz, 3H).

Example 135

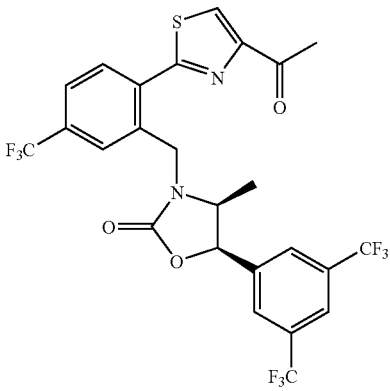 [SMILES: CC(=O)c1csc(-c2ccc(C(F)(F)F)cc2CN2C(=O)O[C@H](c3cc(C(F)(F)F)cc(C(F)(F)F)c3)[C@@H]2C)n1]

(4S,5R)-3-[2-(4-acetyl-1,3-thiazol-2-yl)-5-(trifluoromethyl)benzyl]-5-[3,5-bis(trifluoromethyl)phenyl]-4-methyl-1,3-oxazolidin-2-one To a 0° C. solution of (4S,5R)-5-[3,5-bis(trifluoromethyl)phenyl]-3-[2-[4-(1-hydroxyethyl)-1,3-thiazol-2-yl]-5-(trifluoromethyl)benzyl]-4-methyl-1,3-oxazolidin-2-one (Example 134) (31.0 mg, 0.052 mmol) in CH$_2$Cl$_2$ (6 mL) was added DMP (55 mg, 0.130 mmol). The reaction was warmed to room temperature and stirred for 45 minutes. Next, the reaction was diluted with EtOAc (40 mL) and washed with 1N NaOH (2×15 mL) and brine (2×15 mL). The organic layer was dried over Na$_2$SO$_4$, filtered, and concentrated. Purification of the residue by flash chromatography on silica gel (40% EtOAc/hexanes) afforded (4S,5R)-3-[2-(4-acetyl-1,3-thiazol-2-yl)-5-(trifluoromethyl)benzyl]-5-[3,5-bis(trifluoromethyl)phenyl]-4-methyl-1,3-oxazolidin-2-one. R$_f$=0.26 (40% EtOAc/hexanes). LCMS=597.1 (M+1)$^+$. $^1$H NMR (CDCl$_3$, 600 MHz) δ 8.27 (s, 1H), 7.89 (s, 1H), 7.77-7.82 (m, 4H), 7.71 (d, J=7.9 Hz, 1H), 5.68 (d, J=7.9 Hz, 1H), 5.22 (d, J=16.3 Hz, 1H), 4.85 (d, J=16.4 Hz, 1H), 4.08 (m, 1H), 2.70 (s, 3H), 0.71 (d, J=6.6 Hz, 3H).

Example 136

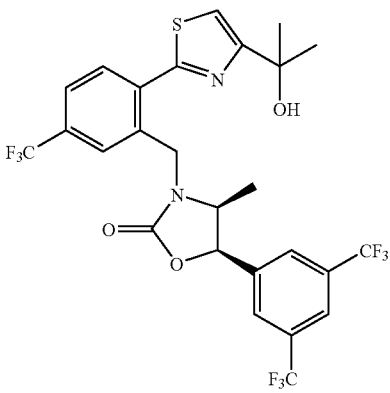 [SMILES: C[C@H]1[C@@H](c2cc(C(F)(F)F)cc(C(F)(F)F)c2)OC(=O)N1Cc1cc(C(F)(F)F)ccc1-c1nc(C(C)(C)O)cs1]

(4S,5R)-5-[3,5-bis(trifluoromethyl)phenyl]-3-[2-[4-(1-hydroxy-1-methylethyl)-1,3-thiazol-2-yl]-5-(trifluoromethyl)benzyl]-4-methyl-1,3-oxazolidin-2-one To a −40° C. solution of (4S,5R)-3-[2-(4-acetyl-1,3-thiazol-2-yl)-5-(trifluoromethyl)benzyl]-5-[3,5-bis(trifluoromethyl)phenyl]-4-methyl-1,3-oxazolidin-2-one (Example 135) (38.1 mg, 0.064 mmol) in THF/heptanes (1:1, 8 mL) was added MeMgBr (21 µL of a 3M solution in Et$_2$O, 0.07 mmol). The temperature was maintained between −40° C. and −20° C. and the reaction was monitored closely by TLC; additional MeMgBr was added dropwise until nearly all starting ketone was consumed. At this point, the reaction was quenched by pouring it into saturated NH$_4$Cl (15 mL). The mixture was extracted with EtOAc (50 mL) and the organic layer was washed with water and brine (15 mL each). The organic layer was dried over Na$_2$SO$_4$, filtered, and concentrated. Purification of the residue by flash chromatography on silica gel (10 to 60% EtOAc/hexanes) afforded (4S,5R)-5-[3,5-bis(trifluoromethyl)phenyl]-3-[2-[4-(1-hydroxy-1-methylethyl)-1,3-thiazol-2-yl]-5-(trifluoromethyl)benzyl]-4-methyl-1,3-oxazolidin-2-one. R$_f$=0.20 (40% EtOAc/hexanes). LCMS=613 (M+1)$^+$. $^1$H NMR (CD$_2$Cl$_2$, 500 MHz) δ 7.90 (s, 1H), 7.85 (d, J=8.0 Hz, 1H), 7.77 (s, 3H), 7.71 (d, J=8.3 Hz, 1H), 7.32 (s, 1H), 5.59 (d, J=8.0 Hz, 1H), 5.28 (d, J=15.8 Hz, 1H), 4.74 (d, J=15.8 Hz, 1H), 3.89 (m, 1H), 3.01 (bs, 1H), 1.63 (s, 3H), 1.62 (s, 3H), 0.64 (d, J=6.5 Hz, 3H).

Example 137

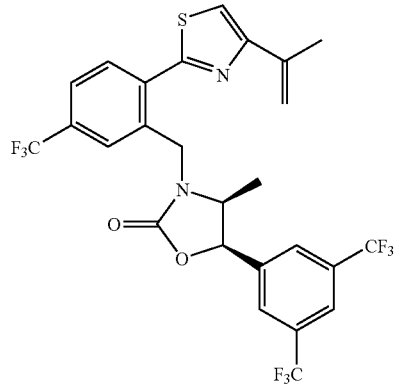 [SMILES: C=C(C)c1csc(-c2ccc(C(F)(F)F)cc2CN2C(=O)O[C@H](c3cc(C(F)(F)F)cc(C(F)(F)F)c3)[C@@H]2C)n1]

(4S,5R)-5-[3,5-bis(trifluoromethyl)phenyl]-3-[2-(4-isopropenyl-1,3-thiazol-2-yl)-5-(trifluoromethyl)benzyl]-4-methyl-1,3-oxazolidin-2-one To a solution of (4S,5R)-5-[3,5-bis(trifluoromethyl)phenyl]-3-[2-[4-(1-hydroxy-1-methylethyl)-1,3-thiazol-2-yl]-5-(trifluoromethyl)benzyl]-4-methyl-1,3-oxazolidin-2-one (example 136) (9.5 mg, 0.015 mmol) in toluene (4 mL) was added p-toluenesulfonic acid monohydrate (20 mg, 0.105 mmol). The reaction was heated to 80° C. for 30 minutes and then cooled to room temperature, diluted with EtOAc (35 mL), and washed with saturated NaHCO$_3$ and brine (15 mL each). The organic layer was dried over Na$_2$SO$_4$, filtered, and concentrated. Purification of the residue by flash chromatography on silica gel (25% EtOAc/hexanes) afforded (4S,5R)-5-[3,5-bis(trifluoromethyl)phenyl]-3-[2-(4-isopropenyl-1,3-thiazol-2-yl)-5-(trifluoromethyl)benzyl]-4-methyl-1,3-oxazolidin-2-one. R$_f$=0.55 (40% EtOAc/hexanes). LCMS=595.1 (M+1)$^+$. $^1$H NMR (CD$_2$Cl$_2$, 500 MHz) δ 7.91 (s, 1H), 7.78-7.83 (m, 4H), 7.68 (d, J=8.5 Hz, 1H), 7.33 (s, 1H), 5.95 (d, J=0.9 Hz, 1H), 5.66 (d, J=8.0 Hz, 1H), 5.24 (m, 1H), 5.07 (d, J=16.4 Hz, 1H), 5.00 (d, J=16.3 Hz, 1H), 4.03 (m, 1H), 2.17 (s, 3H), 0.63 (d, J=6.4 Hz, 3H).

Example 138

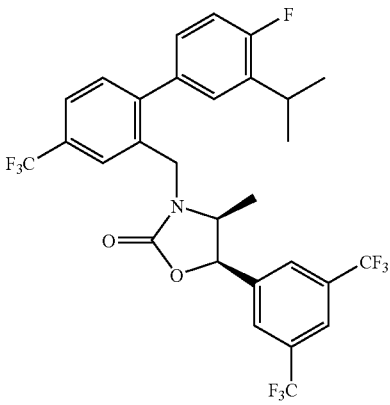 [SMILES: CC(C)c1cc(-c2ccc(C(F)(F)F)cc2CN2C(=O)O[C@H](c3cc(C(F)(F)F)cc(C(F)(F)F)c3)[C@@H]2C)ccc1F]

(4S,5R)-5-[3,5-bis(trifluoromethyl)phenyl]-3-{[4'-fluoro-3'-isopropyl-4-(trifluoromethyl)biphenyl-2-yl]methyl}-4-methyl-1,3-oxazolidin-2-one To a solution of (4S,5R)-5-[3,5-bis(trifluoromethyl)phenyl]-3-{[4'-fluoro-3'-isopropenyl-4-(trifluoromethyl)biphenyl-2-yl]methyl}-4-methyl-1,3-oxazolidin-2-one (Example 119) (18.8 mg, 0.031 mmol) in EtOH (4.5 mL) was added 10% Pd/C (15 mg). The reaction was placed under a H$_2$ atmosphere (balloon) and stirred vigorously. After 45 minutes, the catalyst was removed by filtration. The filtrate was concentrated, and the residue was purified by flash chromatography on silica gel with 15% EtOAc/hexanes. Further purification by PTLC with 75% CH$_2$Cl$_2$/hexanes afforded (4S,5R)-5-[3,5-bis(trifluoromethyl)phenyl]-3-{[4'-fluoro-3'-isopropyl-4-(trifluoromethyl)biphenyl-2-yl]methyl}-4-methyl-1,3-oxazolidin-2-one. R$_f$=0.35 (15% EtOAc/hexanes). LCMS=608.2 (M+1)$^+$. $^1$H NMR (CDCl$_3$, 500 MHz) δ 7.86 (s, 1H), 7.71 (s, 1H), 7.70 (s, 2H), 7.64 (d, J=8.0 Hz, 1H), 7.41 (d, J=8.0 Hz, 1H), 7.15 (m, 1H), 7.08-7.12 (m, 2H), 5.52 (d, J=8.0 Hz, 1H), 4.89 (d, J=15.7 Hz, 1H), 4.18 (d, J=15.8 Hz, 1H), 3.76 (m, 1H), 3.28 (m, 1H), 1.25-1.29 (m, 6H), 0.42 (d, J=6.4 Hz, 3H).

Example 139

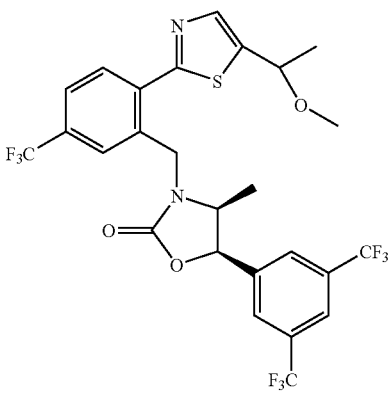 [SMILES: COC(C)c1cnc(-c2ccc(C(F)(F)F)cc2CN2C(=O)O[C@H](c3cc(C(F)(F)F)cc(C(F)(F)F)c3)[C@@H]2C)s1]

(4S,5R)-5-[3,5-bis(trifluoromethyl)phenyl]-3-[2-[5-(1-methoxyethyl)-1,3-thiazol-2-yl]-5-(trifluoromethyl)benzyl]-4-methyl-1,3-oxazolidin-2-one To a 0° C. solution of (4S,5R)-5-[3,5-bis(trifluoromethyl)phenyl]-3-[2-[5-(1-hydroxyethyl)-1,3-thiazol-2-yl]-5-(trifluoromethyl)benzyl]-4-methyl-1,3-oxazolidin-2-one (Example 154) (13.2 mg, 0.0221 mmol) in THF (1 mL) was added NaHMDS (26.5 μL of a 1M solution in THF, 0.0265 mmol) followed by MeI (1 drop). After 1.5 hours, additional NaHMDS (15 μL of a 1M solution in THF, 0.015 mmol) and MeI (1 drop) were added to the reaction. The reaction was warmed to room temperature for 20 minutes and then quenched by pouring into saturated NH$_4$Cl (10 mL). The mixture was extracted with EtOAc (35 mL) and the organic layer was washed with water and brine (15 mL each). The organic layer was dried over Na$_2$SO$_4$, filtered, and concentrated. Purification of the residue by flash chromatography on silica gel (15 to 75% EtOAc/hexanes) afforded (4S,5R)-5-[3,5-bis(trifluoromethyl)phenyl]-3-[2-[5-(1-methoxyethyl)-1,3-thiazol-2-yl]-5-(trifluoromethyl)benzyl]-4-methyl-1,3-oxazolidin-2-one. R$_f$=0.37 (40% EtOAc/hexanes). LCMS=613.0 (M+1)$^+$. $^1$H NMR (CDCl$_3$, 500 MHz) δ 7.87 (s, 1H), 7.74-7.82 (m, 5H), 7.67 (d, J=8.0 Hz, 1H), 6.63-5.66 (m, 1H), 5.08-5.14 (m, 1H), 4.83-4.88 (m, 1H), 4.64-4.68 (m, 1H), 4.01-4.08 (m, 1H), 3.34 (m, 3H), 1.60 (d, J=6.4 Hz, 3H), 0.69 (d, J=6.7 Hz, 3H).

Examples 140 and 141

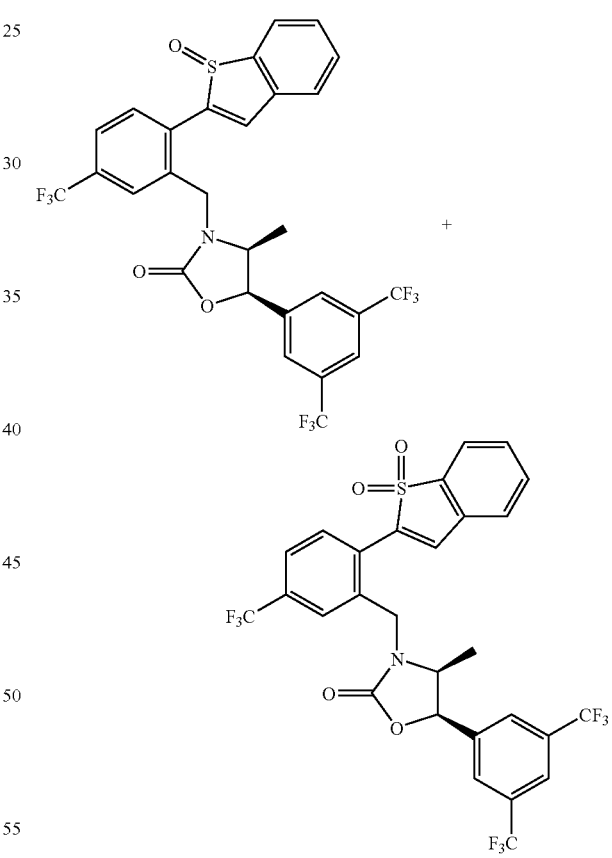

(4S,5R)-5-[3,5-bis(trifluoromethyl)phenyl]-4-methyl-3-[2-(1-oxido-1-benzothien-2-yl)-5-(trifluoromethyl)benzyl]-1,3-oxazolidin-2-one and (4S,5R)-5-[3,5-bis(trifluoromethyl)phenyl]-3-[2-(1,1-dioxido-1-benzothien-2-yl)-5-(trifluoromethyl)benzyl]-4-methyl-1,3-oxazolidin-2-one To a solution of (4S,5R)-3-[2-(1-benzothien-2-yl)-5-(trifluoromethyl)benzyl]-5-[3,5-bis(trifluoromethyl)phenyl]-4- methyl-1,3-oxazolidin-2-one (Example 150) (14.5 mg, 0.024 mmol) in CH$_2$Cl$_2$ (2 mL) was added m-CPBA (16 mg, 77% purity, 0.071 mmol). The reaction was stirred at room temperature for 3 hours, and then diluted with EtOAc (40 mL) and washed with aq. NaHSO$_3$ (15 mL), saturated NaHCO$_3$ (15 mL) and brine (15 mL). The organic layer was dried over Na$_2$SO$_4$, filtered, and concentrated. Purification of the residue by PTLC (25% EtOAc/hexanes, 2 elutions) afforded (4S,5R)-5-[3,5-bis(trifluoromethyl)phenyl]-3-[2-(1,1-dioxido-1-benzothien-2-yl)-5-(trifluoromethyl)benzyl]-4-methyl-1,3-oxazolidin-2-one and 2.2 mg (15%) of (4S,5R)-5-[3,5-bis(trifluoromethyl)phenyl]-4-methyl-3-[2-(1-oxido-1-benzothien-2-yl)-5-(trifluoromethyl)benzyl]-1,3-oxazolidin-2-one. Data for 141: R$_f$=0.09 (25% EtOAc/hexanes). LCMS=636.2 (M+1)$^+$. $^1$H NMR (CDCl$_3$, 500 MHz) δ 7.96 (d, J=8.0 Hz, 1H), 7.83 (s, 1H), 7.68-7.77 (m, 5H), 7.63 (m, 1H), 7.57 (m, 1H), 7.50 (d, J=7.6 Hz, 1H), 7.28 (s, 1H), 5.75 (d, J=8.0 Hz, 1H), 5.21 (d, J=15.8 Hz, 1H), 4.21 (d, J=15.8 Hz, 1H), 4.01 (m, 1H), 0.70 (d, J=6.7 Hz, 3H). Data for 140: R$_f$=0.06 (25% EtOAc/hexanes). LCMS=620.2 (M+1)$^+$. $^1$H NMR (CDCl$_3$, 500 MHz) δ 7.15-7.95 (m, 11H), 5.72-5.75 (m, 1H), 5.36 (d, J=15.6 Hz), 5.07 (d, J=15.8 Hz), 4.41 (d, J=16.0 Hz), 4.22 (d, J=15.8 Hz), 3.88-4.08 (m, 1H), 0.68 (d, J=6.6 Hz), 0.61 (d, J=6.6 Hz).

Example 142

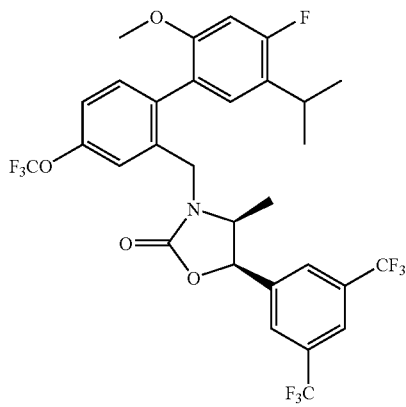 [SMILES: COc1cc(F)c(C(C)C)cc1-c1ccc(OC(F)(F)F)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-{[4'-fluoro-5'-isopropyl-2'-methoxy-4-(trifluoromethoxy)biphenyl-2-yl]-methyl}-4-methyl-1,3-oxazolidin-2-one Step A: 2-(bromomethyl)-1-nitro-4-(trifluoromethoxy)benzene Fuming nitric acid (5 mL) was cooled to 0° C. and 3-(trifluoromethyl)benzyl bromide (1 mL, 6.16 mmol) was added. After 15 minutes, the reaction was poured into ice water (100 mL) and extracted with EtOAc (200 mL). The organic layer was washed with water, saturated NaHCO$_3$, and brine (75 mL each). The organic layer was dried over Na$_2$SO$_4$, filtered, and concentrated. Purification of the residue by flash chromatography on silica gel (0 to 15% EtOAc/hexanes) afforded 2-(bromomethyl)-1-nitro-4-(trifluoromethoxy)benzene R$_f$=0.54 (15% EtOAc/hexanes). $^1$H NMR (CDCl$_3$, 500 MHz) δ 8.14 (d, J=8.9 Hz, 1H), 7.43 (m, 1H), 7.31 (m, 1H), 4.82 (s, 2H).

Step B: (4S,5R)-5-[3,5-bis(trifluoromethyl)phenyl]-4-methyl-3-[2-nitro-5-(trifluoromethoxy)benzyl]-1,3-oxazolidin-2-one To a solution of (4S,5R)-5-[3,5-bis(trifluoromethyl)phenyl]-4-methyl-1,3-oxazolidin-2-one (840 mg, 2.68 mmol) in DMA (25 mL) was added NaHMDS (2.68 mL of a 1M solution in THF, 2.68 mmol). The reaction was stirred at room temperature for 5 minutes, and then 2-(bromomethyl)-1-nitro-4-(trifluoromethoxy)benzene (967 mg, 3.22 mmol) was added by cannula in DMA (5 mL). After 15 minutes, the reaction was poured into saturated NH$_4$Cl (50 mL). The mixture was extracted with EtOAc (150 mL) and the organic layer was washed with water and brine (40 mL each). The organic layer was dried over Na$_2$SO$_4$, filtered, and concentrated. Purification of the residue by flash chromatography on silica gel (5 to 25% EtOAc/hexanes) afforded (4S,5R)-5-[3,5-bis(trifluoromethyl)phenyl]-4-methyl-3-[2-nitro-5-(trifluoromethoxy)benzyl]-1,3-oxazolidin-2-one. R$_f$=0.10 (15% EtOAc/hexanes). LCMS=533.2 (M+1)$^+$. $^1$H NMR (CDCl$_3$, 500 MHz) δ 8.16 (d, J=8.9 Hz, 1H), 7.92 (s, 1H), 7.80 (s, 2H), 7.44 (s, 1H), 7.33 (d, J=8.9 Hz, 1H), 5.78 (d, J=7.8 Hz, 1H), 4.94 (d, J=17.0 Hz, 1H), 4.79 (d, J=16.9 Hz, 1H), 4.25 (m, 1H), 0.81 (d, J=6.7 Hz, 3H).

Step C: (4S,5R)-3-[2-amino-5-(trifluoromethoxy)benzyl]-5-[3,5-bis(trifluoromethyl)phenyl]-4-methyl-1,3-oxazolidin-2-one To a solution of (4S,5R)-5-[3,5-bis(trifluoromethyl)phenyl]-4-methyl-3-[2-nitro-5-(trifluoromethoxy)benzyl]-1,3-oxazolidin-2-one (1.07 g, 2.01 mmol) in EtOAc (30 mL) was added PtO$_2$ (100 mg, 0.44 mmol). The reaction was placed under a H$_2$ atmosphere (balloon) and stirred vigorously. After 1 hour, the catalyst was removed by filtration, and the filtrate was concentrated. Purification of the residue by flash chromatography (5 to 40% EtOAc/hexanes) afforded (4S,5R)-3-[2-amino-5-(trifluoromethoxy)benzyl]-5-[3,5-bis(trifluoromethyl)phenyl]-4-methyl-1,3-oxazolidin-2-one. R$_f$=0.45 (40% EtOAc/hexanes). LCMS=503.2 (M+1)$^+$. $^1$H NMR (CDCl$_3$, 600 MHz) δ 7.89 (s, 1H), 7.75 (s, 2H), 7.03 (dd, J=8.7, 2.0 Hz, 1H), 6.90 (d, J=2.1 Hz, 1H), 6.67 (d, J=8.7 Hz, 1H), 5.67 (d, J=8.5 Hz, 1H), 4.73 (d, J=15.4 Hz, 1H), 4.35 (bs, 2H), 4.09 (d, J=15.4 Hz, 1H), 4.04 (m, 1H), 0.78 (d, J=6.6 Hz, 3H).

Step D: (4S,5R)-5-[3,5-bis(trifluoromethyl)phenyl]-3-[2-iodo-5-(trifluoromethoxy)benzyl]-4-methyl-1,3-oxazolidin-2-one To a solution of (4S,5R)-3-[2-amino-5-(trifluoromethoxy)benzyl]-5-[3,5-bis(trifluoromethyl)phenyl]-4-methyl-1,3-oxazolidin-2-one (582 mg, 1.16 mmol) in CHCl$_3$ (35 mL) was added t-butyl nitrite (275 µL, 2.32 mmol). After 10 minutes, I$_2$ (736 mg, 2.9 mmol) was added. The reaction was stirred at room temperature for 30 minutes, and then heated to 65° C. for 2 hours. The reaction was then cooled to room temperature, diluted with EtOAc (150 mL) and washed with aqueous NaHSO$_3$, water, brine, saturated NaHCO$_3$, and brine (50 mL each). The organic layer was dried over Na$_2$SO$_4$, filtered, and concentrated. Purification of the residue by flash chromatography on silica gel (2 to 15% EtOAc/hexanes) afforded (4S,5R)-5-[3,5-bis(trifluoromethyl)phenyl]-3-[2-iodo-5-(trifluoromethoxy)benzyl]-4-methyl-1,3-oxazolidin-2-one. R$_f$=0.30 (15% EtOAc/hexanes). LCMS=614.1 (M+1)$^+$. $^1$H NMR (CDCl$_3$, 500 MHz) δ 7.89-7.91 (m, 2H), 7.79 (s, 2H), 7.23 (m, 1H), 6.95 (m, 1H), 5.75 (d, J=8.0 Hz, 1H), 4.81 (d, J=15.8 Hz, 1H), 4.32 (d, J=15.8 Hz, 1H), 4.07 (m, 1H), 0.78 (d, J=6.6 Hz, 3H).

Step E: (4S,5R)-5-[3,5-bis(trifluoromethyl)phenyl]-3-{[4'-fluoro-5'-isopropyl-2'-methoxy-4-(trifluoromethoxy)biphenyl-2-yl]methyl}-4-methyl-1,3-oxazolidin-2-one In a microwave tube were placed (4S,5R)-5-[3,5-bis(trifluoromethyl)phenyl]-3-[2-iodo-5-(trifluoromethoxy)benzyl]-4-methyl-1,3-oxazolidin-2-one (41.6 mg, 0.0679 mmol), (4-fluoro-5-isopropyl-2-methoxyphenyl)boronic acid (18 mg, 0.085 mmol), DME (305 µL), EtOH (100 µL), and 1M aqueous $Na_2CO_3$ (140 µL, 0.140 mmol). The mixture was degassed with $N_2$. Next, $Pd(PPh_3)_4$ (4 mg, 3.4×10$^{-3}$ mmol) was added and the mixture was degassed again with $N_2$. The tube was sealed and irradiated in a microwave for 10 minutes at 150° C. and 200 W. The reaction was then cooled to room temperature, diluted with EtOAc (40 mL), and washed with water and brine (15 mL each). The organic layer was dried over $Na_2SO_4$, filtered, and concentrated. Purification of the residue by flash chromatography on silica gel (2 to 15% EtOAc/hexanes) afforded (4S,5R)-5-[3,5-bis(trifluoromethyl)phenyl]-3-{[4'-fluoro-5'-isopropyl-2'-methoxy-4-(trifluoromethoxy)biphenyl-2-yl]methyl}-4-methyl-1,3-oxazolidin-2-one. $R_f$=0.24 (15% EtOAc/hexanes). LCMS=654.3 (M+1)$^+$. $^1$H NMR (CDCl$_3$, 500 MHz, rotamers present) δ 7.85 (s, 1H), 7.69 (s, 2H), 7.21-7.30 (m, 4H), 6.95-7.00 (m, 1H), 6.65-6.68 (m, 1H), 5.59 (d, J=8.0 Hz), 5.41 (d, J=8.0 Hz), 4.74-4.81 (m, 1H), 3.75-4.09 (m, 5H), 3.19 (m, 1H), 1.16-1.27 (m, 6H), 0.51 (d, J=6.7 Hz), 0.36 (d, J=6.6 Hz).

Following the general procedures outlined above, the compounds in Table 6 were prepared:

TABLE 6

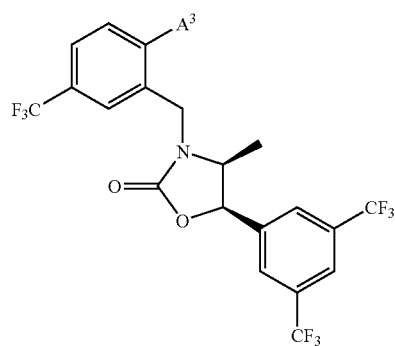

| Example | A³ | LCMS (M + 1)⁺ |
|---|---|---|
| 143 | 2-methoxyphenyl | 578.1 |
| 144 | 5-fluoro-2-methoxyphenyl | 596.1 |
| 145 | 4-fluorophenyl | 566.1 |
| 146 | 3-chloro-4-fluorophenyl | 600.1 |
| 147 | 2-chlorophenyl | 582.2 |
| 148 | 2-chloro-4-fluorophenyl | 600.1 |
| 149 | N-triisopropylsilyl-pyrrol-3-yl | 693.3 |
| 150 | benzothiophen-2-yl | 604.2 |
| 151 | benzothiophen-3-yl | 604.2 |
| 152 | 3-methoxy-5-fluoro-6-isopropenylpyridin-2-yl | 637.2 |

TABLE 6-continued

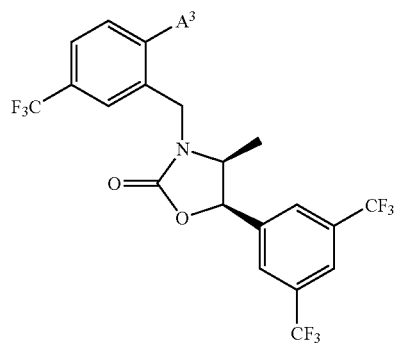

| Example | A³ | LCMS (M + 1)⁺ |
|---|---|---|
| 153 | (3-isobutyl-pyrrol-1-yl) | 593.2 |
| 154 | (2-(1-hydroxyethyl)thiazol-5-yl) | 599.1 |
| 155 | (6-trifluoromethylpyridin-2-yl) | 617.1 |
| 156 | (2-methoxy-5-chlorophenyl) | 612.2 |
| 157 | (pyridin-4-yl) | 549.3 |
| 158 | (pyridin-2-yl) | 549.2 |
| 159 | (pyrazin-2-yl) | 550.2 |
| 160 | (pyrimidin-2-yl) | 550.4 |

TABLE 6-continued

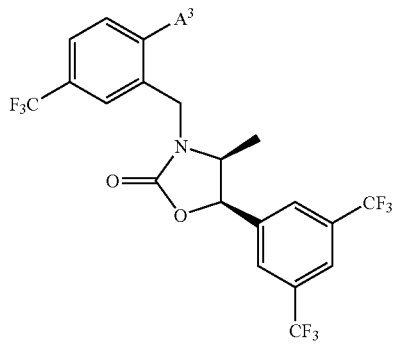

| Example | A³ | LCMS (M + 1)⁺ |
|---|---|---|
| 161 | (4-methylpyridin-2-yl) | 563.3 |
| 162 | (2-methylpyridin-4-yl) | 563.3 |
| 163 | (6-methylpyridin-2-yl) | 563.4 |
| 164 | (2-chloropyridin-4-yl) | 583.1 |
| 165 | (3-methylpyridin-2-yl) | 563.2 |
| 166 | (2-methoxypyrimidin-4-yl) | 579.2 |
| 167 | (5-methylpyridin-2-yl) | 563.2 |
| 168 | (5-fluoropyridin-2-yl) | 567.2 |

TABLE 6-continued

[Structure: benzyl group with F3C and A3 substituents attached to N of oxazolidinone; C5 position bears 3,5-bis(trifluoromethyl)phenyl group; C4 position bears methyl group]

| Example | A³ | LCMS (M + 1)⁺ |
|---|---|---|
| 169 | 5-chloro-pyridin-2-yl | 583.1 |
| 170 | 3,6-dichloro-pyridazin-4-yl | 618.1 |
| 171 | 2-chloro-pyridin-3-yl | 583.1 |
| 172 | 3,5-difluoro-pyridin-2-yl | 585.2 |
| 173 | 5-chloro-3-methyl-pyridin-2-yl | 597.2 |
| 174 | 3-methoxy-6-methyl-pyrazin-2-yl | 593.2 |
| 175 | 3-methoxy-6-(prop-1-en-2-yl)-pyridin-2-yl | 619.2 |
| 176 | 6-chloro-5-fluoro-3-methoxy-pyridin-2-yl | 631.1 |

TABLE 6-continued

[Structure: same as above]

| Example | A³ | LCMS (M + 1)⁺ |
|---|---|---|
| 177 | 3-nitro-6-(prop-1-en-2-yl)-pyridin-2-yl | 634.1 |
| 178 | 4-((tri-tert-butylsilyloxy)methyl)thiazol-2-yl | 699.2 |
| 179 | 4-acetyl-thiazol-2-yl | 597.1 |
| 180 | 4-(2-hydroxypropan-2-yl)-thiazol-2-yl | 613.1 |
| 181 | 4-(prop-1-en-2-yl)-thiazol-2-yl | 595.1 |
| 182 | 6-isopropyl-pyridin-2-yl | 591.2 |
| 183 | 4-isopropyl-thiazol-2-yl | 597.1 |
| 184 | 4-isopropyl-thiazol-2-yl | 597.1 |

TABLE 6-continued

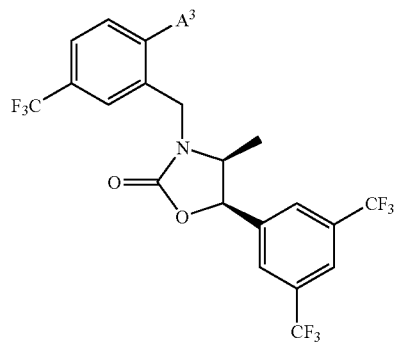

| Example | A³ | LCMS (M + 1)⁺ |
|---------|-----|---------------|
| 185 | (2-isopropyl-thiazol-4-yl) | 597.1 |
| 186 | (3-methoxy-6-isopropyl-pyridin-2-yl) | 621.2 |
| 187 | (3-methoxy-5-fluoro-6-isopropyl-pyridin-2-yl) | 639.2 |

TABLE 6-continued

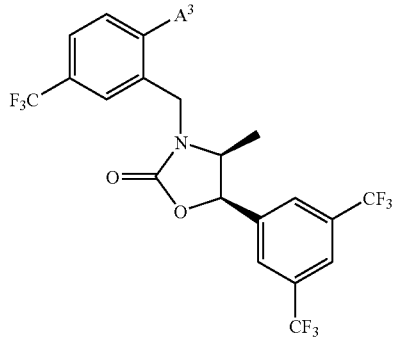

| Example | A³ | LCMS (M + 1)⁺ |
|---------|-----|---------------|
| 188 | (1-oxo-benzo[b]thiophen-3-yl) | 620.2 |
| 189 | (1,1-dioxo-benzo[b]thiophen-3-yl) | 636.2 |

Following the general procedures outlined above, the compounds in Table 7 were prepared:

TABLE 7

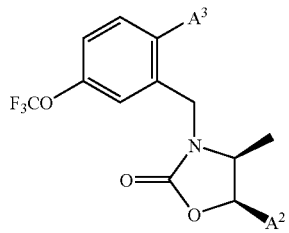

| Example | A³ | A² | LCMS (M + 1)⁺ |
|---------|-----|-----|---------------|
| 190 | (4-methoxy-2-fluoro-5-isopropyl-phenyl) | (3,5-dichlorophenyl) | 586.3 |
| 191 | (2,5-dichlorophenyl) | (3,5-dichlorophenyl) | 566.1 |

TABLE 7-continued

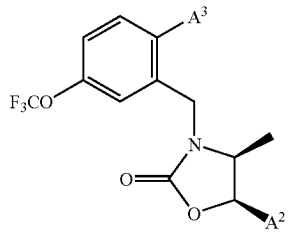

| Example | A³ | A² | LCMS (M + 1)⁺ |
|---|---|---|---|
| 192 | 2-Cl, 5-Cl phenyl | 3,5-diF phenyl | 554.3 |
| 193 | 2-OMe, 4-F, 5-iPr phenyl | 3,5-diF phenyl | 554.3 |
| 194 | 2-Cl, 5-Cl phenyl | 3,5-di(CF₃) phenyl | 632.2 |
| 195 | 2-Cl, 5-iPr phenyl | 3,5-di(CF₃) phenyl | 640.2 |

INTERMEDIATE 9

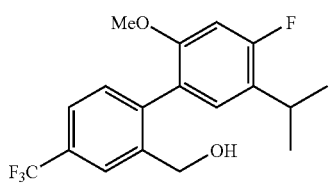

[4'-fluoro-5'-isopropyl-2'-methoxy-4-(trifluoromethyl)biphenyl-2-yl]methanol

A mixture of [2-iodo-5-(trifluoromethyl)phenyl]methanol (EXAMPLE 69) (3.09 g, 10.2 mmol), (4-fluoro-5-isopropyl-2-methoxyphenyl)boronic acid (4.34 g, 20.5 mmol), (Ph₃P)₄Pd (1.42 g, 1.23 mmol) and Na₂CO₃ (9.11 g, 85.9 mmol) in benzene/EtOH/H₂O (7:1:3, 250 mL) was heated at reflux for 24 h under N₂. After cooling to room temperature, the aqueous phase was separated and extracted with CH₂Cl₂ (3×50 mL). The combined organic layers were dried (Na₂SO₄) and concentrated in vacuo to give the crude product. This was purified by flash chromatography (Si, 65×200 mm, 0-20% EtOAc in hexanes gradient) to afford 4'-fluoro-5'-isopropyl-2'-methoxy-4-(trifluoromethyl)biphenyl-2-yl]methanol. $R_f$=0.50 (20% EtOAc in hexanes). $^1$H NMR (500 MHz, CDCl₃) δ 7.86 (s, 1H), 7.59 (d, J=6.7 Hz, 1H), 7.30 (d, J=7.9 Hz, 1H), 6.99 (d, J=8.6 Hz, 1H), 6.68 (d, J=12.0 Hz, 1H), 4.52 (br s, 1H), 4.46 (br s, 1H), 3.73 (s, 3H), 3.25-3.17 (m, 1H), 1.82 (br s, 1H), 1.24 (d, J=6.8 Hz, 6H).

INTERMEDIATE 10

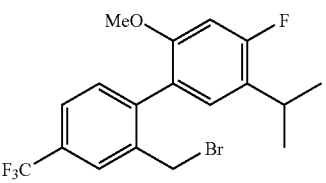

2'-(bromomethyl)-4-fluoro-5-isopropyl-2-methoxy-4'-(trifluoromethyl)biphenyl

A solution of triphenylphosphine (3.11 g, 11.8 mmol) in dry CH₂Cl₂ (7 mL) was added by cannula to a stirred solution of carbon tetrabromide (3.93 g, 11.8 mmol) and 4'-fluoro-5'-isopropyl-2'-methoxy-4-(trifluoromethyl)biphenyl-2-yl]methanol (3.38 g, 9.87 mmol) in dry CH$_2$Cl$_2$ (56 mL) at 0° C. under N$_2$. The reaction was allowed to warm to room temperature. After 2 h, the reaction mixture was concentrated in vacuo to give the crude product. This was purified by flash chromatography (Si, 65×200 mm, 0-20% EtOAc in hexanes gradient) to afford 2'-(bromomethyl)-4-fluoro-5-isopropyl-2-methoxy-4'-(trifluoromethyl)biphenyl. $^1$H NMR (500 MHz, CDCl$_3$) δ 7.83 (s, 1H), 7.61 (d, J=8.0 Hz, 1H), 7.35 (d, J=8.0 Hz, 1H), 7.15 (d, J=8.6 Hz, 1H), 6.72 (d, J=12.0 Hz, 1H), 4.43 (br d, J=10.0 Hz, 1H), 4.30 (br d, J=10.2 Hz, 1H), 3.76 (s, 3H), 3.30-3.22 (m, 1H), 1.29 (d, J=6.9 Hz, 6H).

INTERMEDIATE 11

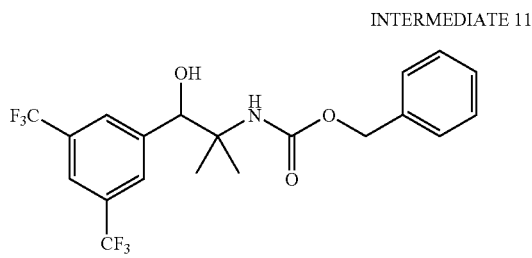 [SMILES: CC(C)(NC(=O)OCc1ccccc1)C(O)c1cc(C(F)(F)F)cc(C(F)(F)F)c1]

5-[3,5-bis(trifluoromethyl)phenyl]-3-{[4'-fluoro-5'-isopropyl-2'-methoxy-4-(trifluoromethyl)biphenyl-2-yl]methyl}-4,4-dimethyl-1,3-oxazolidin-2-one Step A: benzyl {2-[methoxy(methyl)amino]-1,1-dimethyl-2-oxoethyl}carbamate N-Methylmorpholine (682 mg, 741 µL, 6.74 mmol) and isobutylchloroformate (460 mg, 441 µL, 3.37 mmol) were added successively to a stirred solution of N-carbobenzyloxy-2-methylalanine (0.64 g, 2.69 mmol) in dry CH$_2$Cl$_2$ at 0° C. under N$_2$. The resulting cloudy mixture was stirred at 0° C. for 90 min. N,O-Dimethylhydroxylamine hydrochloride (316 mg, 3.24 mmol) was added portionwise and the mixture was warmed to room temperature and stirred for 3 h. The mixture was poured into 1N HCl (30 mL) and extracted with CH$_2$Cl$_2$ (3×40 mL). The combined extracts were washed with 1N HCl (30 mL), dried (Na$_2$SO$_4$) and concentrated in vacuo to give the crude product. This was purified by flash chromatography (Si, 40×160 mm, 0-80% EtOAc in hexanes gradient) to afford benzyl {2-[methoxy(methyl)amino]-1,1-dimethyl-2-oxoethyl}carbamate. R$_f$=0.47 (50% EtOAc in hexanes). LCMS calc.=303.1; found=303.2 (M±Na)$^+$. $^1$H NMR (500 MHz, CDCl$_3$) δ 7.37-7.29 (m, 5H), 5.82 (s, 1H), 5.09 (s, 2H), 3.60 (s, 3H), 3.18 (s, 3H), 1.60 (s, 6H).

Step B: benzyl (1,1-dimethyl-2-oxoethyl)carbamate

Diisobutylaluminum hydride (1.77 mL, 1M solution in toluene, 0.708 mmol) was added to a stirred solution of benzyl {2-[methoxy(methyl)amino]-1,1-dimethyl-2-oxoethyl}carbamate (198.5 mg, 0.708 mmol) in dry THF (7.1 mL) at −78° C. under N$_2$. The reaction was stirred at −78° C. for 4 h. MeOH (100 mL) and 1N HCl (250 µL) were added and the reaction was allowed to warm to room temperature. The mixture was diluted with Et$_2$O (50 mL) and washed with 1N HCl (2×50 mL), 50% saturated NaHCO$_3$ (50 mL) and water (50 mL), then dried (MgSO$_4$) and concentrated in vacuo to give benzyl (1,1-dimethyl-2-oxoethyl)carbamate. R$_f$=0.40 (20% EtOAc in hexanes). LCMS calc.=244.1; found=244.1 (M+Na)$^+$. $^1$H NMR (500 MHz, CDCl$_3$) δ 9.43 (s, 1H), 7.38-7.30 (m, 5H), 5.34 (s, 1H), 5.09 (s, 2H), 1.37 (s, 6H).

Step C: benzyl {2-[3,5-bis(trifluoromethyl)phenyl]-2-hydroxy-1,1-dimethylethyl}carbamate Ethylmagnesium bromide (1.63 mL, 1M in THF, 1.63 mmol) was added dropwise to a stirred solution of 1-iodo-3,5-bis(trifluoromethyl)benzene (608 mg, 317 µL, 1.79 mmol) in dry THF (1 mL) at room temperature under N$_2$ and the reaction was stirred for 30 min. The resulting solution was added to a stirred solution of benzyl (1,1-dimethyl-2-oxoethyl)carbamate (163.5 mg, 0.739 mmol) in dry THF (1 mL) at −20° C. and the reaction was allowed to warm to room temperature over 3 h. Saturated NH$_4$Cl (10 mL) and water (10 mL) were added and the mixture was extracted with EtOAc (3×20 mL). The combined extracts were dried (Na$_2$SO$_4$) and concentrated in vacuo to give the crude product. This was purified by flash chromatography (Si, 25×160 mm, 0-40% EtOAc in hexanes gradient) to afford benzyl {2-[3,5-bis(trifluoromethyl)phenyl]-2-hydroxy-1,1-dimethylethyl}carbamate. R$_f$=0.40 (20% EtOAc in hexanes). LCMS calc.=436.1; found=436.0 (M+1)$^+$. $^1$H NMR (600 MHz, CDCl$_3$) δ 7.80 (s, 1H), 7.77 (s, 2H), 7.39-7.33 (m, 5H), 5.12-5.08 (m, 2H), 1.36 (s, 1H), 4.90 (d, J=4.4 Hz, 1H), 4.81 (s, 1H), 1.36 (s, 3H), 1.23 (s, 3H).

INTERMEDIATE 12

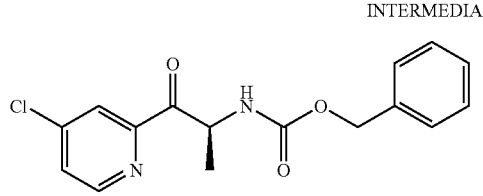

benzyl [(1S)-2-(4-chloropyridin-2-yl)-1-methyl-2-oxoethyl]carbamate

A solution of 2-(dimethylamino)ethanol (471 mg, 531 mL, 5.28 mmol) in dry hexanes (3.3 mL) was cooled to −5° C. and n-butyllithium (1.6 M in hexanes, 6.60 mL, 10.6 mmol) was added dropwise under N$_2$. After 30 min at 0° C., the solution was cooled to −78° C. and a solution of 4-chloropyridine (obtained by washing a solution of the corresponding HCl salt (264 mg, 1.76 mmol) in CH$_2$Cl$_2$ (20 mL) with saturated K$_2$CO$_3$ (10 mL), then back extracting with CH$_2$Cl$_2$ (2×20 mL), combining the organic layers, drying (Na$_2$SO$_4$) and concentrating in vacuo) in hexanes (3.3 mL) was added dropwise by cannula. The solution became dark red in color and after 1 h at −78° C., a solution of the electrophile (prepared by adding isopropylmagnesium chloride (2M in THF, 1.29 mL, 2.59 mmol) to a solution of benzyl {(1S)-2-[methoxy(methyl)amino]-1-methyl-2-oxoethyl}carbamate (702 mg, 2.64 mmol) in dry THF (3.5 mL) at −15° C. under N$_2$ and stirring for 15 min) was added by cannula. The reaction was allowed to warm slowly to room temperature overnight. Water (25 mL) and saturated NH$_4$Cl (50 mL) were added and the mixture was extracted with EtOAc (3×50 mL). The combined extracts were dried (MgSO$_4$) and concentrated in vacuo to give the crude product. This was purified by flash chromatography (Si, 40×160 mm, 0-30% EtOAc in hexanes gradient) to afford benzyl [(1S)-2-(4-chloropyridin-2-yl)-1-methyl-2-oxoethyl]carbamate. R$_f$=0.46 (20% EtOAc in hexanes).

LCMS calc.=319.1; found=319.3 (M+1)+. 1H NMR (500 MHz, CDCl3) δ 8.58 (d, J=5.0 Hz, 1H), 8.04 (s, 1H), 7.47 (dd, J=5.2, 2.0 Hz, 1H), 7.35-7.30 (m, 5H), 5.78 (s, 1H), 5.72 (m, 1H), 5.11 (m, 2H), 1.47 (d, J=7.0 Hz, 3H).

INTERMEDIATE 13

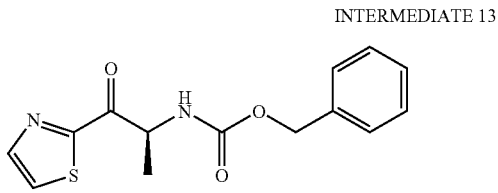 [SMILES: C[C@H](NC(=O)OCc1ccccc1)C(=O)c1nccs1]

benzyl [(1S)-1-methyl-2-oxo-2-(1,3-thiazol-2-yl)ethyl]carbamate n-Butyllithium (1.6M in hexanes, 1.76 mL, 2.83 mmol) was added dropwise to a stirred solution of 2-bromothiazole (462 mg, 251 μL, 2.82 mmol) in dry THF (13 mL) at −78° C. under N2 and the reaction was stirred at −78° C. for 45 min. Separately, isopropylmagnesium chloride (2M in THF, 0.94 mL, 1.99 mmol) was added to a stirred solution of benzyl {(1S)-2-[methoxy(methyl)amino]-1-methyl-2-oxoethyl}carbamate (500 mg, 1.88 mmol) in dry THF (4 mL) at −15° C. under N2. This solution was stirred for 15 min at −15° C. and was added dropwise to the above 2-lithiothiazole solution at −78° C. The reaction was allowed to warm to room temperature overnight and saturated NH4Cl (20 mL) and water (10 mL) were added and the mixture was extracted with EtOAc (3×30 mL). The combined extracts were washed with brine, dried (Na2SO4) and concentrated in vacuo to give the crude product. This was purified by flash chromatography (Si, 25×160 mm, 0-50% EtOAc in hexanes gradient) to afford benzyl [(1S)-1-methyl-2-oxo-2-(1,3-thiazol-2-yl)ethyl]carbamate. R$_f$=0.28 (20% EtOAc in hexanes). LCMS calc.=291.1; found=291.3 (M+1)+. 1H NMR (600 MHz, CDCl3) δ 8.03 (s, 1H), 7.70 (d, J=3.1 Hz, 1H), 7.34-7.29 (m, 5H), 5.79 (d, J=6.6 Hz, 1H), 5.53-5.49 (m, 1H), 5.14-5.08 (m, 2H), 1.55 (d, J=6.4 Hz, 3H).

INTERMEDIATE 14

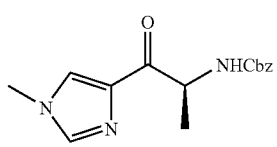

Benzyl [(1S)-1-methyl-2-(1-methyl-1H-imidazol-4-yl)-2-oxoethyl]carbamate

A solution of benzyl {(1S)-2-[methoxy(methyl)amino]-1-methyl-2-oxoethyl}carbamate (64 mg, 0.24 mmol) in CH2Cl2 (1 mL) was cooled to −20° C. under N2, and isopropylmagnesium chloride (120 μL of a 2.0 M solution in THF) was added dropwise. The mixture was stirred at −20° C. for 20 min. In a separate flask ethylmagnesium bromide (480 μL of a 2.0 M solution in Et2O) was added to a solution of 4-iodo-1-methyl-1-H-imidazole (109 mg, 0.48 mmol) in dry CH2Cl2 (1.5 mL) at room temperature. The resulting mixture was stirred for 20 min and then added by cannula to the solution above slowly. The resulting solution was left to stir overnight. Saturated NH4Cl was added to the reaction solution. The mixture was diluted with water and the aqueous phase was extracted with CH2Cl2 (2×25 mL). The combined organic extracts were dried (Na2SO4) and concentrated in vacuo. Flash chromatography of the residue yielded benzyl [(1S)-1-methyl-2-(1-methyl-1H-imidazol-4-yl)-2-oxoethyl]carbamate. LCMS calc.=288.14; found=288.3 (M+1)+. 1H NMR (500 MHz, CDCl3) δ 7.65 (s, 1 H); 7.47 (s, 1 H); 7.35-7.28 (m, 5 H); 5.93 (d, J=6.9 Hz, 1 H); 5.29-5.25 (m, 1 H); 5.13 (s, 2 H); 3.73 (s, 3 H); 1.26 (d, J=7.1 Hz, 3H).

INTERMEDIATE 15

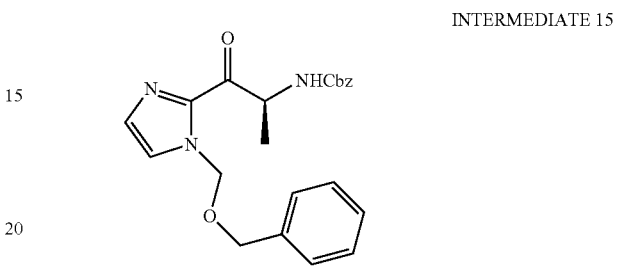

Benzyl ((1S)-2-{1-[(benzyloxy)methyl]-1H-imidazol-2-yl}-1-methyl-2-oxoethyl)carbamate Step A: 1-[(benzyloxy)methyl]-1H-imidazole A mixture of chloromethylether (4.3 mL, 29 mmol) and imidazole (6 g, 58 mmol) in acetonitrile (200 mL) was heated at reflux for 3.5 h. The solvent was removed in vacuo. The resulting oily residue was partitioned between CH2Cl2 (300 mL) and water (150 mL). Then the organic extract was washed with water (2×150 mL), dried (Na2SO4) and concentrated in vacuo to yield 1-[(benzyloxy)methyl]-1H-imidazole used without further purification. LCMS calc.=189.10; found=189.1 (M+1)+. 1H NMR (500 MHz, CDCl3) δ 7.63 (s, 1 H); 7.40-7.30 (m, 5 H); 7.16 (t, J=6.5 Hz, 1 H); 7.09 (t, J=10.6 Hz, 1 H); 5.34 (s, 2 H); 4.45 (s, 2 H).

Step B: benzyl ((1S)-2-{1-[(benzyloxy)methyl]-1H-imidazol-2-yl}-1-methyl-2-oxoethyl)carbamate To a solution of 1-[(benzyloxy)methyl]-1H-imidazole (706 mg, 3.75 mmol) in THF (4 mL) at −78° C. under N2, was added n-Butyllithium (2.3 mL of a 1.6 M solution in hexanes). The mixture was stirred at −78° C. for 30 min. To a solution of benzyl {(1S)-2-[methoxy(methyl)amino]-1-methyl-2-oxoethyl}carbamate (200 mg, 0.75 mmol) in THF (2 mL) under N2 at −15° C., was added isopropylmagnesium chloride (375 μL of a 2.0 M solution in THF). The resulting mixture was stirred at −15° C. for 15 min. This mixture was then added, by cannula to the solution above at −78° C. The mixture stirred at −78° C. for about 3 h, then warmed up gradually to room temperature and stirred overnight. The mixture was quenched with saturated NH4Cl. The aqueous layer was extracted with CH2Cl2 (3×25 mL). The organic layers were combined, dried (Na2SO4) and concentrated in vacuo. The residue was purified by flash chromatography to afford benzyl ((1S)-2-{1-[(benzyloxy)methyl]-1H-imidazol-2-yl}-1-methyl-2-oxoethyl)carbamate contaminated with about 30% of the unreacted starting material benzyl {(1S)-2-[methoxy(methyl)amino]-1-methyl-2-oxoethyl}carbamate. The mixture was carried forward to the next step without further purification. LCMS calc.=394.18; found=394.2 (M+1)+.

INTERMEDIATE 16

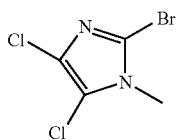

2-bromo-4,5-dichloro-1-methyl-1H-imidazole

A mixture of 2-bromo-4,5-dichloroimidazole (1 g, 4.6 mmol), methyl iodide (346 μL, 5.56 mmol), potassium carbonate (1.27 g, 9.2 mmol) and tetrabutylammonium bromide (148 mg, 0.46 mmol) in acetonitrile (2 mL) was stirred vigorously at 70-80° C. for 1.0 h. After cooling to room temperature, the inorganic salts were filtered off and washed with acetonitrile. The filtrate was evaporated and the residue was purified by flash chromatography (Si) to afford 2-bromo-4,5-dichloro-1-methyl-1H-imidazole as a white solid. LCMS calc.=230.89; found=230.9 (M+1)+. 1H NMR (500 MHz, CDCl3) δ 3.61 (s, 3 H).

INTERMEDIATE 17

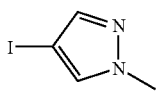

4-iodo-1-methyl-1H-pyrazole

To a solution of 18-crown-6 (132 mg, 0.5 mmol) in Et2O (8 mL) under N2, was added potassium tert-butoxide (616 mg, 5.5 mmol). The mixture was stirred while 4-iodopyrazole (1 g, 5 mmol) was introduced in a single portion at room temperature. The reaction was cooled to 0° C. and a solution of iodomethane (342 μL, 5.5 mmol) in Et2O (2 mL) was added dropwise at 0° C. The resulting mixture was warmed to room temperature and stirred overnight. The reaction was then diluted with water and extracted with Et2O (2×50 mL). The combined organic layers were washed with brine (45 mL), dried over anhydrous Na2SO4 and concentrated in vacuo. Flash chromatography gave 4-iodo-1-methyl-1H-pyrazole. LCMS calc.=208.96; found=209.0 (M+1)+. 1H NMR (500 MHz, CDCl3) δ 7.52 (s, 1H); 7.43 (s, 1 H); 3.95 (s, 3 H).

INTERMEDIATE 18

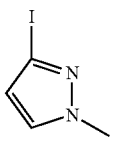

3-iodo-1-methyl-1H-pyrazole 1-methyl-1-H-pyrazole-3-amine (250 mg, 2.57 mmol) was heated at reflux for 3 h with tert-butylnitrile (336 μL, 2.83 mmol) in diiodomethane (5 mL). The solvent and volatile material was removed in vacuo and the resulting residue was purified by flash chromatography (Si) to yield 3-iodo-1-methyl-1H-pyrazole. LCMS calc.=208.96; found=209.0 (M+1)+. 1H NMR (500 MHz, CDCl3) δ 7.21 (d, J=2.1 Hz, 1 H); 6.42 (d, J=2.2 Hz, 1 H); 3.94 (s, 3 H).

INTERMEDIATES 19, 20

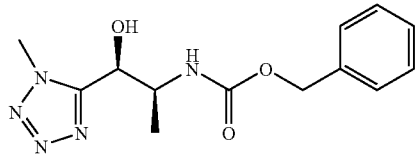

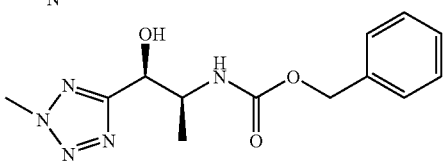

(4S,5S)-3-{[4'-fluoro-5'-isopropyl-2'-methoxy-4-(trifluoromethyl)biphenyl-2-yl]methyl}-4-methyl-5-(1-methyl-1H-tetrazol-5-yl)-1,3-oxazolidin-2-one and (4S,5S)-3-{[4'-fluoro-5'-isopropyl-2'-methoxy-4-(trifluoromethyl)biphenyl-2-yl]methyl}-4-methyl-5-(2-methyl-2H-tetrazol-5-yl)-1,3-oxazolidin-2-one Step A: benzyl [(1S,2S)-2-{[tert-butyl(dimethyl)silyl]oxy}-1-methyl-2-(1H-tetrazol-5-yl)ethyl]carbamate and benzyl [(1S,2S)-2-{[tert-butyl(dimethyl)silyl]oxy}-1-methyl-2-(2H-tetrazol-5-yl)ethyl]carbamate A mixture of benzyl ((1S,2S)-2-{[tert-butyl(dimethyl)silyl]oxy}-2-cyano-1-methylethyl)carbamate (106.6 mg, 0.306 mmol), triethylamine hydrochloride (211 mg, 1.53 mmol) and sodium azide (99.4 mg, 1.56 mmol) in dry toluene (6 mL) was heated at relux under N2 for 20 h and at room temperature for 2 days. The reaction was diluted with 1N HCl (20 mL) and extracted with EtOAc (3×20 mL). The combined extracts were dried (Na2SO4) and concentrated in vacuo to afford the crude product. This was carried forward with no further purification. LCMS calc.=392.2; found=392.1 (M+1)+.

Step B: benzyl [(1S,2S)-2-{[tert-butyl(dimethyl)silyl]oxy}-1-methyl-2-(1-methyl-1H-tetrazol-5-yl)ethyl]carbamate and benzyl [(1S,2S)-2-{[tert-butyl(dimethyl)silyl]oxy}-1-methyl-2-(2-methyl-2H-tetrazol-5-yl)ethyl]carbamate (Trimethylsilyl)diazomethane (2M in hexanes, 459 μL, 0.918 mmol) was added dropwise to a solution of the crude benzyl [(1S,2S)-2-{[tert-butyl(dimethyl)silyl]oxy}-1-methyl-2-(1H-tetrazol-5-yl)ethyl]carbamate and benzyl [(1S,2S)-2-{[tert-butyl(dimethyl)silyl]oxy}-1-methyl-2-(2H-tetrazol-5-yl)ethyl]carbamate in CH2Cl2/MeOH (3:2, 5 mL) at room temperature under N2. After 15 min and gas evolution had ceased, the reaction mixture was concentrated in vacuo to give the crude product. This was purified by flash chromatography (Si, 12×160 mm, 0-70% EtOAc in hexanes gradient) to afford benzyl [(1S,2S)-2-{[tert-butyl(dimethyl)silyl]oxy}-1-methyl-2-(1-methyl-1H-tetrazol-5-yl)ethyl]carbamate and benzyl [(1S,2S)-2-{[tert-butyl(dimethyl)silyl]oxy}-1-methyl-2-(2-methyl-2H-tetrazol-5-yl)ethyl]carbamate, as a 2:1 mixture of regioisomers. LCMS calc.=406.2; found=406.2 (M+1)+.

Step C: benzyl [(1S,2S)-2-hydroxy-1-methyl-2-(1-methyl-1H-tetrazol-5-yl)ethyl]carbamate and benzyl [(1S,2S)-2-hydroxy-1-methyl-2-(2-methyl-2H-tetrazol-5-yl)ethyl]carbamate Tetrabutylammonium fluoride (1M, in THF, 177 µL, 0.177 mmol) was added dropwise to a stirred solution of benzyl [(1S,2S)-2-{[tert-butyl(dimethyl)silyl]oxy}-1-methyl-2-(1-methyl-1H-tetrazol-5-yl)ethyl]carbamate and benzyl [(1S,2S)-2-{[tert-butyl(dimethyl)silyl]oxy}-1-methyl-2-(2-methyl-2H-tetrazol-5-yl)ethyl]carbamate (2:1 mixture of regioisomers, 65.2 mg, 0.161 mmol) in THF (2 mL) at 0° C. The reaction was stirred for 2 h at 0° C., diluted with saturated NH$_4$Cl (10 mL) and extracted with EtOAc (3×30 mL). The combined extracts were dried (Na$_2$SO$_4$) and concentrated in vacuo to give the crude product. This was purified by flash chromatography (Si, 12×160 mm, 0-80% EtOAc in hexanes gradient) to afford benzyl [(1S,2S)-2-hydroxy-1-methyl-2-(2-methyl-2H-tetrazol-5-yl)ethyl]carbamate and benzyl [(1S,2S)-2-hydroxy-1-methyl-2-(1-methyl-1H-tetrazol-5-yl)ethyl]carbamate. 2-methyl isomer (INTERMEDIATE 20): LCMS calc.=292.1; found=292.1 (M+1)$^+$. $^1$H NMR (500 MHz, CDCl$_3$) δ 7.33-7.29 (m, 5H), 5.59 (d, J=8.5 Hz, 1H), 5.09-5.00 (m, 5H), 4.49 (m, 1H), 4.26 (s, 3H), 1.07 (d, J=6.9 Hz, 3H). 1-methyl isomer (INTERMEDIATE 19): LCMS calc.=292.1; found=292.1 (M+1)$^+$. $^1$H NMR (500 MHz, CDCl$_3$) δ 7.33-7.29 (m, 5H), 5.72 (s, 1H), 5.07 (m, 3H), 4.99 (m, 2H), 4.18 (m, 1H), 4.10 (s, 3H), 1.24 (d, J=6.7 Hz, 3H).

Example 196

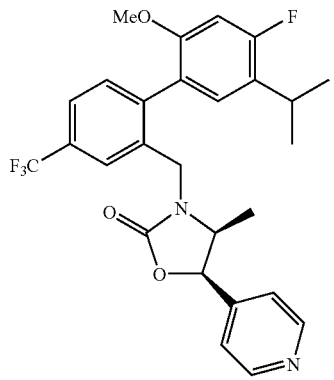 [SMILES: COc1cc(F)c(C(C)C)cc1-c1ccc(C(F)(F)F)cc1CN1C(=O)O[C@H](c2ccncc2)[C@@H]1C]

(4S,5R)-3-{[4'-fluoro-5'-isopropyl-2'-methoxy-4-(trifluoromethyl)biphenyl-2-yl]-methyl}-4-methyl-5-pyridin-4-yl-1,3-oxazolidin-2-one Step A: benzyl [(1S)-1-methyl-2-oxo-2-pyridin-4-ylethyl]carbamate A solution of isopropylmagnesium chloride (1.6 mL, 1M in THF, 3.23 mmol) was added dropwise to a stirred solution of benzyl {(1S)-2-[methoxy(methyl)amino]-1-methyl-2-oxoethyl}carbamate (EXAMPLE 17, Step 1) (879 mg, 3.30 mmol) in dry THF (4.2 mL) at −15° C. under N$_2$. The reaction was stirred at −15° C. for 30 min then a suspension of 4-pyridylmagnesium bromide in dry THF (prepared by adding ethyl magnesium bromide (6 mL, 2M in THF, 6.00 mmol) to a stirred solution of 4-iodopyridine (1.35 g, 6.60 mmol) in dry THF (45 mL) at room temperature under N$_2$ and stirring for 30 min) was added dropwise by cannula. The reaction was allowed to warm to room temperature and was stirred for 5 h. 1N HCl (15 mL) was added to quench the reaction and the mixture was adjusted to basic pH with saturated NaHCO$_3$. The mixture was extracted with EtOAc (2×50 mL) and CH$_2$Cl$_2$ (3×50 mL). The EtOAc and CH$_2$Cl$_2$ extracted were washed with brine separately, dried (Na$_2$SO$_4$), combined and concentrated in vacuo to give the crude product. This was purified by flash chromatography (Si, 40×160 mm, 0-100% EtOAc in hexanes gradient) to afford benzyl [(2R)-1-methyl-2-oxo-2-pyridin-4-ylethyl]carbamate, as a colorless solid. R$_f$=0.33 (50% EtOAc/hexanes). LCMS calc.=285.1; found=285.3 (M+1)$^+$. $^1$H NMR (500 MHz, CDCl$_3$) δ 8.85 (d, J=3.3 Hz, 2H), 7.76 (d, J=5.5 Hz, 2H), 7.36-7.32 (m, 5H), 5.70 (d, J=6.8 Hz, 1H), 5.31-5.25 (m, 1H), 5.13 (s, 2H), 1.43 (s, 3H).

Step B: benzyl [(1S,2R)-2-hydroxy-1-methyl-2-pyridin-4-ylethyl]carbamate

Lithium tri-tert-butoxyaluminum hydride (964 mg, 3.79 mmol) was added to a solution of benzyl [(2R)-1-methyl-2-oxo-2-pyridin-4-ylethyl]carbamate (539.1 mg, 1.90 mmol) in dry EtOH (40 mL) at −78° C. under N$_2$. The reaction was stirred at −78° C. for 2 h. 2% Aqueous acetic acid was added to quench the reaction and the mixture was adjusted to basic pH with saturated NaHCO$_3$ (~50 mL). The mixture was extracted with EtOAc (3×100 mL) and the combined extracts were washed with brine (50 mL), dried (Na$_2$SO$_4$) and concentrated in vacuo to give the crude product. This was purified by flash chromatography (Si, 40×160 mm, 0-100% EtOAc in hexanes gradient) to afford benzyl [(1S,2R)-2-hydroxy-1-methyl-2-pyridin-4-ylethyl]carbamate as a colorless solid. R$_f$=0.49 (EtOAc). LCMS calc.=287.1; found=287.3 (M+1)$^+$. $^1$H NMR (500 MHz, CDCl$_3$) δ 8.41 (d, J=5.7 Hz, 2H), 7.36-7.32 (m, 7H), 5.27 (d, J=7.4 Hz, 1H), 5.10 (s, 2H), 4.89 (s, 1H), 4.02 (br s, 1H), 0.96 (d, J=6.7 Hz, 3H).

Step C: (4S,5R)-3-{[4'-fluoro-5'-isopropyl-2'-methoxy-4-(trifluoromethyl)biphenyl-2-yl]methyl}-4-methyl-5-pyridin-4-yl-1,3-oxazolidin-2-one Sodium hydride (52.4 mg, 60% dispersion in mineral oil, 1.31 mmol) was added to a solution of benzyl [(1S,2R)-2-hydroxy-1-methyl-2-pyridin-4-ylethyl]carbamate 150 mg, 0.524 mmol) in dry THF (6 mL) at room temperature under N$_2$. After stirring for 30 min at room temperature a solution of 2-(bromomethyl)-5'-isopropyl-2'-methoxy-4-(trifluoromethyl)biphenyl (255 mg, 0.629 mmol) in dry THF (3 mL) was added by cannula. The reaction mixture was stirred overnight at room temperature. Saturated NH$_4$Cl (10 mL) was added and the mixture was extracted with EtOAc (3×20 mL). The combined extracts were dried (Na$_2$SO$_4$) and concentrated in vacuo to give the crude product. This was purified by flash chromatography (Si, 25×160 mm, 0-70% EtOAc in hexanes gradient) to afford (4S,5R)-3-{[4'-fluoro-5'-isopropyl-2'-methoxy-4-(trifluoromethyl)biphenyl-2-yl]methyl}-4-methyl-5-pyridin-4-yl-1,3-oxazolidin-2-one as a colorless oil. R$_f$=0.49 (EtOAc). LCMS calc.=503.2; found=503.3 (M+1)$^+$. $^1$H NMR (600 MHz, CDCl$_3$, 1:1 mixture of atropisomers) δ 8.61 (d, J=4.1 Hz, 2H), 7.68 (s, 0.5H), 7.61 (s, 1H), 7.60 (s, 0.5H), 7.33 (dd, J=7.4, 3.8, Hz, 1H), 7.16 (br s, 2H), 6.97 (dd, J=17.8, 8.4 Hz, 1H), 6.67 (dd, J=12.0, 3.4 Hz, 1H), 5.44 (d, J=8.2 Hz, 0.5H), 5.28 (d, J=8.0 Hz, 0.5H), 4.79 (d, J=15.8 Hz, 0.5H), 4.76 (d, J=15.8 Hz, 0.5H), 4.15-4.09 (m, 1H), 3.88 (d, J=15.8 Hz, 0.5H), 3.79-3.70 (m, 0.5H), 3.74 (s, 3H), 3.23-3.17 (m, 1H), 1.26-1.16 (m, 6H), 0.52 (d, J=6.5 Hz, 1.5H), 0.38 (d, J=6.5 Hz, 1.5H).

Example 197

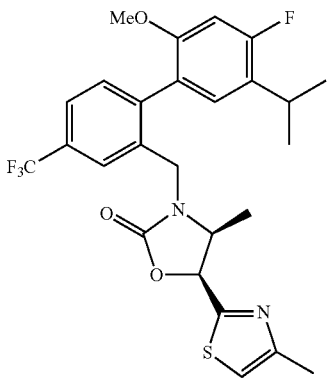 [SMILES: COc1cc(F)c(C(C)C)cc1-c1ccc(C(F)(F)F)cc1CN1C(=O)O[C@H](c2nc(C)cs2)[C@@H]1C]

(4S,5S)-3-{[4'-fluoro-5'-isopropyl-2'-methoxy-4-(trifluoromethyl)biphenyl-2-yl]methyl}-4-methyl-5-(4-methyl-1,3-thiazol-2-yl)-1,3-oxazolidin-2-one Step A: benzyl [(1S)-1-methyl-2-oxoethyl]carbamate Dimethylsulfoxide (1.01 g, 918 µL, 12.9 mmol) was added dropwise to a stirred solution of oxalyl chloride (790 mg, 543 µL, 6.23 mmol) in dry $CH_2Cl_2$ (12.6 mL) at −78° C. under $N_2$ and the reaction was stirred for 15 min. A solution of benzyl [(1S)-2-hydroxy-1-methylethyl]carbamate (965 mg, 4.61 mmol) in dry $CH_2Cl_2$ (12.6 mL) was added dropwise by cannula and the mixture was stirred at −78° C. for 30 min. Triethylamine (1.34 g, 1.85 mL, 13.2 mmol) was added and the reaction was allowed to warm to room temperature and was stirred for 2 h. Water (15 mL) was added and the aqueous phase was separated and extracted with $CH_2Cl_2$ (3×15 mL). The combined organic extracts were washed with saturated $NaHCO_3$ and brine, then dried ($MgSO_4$) and concentrated in vacuo to afford benzyl [(1S)-1-methyl-2-oxoethyl]carbamate as a colorless oil. $R_f$=0.75 (50% EtOAc in hexanes). $^1$H NMR (500 MHz, $CDCl_3$) δ 9.58 (s, 1H), 7.39-7.35 (m, 5H), 5.39 (br s, 1H), 5.15 (s, 2H), 4.33 (m, 1H), 1.40 (d, J=7.1 Hz, 3H).

Step B: benzyl [(1S)-2-cyano-2-hydroxy-1-methylethyl]carbamate

Diethylaluminum cyanide (4.53 mL, 1M in toluene, 4.53 mmol) was added dropwise to a stirred solution of benzyl [(1S)-1-methyl-2-oxoethyl]carbamate (0.853 g, 4.12 mmol) in dry toluene (33 mL) at −78° C. under $N_2$. The mixture was stirred at −78° C. for 6 h and then allowed to warm to room temperature overnight. Saturated $NH_4Cl$ (20 mL) and water (10 mL) were added then the mixture was extracted with EtOAc (3×50 mL). The combined extracts were dried ($Na_2SO_4$) and concentrated in vacuo to afford the crude product. This was purified by flash chromatography (Si, 40×160 mm, 0-40% EtOAc in hexanes gradient) to afford benzyl [(1S)-2-cyano-2-hydroxy-1-methylethyl]carbamate as a 3:1 mixture of diastereoisomers. $R_f$=0.63 (50% EtOAc in hexanes). LCMS calc.=257.1; found=257.1 (M+1)$^+$. $^1$H NMR (500 MHz, $CDCl_3$) major diastereoisomer: δ 7.39-7.31 (m, 5H), 5.11 (m, 2H), 4.60 br (s, 1H), 3.96 (m, 1H), 1.34 (d, J=6.7 Hz, 3H), minor diastereoisomer: δ 7.39-7.31 (m, 5H), 5.14 (m, 2H), 4.50 br (s, 1H), 4.10 (m, 1H), 1.30 (d, J=7.0 Hz, 3H).

Step C: benzyl ((1S,2S)-2-{[tert-butyl(dimethyl)silyl]oxy}-2-cyano-1-methylethyl)carbamate tert-Butyldimethylsilyl chloride (471 mg, 3.12 mmol) and imidazole (483 mg, 7.10 mmol) were added successively to a stirred solution of benzyl [(1S)-2-cyano-2-hydroxy-1-methylethyl]carbamate (665 mg, 2.84 mmol) in dry $CH_2Cl_2$ (13 mL) at room temperature under $N_2$ and the mixture was stirred overnight. Water (30 mL) was added and the mixture was extracted with $Et_2O$ (3×30 mL). The combined extracts were dried ($MgSO_4$) and concentrated in vacuo to give the crude product. This was purified by flash chromatography (Si, 40×160 mm, 0-15% EtOAc in hexanes gradient) to afford benzyl ((1S,2R)-2-{[tert-butyl(dimethyl)silyl]oxy}-2-cyano-1-methylethyl)carbamate and benzyl ((1S,2S)-2-{[tert-butyl(dimethyl)silyl]oxy}-2-cyano-1-methylethyl)carbamate. (1S,2R)-diastereoisomer: $R_f$=0.29 (10% EtOAc in hexanes). LCMS calc.=349.2; found=349.1 (M+1)$^+$. $^1$H NMR (500 MHz, $CDCl_3$) δ 7.39-7.33 (m, 5H), 5.16 (d, J=12.1 Hz, 1H), 5.07 (d, J=12.1 Hz, 1H), 4.89 (br d, J=6.6 Hz, 1H), 4.68 (br, d, 3.6 Hz, 1H), 3.92 (m, 1H), 1.31 (d, J=6.7 Hz, 3H), 0.91 (s, 9H), 0.21 (s, 3H), 0.17 (s, 3H). (1S,2S)-diastereoisomer: $R_f$=0.24 (10% EtOAc in hexanes). LCMS calc.=349.2; found=349.1 (M+1)$^+$. $^1$H NMR (500 MHz, $CDCl_3$) δ 7.38-7.32 (m, 5H), 5.10 (s, 2H), 4.76 (br d, J=6.9 Hz, 1H), 4.63 (br s, 1H), 4.00 (m, 1H), 1.31 (d, J=6.8 Hz, 3H), 0.90 (d, J=2.9 Hz, 9H), 0.17 (s, 3H), 0.08 (s, 3H).

Step D: benzyl ((1S,2S)-3-amino-2-{[tert-butyl(dimethyl)silyl]oxy}-1-methyl-3-thioxopropyl)carbamate A mixture of benzyl ((1S,2S)-2-{[tert-butyl(dimethyl)silyl]oxy}-2-cyano-1-methylethyl)carbamate (115.6 mg, 0.287 mmol), diethyldithiophosphate (1 mL) and water (3 drops) was stirred overnight at room temperature. The reaction mixture was partitioned between saturated $NaHCO_3$ (40 mL) and EtOAc (40 mL). The aqueous layer was separated and extracted with EtOAc (2×40 mL). The combined extracts were dried ($Na_2SO_4$) and concentrated in vacuo to give the crude product. This was purified by flash chromatography (Si, 12×160 mm, 0-40% EtOAc in hexanes gradient) to afford benzyl ((1S,2S)-3-amino-2-{[tert-butyl(dimethyl)silyl]oxy}-1-methyl-3-thioxopropyl)carbamate as a colorless oil. $R_f$=0.30 (20% EtOAc in hexanes). LCMS calc.=383.2; found=383.1 (M+1)$^+$. $^1$H NMR (500 MHz, $CDCl_3$) δ 8.36 (s, 1H), 7.87 (s, 1H), 7.37-7.29 (m, 5H), 5.13 (m, 2H), 4.85 (d, J=8.2 Hz, 1H), 4.72 (s, 1H), 4.47 (m, 1H), 1.05 (d, J=6.7 Hz, 3H), 0.96 (s, 9H), 0.08 (s, 3H), 0.07 (s, 3H).

Step E: benzyl [(1S,2S)-2-hydroxy-1-methyl-2-(4-methyl-1,3-thiazol-2-yl)ethyl]carbamate A solution of benzyl ((1S,2S)-3-amino-2-{[tert-butyl(dimethyl)silyl]oxy}-1-methyl-3-thioxopropyl)carbamate (96.8 mg, 0.253 mmol) and chloroacetone (117 mg, 101 µL, 1.27 mmol) in dry EtOH (5 mL) was heated at reflux under $N_2$ for 20 h, then stirred at room temperature for 2 days. The reaction mixture was concentrated in vacuo to give the crude product. This was purified by flash chromatography (Si, 12×160 mm, 0-100% EtOAc in hexanes gradient) to afford benzyl [(1S, 2S)-2-hydroxy-1-methyl-2-(4-methyl-1,3-thiazol-2-yl)ethyl]carbamate. $R_f$=0.44 (50% EtOAc in hexanes). LCMS calc.=307.1; found=307.1 (M+1)$^+$. $^1$H NMR (500 MHz, $CDCl_3$) δ 7.31 (m, 5H), 6.80 (s, 1H), 5.49 (br s, 1H), 5.06 (m, 3H), 4.26-4.18 (m, 1H), 2.38 (s, 3H), 1.09 (d, J=6.5 Hz, 3H).

Step F: (4S,5S)-4-methyl-5-(4-methyl-1,3-thiazol-2-yl)-1,3-oxazolidin-2-one

A solution of benzyl [(1S,2S)-2-hydroxy-1-methyl-2-(4-methyl-1,3-thiazol-2-yl)ethyl]carbamate (53.4 mg, 0.174 mmol) in 7.5 N aqueous KOH (1 mL), MeOH, (2 mL) and THF (4 mL) was stirred at room temperature overnight. The reaction mixture was acidified with 3N HCl and extracted with EtOAc (3×20 mL). The combined extracts were washed with brine, dried (Na₂SO₄) and concentrated in vacuo to afford the product. LCMS calc.=199.1; found=199.1 (M+1)⁺. ¹H NMR (500 MHz, CDCl₃) δ 6.92 (s, 1H), 6.82 (s, 1H), 5.91 (d, J=8.2 Hz, 1H), 4.39-4.35 (m, 1H), 2.44 (s, 3H), 0.95 (d, J=6.4 Hz, 3H).

Step G: (4S,5S)-3-{[4'-fluoro-5'-isopropyl-2'-methoxy-4-(trifluoromethyl)biphenyl-2-yl]methyl}-4-methyl-5-(4-methyl-1,3-thiazol-2-yl)-1,3-oxazolidin-2-one Sodium hydride (60% dispersion in mineral oil, 8.1 mg, 0.202 mmol) was added to a stirred solution of (4S,5S)-4-methyl-5-(4-methyl-1,3-thiazol-2-yl)-1,3-oxazolidin-2-one (33.4 mg, 0.168 mmol) in dry THF (1 mL) at room temperature under N₂. The reaction was stirred for 15 min then a solution of 2'-(bromomethyl)-4-fluoro-5-isopropyl-2-methoxy-4'-(trifluoromethyl)biphenyl (81.0 mg, 0.202 mmol) in dry THF (2 mL) was added by cannula. The reaction was stirred at room temperature overnight. Saturated NH₄Cl (10 mL) was added and the mixture was extracted with EtOAc (3×20 mL). The combined extracts were dried (Na₂SO₄) and concentrated in vacuo to give the crude product. This was purified by flash chromatography (Si, 25×160 mm, 0-70% EtOAc in hexanes gradient) and chiral HPLC (IA column, 20×250 mm, 5% i-PrOH in heptane) to afford (4S,5S)-3-{[4'-fluoro-5'-isopropyl-2'-methoxy-4-(trifluoromethyl)biphenyl-2-yl]methyl}-4-methyl-5-(4-methyl-1,3-thiazol-2-yl)-1,3-oxazolidin-2-one. R_f=0.18 (20% EtOAc in hexanes). LCMS calc.=523.2; found=523.1 (M+1)⁺. ¹H NMR (500 MHz, CDCl₃, 1:1 mixture of atropisomers) δ 7.68 (s, 0.5H), 7.63 (s, 0.5H), 7.59 (d, J=8.0 Hz, 1H), 7.32 (d, J=7.9 Hz, 1H), 6.99 (d, J=8.5 Hz, 0.5H), 6.95 (d, J=8.5 Hz, 0.5H), 6.88 (s, 1H), 6.68 (d, J=5.0 Hz, 0.5H), 6.66 (d, J=4.9 Hz, 0.5H), 5.70 (d, J=8.3 Hz, 0.5H), 5.55 (d, J=8.2 Hz, 0.5H), 4.72 (d, J=15.9 Hz, 0.5H), 4.64 (d, J=15.9 Hz, 0.5H), 4.20 (d, J=15.9 Hz, 0.5H), 3.95 (d, J=15.9 Hz, 0.5H), 3.91-3.83 (m, 1H), 3.75 (s, 1.5H), 3.74 (s, 1.5H), 3.23-3.15 (m, 1H), 2.40 (s, 3H), 1.26-1.18 (m, 6H), 0.65 (d, J=6.5 Hz, 1.5H), 0.55 (d, J=6.5 Hz, 1.5H).

Following the general procedures outlined above, the compounds in Table 8 were prepared. Example 198 was made as a reference compound.

TABLE 8

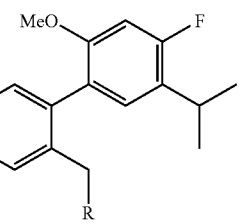

| Example | R | LCMS (M + 1)⁺ |
|---------|---|----------------|
| 198 | | 426.1 |
| 199 | | 570.2, 572.1, 574.2 |
| 200 | | 520.3 |
| 201 | | 516.3 |
| 202 | | 536.3 |
| 203 | | 532.3 |
| 204 | | 570.3 |

TABLE 8-continued

| Example | R | LCMS (M + 1)+ |
|---|---|---|
| 205 | 3-(trifluoromethoxy)phenyl oxazolidinone | 586.3 |
| 206 | 3-cyanophenyl oxazolidinone | 527.3 |
| 207 | 3-cyanophenyl oxazolidinone (diastereomer) | 527.3 |
| 208 | 3-(methylthio)phenyl oxazolidinone | 548.3 |
| 209 | 3-(dimethylamino)phenyl oxazolidinone | 545.4 |
| 210 | 3-(1,3-dioxan-2-yl)phenyl oxazolidinone | 588.5 |
| 211 | benzo[1,3]dioxol-5-yl oxazolidinone | 546.3 |
| 212 | 3,4-difluorophenyl oxazolidinone | 538.3 |
| 213 | 3-chloro-4-fluorophenyl oxazolidinone | 554.3 |
| 214 | 3,5-difluorophenyl oxazolidinone | 538.3 |
| 215 | 3-chloro-5-fluorophenyl oxazolidinone | 554.3 |
| 216 | 3,5-dimethoxyphenyl oxazolidinone | 562.4 |

TABLE 8-continued

| Example | R | LCMS (M + 1)+ |
|---|---|---|
| 217 | 3,4,5-trifluorophenyl-oxazolidinone | 556.3 |
| 218 | 3,5-dichlorobenzyl-oxazolidinone | 584.3 |
| 219 | 3,5-bis(trifluoromethyl)phenyl-oxazolidinone | 624.3 |
| 220 | 3,5-bis(trifluoromethyl)phenyl-dimethyl-oxazolidinone | 652.2 |
| 221 | cyclohexyl-oxazolidinone | 508.4 |
| 222 | cyclopentyl-oxazolidinone | 494.4 |
| 223 | pyridin-2-yl-oxazolidinone | 503.2 |
| 224 | pyridin-4-yl-oxazolidinone | 503.3 |
| 225 | pyridin-3-yl-oxazolidinone | 503.3 |
| 226 | pyridin-3-yl-oxazolidinone | 503.3 |
| 227 | thiophen-3-yl-oxazolidinone | 508.3 |
| 228 | thiophen-2-yl-oxazolidinone | 508.3 |

TABLE 8-continued

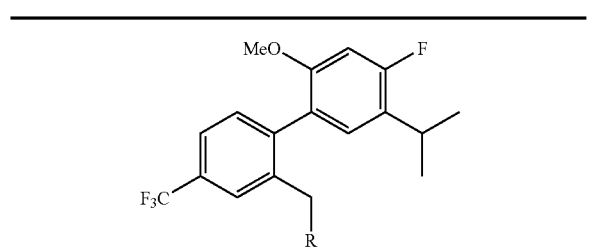

| Example | R | LCMS (M + 1)+ |
|---|---|---|
| 229 | (4-methyl-oxazolidinone-5-yl)-(5-chlorothiophen-2-yl) | 542.3, 544.3 |
| 230 | (4-methyl-oxazolidinone-5-yl)-(pyrazin-2-yl) | 504.3 |
| 231 | (4-methyl-oxazolidinone-5-yl)-(pyrazin-2-yl) | 504.3 |
| 232 | (4-methyl-oxazolidinone-5-yl)-(4-chloropyridin-2-yl) | 537.3, 539.3 |
| 233 | (4-methyl-oxazolidinone-5-yl)-(thiazol-2-yl) | 509.2 |
| 234 | (4-methyl-oxazolidinone-5-yl)-(pyrimidin-5-yl) | 504.4 |

TABLE 8-continued

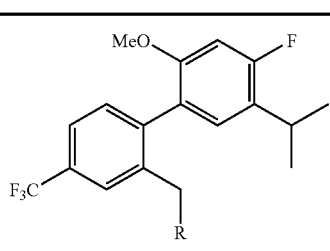

| Example | R | LCMS (M + 1)+ |
|---|---|---|
| 235 | (4-methyl-oxazolidinone-5-yl)-(4-methylthiazol-2-yl) | 523.1 |
| 236 | (4-methyl-oxazolidinone-5-yl)-(2-methyltetrazol-5-yl) | 508.1 |
| 237 | (4-methyl-oxazolidinone-5-yl)-(1-methyltetrazol-5-yl) | 508.1 |
| 238 | (4-methyl-oxazolidinone-5-yl)-(1-methylimidazol-2-yl) | 506.4 |
| 239 | (4-methyl-oxazolidinone-5-yl)-(1-methylimidazol-4-yl) | 506.3 |
| 240 | (4-methyl-oxazolidinone-5-yl)-(1-methylimidazol-5-yl) | 506.2 |

TABLE 8-continued
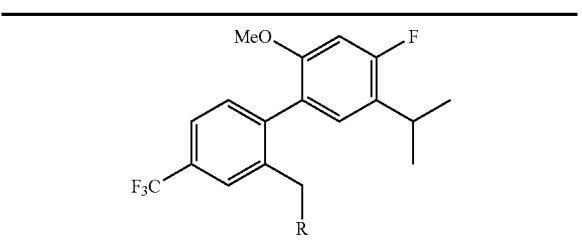
| Example | R | LCMS (M + 1)+ |
|---|---|---|
| 241 | | 520.3 |
| 242 | | 520.3 |
| 243 | | 574.1 |
| 244 | | 612.3 |
| 245 | | 506.2 |
TABLE 8-continued
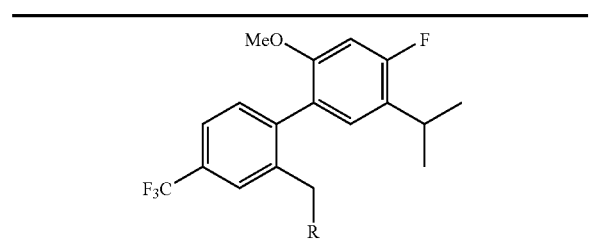
| Example | R | LCMS (M + 1)+ |
|---|---|---|
| 246 | | 506.2 |
| 247 | | 506.2 |
| 248 | | 520.2 |
| 249 | | 574.2 |
| 250 | | 574.2 |
| 251 | | 507.2 |

TABLE 8-continued

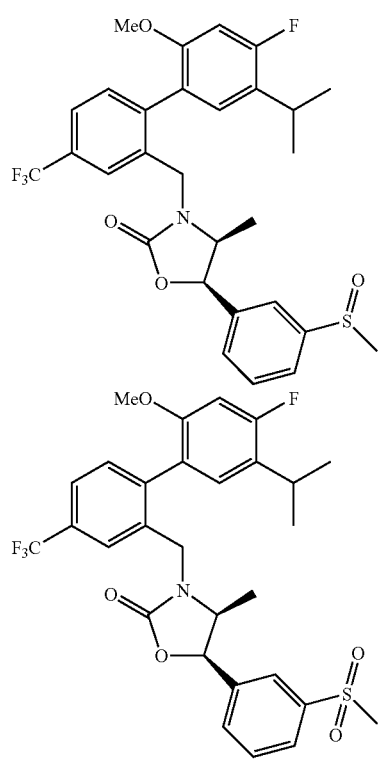

| Example | R | LCMS (M + 1)+ |
|---------|---|---------------|
| 252 | | 507.2 |

Example 253, 254

(4S,5R)-3-{[4'-fluoro-5'-isopropyl-2'-methoxy-4-(trifluoromethyl)biphenyl-2-yl]methyl}-4-methyl-5-[3-(methylsulfinyl)phenyl]-1,3-oxazolidin-2-one
(EXAMPLE 253)

(4S,5R)-3-{[4'-fluoro-5'-isopropyl-2'-methoxy-4-(trifluoromethyl)biphenyl-2-yl]methyl}-4-methyl-5-[3-(methylsulfonyl)phenyl]-1,3-oxazolidin-2-one
(EXAMPLE 254)

To a solution of (4S,5R)-3-{[4'-fluoro-5'-isopropyl-2'-methoxy-4-(trifluoromethyl)biphenyl-2-yl]methyl}-4-methyl-5-[3-(methylthio)phenyl]-1,3-oxazolidin-2-one (EXAMPLE 208) (25 mg, 0.0457 mmol) in dry dichloromethane (1.5 mL) under $N_2$ at 0° C., was added dropwise a solution of 3-chloroperoxybenzoic acid (77%, 26 mg, 0.114 mmol) in $CH_2Cl_2$ (0.5 mL). After addition the mixture was left to warm to room temperature and stirred for 2 h. The reaction mixture was quenched with saturated $Na_2SO_3$ (15 mL). The aqueous layer was extracted with $Et_2O$ (3×20 mL). The combined organic extracts were washed with saturated $NaHCO_3$, dried ($Na_2SO_4$) and concentrated in vacuo. The crude material was purified by flash chromatography (Si, 12×160 mm, 0-60% EtOAc in hexanes gradient) to afford (4S,5R)-3-{[4'-fluoro-5'-isopropyl-2'-methoxy-4-(trifluoromethyl)biphenyl-2-yl]methyl}-4-methyl-5-[3-(methylsulfinyl)phenyl]-1,3-oxazolidin-2-one and (4S,5R)-3-{[4'-fluoro-5'-isopropyl-2'-methoxy-4-(trifluoromethyl)biphenyl-2-yl]methyl}-4-methyl-5-[3-(methylsulfonyl)phenyl]-1,3-oxazolidin-2-one. EXAMPLE 253: LCMS calc.=564.19; found=564.3 (M+1)+. $^1$H NMR (500 MHz, CDCl$_3$, 1:1 mixture of atropisomers) δ 7.73 (s, 0.5 H); 7.66-7.52 (m, 4.5 H); 7.42 (s, 0.5 H); 7.40 (s, 0.5 H); 7.37 (d, J=3.4 Hz, 0.5 H); 7.36 (d, J=3.5 Hz, 0.5 H); 7.02 (d, J=8.4 Hz, 0.5 H); 6.99 (d, J=8.4 Hz, 0.5 H); 6.71 (d, J=3.1 Hz, 0.5 H); 6.69 (d, J=2.9 Hz, 0.5 H); 5.59 (d, J=5.9 Hz, 0.5 H); 5.57 (d, J=5.9 Hz, 0.5 H); 5.42 (t, J=8.4 Hz, 1 H); 4.85 (d, J=3.4 Hz, 0.5 H); 4.82 (d, J=3.4 Hz, 0.5 H); 4.80 (d, J=7.8 Hz, 0.5 H); 4.77 (d, J=7.7 Hz, 0.5 H); 4.16 (d, J=15.8 Hz, 0.5 H); 3.92 (d, J=15.8 Hz, 0.5 H); 3.76 (s, 3 H); 3.85-3.72 (m, 1 H); 3.26-3.19 (m, 1 H); 2.73 (d, J=4.7 Hz, 3 H); 1.30-1.26 (m, 4.5 H); 1.20 (d, J=6.9 Hz, 1.5 H); 0.55 (d, J=6.7 Hz, 0.75 H); 0.52 (d, J=6.7 Hz, 0.75 H); 0.41 (d, J=4.0 Hz, 0.75 H); 0.39 (d, J=4.1 Hz, 0.75 H). EXAMPLE 254: LCMS calc.=580.17; found=580.3 (M+1)+. $^1$H NMR (500 MHz, CDCl$_3$, 1:1 mixture of atropisomers) δ 7.95 (s, 0.5 H); 7.94 (s, 0.5 H); 7.81 (s, 0.5 H); 7.80 (s, 0.5 H); 7.73 (s, 0.5 H); 7.65-7.58 (m, 3 H); 7.57 (s, 0.5 H); 7.38 (d, J=3.5 Hz, 0.5 H); 7.36 (d, J=3.8 Hz, 0.5 H); 7.02 (d, J=8.4 Hz, 0.5 H); 6.99 (d, J=8.4 Hz, 0.5 H); 6.72 (s, 0.5 H); 6.69 (d, J=8.1 Hz, 0.5 H); 5.42 (d, J=8.0 Hz, 0.5 H); 4.86 (d, J=15.9 Hz, 0.5 H); 4.81 (d, J=15.9 Hz, 0.5 H); 4.17 (d, J=15.8 Hz, 0.5 H); 3.91 (d, J=15.8 Hz, 0.5 H); 3.81-3.75 (m, 1 H); 3.78 (s, 3 H); 3.27-3.19 (m, 1 H); 3.07 (s, 3 H); 1.30-1.26 (m, 4.5 H); 1.21 (t, J=8.7 Hz, 1.5 H); 0.53 (d, J=6.5 Hz, 1.5 H); 0.39 (d, J=6.5 Hz, 1.5 H).

Example 255

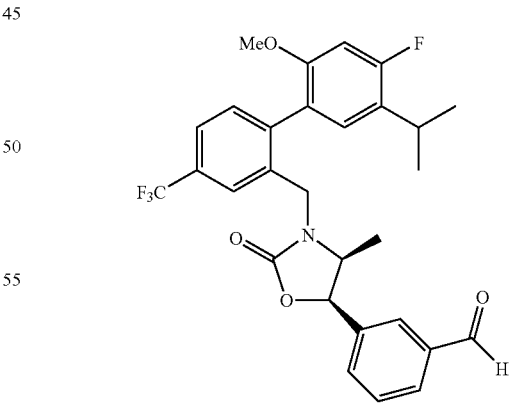

3-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)benzaldehyde The solution of (4S,5R)-5-[3-(1,3-dioxan-2-yl)phenyl]-3-{[4'-fluoro-5'-isopropyl-2'-methoxy-4-(trifluoromethyl)biphenyl-2-yl]methyl}-4-methyl-1,3-oxazolidin-2-one (EXAMPLE 210) (380 mg, 0.647 mmol) in THF and 1N HCl (3:1) (4 mL) was stirred at room temperature for 2 h. The reaction mixture was diluted with EtOAc and washed with NaHCO₃ and brine. The organic layer was dried and concentrated in vacuo. The crude material was purified by flash chromatography (Si) to provide 3-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)benzaldehyde. LCMS calc.=530.19; found=530.4 (M+1)⁺. ¹H NMR (500 MHz, CDCl₃, 1:1 mixture of atropisomers) δ 10.03 (s, 1 H); 7.88 (s, 0.5 H); 7.87 (s, 0.5 H); 7.77-7.52 (m, 5 H); 7.37 (d, J=3.5 Hz, 0.5 H); 7.36 (d, J=3.4 Hz, 0.5 H); 7.02 (d, J=8.4 Hz, 0.5 H); 6.99 (d, J=8.4 Hz, 0.5 H); 6.71 (d, J=3.5 Hz, 0.5 H); 6.69 (d, J=3.4 Hz, 0.5 H); 4.17 (d, J=15.8 Hz, 0.5 H); 6.98 (d, J=15.8 Hz, 0.5 H); 3.78 (s, 3 H); 3.85-3.71 (m, 1 H); 3.26-3.19 (m, 1 H); 1.30-1.26 (m, 4.5 H); 1.19 (d, J=6.9 Hz, 1.5 H); 0.53 (d, J=6.6 Hz, 1.5 H); 0.40 (d, J=6.6 Hz, 1.5 H).

Example 256

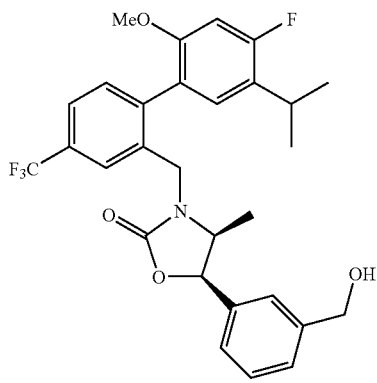 [SMILES: COc1cc(F)c(C(C)C)cc1-c1ccc(C(F)(F)F)cc1CN1C(=O)O[C@H](c2cccc(CO)c2)[C@@H]1C]

(4S,5R)-3-{[4'-fluoro-5'-isopropyl-2'-methoxy-4-(trifluoromethyl)biphenyl-2-yl]methyl}-5-[3-(hydroxy)-3-{[4'-fluoro-5'-isopropyl-2'-methoxy-4-(trifluoromethyl)biphenyl-2-yl]methyl}-5-[3-(hydroxy To a solution of 3-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)benzaldehyde (12 mg, 0.023 mmol) in anhydrous EtOH (1 mL) at 0° C. under N₂, was added NaBH₄ (4.5 mg, 0.119 mmol) as a powder. The solution was warmed to room temperature and stirred for 1 h. The mixture was quenched with 2% HOAc and diluted with water. The aqueous layer was extracted with EtOAc (3×10 mL). The combined organic extracts were washed with saturated NaHCO₃ (12 mL) and brine (12 mL), dried (Na₂SO₄) and concentrated in vacuo. The crude material was purified by flash chromatography to yield (4S,5R)-3-{[4'-fluoro-5'-isopropyl-2'-methoxy-4-(trifluoromethyl)biphenyl-2-yl]methyl}-5-[3-(hydroxy)-3-{[4'-fluoro-5'-isopropyl-2'-methoxy-4-(trifluoromethyl)biphenyl-2-yl]methyl}-5-[3-(hydroxy. LCMS calc.=532.0; found=532.4 (M+1)⁺. ¹H NMR (500 MHz, CDCl₃, 1:1 mixture of atropisomers) δ 7.73 (s, 0.5 H); 7.67 (s, 0.5 H); 7.64 (s, 0.5 H); 7.62 (s, 0.5 H); 7.42-7.32 (m, 3 H); 7.24 (s, 1 H); 7.15 (s, 0.5 H); 7.14 (s, 0.5 H); 7.01 (d, J=8.4 Hz, 0.5 H); 6.98 (d, J=8.5 Hz, 0.5 H); 6.71 (s, 0.5 H); 6.68 (s, 0.5 H); 5.51 (d, J=8.1 Hz, 0.5 H); 5.37 (d, J=8.0 Hz, 0.5 H); 4.81 (d, J=15.9 Hz, 0.5 H); 4.74 (d, J=16 Hz, 0.5 H); 4.73 (s, 2 H); 4.15 (d, J=15.9 Hz, 1 H); 3.92 (d, J=15.9 Hz, 1 H); 3.77 (s, 3.0 H); 3.79-3.74 (m, 0.5 H); 3.74-3.68 (m, 0.5 H); 3.25-3.18 (m, 1 H); 1.29-1.25 (m, 4.5 H); 1.19 (d, J=6.9 Hz, 1.5 H); 0.53 (d, J=6.4 Hz, 1.5 H); 0.40 (d, J=6.4 Hz, 1.5 H).

Example 257

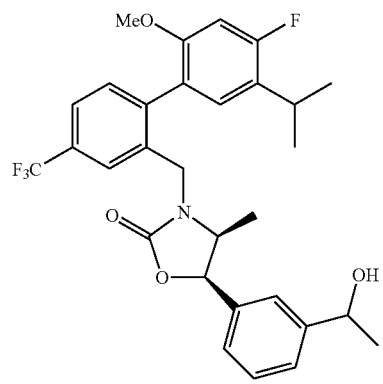 [SMILES: COc1cc(F)c(C(C)C)cc1-c1ccc(C(F)(F)F)cc1CN1C(=O)O[C@H](c2cccc(C(C)O)c2)[C@@H]1C]

(4S,5R)-3-{[4'-fluoro-5'-isopropyl-2'-methoxy-4-(trifluoromethyl)biphenyl-2-yl]methyl}-5-[3-(1-hydro)-xyethyl)phenyl]-4-methyl-1,3-oxazolidin-2-one To a solution of 3-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)benzaldehyde (11 mg, 0.021 mmol) in THF (1 mL) at −78° C. under N₂, was added methylmagnesium bromide (30 μL of a 3.0 M solution in Et₂O). The mixture was stirred at −78° C. for 2 h. The mixture was quenched with saturated NH₄Cl (10 mL). The aqueous layer was extracted with EtOAc (3×10 mL). The combined organic layers were washed with brine (15 mL), dried (Na₂SO₄) and concentrated in vacuo to give the crude product. This was purified by flash chromatography (Si) to afford (4S,5R)-3-{[4'-fluoro-5'-isopropyl-2'-methoxy-4-(trifluoromethyl)biphenyl-2-yl]methyl}-5-[3-(1-hydro)-xyethyl)phenyl]-4-methyl-1,3-oxazolidin-2-one. LCMS calc.=546.22; found=546.4 (M+1)⁺. ¹H NMR (500 MHz, CDCl₃, 1:1 mixture of atropisomers) δ 7.74 (s, 0.5 H); 7.67 (s, 0.5 H); 7.64 (s, 0.5 H); 7.63 (s, 0.5 H); 7.36 (m, 3 H); 7.24 (s, 1 H); 7.15 (s, 0.5 H); 7.14 (s, 0.5 H); 7.01 (d, J=8.5 Hz, 0.5 H); 6.99 (d, J=8.5 Hz, 0.5 H); 6.71 (s, 0.5 H); 6.68 (s, 0.5 H); 5.52 (d, J=8.0 Hz, 0.5 H); 5.36 (d, J=7.9 Hz, 0.5 H); 4.92 (q, J=6.4 Hz, 1 H); 4.83 (d, J=15.7, 0.5 H); 4.77 (d, J=16.0, 0.5 H); 4.16 (d, J=15.5 Hz, 0.5H); 3.92 (d, J=15.5 Hz, 0.5 H); 3.77 (d, J=7.1 Hz, 3 H); 3.81-3.68 (m, 1 H); 3.25-3.18 (m, 1 H); 1.64 (br, s, 1 H); 1.49 (d, J=6.4 Hz, 3 H); 1.30-1.26 (m, 4.5 H); 1.19 (d, J=6.9 Hz, 1.5 H); 0.53 (d, J=6.5 Hz, 1.5 H); 0.40 (d, J=6.5 Hz, 1.5 H).

Following the general procedures outlined above, the compounds in Table 9 were prepared:

TABLE 9

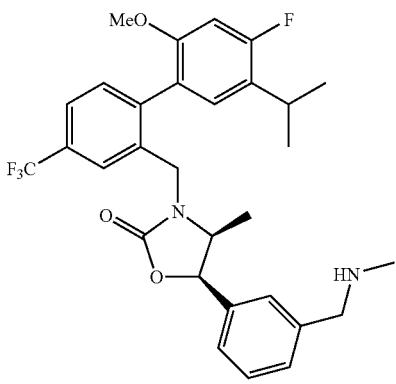 [SMILES: CNCc1cccc([C@H]2OC(=O)N(Cc3cc(C(F)(F)F)ccc3-c3cc(C(C)C)c(F)cc3OC)[C@H]2C)c1]

| Example | R | LCMS (M + 1)+ |
|---------|------|---------------|
| 258 | Et | 560.4 |
| 259 | n-Pr | 574.4 |

Example 260

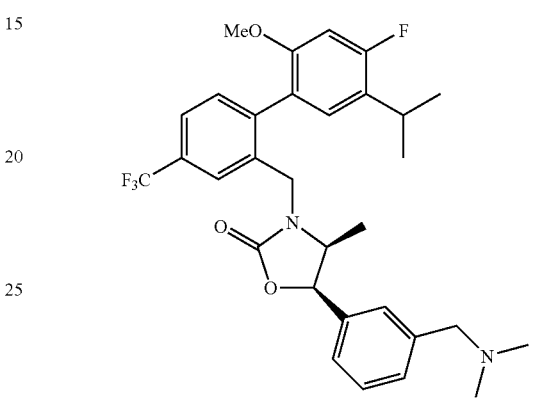

(4S,5R)-3-{[4'-fluoro-5'-isopropyl-2'-methoxy-4-(trifluoromethyl)biphenyl-2-yl]-methyl}-4-methyl-5-{3-[(methylamino)methyl]phenyl}-1,3-oxazolidin-2-one To a solution of 3-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)benzaldehyde (15 mg, 0.028 mmol) in 1,2-dichloroethane (1 mL) was added methylamine (1 mL of a 2.0 M solution in THF). The resulting mixture was treated with sodium triacetoxyborohydride (34.8 mg, 0.16 mmol) and AcOH (0.05 mL). The mixture was stirred under $N_2$ at room temperature for 5 days. The reaction mixture was quenched with 1N NaOH and the aqueous layer was extracted with ether (3×15 mL). The ether extracts were washed with brine, dried ($Na_2SO_4$) and concentrated in vacuo. The residue was purified by flash chromatography (Si) to afford (4S,5R)-3-{[4'-fluoro-5'-isopropyl-2'-methoxy-4-(trifluoromethyl)biphenyl-2-yl]methyl}-4-methyl-5-{3-[(methylamino)methyl]phenyl}-1,3-oxazolidin-2-one. LCMS calc.=545.23; found=545.4 (M+1)+. $^1$H NMR (500 MHz, $CDCl_3$, 1:1 mixture of atropisomers) δ 7.74 (s, 0.5 H); 7.67 (s, 0.5 H); 7.64 (s, 0.5 H); 7.62 (s, 0.5 H); 7.33 (m, 3 H); 7.20 (s, 1 H); 7.13 (s, 0.5 H); 7.12 (s, 0.5 H); 7.01 (d, J=8.4 Hz, 0.5 H); 6.98 (d, J=8.5 Hz, 0.5 H); 6.71 (d, J=2.9 Hz, 0.5 H); 6.68 (d, J=2.8 Hz, 0.5 H); 5.51 (d, J=8.1 Hz, 0.5 H); 5.37 (d, J=8.0 Hz, 0.5 H); 4.82 (d, J=15.9 Hz, 0.5 H); 4.75 (d, J=15.9 Hz, 0.5 H); 4.16 (d, J=15.9 Hz, 0.5 H); 3.92 (d, J=15.9 Hz, 0.5H); 3.77 (m, 5.5 H); 3.70 (t, J=6.6 Hz, 0.5 H); 3.25-3.18 (m, 1H); 2.45 (s, 3H); 1.93 (br, s, 1 H); 1.27 (m, 4.5 H); 1.19 (d, J=6.9 Hz, 1.5 H); 0.53 (d, J=6.5 Hz, 1.5 H); 0.40 (d, J=6.5 Hz, 1.5 H).

Example 261

(4S,5R)-5-{3-[(dimethylamino)methyl]-phenyl}-3-{[4'-fluoro-5'-isopropyl-2'-methoxy-4-(trifluoromethyl)biphenyl-2-yl]-methyl}-4-methyl-1,3-oxazolidin-2-one To a solution of 3-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)benzaldehyde (15 mg, 0.028 mmol) in EtOH (1 mL) was added dimethylamine (140 μL of a 2.0 M solution in MeOH) and titanium isopropoxide (79 μL, 0.28 mmol). The resulting white suspension was stirred overnight. Sodium borohydride (7.1 mg, 0.188 mmol) was added and the mixture was stirred overnight. The reaction was quenched by pouring the mixture into 2N aqueous ammonia (2 mL). The resulting inorganic precipitate was filtered and washed with dichloromethane. The combined filtrates were extracted with dichloromethane (2×15 mL). The extracts were dried ($Na_2SO_4$) and concentrated in vacuo. The residue was purified by flash chromatography (Si) to give (4S,5R)-5-{3-[(dimethylamino)methyl]phenyl}-3-{[4'-fluoro-5'-isopropyl-2'-methoxy-4-(trifluoromethyl)biphenyl-2-yl]methyl}-4-methyl-1,3-oxazolidin-2-one. LCMS calc.=559.25; found=559.4 (M+1)+. $^1$H NMR (500 MHz, $CDCl_3$, 1:1 mixture of atropisomers) δ 7.74 (s, 0.5 H); 7.67 (s, 0.5 H); 7.64 (s, 0.5 H); 7.62 (s, 0.5 H); 7.37-7.29 (m, 3 H); 7.18 (s, 1 H); 7.16 (s, 0.5 H); 7.13 (s, 0.5 H); 7.01 (d, J=8.4 Hz, 0.5 H); 6.99 (d, J=8.5 Hz, 0.5 H); 6.71 (d, J=3.0 Hz, 0.5 H); 6.68 (d, J=2.9 Hz, 0.5 H); 5.52 (d, J=8.1 Hz, 0.5 H); 5.37 (d, J=8.0 Hz, 0.5 H); 4.82 (d, J=15.9 Hz, 0.5 H); 4.77 (d, J=16.0 Hz, 0.5 H); 4.15 (d, J=16.0 Hz, 0.5 H); 3.91 (d, J=15.9 Hz, 0.5 H); 3.76 (s, 3 H); 3.80-3.73 (m, 0.5 H); 3.72-3.68 (m, 0.5H); 3.43 (s, 2H); 3.25-3.18 (m, 1 H); 2.23 (s, 6 H); 1.27 (m, 4.5 H); 1.19 (d, J=6.9 Hz, 1.5 H); 0.53 (d, J=6.5 Hz, 1.5 H); 0.39 (d, J=6.6 Hz, 1.5 H).

Example 262

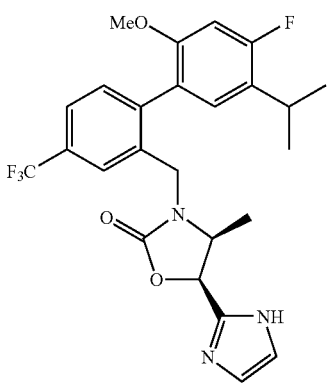 [SMILES: COc1cc(F)c(C(C)C)cc1-c1ccc(C(F)(F)F)cc1CN1C(=O)O[C@H](c2ncc[nH]2)[C@@H]1C]

(4S,5R)-3-{[4'-fluoro-5'-isopropyl-2'-methoxy-4-(trifluoromethyl)biphenyl-2-yl]methyl}-5-(1H-imidazol-2-yl)-4-methyl-1,3-oxazolidin-2-one A mixture of (4S,5S)-5-{1-[(benzyloxy)methyl]-1H-imidazol-2-yl}-3-{[4'-fluoro-5'-isopropyl-2'-methoxy-4-(trifluoromethyl)biphenyl-2-yl]methyl}-4-methyl-1,3-oxazolidin-2-one (EXAMPLE 244) (16.9 mg, 0.028 mmol), 20% palladium hydroxide on carbon (8.3 mg) and 1N HCl (28 uL) in MeOH (1 mL) was stirred under hydrogen (balloon) overnight, after which time it was filtered through Celite and concentrated in vacuo. The crude material was purified by flash chromatography to afford (4S,5R)-3-{[4'-fluoro-5'-isopropyl-2'-methoxy-4-(trifluoromethyl)biphenyl-2-yl]methyl}-5-(1H-imidazol-2-yl)-4-methyl-1,3-oxazolidin-2-one. LCMS calc.=492.18; found=492.2 (M+1)$^+$. $^1$H NMR (500 MHz, CDCl$_3$, 1:1 mixture of atropisomers) δ 7.71 (s, 0.5 H); 7.67 (s, 0.5 H); 7.65 (s, 0.5 H); 7.64 (s, 0.5 H); 7.37 (d, J=3.2 Hz, 0.5 H); 7.35 (d, J=3.3 Hz, 0.5 H); 7.09 (d, 2 H); 7.02 (d, J=8.4 Hz, 0.5 H); 6.99 (d, J=8.5 Hz, 0.5 H); 6.72 (d, J=4.3 Hz, 0.5 H); 6.69 (d, J=4.2 Hz, 0.5H); 5.76 (d, J=8.3 Hz, 0.5 H); 5.64 (d, J=8.7 Hz, 0.5 H); 4.72 (d, J=15.8 Hz, 0.5 H); 4.68 (d, J=15.8 Hz, 0.5 H); 4.20 (d, J=15.7 Hz, 0.5 H); 4.01 (d, J=15.7 Hz, 0.5 H); 3.90 (br, s, 1H); 3.79-3.72 (m, 4H); 3.25-3.18 (m, 1 H); 1.28-1.22 (m, 6 H); 0.67 (d, J=6.5 Hz, 1.5 H); 0.59 (d, J=6.5 Hz, 1.5 H).

Example 263

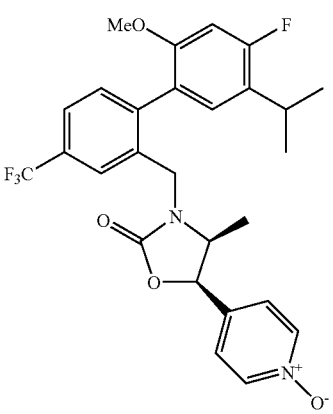 [SMILES: COc1cc(F)c(C(C)C)cc1-c1ccc(C(F)(F)F)cc1CN1C(=O)O[C@H](c2cc[n+]([O-])cc2)[C@@H]1C]

(4S,5R)-3-{[4'-fluoro-5'-isopropyl-2'-methoxy-4-(trifluoromethyl)biphenyl-2-yl]-methyl}-4-methyl-5-(1-oxidopyridin-4-yl)-1,3-oxazolidin-2-one m-Chlorobenzoic acid (77%, 47.9 mg, 0.214 mmol) was added to a solution of (4S,5R)-3-{[4'-fluoro-5'-isopropyl-2'-methoxy-4-(trifluoromethyl)biphenyl-2-yl]methyl}-4-methyl-5-pyridin-4-yl-1,3-oxazolidin-2-one (53.7, 0.107 mmol) in dry CH$_2$Cl$_2$ (10.8 mL) at 0° C. After 15 min at 0° C., the reaction was stirred at room temperature for 3 h. The reaction was diluted with CH$_2$Cl$_2$ (40 mL) and washed with saturated Na$_2$SO$_3$ (20 mL) and saturated K$_2$CO$_3$ (2×20 mL). The organic layer was dried (Na$_2$SO$_4$) and concentrated in vacuo to afford (4S,5R)-3-{[4'-fluoro-5'-isopropyl-2'-methoxy-4-(trifluoromethyl)biphenyl-2-yl]methyl}-4-methyl-5-(1-oxidopyridin-4-yl)-1,3-oxazolidin-2-one as an oil. LCMS calc.=519.2; found=519.3 (M+1)$^+$.

Example 264

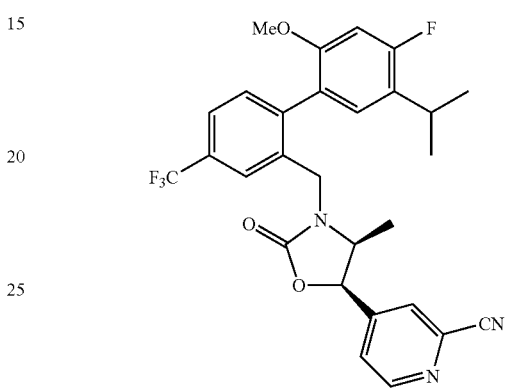

4-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)pyridine-2-carbonitrile Trimethylsilyl cyanide (39.9 mg, 54 μL, 0.402 mmol) was added to a stirred solution of (4S,5R)-3-{[4'-fluoro-5'-isopropyl-2'-methoxy-4-(trifluoromethyl)biphenyl-2-yl]methyl}-4-methyl-5-(1-oxidopyridin-4-yl)-1,3-oxazolidin-2-one (37.9 mg, 0.0732 mmol) in dry CH$_2$Cl$_2$ (2 mL) at room temperature under N$_2$. The reaction was stirred for 5 min and benzoyl chloride (20.5 mg, 17 μL, 0.146 mmol) was added. The reaction was stirred at room temperature overnight. 50% Saturated K$_2$CO$_3$ (10 mL) was added and the mixture was diluted with CH$_2$Cl$_2$ (20 mL). The aqueous layer was separated and extracted with CH$_2$Cl$_2$ (2×10 mL). The combined organic extracts were dried (K$_2$CO$_3$) and concentrated in vacuo to give the crude product. This was purified by flash chromatography (Si, 12×160 mm, 0-70% EtOAc in hexanes gradient) to afford the product (11.6 mg, 30%), as a colorless oil. This was resolved into its enantiomers by chiral HPLC (AD column, 20×250 mm, 10% i-PrOH in heptane) to give 4-((4S,5R)-3-{[4'-fluoro-5'-isopropyl-2'-methoxy-4-(trifluoromethyl)biphenyl-2-yl]methyl}-4-methyl-2-oxo-1,3-oxazolidin-5-yl)pyridine-2-carbonitrile and 4-((4R,5S)-3-{[4'-fluoro-5'-isopropyl-2'-methoxy-4-(trifluoromethyl)biphenyl-2-yl]methyl}-4-methyl-2-oxo-1,3-oxazolidin-5-yl)pyridine-2-carbonitrile. R$_f$=0.72 (50% EtOAc in hexanes). LCMS calc.=528.2; found=528.3 (M+1)$^+$. $^1$H NMR (500 MHz, CDCl$_3$, 1:1 mixture of atropisomers) δ 8.73 (s, 1H), 7.67-7.59 (m, 2H), 7.55 (d, J=3.3 Hz, 1H), 7.40 (d, J=4.2 Hz, 1H), 7.35 (dd, J=7.8, 3.3 Hz, 1H), 6.99 (d, J=8.4 Hz, 1H), 6.95 (d, J=8.4 Hz, 1H), 6.69 (d, J=3.1 Hz, 1H), 6.67 (d, J=3.1 Hz, 1H), 5.47 (d, J=8.1 Hz, 0.5H), 5.30 (d, J=8.1 Hz, 0.5H), 4.81 (t, J=15.1 Hz, 1H), 4.11 (d, J=15.8 Hz, 0.5H), 3.89 (d, J=15.8 Hz, 0.5H), 3.83-3.73 (m, 1H), 3.76 (s, 3H), 3.24-3.16 (m, 1H), 1.27-1.17 (m, 6H), 0.54 (d, J=6.5 Hz, 1.5H), 0.39 (d, J=6.5 Hz, 1.5H).

Example 265

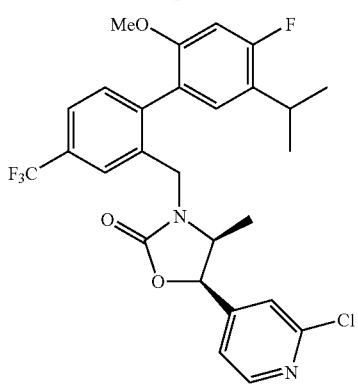 [SMILES: COc1cc(F)c(C(C)C)cc1-c1ccc(C(F)(F)F)cc1CN1C(=O)O[C@H](c2ccnc(Cl)c2)[C@@H]1C]

(4S,5R)-5-(2-chloropyridin-4-yl)-3-{[4'-fluoro-5'-isopropyl-2'-methoxy-4-(trifluoromethyl)biphenyl-2-yl]-methyl}-4-methyl-1,3-oxazolidin-2-one A solution of (4S,5R)-3-{[4'-fluoro-5'-isopropyl-2'-methoxy-4-(trifluoromethyl)biphenyl-2-yl]methyl}-4-methyl-5-(1-oxidopyridin-4-yl)-1,3-oxazolidin-2-one (53.7 mg, 0.104 mmol) in phosphorous oxychloride (4 mL) was heated at reflux under $N_2$ for 2 h. The reaction mixture was cooled to room temperature, concentrated in vacuo, diluted with EtOAc (20 mL) and water (5 mL), then washed with saturated $NaHCO_3$ (10 mL). The aqueous layer was extracted with EtOAc (2×20 mL). The combined organic layers were dried ($Na_2SO_4$) and concentrated in vacuo to give the crude product. This was purified by flash chromatography (Si, 12×160 mm, 0-70% EtOAc in hexanes gradient) to afford the product as a colorless oil. This was resolved into its enantiomers by chiral HPLC (AD column, 20×250 mm, 5% i-PrOH in heptane) to afford (4S,5R)-5-(2-chloropyridin-4-yl)-3-{[4'-fluoro-5'-isopropyl-2'-methoxy-4-(trifluoromethyl)biphenyl-2-yl]methyl}-4-methyl-1,3-oxazolidin-2-one. $R_f$=0.17 (20% EtOAc in hexanes). LCMS calc.=537.2; found=537.3 $(M+1)^+$. $^1H$ NMR (500 MHz, $CDCl_3$, 1:1 mixture of atropisomers) δ 8.40 (br s, 1H), 7.70 (s, 0.5H), 7.63 (s, 1.5H), 7.37 (m, 1H), 7.24 (br s, 1H), 7.10 (br s, 1H), 7.01 (d, J=8.2 Hz, 0.5H), 6.98 (d, J=8.2 Hz, 0.5H), 6.72-6.68 (m, 1H), 5.44 (d, J=8.1 Hz, 0.5H), 5.29 (d, J=8.1 Hz, 0.5H), 4.81 (t, J=16.9 Hz, 1H), 4.14 (d, J=15.9 Hz, 0.5H), 3.91 (d, J=15.9 Hz, 0.5H), 3.81-3.71 (m, 1H), 3.76 (s, 3H), 3.27-3.19 (m, 1H), 1.29-1.19 (m, 6H), 0.58 (d, J=6.5 Hz, 1.5H), 0.44 (d, J=6.5 Hz, 1.5H).

Example 266

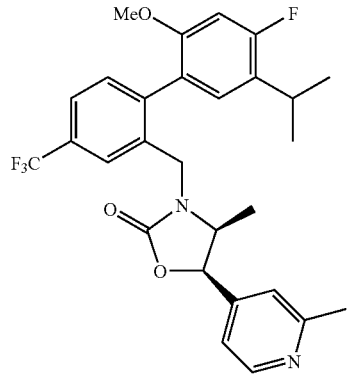 [SMILES: COc1cc(F)c(C(C)C)cc1-c1ccc(C(F)(F)F)cc1CN1C(=O)O[C@H](c2ccnc(C)c2)[C@@H]1C]

(4S,5R)-3-{[4'-fluoro-5'-isopropyl-2'-methoxy-4-(trifluoromethyl)biphenyl-2-yl]methyl}-4-methyl-5-(2-methylpyridin-4-yl)-1,3-oxazolidin-2-one A solution of (4S,5R)-5-(2-chloropyridin-4-yl)-3-{[4'-fluoro-5'-isopropyl-2'-methoxy-4-(trifluoromethyl)biphenyl-2-yl]methyl}-4-methyl-1,3-oxazolidin-2-one (20.9 mg, 0.0389 mmol), trimethylboroxin (14.7 mg, 16 µL, 0.116 mmol), $Cs_2CO_3$ (38.0 mg, 0.117 mmol) and $(Ph_3P)_4Pd$ (9.0 mg, 0.00778 mmol) in dry 1,4-dioxane (1 mL) was heated at reflux overnight. The reaction mixture was filtered through a plug of Celite and washed with EtOAc. The filtrate was concentrated in vacuo to afford the crude product. This was purified by flash chromatography (Si, 12×160 mm, 0-70% EtOAc in hexanes gradient) to afford the product as a colorless oil. This was resolved into its enantiomers by chiral HPLC (AD column, 20×250 mm, 10% i-PrOH in heptane) to afford (4S,5R)-3-{[4'-fluoro-5'-isopropyl-2'-methoxy-4-(trifluoromethyl)biphenyl-2-yl]methyl}-4-methyl-5-(2-methylpyridin-4-yl)-1,3-oxazolidin-2-one and (4R,5S)-3-{[4'-fluoro-5'-isopropyl-2'-methoxy-4-(trifluoromethyl)biphenyl-2-yl]methyl}-4-methyl-5-(2-methylpyridin-4-yl)-1,3-oxazolidin-2-one. $R_f$=0.22 (50% EtOAc in hexanes). LCMS calc.=517.2; found=517.1 $(M+1)^+$. $^1H$ NMR (500 MHz, $CDCl_3$, 1:1 mixture of atropisomers) δ 8.48 (d, J=4.9 Hz, 1H), 7.69 (s, 0.5H), 7.61 (s, 1H), 7.60 (s, 0.5H), 7.33 (m, 1H), 7.05 (s, 1H), 6.99-6.93 (m, 2H), 6.69 (d, J=3.2 Hz, 1H), 6.66 (d, J=3.2 Hz, 1H), 5.40 (d, J=8.1 Hz, 0.5H), 5.24 (d, J=8.1 Hz, 0.5H), 4.79 (d, J=15.9 Hz, 0.5H), 4.74 (d, J=15.9 Hz, 0.5H), 4.13 (d, J=15.9 Hz, 0.5H), 3.89 (d, J=15.9 Hz, 0.5H), 3.78-3.66 (m, 1H), 3.75 (s, 3H), 3.23-3.17 (m, 1H), 2.56 (s, 3H), 1.25-1.17 (m, 6H), 0.53 (d, J=6.5 Hz, 1.5H), 0.39 (d, J=6.5 Hz, 1.5H).

Following the general procedures outlined above, the compounds in Table 10 were prepared:

TABLE 10

| Example | R | LCMS (M + 1)+ |
|---|---|---|
| 267 | ![structure with oxazolidinone and pyridine N-oxide] | 519.3 |
| 268 | ![structure with oxazolidinone and 6-chloropyridin-2-yl] | 537.3, 539.2 |

Following the general procedures outlined above, the compounds in Table 11 were prepared:

TABLE 11
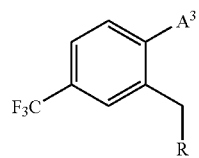
| Example | R | A³ | LCMS (M + 1)⁺ |
|---|---|---|---|
| 269 | (4-methyl-2-oxo-oxazolidin-3-yl with 3,5-dichlorophenyl at 5-position) | 2-Cl, 4-F, 5-methyl phenyl | 546.1, 548.1, 550.1 |
| 270 | (4-methyl-2-oxo-oxazolidin-3-yl with 3,5-dichlorophenyl at 5-position) | 2-Cl, 5-Cl phenyl | 548.1, 550.1, 552.1, 554.1 |
| 271 | (4-methyl-2-oxo-oxazolidin-3-yl with 3,5-difluorophenyl at 5-position) | 2-Cl, 4-F, 5-methyl phenyl | 514.2, 516.2 |
| 272 | (4-methyl-2-oxo-oxazolidin-3-yl with 3,5-difluorophenyl at 5-position) | 2-Cl, 5-Cl phenyl | 516.2, 518.1, 520.2 |

Following the general procedures outlined above, the compounds in Table 12 were prepared:

TABLE 12

| Example | R | LCMS (M + 1)+ |
|---|---|---|
| 273 | | 518.2 |
| 274 | | 572.2 |
| 275 | | 492.1 |
| 276 | | 506.2 |
| 277 | | 495.0, 497.0 |
| 278 | | 502.0, 504.0, 506.1 |

TABLE 12-continued

| Example | R | LCMS (M + 1)+ |
|---|---|---|
| 279 | | 495.0, 497.0 |
| 280 | | 489.0, 491.0 |

Example 281

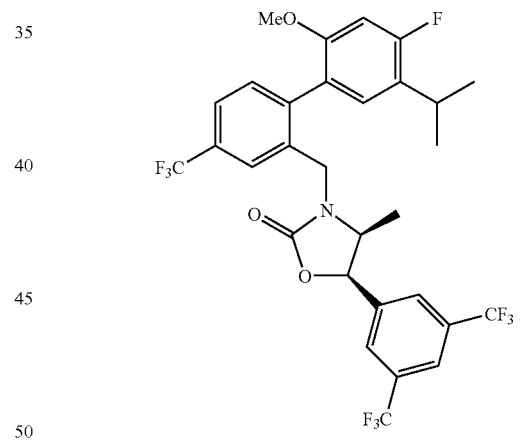

(4S,5R)-5-[3,5-bis(trifluoromethyl)phenyl]-3-{[4'-fluoro-2'-hydroxy-5'-isopropyl-4-(trifluoromethyl)biphenyl-2-yl]-methyl}-4-methyl-1,3-oxazolidin-2-one Step A: 4-fluoro-2'-(iodomethyl)-5-isopropyl-4'-(trifluoromethyl)biphenyl-2-ol A solution of [4'-fluoro-5'-isopropyl-2'-methoxy-4-(trifluoromethyl)biphenyl-2-yl]methanol (71.5 mg, 0.209 mmol) and iodine (610 mg, 2.40 mmol) in phenyltrimethylsilane (877 µL) was heated at 110° C. in a sealed tube overnight. The reaction was cooled to room temperature, diluted with 1N HCl (10 mL) and extracted with EtOAc (3×20 mL). The combined extracts were washed with 10% $Na_2S_2O_3$ (20 mL), dried (Na₂SO₄) and concentrated in vacuo to give the crude product. This was purified by flash chromatography (Si, 12×160 mm, 0-20% EtOAc in hexanes gradient) to afford 4-fluoro-2'-(iodomethyl)-5-isopropyl-4'-(trifluoromethyl)biphenyl-2-ol. $R_f$=0.65 (20% EtOAc in hexanes). ¹H NMR (500 MHz, CDCl₃) δ 7.81 (s, 1H), 7.60 (d, J=7.9 Hz, 1H), 7.34 (d, J=7.9 Hz, 1H), 7.10 (d, J=8.3 Hz, 1H), 6.69 (d, J=11.1 Hz, 1H), 4.82 (s, 1H), 4.41 (d, J=9.4 Hz, 1H), 4.23 (d, J=9.3 Hz, 1H), 3.27-3.19 (m, 1H), 1.27 (br s, 6H).

Step B: 2-{[4-fluoro-2'-(iodomethyl)-5-isopropyl-4'-(trifluoromethyl)biphenyl-2-yl]oxy}tetrahydro-2H-pyran p-Toluenesulfonic acid (2.8 mg, 0.0145 mmol) was added to a solution of 4-fluoro-2'-(iodomethyl)-5-isopropyl-4'-(trifluoromethyl)biphenyl-2-ol (63.4 mg, 0.145 mmol) and 3,4-dihydro-2H-pyran (60.8 mg, 66 µL, 0.723 mmol) in dry CH₂Cl₂ (7.2 mL) at room temperature under N₂ and the reaction was stirred for 3 days. The reaction mixture was diluted with saturated NaHCO₃ (20 mL) and extracted with CH₂Cl₂ (3×20 mL). The combined extracts were dried (Na₂SO₄) and concentrated in vacuo to give the crude product. This was purified by flash chromatography (Si, 12×160 mm, 0-20% EtOAc in hexanes gradient) to afford 2-{[4-fluoro-2'-(iodomethyl)-5-isopropyl-4'-(trifluoromethyl)biphenyl-2-yl]oxy}tetrahydro-2H-pyran. $R_f$=0.74 (10% EtOAc in hexanes). ¹H NMR (500 MHz, CDCl₃) δ 7.75 (s, 1H), 7.62 (d, J=8.3 Hz, 0.5H), 7.59 (d, J=8.3 Hz, 0.5H), 7.53 (t, J=7.3 Hz, 0.5H), 7.41 (s, 0.5H), 7.32 (d, J=7.9 Hz, 0.5H), 7.25 (d, J=7.9 Hz, 0.5H), 7.15 (t, J=9.4 Hz, 0.5H), 6.99 (d, J=12.2 Hz, 0.5H), 6.94 (d, J=12.2 Hz, 0.5H), 6.69 (d, J=11.0 Hz, 0.5H), 5.37 (s, 0.5H), 5.23 (s, 0.5H), 5.13 (s, 1H), 4.45 (d, J=9.6 Hz, 0.5H), 4.40 (d, J=9.6 Hz, 0.5H), 4.31 (d, J=9.6 Hz, 0.5H), 4.23 (d, J=9.6 Hz, 0.5H) 3.76 (m, 0.5H), 3.66-3.54 (m, 1.5H), 3.29-3.21 (m, 1H), 1.68-1.44 (m, 4H) 1.32-1.26 (m, 6H).

Step C: (4S,5R)-5-[3,5-bis(trifluoromethyl)phenyl]-3-{[4'-fluoro-2'-hydroxy-5'-isopropyl-4-(trifluoromethyl)biphenyl-2-yl]-methyl}-4-methyl-1,3-oxazolidin-2-one Sodium hydride (60% dispersion in mineral oil, 1.9 mg, 0.0485 mmol) was added to a stirred solution of (4S,5R)-5-[3,5-bis(trifluoromethyl)phenyl]-4-methyl-1,3-oxazolidin-2-one in dry DMF (1 mL) and the reaction was stirred for 30 min, A solution of 2-{[4-fluoro-2'-(iodomethyl)-5-isopropyl-4'-(trifluoromethyl)biphenyl-2-yl]oxy}tetrahydro-2H-pyran (16.9 mg, 0.324 mmol) in dry DMF (1 mL) was added by cannula and the reaction was stirred at room temperature overnight. The reaction was diluted with saturated NH₄Cl (10 mL) and water (5 mL) and extracted with EtOAc (3×20 mL). The combined extracts were dried (Na₂SO₄) and concentrated in vacuo to give the crude product. A solution of the crude product and p-toluenesulfonic acid (0.6 mg, 0.00324 mmol) in MeOH (5 mL) was stirred at room temperature overnight. The reaction mixture was concentrated in vacuo to give the crude product. This was purified by flash chromatography (Si, 12×160 mm, 0-35% EtOAc in hexanes gradient) to afford (4S,5R)-5-[3,5-bis(trifluoromethyl)phenyl]-3-{[4'-fluoro-2'-hydroxy-5'-isopropyl-4-(trifluoromethyl)biphenyl-2-yl]methyl}-4-methyl-1,3-oxazolidin-2-one. $R_f$=0.33 (20% EtOAc in hexanes). LCMS calc.=624.2; found=624.3 (M+1)⁺. ¹H NMR (500 MHz, CDCl₃, 1:1 mixture of atropisomers) δ 7.86 (s, 1H), 7.67 (m, 4H), 7.42 (d, J=7.1 Hz, 0.5H), 7.41 (d, J=7.1 Hz, 0.5H), 6.95 (d, J=7.3 Hz, 0.5H), 6.94 (d, J=7.3 Hz, 0.5H), 6.70 (d, J=5.6 Hz, 0.5H), 6.68 (d, J=5.6 Hz, 0.5H), 5.66 (d, J=8.0 Hz, 0.5H), 5.36 (d, J=8.1 Hz, 0.5H), 4.93 (d, J=15.8 Hz, 0.5H), 4.88 (d, J=15.8 Hz, 0.5H), 4.18 (d, J=15.8 Hz, 0.5H), 4.00 (d, J=15.8 Hz, 0.5H), 3.87-3.83 (m, 0.5H), 3.77-3.71 (m, 0.5H), 3.22-3.14 (m, 1H), 1.77 (br s, 1H), 1.27-1.17 (m, 6H), 0.57 (d, J=6.5 Hz, 1.5H), 0.45 (d, J=6.5 Hz, 1.5H).

Following the general procedures outlined above, the compounds in Table 13 were prepared:

TABLE 13

| Example | R | LCMS (M + 1)⁺ |
|---------|---|---------------|
| 282 | (structure shown) | 624.3 |

Example 283

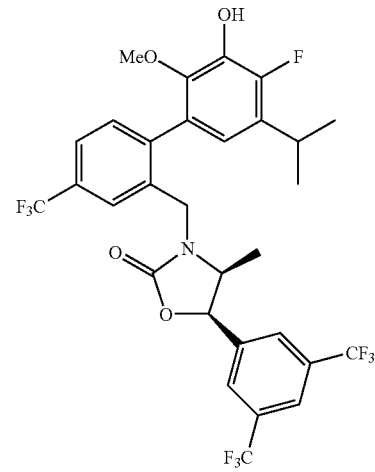 [SMILES: COc1c(-c2ccc(C(F)(F)F)cc2CN2C(=O)O[C@H](c3cc(C(F)(F)F)cc(C(F)(F)F)c3)[C@@H]2C)cc(C(C)C)c(F)c1O]

(4S,5R)-5-[3,5-bis(trifluoromethyl)phenyl]-3-{[4'-fluoro-3'-hydroxy-5'-isopropyl-2'-methoxy-4-(trifluoromethyl)biphenyl-2-yl]methyl}-4-methyl-1,3-oxazolidin-2-one

Step A: tert-butyl{[4'-fluoro-5'-isopropyl-2'-methoxy-4-(trifluoromethyl)biphenyl-2-yl]-methoxy}dimethylsilane tert-Butyldimethylsilyl chloride (0.48 g, 3.21 mmol) and imidazole (0.50 g, 7.30 mmol) were added successively to a stirred solution of [4'-fluoro-5'-isopropyl-2'-methoxy-4-(trifluoromethyl)biphenyl-2-yl]methanol (1.00 g, 2.93 mmol) in dry $CH_2Cl_2$ (13.4 mL) at room temperature under $N_2$ and the reaction was stirred overnight. Water (50 mL) was added and the mixture was extracted with EtOAc (3×50 mL). The combined extracts were dried ($MgSO_4$) and concentrated in vacuo to give the crude product. This was purified by flash chromatography (Si, 25×160 mm, 1% EtOAc in hexanes) to afford tert-butyl {[4'-fluoro-5'-isopropyl-2'-methoxy-4-(trifluoromethyl)biphenyl-2-yl]methoxy}dimethylsilane as a colorless oil. $R_f$=0.16 (1% EtOAc in hexanes). LCMS calc.=457.2; found=457.2 (M+1)$^+$. $^1$H NMR (500 MHz, $CDCl_3$) δ 7.94 (s, 1H), 7.57 (d, J=7.8 Hz, 1H), 7.29 (d, J=7.6 Hz, 1H), 7.00 (d, J=8.6 Hz, 1H), 6.69 (d, J=12.1 Hz, 1H), 4.63 (br s, 1H), 4.50 (br s, 1H), 3.75 (s, 3H), 3.29-3.21 (m, 1H), 1.28 (d, J=6.9 Hz, 6H), 0.93 (s, 9H), 0.03 (s, 6H).

Step B: 2'-({[tert-butyl(dimethyl)silyl]oxy}methyl)-4-fluoro-5-isopropyl-2-methoxy-4'-(trifluoromethyl)biphenyl-3-ol n-Butyllithium (1.6M in hexanes, 261 μL 0.417 mmol) was added dropwise over 30-45 min with a syringe pump to a stirred solution of tert-butyl{[4'-fluoro-5'-isopropyl-2'-methoxy-4-(trifluoromethyl)biphenyl-2-yl]methoxy}dimethylsilane (200 mg, 0.438 mmol) in dry THF (0.5 mL) at −78° C. under $N_2$. The reaction was stirred for a further 2 h at −78° C. after the addition to give a violet colored solution. Trimethyl borate (43.4 mg, 47 μL, 0.417 mmol) was added dropwise and the reaction was stirred at −78° C. for 3 h. The reaction mixture was warmed to 0° C. and acetic acid (25.1 mg, 24 μL, 0.626 mmol) was added quickly followed by 30% aqueous hydrogen peroxide (52 μL, 0.459 mmol) dropwise. The reaction was stirred at room temperature overnight, diluted with water (10 mL) and extracted with $Et_2O$ (3×20 mL). The combined extracts were washed with 50% saturated $FeSO_4$ (20 mL), dried ($Na_2SO_4$) and concentrated in vacuo to give the crude product. This was purified by flash chromatography (Si, 12×160 mm, 0-100% EtOAc in hexanes gradient) to afford T-({[tert-butyl(dimethyl)silyl]oxy}methyl)-4-fluoro-5-isopropyl-2-methoxy-4'-(trifluoromethyl)biphenyl-3-ol. $R_f$=0.32 (10% EtOAc in hexanes). LCMS calc.=473.1; found=473.2 (M+1)$^+$. $^1$H NMR (600 MHz, $CDCl_3$) δ 7.95 (s, 1H), 7.56 (d, J=7.8 Hz, 1H), 7.35 (d, J=7.9 Hz, 1H), 6.53 (d, J=7.8 Hz, 1H), 5.65 (s, 1H), 4.68 (br s, 1H), 4.54 (br s, 1H), 3.42 (s, 3H), 3.26-3.20 (m, 1H), 1.25 (d, J=6.9 Hz, 6H), 0.90 (s, 9H), 0.02 (s, 6H).

Step C: 4-fluoro-2'-(hydroxymethyl)-5-isopropyl-2-methoxy-4'-(trifluoromethyl)biphenyl-3-ol tert-Butylammonium fluoride (1M in THF, 179 μL, 0.179 mmol) was added dropwise to a stirred solution of 2'-({[tert-butyl(dimethyl)silyl]oxy}methyl)-4-fluoro-5-isopropyl-2-methoxy-4'-(trifluoromethyl)biphenyl-3-ol (76.8 mg, 0.163 mmol) in THF (2 mL) at 0° C. and the reaction was allowed to warm to room temperature overnight. Saturated $NH_4Cl$ (10 ml) was added and the mixture was extracted with EtOAc (3×20 mL). The combined extracts were dried ($Na_2SO_4$) and concentrated in vacuo to give the crude product. This was purified by flash chromatography (Si, 12×160 mm, 0-40% EtOAc in hexanes gradient) to afford 4-fluoro-2'-(hydroxymethyl)-5-isopropyl-2-methoxy-4'-(trifluoromethyl)biphenyl-3-ol. $R_f$=0.26 (20% EtOAc in hexanes). $^1$H NMR (600 MHz, $CDCl_3$) δ 7.85 (s, 1H), 7.63 (d, J=7.9 Hz, 1H), 7.41 (d, J=8.0 Hz, 1H), 6.53 (d, J=7.7 Hz, 1H), 4.50 (br s, 1H), 4.47 (s, 1H), 3.42 (s, 3H), 3.25-3.19 (m, 1H), 1.24 (br s, 6H).

Step D: 2'-(bromomethyl)-4-fluoro-5-isopropyl-2-methoxy-4'-(trifluoromethyl)biphenyl-3-ol A solution of triphenylphosphine (102.8 mg, 0.392 mmol) in dry $CH_2Cl_2$ (2 mL) was added by cannula to a stirred solution of carbon tetrabromide (130 mg, 0.392 mmol) and 4-fluoro-2'-(hydroxymethyl)-5-isopropyl-2-methoxy-4'-(trifluoromethyl)biphenyl-3-ol (58.5 mg, 0.163 mmol) in dry $CH_2Cl_2$ (2 mL) at 0° C. under $N_2$ and the reaction was stirred at room temperature overnight. The reaction mixture was concentrated in vacuo to give the crude product. This was purified by flash chromatography (Si, 12×160 mm, 0-40% EtOAc in hexanes gradient) to afford 2'-(bromomethyl)-4-fluoro-5-isopropyl-2-methoxy-4'-(trifluoromethyl)biphenyl-3-ol. $R_f$=0.55 (20% EtOAc in hexanes). $^1$H NMR (600 MHz, $CDCl_3$) δ 7.84 (s, 1H), 7.61 (d, J=7.9 Hz, 1H), 7.42 (d, J=8.0 Hz, 1H), 6.69 (d, J=7.8 Hz, 1H), 5.59 (s, 1H), 4.50 (d, J=9.6 Hz, 1H), 4.39 (d, J=9.7 Hz, 1H), 3.47 (s, 3H), 3.29-3.23 (m, 1H), 1.27 (d, J=6.9 Hz, 6H).

Step E: 2-{[2'-(bromomethyl)-4-fluoro-5-isopropyl-2-methoxy-4'-(trifluoromethyl)biphenyl-3-yl]oxy}tetrahydro-2H-pyran 3,4-Dihydro-2H-pyran (51.9 mg, 56 μL, 0.617 mmol) was added to a stirred solution of p-toluenesulfonic acid (2.3 mg, 0.0123 mmol) and 2'-(bromomethyl)-4-fluoro-5-isopropyl-2-methoxy-4'-(trifluoromethyl)biphenyl-3-ol (52.0 mg, 0.123 mmol) in dry $CH_2Cl_2$ (6.1 mL) at room temperature under $N_2$ and the reaction was stirred overnight. The reaction mixture was diluted with $CH_2Cl_2$ (45 mL) and washed with saturated $NaHCO_3$ (5 mL) and 30% saturated $Na_2SO_3$ (5 mL), dried ($Na_2SO_4$) and concentrated in vacuo to give the crude product. This was purified by flash chromatography (Si, 12×160 mm, 0-40% EtOAc in hexanes gradient) to afford 2-{[2'-(bromomethyl)-4-fluoro-5-isopropyl-2-methoxy-4'-(trifluoromethyl)biphenyl-3-yl]oxy}tetrahydro-2H-pyran. $R_f$=0.59 (20% EtOAc in hexanes). $^1$H NMR (600 MHz, $CDCl_3$) 7.82 (s, 1H), 7.60 (d, J=7.0 Hz, 1H), 7.41 (d, J=8.0 Hz, 1H), 6.67 (d, J=7.8 Hz, 1H), 5.77 (s, 1H), 4.97 (dd, J=4.9, 2.9 Hz, 1H), 4.49 (d, J=9.8 Hz, 1H), 4.37 (d, J=9.8 Hz, 1H), 3.89-3.87 (m, 1H), 3.61-3.49 (m, 1H), 3.46 (s, 3H), 3.27-3.21 (m, 1H), 1.89-1.83 (m, 1H), 1.78-1.70 (m, 1H) 1.64-1.48 (m, 3H), 1.26 (d, J=6.8 Hz, 6H).

Step F: (4S,5R)-5-[3,5-bis(trifluoromethyl)phenyl]-3-{[4'-fluoro-3'-hydroxy-5'-isopropyl-2'-methoxy-4-(trifluoromethyl)biphenyl-2-yl]methyl}-4-methyl-1,3-oxazolidin-2-one Sodium hydride (60% dispersion in mineral oil, 14.7 mg, 0.368 mmol) was added to a stirred solution of (4S,5R)-5-[3,5-bis(trifluoromethyl)phenyl]-4-methyl-1,3-oxazolidin-2-one (57.7 mg, 0.184 mmol) in dry THF (2 mL) at room temperature. After 30 min a solution of 2'-(bromomethyl)-4-fluoro-5-isopropyl-2-methoxy-4'-(trifluoromethyl)biphenyl-3-ol (62.0 mg, 0.123 mmol) in dry THF (2 mL) was added by cannula and the reaction mixture was stirred overnight. Saturated $NH_4Cl$ (10 mL) was added and the mixture was extracted with EtOAc (3×20 mL). The combined extracts were dried ($Na_2SO_4$) and concentrated in vacuo to give the crude product. This was purified by flash chromatography (Si, 12×160 mm, 0-40% EtOAc in hexanes gradient) to afford (4S,5R)-5-[3,5-bis(trifluoromethyl)phenyl]-3-{[4'-fluoro-3'- hydroxy-5'-isopropyl-2'-methoxy-4-(trifluoromethyl)biphenyl-2-yl]methyl}-4-methyl-1,3-oxazolidin-2-one. R$_f$=0.25 (20% EtOAc in hexanes). LCMS calc.=654.2; found=654.2 (M+1)$^+$. $^1$H NMR (500 MHz, CDCl$_3$, 1:1 mixture of atropisomers) δ 7.86 (m, 1H), 7.73-7.63 (m, 4H) 7.44 (m, 1H), 6.55 (d, J=7.6 Hz, 0.5H), 6.52 (d, J=7.7 Hz, 0.5H), 5.71 (br s, 1H), 5.60 (d, J=8.0 Hz, 0.5H), 5.54 (d, J=8.0 Hz, 0.5H), 4.87 (d, J=16.0 Hz, 0.5H), 4.72 (d, J=16.1 Hz, 0.5H), 4.23 (d, J=16.1 Hz, 0.5H), 3.98 (d, J=15.9 Hz, 0.5H), 3.93-3.85 (m, 0.5H), 3.77-3.71 (m, 0.5H), 3.51 (s, 1.5H), 3.47 (s, 1.5H), 3.25-3.17 (m, 1H), 1.26-1.18 (m, 6H), 0.58 (d, J=6.5 Hz, 1.5H), 0.38 (d, J=6.6 Hz, 1.5H).

Example 284

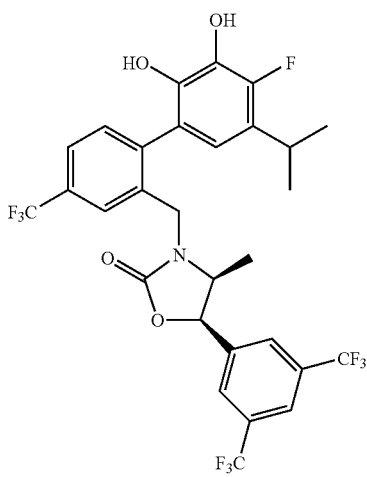 [SMILES: CC(C)c1cc(-c2ccc(C(F)(F)F)cc2CN2C(=O)O[C@H](c3cc(C(F)(F)F)cc(C(F)(F)F)c3)[C@@H]2C)c(O)c(O)c1F]

(4S,5R)-5-[3,5-bis(trifluoromethyl)phenyl]-3-{[4'-fluoro-2',3'-dihydroxy-5'-isopropyl-4-(trifluoromethyl)biphenyl-2-yl]methyl}-4-methyl-1,3-oxazolidin-2-one Boron tribromide (17.4 mg, 6.6 µL, 0.0692 mmol) was added to a stirred solution of (4S,5R)-5-[3,5-bis(trifluoromethyl)phenyl]-3-{[4'-fluoro-3'-hydroxy-5'-isopropyl-2'-methoxy-4-(trifluoromethyl)biphenyl-2-yl]methyl}-4-methyl-1,3-oxazolidin-2-one (22.6 mg, 0.0346 mmol) in dry CH$_2$Cl$_2$ (1 mL) at −78° C. at room temperature under N$_2$ and the reaction was stirred for 8 h. The reaction was diluted with water (5 mL) and extracted with EtOAc (3×20 mL). The combined extracts were dried (Na$_2$SO$_4$) and concentrated in vacuo to give the crude product. This was purified by chiral HPLC (IA column, 20×250 mm, 15% i-PrOH in heptane) to afford (4S,5R)-5-[3,5-bis(trifluoromethyl)phenyl]-3-{[4'-fluoro-2',3'-dihydroxy-5'-isopropyl-4-(trifluoromethyl)biphenyl-2-yl]methyl}-4-methyl-1,3-oxazolidin-2-one. R$_f$=0.24 (20% EtOAc in hexanes). LCMS calc.=640.2; found=640.2 (M+1)$^+$. $^1$H NMR (600 MHz, CDCl$_3$, 1:1 mixture of atropisomers) δ 7.85 (s, 1H), 7.70-7.62 (m, 4H), 7.41 (m, 1H), 6.52 (s, 0.5H), 6.51 (s, 0.5H), 6.20 (br s, 2H), 5.65 (d, J=7.9 Hz, 0.5H), 5.38 (d, J=8.0 Hz, 0.5H), 5.00 (d, J=15.5 Hz, 0.5H), 4.92 (d, J=15.6 Hz, 0.5H), 4.15 (d, J=15.5 Hz, 0.5H), 4.02 (d, J=15.6 Hz, 0.5H), 3.88 (t, J=6.7 Hz, 0.5H), 3.77 (t, J=6.7 Hz, 0.5H), 3.19-3.13 (m, 1H), 1.26-1.17 (m, 6H), 0.59 (d, J=6.1 Hz, 1.5H), 0.48 (d, J=6.2 Hz, 1.5H).

INTERMEDIATE 20

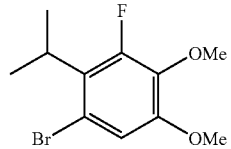

Step A:
2-(2-fluoro-3,4-dimethoxyphenyl)propan-2-ol

A solution of methylmagnesium chloride (3M in THF, 1.74 mL, 5.22 mmol) was added dropwise to a stirred solution of 1-(2-fluoro-3,4-dimethoxyphenyl)ethanone (*J. Chem. Soc. Perkin Trans.* 2 1994, 547-555) (646 mg, 3.26 mmol) in heptane (3.1 mL) and THF (1.4 mL) at −20° C. under N$_2$. The reaction was allowed to warm to room temperature and was stirred for 4 h. 50% Saturated NH$_4$Cl (20 mL) was added and the mixture was extracted with EtOAc (3×20 mL). The combined extracts were dried (Na$_2$SO$_4$) and concentrated in vacuo to give 2-(2-fluoro-3,4-dimethoxyphenyl)propan-2-ol as a colorless oil. LCMS calc.=197.1; found=197.1 (M−OH)$^+$. $^1$H NMR (600 MHz, CDCl$_3$) δ 7.14 (t, J=8.8 Hz, 1H), 6.61 (dd, J=8.8, 1.4 Hz, 1H), 3.86 (s, 3H), 3.83 (s, 3H), 2.56-2.25 (br s, 1H), 1.58 (s, 6H).

Step B: 2-fluoro-1-isopropyl-3,4-dimethoxybenzene

A suspension of 10% palladium on carbon (69.8 mg) in a solution of 2-(2-fluoro-3,4-dimethoxyphenyl)propan-2-ol (698 mg, 3.26 mmol) in 5N HCl (0.7 mL) and EtOH (5.6 mL) was stirred at room temperature under H$_2$ (15 psi) overnight. The mixture was filtered through a plug of Celite and washed with EtOAc (~75 mL). The filtrate was washed with 50% saturated brine (10 mL), dried (MgSO$_4$) and concentrated in vacuo to afford 2-fluoro-1-isopropyl-3,4-dimethoxybenzene. $^1$H NMR (500 MHz, CDCl$_3$) δ 6.86 (t, J=8.3 Hz, 1H), 6.63 (dd, J=8.7, 1.5 Hz, 1H), 3.89 (s, 3H), 3.84 (s, 3H), 3.19-3.11 (m, 1H), 1.22 (d, J=6.8 Hz, 6H).

Step C:
1-bromo-3-fluoro-2-isopropyl-4,5-dimethoxybenzene

Bromine (80.6 mg, 26 µL, 0.504 mmol) was added to a solution of 2-fluoro-1-isopropyl-3,4-dimethoxybenzene (50.0 mg, 0.252 mmol) and potassium acetate (49.5 mg, 0.504 mmol) in acetic acid (1 mL) at room temperature and the reaction was stirred overnight. The reaction was diluted with water (10 mL) and saturated Na$_2$SO$_3$ (10 mL), then extracted with EtOAc (3×20 mL). The combined extracts were washed with saturated NaHCO$_3$ (2×10 mL), dried (MgSO$_4$) and concentrated in vacuo to afford 1-bromo-3-fluoro-2-isopropyl-4,5-dimethoxybenzene. $^1$H NMR (600 MHz, CDCl$_3$) δ 6.86 (d, J=2.0 Hz, 1H), 3.87 (s, 3H), 3.81 (s, 3H), 3.43-3.34 (m, 1H), 1.31-1.29 (dd, J=7.1, 1.4 Hz, 6H).

Following the general procedures outlined above, the compounds in Table 14 were prepared:

TABLE 14

![Structure with A³ group, F₃C, oxazolidinone, and 3,5-bis(CF₃)phenyl]

| Example | A³ | LCMS (M + 1)⁺ |
|---|---|---|
| 285 | ![isopropyl, F, OMe, OMe - atropisomer A] | 668.1 |
| 286 | ![isopropyl, F, OMe, OMe - atropisomer B] | 668.1 |
| 287 | ![isopropyl, F, OH, OH - atropisomer A] | 640.1 |
| 288 | ![isopropyl, F, OH, OH - atropisomer B] | 640.1 |

Example 289

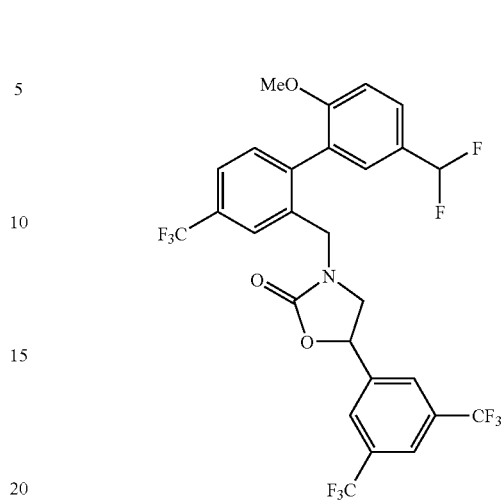

5-[3,5-bis(trifluoromethyl)phenyl]-3-{[5'-(difluoromethyl)-2'-methoxy-4-(trifluoromethyl)biphenyl-2-yl]methyl}-1,3-oxazolidin-2-one Step A: 2'-({5-[3,5-bis(trifluoromethyl)phenyl]-2-oxo-1,3-oxazolidin-3-yl}methyl)-6-methoxy-4'-(trifluoromethyl)biphenyl-3-carbaldehyde A mixture of 5-[3,5-bis(trifluoromethyl)phenyl]-3-[2-iodo-5-(trifluoromethyl)benzyl]-1,3-oxazolidin-2-one (Example 66, 50 mg; 0.0858 mmol), 5-formyl-2-methoxyphenyl boronic acid (46 mg; 0.257 mmol), tetrakis(triphenylphosphine)palladium (0) (12 mg; 0.0103 mmol), and sodium carbonate (74 mg) in benzene/ethanol/water (2.8/0.4/1.2 mL) was heated at reflux for 60 h. The reaction was diluted with EtOAc (30 mL) and washed successively with $H_2O$ (10 mL) and brine (10 mL), dried over $MgSO_4$, filtered, and concentrated in vacuo. The crude product was purified by flash silica gel chromatography (0-50% EtOAc/hexanes gradient) to afford 2'-({5-[3,5-bis(trifluoromethyl)phenyl]-2-oxo-1,3-oxazolidin-3-yl}methyl)-6-methoxy-4'-(trifluoromethyl)biphenyl-3-carbaldehyde as a yellow oil. LCMS=592.1 (M+1)⁺. $^1$H NMR (CDCl₃, 500 MHz, mixture of atropisomers): δ 9.98 (s, 1 H), 7.99-7.96 (m, 1 H), 7.90 (s, 1 H), 7.75 (s, 2 H), 7.69-7.64 (m, 2 Hz), 7.53 (s, 1 H), 7.41-7.38 (m, 1 H), 7.17-7.14 (m, 1 H), 5.37 (t, J=8.2 Hz, 1 H), 4.59 (d, J=15.3 Hz, 1 H), 4.37 (d, J=15.6 Hz, 1 H), 3.92 (s, 3 H), 3.67-3.64 (m, 1 Hz), 3.19-3.16 (m, 1 H).

Step B: 5-[3,5-bis(trifluoromethyl)phenyl]-3-{[5'-(difluoromethyl)-2'-methoxy-4-(trifluoromethyl)biphenyl-2-yl]methyl}-1,3-oxazolidin-2-one Diethylaminosulfur trifluoride (22 μL, 0.1675 mmol) was added dropwise to a stirred solution of 2'-({5-[3,5-bis(trifluoromethyl)phenyl]-2-oxo-1,3-oxazolidin-3-yl}methyl)-6-methoxy-4'-(trifluoromethyl)biphenyl-3-carbaldehyde (Step A, 50 mg, 0.0838 mmol) in $CH_2Cl_2$ (1 mL) at 0° C. The reaction stirred at room temperature for 14 h. The reaction was quenched with $H_2O$ at 0° C., diluted with $CH_2Cl_2$ (10 mL), washed with $H_2O$ (10 mL) and brine (10 mL), dried over $Na_2SO_4$, filtered, and concentrated in vacuo. The crude product was purified by flash silica gel chromatography (0-25% EtOAc/hexanes gradient) to afford 5-[3,5-bis(trifluoromethyl)phenyl]-3-{[5'-(difluoromethyl)-2'-methoxy-4-(trifluoromethyl)biphenyl-2-yl]methyl}-1,3-oxazolidin-2-one as a clear glass. LCMS=594.2 (M−19)+. 1H NMR (benzene-d6, 500 MHz, mixture of atropisomers): δ 7.64 (s, 1 H), 7.38-7.36 (m, 2 H), 7.30-7.26 (m, 2 H), 7.14-7.11 (m, 2 H), 6.85 (d, J=8 Hz, 1 H), 6.45 (d, J=8.5 Hz, 1 H), 6.37-6.13 (m, 1 H), 4.46-4.38 (m, 2 H), 3.79-3.76 (m, 1 H), 3.21 (s, 3 H), 2.36 (t, J=8.7 Hz, 1 H), 2.05 (t, J=8.4 Hz, 1 H).

This compound was separated into its enantiomers (5S)-5-[3,5-bis(trifluoromethyl)phenyl]-3-{[5'-(difluoromethyl)-2'-methoxy-4-(trifluoromethyl)biphenyl-2-yl]methyl}-1,3-oxazolidin-2-one and (5R)-5-[3,5-bis(trifluoromethyl)phenyl]-3-{[5'-(difluoromethyl)-2'-methoxy-4-(trifluoromethyl)biphenyl-2-yl]methyl}-1,3-oxazolidin-2-one using chiral HPLC (15% IPA/heptane, AS column).

Example 290

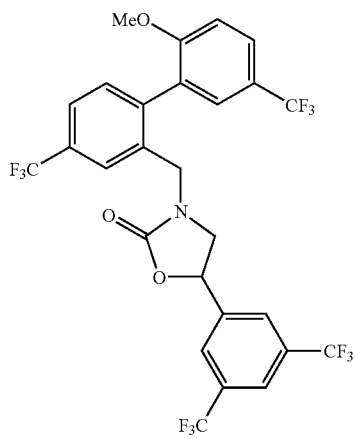 [SMILES: COc1ccc(C(F)(F)F)cc1-c1ccc(C(F)(F)F)cc1CN1CC(c2cc(C(F)(F)F)cc(C(F)(F)F)c2)OC1=O]

5-[3,5-bis(trifluoromethyl)phenyl]-3-{[2'-methoxy-4,5'-bis(trifluoromethyl)biphenyl-2-yl]methyl}-1,3-oxazolidin-2-one Step A:
2-iodo-1-methoxy-4-(trifluoromethyl)benzene To a stirred solution of 2-methoxy-5-(trifluoromethyl) aniline (500 mg, 2.62 mmol) in CH2Cl2 (10 mL) was added t-butyl nitrite (467 μL, 3.93 mmol). The reaction was stirred for 5 min prior to addition of iodine (1.3 g, 5.24 mmol), and then heated at 70° C. for 2 h. The reaction was cooled, diluted with CH2Cl2 (10 mL), washed with sat. Na2S2O3 (10 mL) and brine (10 mL), dried over Na2SO4, filtered and concentrated in vacuo. The crude product was purified by flash silica gel chromatography (hexanes) to afford 2-iodo-1-methoxy-4-(trifluoromethyl)benzene as a light yellow solid. 1H NMR (CDCl3, 500 MHz): δ 8.05 (d, J=2 Hz, 1 H), 7.61 (dd, J=8.7, 1.8 Hz, 1 H), 6.89 (d, J=8.7 Hz, 1 H), 3.97 (s, 3 H).

Step B:
[2-methoxy-5-(trifluoromethyl)phenyl]boronic acid n-Butyl lithium (1.6M in hexanes, 456 μL, 0.729 mmol) was added dropwise to a stirred solution of 2-iodo-1-methoxy-4-(trifluoromethyl)benzene (Step A, 200 mg, 0.662 mmol) in THF (1.5 mL) at −78° C. under an atmosphere of nitrogen. The reaction stirred at −78° C. for 30 min prior to the addition of triisopropyl borate (458 μL, 1.986 mmol). The reaction stirred an additional 2 h at −78° C. and was quenched with sat. NH4Cl. The mixture was extracted with CH2Cl2 and the organic phase was washed with NaHCO3 (15 mL) and brine (15 mL), dried (Na2SO4), filtered, conc. in vacuo to afford [2-methoxy-5-(trifluoromethyl)phenyl]boronic acid which was carried on without purification.

Step C: 5-[3,5-bis(trifluoromethyl)phenyl]-3-{[2'-methoxy-4,5'-bis(trifluoromethyl)-biphenyl-2-yl]-methyl}-1,3-oxazolidin-2-one 5-[3,5-bis(trifluoromethyl)phenyl]-3-[2-iodo-5-(trifluoromethyl)benzyl]-1,3-oxazolidin-2-one (Example 66, 100 mg; 0.171 mmol) was treated with [2-methoxy-5-(trifluoromethyl)phenyl]boronic acid (Step B, 113 mg; 0.514 mmol), tetrakis(triphenylphosphine)palladium (0) (24 mg; 0.0206 mmol), and sodium carbonate (148 mg) as described in Example 291 to afford 5-[3,5-bis(trifluoromethyl)phenyl]-3-{[2'-methoxy-4,5'-bis(trifluoromethyl)-biphenyl-2-yl]methyl}-1,3-oxazolidin-2-one as a clear glass. LCMS=612.1 (M−19)+. 1H NMR (benzene-d6, 500 MHz, mixture of atropisomers): δ 7.61 (s, 1H), 7.40-7.36 (m, 1 H), 7.31 (s, 1 H), 7.27-7.23 (m, 4 H), 6.74-6.72 (m, 1 H), 6.35 (d, J=8.7 Hz, 1 H), 4.42-4.32 (m, 2 H), 3.70 (d, J=15.8 Hz, 1 H), 3.14 (s, 3 H), 2.28 (t, J=8.7 Hz, 1 H), 1.98 (t, J=8.2 Hz, 1 H).

This compound was separated into its enantiomers (5R)-5-[3,5-bis(trifluoromethyl)phenyl]-3-{[2'-methoxy-4,5'-bis(trifluoromethyl)-biphenyl-2-yl]methyl}-1,3-oxazolidin-2-one and (5S)-5-[3,5-bis(trifluoromethyl)phenyl]-3-{[2'-methoxy-4,5'-bis(trifluoromethyl)-biphenyl-2-yl]methyl}-1,3-oxazolidin-2-one using chiral HPLC (5% EtOH/heptane, AS column).

INTERMEDIATE 21

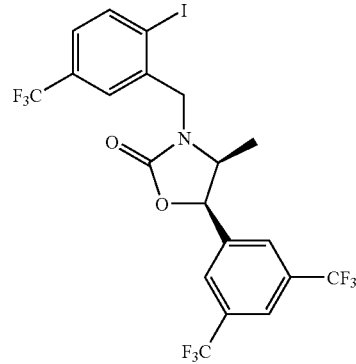

(4S,5R)-5-[3,5-bis(trifluoromethyl)phenyl]-3-[2-iodo-5-(trifluoromethyl)benzyl]-4-methyl-1,3-oxazolidin-2-one (4S,5R)-5-[3,5-bis(trifluoromethyl)phenyl]-4-methyl-1,3-oxazolidin-2-one (400 mg, 1.28 mmol) was treated with NaH (60% in oil, 128 mg, 3.2 mmol) and 2-(bromomethyl)-1-iodo-4-(trifluoromethyl)benzene (Example 70, 466 mg, 1.28 mmol) as described in Example 66 to afford (4S,5R)-5-[3,5-bis(trifluoromethyl)phenyl]-3-[2-iodo-5-(trifluoromethyl)benzyl]-4-methyl-1,3-oxazolidin-2-one as a white solid. LCMS=598.0 (M+1)+. 1H NMR (CDCl3, 500 MHz): δ 8.06 (d, J=8.2 Hz, 1 H), 7.93 (s, 1 H), 7.82 (s, 2 H), 7.61 (s, 1 H), 7.33 (dd, J=8.2, 1.4 Hz, 1 H), 5.79 (d, J=7.8 Hz, 1 H), 4.91 (d, J=16 Hz, 1 H), 4.40 (d, J=16 Hz, 1 H), 4.16-4.06 (m, 1 H), 0.83 (d, J=6.4 Hz, 3 H).

Example 291

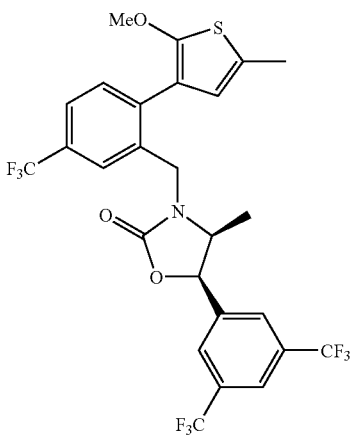 [SMILES: COc1sc(C)cc1-c1ccc(C(F)(F)F)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-[2-(2-methoxy-5-methyl-3-thienyl)-5-(trifluoromethyl)benzyl]-4-methyl-1,3-oxazolidin-2-one

Step A: 3,5-dibromo-2-methoxythiophene

To a stirred solution of 2-methoxythiophene (1 g, 8.76 mmol) in $CH_2Cl_2$ (18 mL) at 0° C. was added N-bromosuccinimide (3.12 g, 17.52 mmol) slowly. The reaction was allowed to warm to room temperature and stirred for 14 h. The reaction was cooled in an ice bath and filtered. The filtrate was washed with sat. $NaHCO_3$ (2×25 mL). The aqueous layer was neutralized with 1N HCl and extracted with $CHCl_3$ (3×25 mL). The combined organic layers were washed with brine (25 mL), dried ($Na_2SO_4$), filtered and concentrated in vacuo. The crude product was purified by flash silica gel chromatography (hexanes) to afford 3,5-dibromo-2-methoxythiophene as a pale pink oil. LCMS=272.9 $(M+)^+$.

Step B: 3-bromo-2-methoxy-5-methylthiophene n-Butyl lithium (2.0M in pentane, 0.97 mL, 1.93 mmol) was added to a stirred solution of 3,5-dibromo-2-methoxythiophene (Step A, 500 mg, 1.84 mmol) in THF (5 mL) at −78° C. under an atmosphere of $N_2$. The reaction stirred at −78° C. for 1 h prior to addition of methyl iodide (114 μL, 1.84 mmol). The reaction was allowed to warm to room temperature and stirred for 20 h. The solvent was removed under reduced pressure and the residue was partitioned between EtOAc (15 mL0 and $H_2O$ (15 mL). The aqueous layer was re-extracted with ether (2×15 mL) and the combined organic layers were washed with $H_2O$ (15 mL) and brine (15 mL), dried ($MgSO_4$), filtered and concentrated in vacuo. The crude product was purified by flash silica gel chromatography (hexanes) to afford 3-bromo-2-methoxy-5-methylthiophene as a yellow oil. $^1H$ NMR ($CDCl_3$, 500 MHz): δ 6.44 (s, 1 H), 3.95 (s, 3 H), 2.41 (s, 3 H).

Step C: (2-methoxy-5-methyl-3-thienyl)boronic acid

A stirred mixture of 3-bromo-2-methoxy-5-methylthiophene (Step B, 296 mg, 1.43 mmol) and triisopropyl borate (396 μL, 2.15 mmol) in toluene/THF (2.3/0.6 mL) was cooled to −70° C. under an atmosphere of $N_2$. n-Butyl lithium (2.0M in pentane, 1.07 mL, 2.15 mmol) was added dropwise via a syringe pump over 1 h. The reaction stirred at −70° C. for 40 min more and was quenched with 2N HCl (2 mL) at −20° C. The reaction was partitioned between EtOAc (15 mL) and $H_2O$ (15 mL). The aqueous layer was extracted with EtOAc (10 mL); the combined organic layers were washed with brine (15 mL), dried ($Na_2SO_4$), filtered, and concentrated in vacuo to afford (2-methoxy-5-methyl-3-thienyl)boronic acid as a yellow oil. This material was used without further purification.

Step D: (4S,5R)-5-[3,5-bis(trifluoromethyl)phenyl]-3-[2-(2-methoxy-5-methyl-3-thienyl)-5-(trifluoromethyl)benzyl]-4-methyl-1,3-oxazolidin-2-one (4S,5R)-5-[3,5-bis(trifluoromethyl)phenyl]-3-[2-iodo-5-(trifluoromethyl)benzyl]-4-methyl-1,3-oxazolidin-2-one (Intermediate 21, 13 mg; 0.0219 mmol) was treated with (2-methoxy-5-methyl-3-thienyl)boronic acid (Step C, 10.4 mg; 0.0657 mmol), tetrakis(triphenylphosphine)palladium (0) (3 mg; 0.0026 mmol), and sodium carbonate (20 mg) as described in Example 291 to afford (4S,5R)-5-[3,5-bis(trifluoromethyl)phenyl]-3-[2-(2-methoxy-5-methyl-3-thienyl)-5-(trifluoromethyl)benzyl]-4-methyl-1,3-oxazolidin-2-one as a yellow glass. LCMS=598.2 $(M+1)^+$. $^1H$ NMR (benzene-$d_6$, 500 MHz): δ 7.75 (s, 1 H), 7.57 (s, 1 H), 7.31-29 (m, 1H), 7.24 (s, 2 H), 7.12-7.10 (m, 1 H), 6.14 (s, 1 H), 4.96 (d, J=16 Hz, 1 H), 4.57 (d, J=8 Hz, 1 H), 3.99 (d, J=15.8 Hz, 1 H), 3.30 (s, 3 H), 2.95-2.92 (m, 1 H), 2.05 (s, 3 H), −0.28 (d, J=6.7 Hz, 3 H).

Following the general procedures outlined above, the compounds in Table 15 were prepared:

TABLE 15

| Compound | $A^3$ | LCMS |
|---|---|---|
| 292 | MeO, CF₂H substituted phenyl | 608.1 $(M-19)^+$ |
| 293 | MeO, F, methyl substituted phenyl | 610.1 $(M+1)^+$ |
| 294 | Cl, F, methyl substituted phenyl | 614.2 $(M+1)^+$ |

TABLE 15-continued

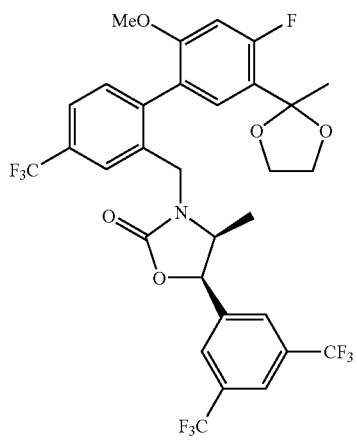 [SMILES: COc1cc(F)c(C2(C)OCCO2)cc1-c1ccc(C(F)(F)F)cc1CN1C(=O)O[C@H](c2cc(C(F)(F)F)cc(C(F)(F)F)c2)[C@@H]1C]

| Compound | $A^3$ | LCMS |
|---|---|---|
| 295 | MeO / F / NO$_2$ substituted phenyl | 682.1 (M + 42)$^+$ |
| 296 | Cl / Cl substituted thiophene | 622.2 (M + 1)$^+$ |
| 297 | MeO substituted thiophene | 584.2 (M + 1)$^+$ |

Example 298

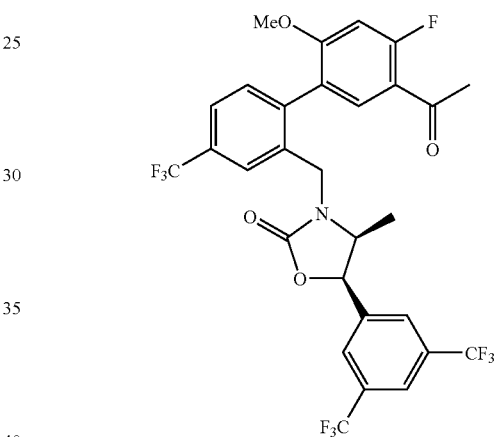

(4S,5R)-5-[3,5-bis(trifluoromethyl)phenyl]-3-{[4'-fluoro-2'-methoxy-5'-(2-methyl-1,3-dioxolan-2-yl)-4-(trifluoromethyl)biphenyl-2-yl]methyl}-4-1,3-oxazolidin-2-one A mixture of (4S,5R)-5-[3,5-bis(trifluoromethyl)phenyl]-3-[2-iodo-5-(trifluoromethyl)benzyl]-4-methyl-1,3-oxazolidin-2-one (Intermediate 21, 7.34 g, 12.29 mol), [4-fluoro-2-methoxy-5-(2-methyl-1,3-dioxolan-2-yl)phenyl]boronic acid (5.5 g, 21.48 mol), tetrakis(triphenylphosphine)palladium (0) (1.7 g; 1.47 mol), and sodium carbonate (10 g) in benzene/EtOH/H$_2$O (203/29/86 mL) was heated at reflux for 14 h. The reaction was quenched with H$_2$O and partitioned between EtOAc (250 mL) and H$_2$O (75 mL). The aqueous layer was re-extracted with EtOAc (3×200 mL). The combined extracts were washed with brine (100 mL), dried (MgSO$_4$), filtered, and concentrated in vacuo. The crude product was purified by flash silica gel chromatography (0-25% EtOAc/hexanes gradient) to afford (4S,5R)-5-[3,5-bis(trifluoromethyl)phenyl]-3-{[4'-fluoro-2'-methoxy-5'-(2-methyl-1,3-dioxolan-2-yl)-4-(trifluoromethyl)biphenyl-2-yl]methyl}-4-1,3-oxazolidin-2-one as an amorphous solid. LCMS=682.2 (M+1)$^+$. $^1$H NMR (CDCl$_3$, 500 MHz, mixture of atropisomers): δ 7.86 (s, 1 H), 7.71 (S, 3 H), 7.65-7.61 (m, 1 H), 7.37-7.34 (m, 1 H), 7.32-7.28 (m, 1 H), 6.75 (dd, J=12.4, 3.6 Hz, 1H), 5.58 (d, J=8.1 Hz, 1 H), 4.89 (d, J=15.8 Hz, 1 H), 4.08-4.04 (m, 2 H), 3.91-3.76 (m, 7 H), 1.73 (d, J=10.5 Hz, 3 H), 0.4 (d, J=6.5 Hz, 3 H).

Example 299

(4S,5R)-3-{[5'-acetyl-4'-fluoro-2'-methoxy-4-(trifluoromethyl)biphenyl-2-yl]methyl}-5-[3,5-bis(trifluoromethyl)phenyl]-4-methyl-1,3-oxazolidin-2-one To a stirred solution of (4S,5R)-5-[3,5-bis(trifluoromethyl)phenyl]-3-{[4'-fluoro-2'-methoxy-5'-(2-methyl-1,3-dioxolan-2-yl)-4-(trifluoromethyl)biphenyl-2-yl]methyl}-4-1,3-oxazolidin-2-one (8 g, 0.0118 mol) in acetone (400 mL) was added p-toluenesulfonic acid monohydrate (670 mg, 0.0035 mol). The reaction stirred at room temperature for 14 h. The reaction was partitioned between EtOAc (250 mL) and sat. NaHCO$_3$ (250 mL). The aqueous layer was re-extracted with EtOAc (3×250 mL) and the combined organic layers were washed with brine (200 mL), dried (MgSO$_4$), filtered, and concentrated in vacuo. The crude product was purified by flash silica gel chromatography (0-25% EtOAc/hexanes gradient) to afford (4S,5R)-3-{[5'-acetyl-4'-fluoro-2'-methoxy-4-(trifluoromethyl)biphenyl-2-yl]-methyl}-5-[3,5-bis(trifluoromethyl)phenyl]-4-methyl-1,3-oxazolidin-2-one as a yellow solid. LCMS=638.2 (M+1)$^+$. $^1$H NMR (CDCl$_3$, 500 MHz, mixture of atropisomers): δ 7.87 (s, 1 H), 7.81-7.79 (m, 1 H), 7.74 (s, 1 H), 7.70 (s, 2 H), 7.59 (s, 1 H), 7.39 (d, J=8 Hz, 1 H), 6.80 (d, J=12.8 Hz, 1 H), 5.27 (d, J=8.2 Hz, 1 H), 4.97 (d, J=15.3 Hz, 1 H), 4.04 (d, J=15.5 Hz, 1 H), 3.94 (s, 3 H), 3.72-3.66 (m, 1 H), 2.67-2.64 (m, 3 H), 0.62 (d, J=6.4 Hz, 3 H).

Example 300

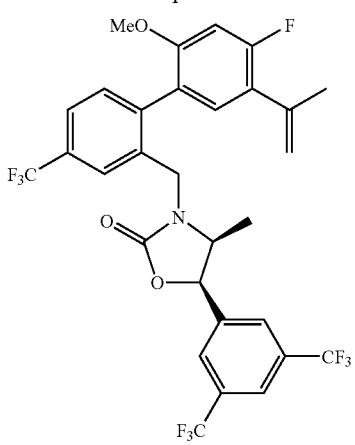

(4S,5R)-5-[3,5-bis(trifluoromethyl)phenyl]-3-{[4'-fluoro-5'-isopropenyl-2'-methoxy-4-(trifluoromethyl)biphenyl-2-yl]methyl}-4-methyl-1,3-oxazolidin-2-one Methyl magnesium iodide (29 µL, 0.085 mmol) was added dropwise to a solution of (4S,5R)-3-{[5'-acetyl-4'-fluoro-2'-methoxy-4-(trifluoromethyl)biphenyl-2-yl]methyl}-5-[3,5-bis(trifluoromethyl)phenyl]-4-methyl-1,3-oxazolidin-2-one (30 mg, 0.047 mmol) in diethyl ether (2 mL) at room temperature. The reaction was carefully heated at reflux 4 h. Additional methyl magnesium iodide (63 µL, 0.19 mmol) and ether (1 mL) was added and the reaction was refluxed for 3 h. The reaction was quenched with sat. NH$_4$Cl and extracted with EtOAc (3×25 mL). The combined extracts were washed with brine (25 mL), dried (Na$_2$SO$_4$), filtered, and concentrated in vacuo. The crude product was purified by flash silica gel chromatography (0-25% EtOAc/hexanes gradient) to afford (4S,5R)-5-[3,5-bis(trifluoromethyl)phenyl]-3-{[4'-fluoro-5'-isopropenyl-2'-methoxy-4-(trifluoromethyl)biphenyl-2-yl]methyl}-4-methyl-1,3-oxazolidin-2-one as a clear glass. LCMS=636.3 (M+1)$^+$. $^1$H NMR (benzene-d$_6$, 500 MHz, mixture of atropisomers): δ 7.59 (s, 1 H), 7.55 (s, 1 H), 7.35 (d, J=8 Hz, 1 H), 7.30-7.27 (m, 2 H), 6.99-6.96 (m, 2 H), 6.45 (d, J=12.9 Hz, 1 H), 5.32 (d, J=16.9 Hz, 1 H), 5.16-5.15 (m, 1 H), 4.90 (d, J=16.3 Hz, 1 H), 4.48 (d, J=7.7 Hz, 1 H), 3.70 (d, J=6.4 Hz, 1 H), 3.16 (s, 3 H), 2.85-2.79 (m, 1 H), 2.12 (s, 3 H), −0.025 (d, J=6.5 Hz, 3 H).

Example 301

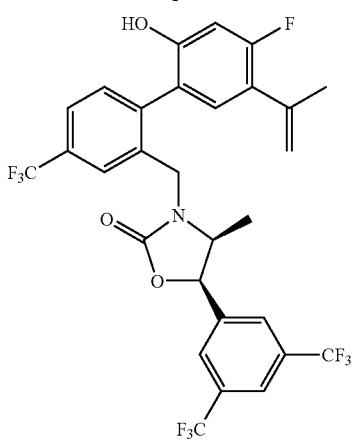

(4S,5R)-5-[3,5-bis(trifluoromethyl)phenyl]-3-{[4'-fluoro-2'-hydroxy-5'-isopropenyl-4-(trifluoromethyl)biphenyl-2-yl]methyl}-4-methyl-1,3-oxazolidin-2-one To a stirred solution of (4S,5R)-5-[3,5-bis(trifluoromethyl)phenyl]-3-{[4'-fluoro-5'-isopropenyl-2'-methoxy-4-(trifluoromethyl)biphenyl-2-yl]methyl}-4-methyl-1,3-oxazolidin-2-one (Example 300, 50 mg, 0.078 mmol) in DMF (450 µL) was added lithium chloride (13.4 mg, 0.315 mmol). The vial was sealed and the reaction was heated at 160° C. for 14 h. 10% NaOH (10 mL) was added and the resultant solution was extracted with ether (3×10 mL). The aqueous layer was acidified to pH~3 with 3N HCl and was re-extracted with ether (3×25 mL). The combined organic extracts were washed with brine (25 mL), dried (MgSO$_4$), filtered, and concentrated in vacuo. The crude product was purified by flash silica gel chromatography (0-25% EtOAc/hexanes gradient) to afford (4S,5R)-5-[3,5-bis(trifluoromethyl)phenyl]-3-{[4'-fluoro-2'-hydroxy-5'-isopropenyl-4-(trifluoromethyl)biphenyl-2-yl]methyl}-4-methyl-1,3-oxazolidin-2-one as a clear glass. LCMS=622.1 (M+1)$^+$. $^1$H NMR (CDCl$_3$, 500 MHz, mixture of atropisomers): δ 7.90 (s, 1 H), 7.76-7.70 (m, 4 H), 7.48-7.45 (m, 1 H), 7.11-7.07 (m, 1 H), 6.75 (d, J=11.7 Hz, 1 H), 5.71 (d, J=7.8 Hz, 1 H), 5.59-5.56 (m, 1 H), 5.25-5.21 (m, 2 H), 4.81 (d, J=15.4 Hz, 1 H), 4.04 (d, J=15.6 Hz, 1 H), 3.97-3.92 (m, 1 H), 2.13 (s, 3 H), 0.58 (d, J=6.6 Hz, 3 H).

Example 302

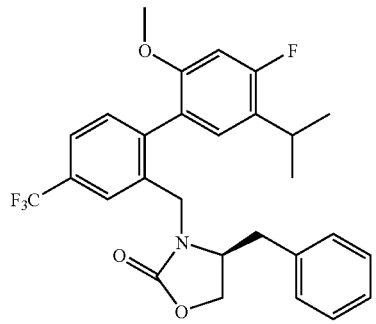 [SMILES: COc1cc(F)c(C(C)C)cc1-c1ccc(C(F)(F)F)cc1CN1C(=O)OC[C@@H]1Cc1ccccc1]

(4S)-4-benzyl-3-{[4'-fluoro-5'-isopropyl-2'-methoxy-4-(trifluoromethyl)biphenyl-2-yl]-methyl}-1,3-oxazolidin-2-one A stirred suspension of sodium hydride (60% in oil, 37 mg, 0.926 mmol) in THF (1 mL) was treated at 0° C. with (S)-4-benzyl-2-oxazolidinone (33 mg, 0.185 mmol) dissolved in THF (1 mL), under an atmosphere of N$_2$. The reaction was stirred for 20 min and a solution of 2'-(bromomethyl)-4-fluoro-5-isopropyl-2-methoxy-4'-(trifluoromethyl)biphenyl (Intermediate 10, 50 mg, 0.124 mmol) in THF (1 mL) was added dropwise. The reaction was stirred at room temperature for 60 h. The reaction was quenched with H$_2$O (1 mL) and partitioned between EtOAc (25 mL) and H$_2$O (10 mL). The aqueous phase was re-extracted with EtOAc (3×15 mL) and the combined organic extracts were washed with brine (25 mL), dried (MgSO$_4$) and concentrated in vacuo to give the crude product. This was purified by flash silica-gel chromatography (0-25% EtOAc/hexanes gradient) to afford (4S)-4-benzyl-3-{[4'-fluoro-5'-isopropyl-2'-methoxy-4-(trifluoromethyl)biphenyl-2-yl]methyl}-1,3-oxazolidin-2-one as a clear glass. LCMS=502.3 (M+1)$^+$. $^1$H NMR (CDCl$_3$, 500 MHz, mixture of atropisomers) δ 7.69-7.64 (m, 1H), 7.58 (s, 1H), 7.39-7.36 (m, 1 H), 7.29-7.24 (m, 3 H), 7.06 (d, J=8.5 Hz, 1H), 6.97-6.91 (m, 2 H), 6.73 (d, J=11.7, 1H), 4.79 (d, J=15.8 Hz, 1H), 4.30 (d, J=15.8 Hz, 1 H), 4.08-4.05 (m, 1H), 3.99-3.97 (m, 1H), 3.76 (s, 3H), 3.65-3.58 (m, 1H), 3.27-3.17 (m, 1 H), 2.81 (dd, J=13.5, 4.1 Hz, 1H), 2.45-2.40 (m, 1 H), 1.30-1.4 (m, 6 H).

Example 303

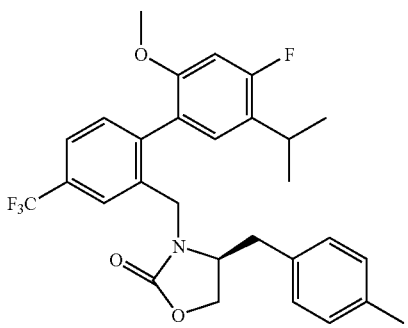 [SMILES: COc1cc(F)c(C(C)C)cc1-c1ccc(C(F)(F)F)cc1CN1C(=O)OC[C@@H]1Cc1ccc(C)cc1]

(4S)-3-{[4'-fluoro-5'-isopropyl-2'-methoxy-4-(trifluoromethyl)biphenyl-2-yl]methyl}-4-(4-methylbenzyl)-1,3-oxazolidin-2-one Step A: (2S)-2-amino-3-(4-methylphenyl)propan-1-ol A mixture of lithium aluminum hydride (254 mg, 6.696 mmol) in THF (20 mL) was heated at reflux for 1 h, then cooled in an ice bath. (S)-4-Methylphenylalanine (500 mg, 2.79 mmol) was added portionwise and the resultant mixture was heated at reflux for 14 h. The excess lithium aluminum hydride was decomposed by successive addition of $H_2O$ (1 mL), 10% aq. NaOH (10 mL) and $H_2O$ (2.5 mL). The mixture was filtered and the solid was washed with THF. The filtrate was concentrated in vacuo and the residue was dissolved in $CHCl_3$ (50 mL), washed with 5% aq. NaOH (25 mL), $H_2O$ (25 mL) and brine (25 mL), dried ($MgSO_4$), filtered, and concentrated in vacuo to afford (2S)-2-amino-3-(4-methylphenyl)propan-1-ol as an off-white solid. $^1H$ NMR ($CD_3OD$, 500 MHz) δ 7.13-7.09 (m, 4H), 3.52 (dd, J=10.7, 4.6 Hz, 1H), 3.36 (dd, J=10.7, 6.9 Hz, 1H), 3.04-2.99 (m, 1 H), 2.73 (dd, J=13.5, 6.2 Hz, 1H), 2.53 (dd, J=13.5, 7.7 Hz, 1H), 2.30 (s, 3 H).

Step B: (4S)-4-(4-methylbenzyl)-1,3-oxazolidin-2-one

A stirred solution of (2S)-2-amino-3-(4-methylphenyl)propan-1-ol (Step A, 460 mg, 2.79 mmol) in $CH_2Cl_2$ (20 mL) at 0° C. was treated with diisopropylethylamine (2.92 mL, 16.74 mmol) and triphosgene (414 mg, 1.39 mmol) under an atmosphere of $N_2$. The reaction stirred at 0° C. for 3 h. The reaction was quenched with sat. $NaHCO_3$ (10 mL) and extracted with EtOAc (4×20 mL). The combined organic layers were washed with brine (25 mL), dried ($MgSO_4$), filtered and concentrated in vacuo. The crude product was purified by flash silica gel chromatography (0-70% EtOAc/hexanes gradient) to afford (4S)-4-(4-methylbenzyl)-1,3-oxazolidin-2-one as a white solid. LCMS=192.2 $(M+1)^+$. $^1H$ NMR ($CDCl_3$, 500 MHz) δ 7.17 (d, J=8 Hz, 2 H), 7.09 (d, J=7.7 Hz, 2 H), 5.39 (br s, 1 H), 4.48 (t, J=8.4 Hz, 1 H), 4.37 (dd, J=8.6, 5.6 Hz, 1 H), 4.11-4.06 (m, 1 H), 2.86 (d, J=7.1 Hz, 2 H), 2.36 (s, 3 H).

Step C: (4S)-3-{[4'-fluoro-5'-isopropyl-2'-methoxy-4-(trifluoromethyl)biphenyl-2-yl]methyl}-4-(4-methylbenzyl)-1,3-oxazolidin-2-one (4S)-4-(4-methylbenzyl)-1,3-oxazolidin-2-one (Step B, 14 mg, 0.074 mmol) was treated with sodium hydride (60% in oil, 6.2 mg, 0.154 mmol) and 2'-(bromomethyl)-4-fluoro-5-isopropyl-2-methoxy-4'-(trifluoromethyl)biphenyl (Intermediate 10, 25 mg, 0.062 mmol) as described in Example 305 to afford (4S)-3-{[4'-fluoro-5'-isopropyl-2'-methoxy-4-(trifluoromethyl)biphenyl-2-yl]methyl}-4-(4-methylbenzyl)-1,3-oxazolidin-2-one as clear gum. LCMS=516.4 $(M+1)^+$. $^1H$ NMR ($CDCl_3$, 500 MHz, mixture of atropisomers) δ 7.65-7.60 (m, 1 H), 7.53 (s, 1 H), 7.35-7.32 (m, 1 H), 7.06-7.20 (m, 2 H), 6.82-6.75 (m, 2 H), 6.69 (d, J=11.7 Hz, 1 H), 4.67 (d, J=15.8 Hz, 1 H), 4.06 (d, J=15.8 Hz, 1 H), 4.04-4.00 (m, 1 H), 3.96-3.93 (m, 1 H), 3.73 (s, 3 H), 3.55-3.48 (m, 1 H), 3.23-3.15 (m, 1 H), 2.63 (dd, J=13.5, 3.6 Hz, 1 H), 2.35 (d, J=13.5 Hz, 1 H), 2.29 (s, 3 H), 1.25-1.13 (m, 6 H).

Following the general procedures outlined above, the compounds in Table 16 were prepared:

TABLE 16

| Compound | $A^2$ | LCMS $(M + 1)^+$ |
|---|---|---|
| 304 | 3-methylbenzyl | 516.4 |
| 305 | 2-methylbenzyl | 516.4 |
| 306 | 3-methoxybenzyl | 532.3 |
| 307 | 2-methoxybenzyl | 532.3 |
| 308 | 3-fluorobenzyl | 520.4 |
| 309 | 2-fluorobenzyl | 520.3 |

TABLE 16-continued

[Structure: biphenyl with OMe, F, isopropyl substituents, CF3, and oxazolidinone with A² substituent]

| Compound | A² | LCMS (M + 1)+ |
|---|---|---|
| 310 | 3-chlorobenzyl | 536.3 |
| 311 | 4-chlorobenzyl | 536.3 |
| 312 | 4-chlorobenzyl | 536.3 |
| 313 | 1-phenylethyl, diastereomer A | 516.4 |
| 314 | 1-phenylethyl, diastereomer B | 516.4 |
| 315 | 1-phenylethyl, diastereomer C | 516.4 |
| 316 | 1-phenylethyl, diastereomer D | 516.4 |

Example 317

(4S,5S)-4-benzyl-3-{[4'-fluoro-5'-isopropyl-2'-methoxy-4-(trifluoromethyl)biphenyl-2-yl]methyl}-5-methyl-1,3-oxazolidin-2-one

Step A:
tert-butyl[1(S)-1-benzyl-2-oxopropyl]carbamate

A stirred solution of N-(tert-butoxycarbonyl)-N-methoxy-N-methyl-L-phenylalaninamide (500 mg, 1.62 mmol) in THF (3 mL) at −15° C. was treated with methyl magnesium bromide (540 μL, 1.62 mmol) under an atmosphere of $N_2$. The reaction stirred at −15° C. for 15 min prior to dropwise addition of methyl magnesium bromide (1.08 mL, 3.24 mmol). The reaction stirred for 14 h at room temperature and was quenched with 1N HCl (5 mL). The mixture was partitioned between $H_2O$ (15 mL) and EtOAc (20 mL) and the aqueous layer was re-extracted with EtOAc (2×20 mL). The combined organic layers were washed with $H_2O$ (20 mL) and brine (20 mL), dried ($Na_2SO_4$), filtered and concentrated in vacuo. The crude product was purified by flash silica gel chromatography to afford tert-butyl[1(S)-1-benzyl-2-oxopropyl]carbamate as a white solid. LCMS=164.2 (M−BOC)+. $^1$H NMR (CDCl$_3$, 500 MHz) δ 7.34-7.26 (m, 3H), 7.18 (d, J=7.1 Hz, 2 H), 5.15 (br s, 1 H), 4.59-4.56 (m, 1 H), 3.14-2.99 (m, 2 H), 2.16 (s, 3 H), 1.44 (s, 9 H).

Step B:
tert-butyl[1(S)-1-benzyl-2-hydroxypropyl]carbamate

A stirred solution of tert-butyl[1(S)-1-benzyl-2-oxopropyl]carbamate (Step A, 150 mg, 0.57 mmol) in dry MeOH (5 mL) at −20° C. was treated with sodium borohydride (44.2 mg, 1.169 mmol). The reaction stirred at −20° C. for 1 h and was quenched with $H_2O$ (1 mL) and concentrated in vacuo. The residue was dissolved in EtOAc (25 mL) and washed sequentially with $H_2O$ (15 mL) and brine (15 mL), dried ($Na_2SO_4$), filtered and concentrated in vacuo. The crude product was purified by preparatory thin-layer chromatography, eluting with 15% acetone/hexanes to afford tert-butyl[(1S,2R)-1-benzyl-2-hydroxypropyl]carbamate (45 mg) and tert-butyl[(1S,2S)-1-benzyl-2-hydroxypropyl]carbamate as white solids. tert-butyl[(1S,2R)-1-benzyl-2-hydroxypropyl]carbamate: LCMS=166.2 (M−BOC)+. $^1$H NMR (CDCl$_3$, 500 MHz) δ 7.34-7.31 (m, 2H), 7.26-7.23 (m, 3 H), 4.81 (br s, 1 H), 3.83 (dq, J=6.4, 2.7 Hz, 1 H), 3.71-3.69 (m, 1 H), 2.90 (d, J=7.3 Hz, 2 H), 1.43 (s, 9 H), 1.22 (d, J=6.5 Hz, 3 H). tert-butyl[(1S,2S)-1-benzyl-2-hydroxypropyl]carbamate: LCMS=166.2 (M−BOC)+. $^1$H NMR (CDCl$_3$, 500 MHz) δ 7.34-7.31 (m, 2 H), 7.26-7.23 (m, 3 H), 4.58 (br s, 1 H), 3.3.93-3.85 (m, 2 H), 2.90 (dd, J=14.2, 5 Hz, 1 H), 2.82-2.73 (m, 1 H), 1.40 (s, 9 H), 1.25 (d, J=6.4 Hz, 3 H).

Step C: (4S,5S)-4-benzyl-3-{[4'-fluoro-5'-isopropyl-2'-methoxy-4-(trifluoromethyl)biphenyl-2-yl]methyl}-5-methyl-1,3-oxazolidin-2-one tert-butyl[(1S,2R)-1-benzyl-2-hydroxypropyl]carbamate (Step B, 39 mg, 0.148 mmol) was treated with sodium hydride (60% in oil, 12 mg, 0.309 mmol) and 2'-(bromomethyl)-4-fluoro-5-isopropyl-2-methoxy-4'-(trifluoromethyl)biphenyl (Intermediate 10, 50 mg, 0.123 mmol) as described in Example 305 to afford (4S,5S)-4-benzyl-3-{[4'-fluoro-5'-isopropyl-2'-methoxy-4-(trifluoromethyl)biphenyl-2-yl]methyl}-5-methyl-1,3-oxazolidin-2-one as a clear glass. LCMS=516.4 (M+1)$^+$. $^1$H NMR (CDCl$_3$, 500 MHz, mixture of atropisomers) δ 7.68 (d, J=11.5 Hz, 1 H), 7.66-7.63 (m, 1 H), 7.39-7.36 (m, 1 H), 7.28-7.23 (m, 3 H), 7.07 (d, J=8.5 Hz, 1 H), 6.94 (d, J=6.9 Hz, 2 H), 6.73 (d, J=4.8 Hz, 1 H), 4.81 (d, J=16 Hz, 1 H) 4.38 (d, J=16.1 Hz, 1 H), 4.28-4.23 (m, 1 H), 3.78 (s, 3 H), 3.29-3.17 (m, 2 H), 2.81 (dd, J=13.3, 3.9 Hz, 1H), 2.38-2.28 (m, 1 H), 1.29-1.13 (m, 6 H), 0.98 (d, J=6.2 Hz, 3 H).

Example 318

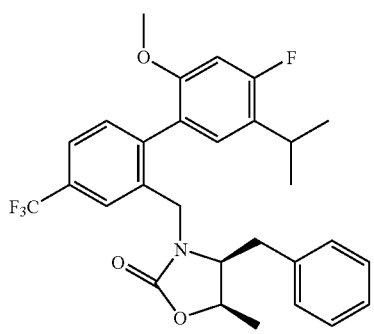 [SMILES: COc1cc(F)c(C(C)C)cc1-c1ccc(C(F)(F)F)cc1CN1C(=O)O[C@H](C)[C@@H]1Cc1ccccc1]

(4S,5R)-4-benzyl-3-{[4'-fluoro-5'-isopropyl-2'-methoxy-4-(trifluoromethyl)biphenyl-2-yl]methyl}-5-methyl-1,3-oxazolidin-2-one tert-butyl[(1S,2S)-1-benzyl-2-hydroxypropyl]carbamate (Example 317, Step B, 39 mg, 0.148 mmol) was treated with sodium hydride (60% in oil, 12 mg, 0.309 mmol) and 2'-(bromomethyl)-4-fluoro-5-isopropyl-2-methoxy-4'-(trifluoromethyl)biphenyl (Intermediate 10, 50 mg, 0.123 mmol) as described in Example 305 to afford (4S,5R)-4-benzyl-3-{[4'-fluoro-5'-isopropyl-2'-methoxy-4-(trifluoromethyl)biphenyl-2-yl]methyl}-5-methyl-1,3-oxazolidin-2-one as a clear glass. LCMS=516.4 (M+1)$^+$. $^1$H NMR (CDCl$_3$, 500 MHz, mixture of atropisomers) δ 7.64-759 (m, 2 H), 7.33-7.30 (m, 1 H), 7.28-7.21 (m, 2 H), 7.16 (s, 1 H), 7.00-6.91 (m, 3 H), 6.67 (d, J=3 Hz, 1 H), 4.70 (d, J=2.7 Hz, 1 H), 4.52-4.47 (m, 1 H), 3.95 (d, J=15.8 Hz, 1 H), 3.70 (s, 3 H), 3.68-3.62 (m, 1 H), 3.24-3.18 (m, 1 H), 2.72-2.53 (m, 2 H), 1.28-1.21 (m, 6H), 1.19 (d, J=6.8 Hz, 3 H).

Example 319

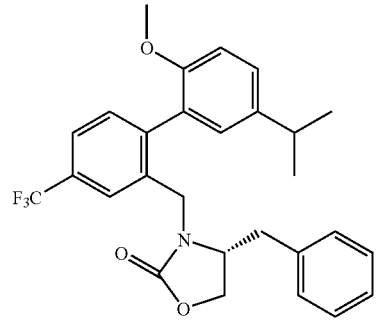 [SMILES: COc1ccc(C(C)C)cc1-c1ccc(C(F)(F)F)cc1CN1C(=O)OC[C@H]1Cc1ccccc1]

(4R)-4-benzyl-3-{[5'-isopropyl-2'-methoxy-4-(trifluoromethyl)biphenyl-2-yl]-methyl}-1,3-oxazolidin-2-one The title compound was prepared according to the procedure described in Example 67 starting from (R)-4-benzyl-2-oxazolidinone (49 mg, 0.27 mmol) and 2-(bromomethyl)-1-iodo-4-(trifluoromethyl)benzene (100 mg, 0.27 mmol) to afford the title compound as a colorless oil. R$_f$=0.35 (15% EtOAc/hexanes). LCMS 484 (M+1)$^+$. $^1$H NMR (CDCl$_3$, 500 MHz) (atropisomers present) δ 7.72 (br s 1H), 7.65 (br s, 1H), 7.42 (m, 1H), 7.32-7.22 (m, 3H), 7.08 (m, 1H), 6.90-6.84 (m, 3H), 4.81 (d, J=15.8 Hz, 1H), 4.35 (d, J=15.8 Hz), 4.28 (t, J=8.7 Hz, 1H), 3.96-3.92 (m, 3H), 3.78 (s, 3H), 3.62-3.52 (m, 1H), 2.94-2.86 (m, 1H), 2.82 (dd, J=9.4, 3.9 Hz, 1H), 2.42 (dd, J=9.6, 3.9 Hz), 1.26 (s, 3H), 1.10 (s, 3H).

Example 320

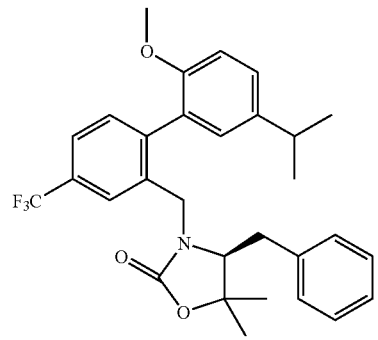 [SMILES: COc1ccc(C(C)C)cc1-c1ccc(C(F)(F)F)cc1CN1C(=O)OC(C)(C)[C@@H]1Cc1ccccc1]

Example 322 was prepared according to the procedure described in Example 14 starting from (S)-4-benzyl-5,5-dimethyl-2-oxazolidinone (10 mg, 0.05 mmol) and 2-(bromomethyl)-5'-isopropyl-2'-methoxy-4-(trifluoromethyl)biphenyl (20 mg, 0.05 mmol) to afford the title compound as a colorless oil. LCMS 512 (M+1)$^+$. $^1$H NMR (CDCl$_3$, 500 MHz) (atropisomers present) δ 7.72 (br s 1H), 7.31 (br s, 1H), 7.12-7.02 (m, 2H), 6.85-6.82 (m, 3H), 6.45-6.35 (m, 4H), 4.61 (d, J=15.8 Hz, 1H), 4.21 (d, J=15.8 Hz), 3.21 (s, 2H), 3.16 (s, 3H), 2.62-2.52 (m, 1H), 2.42-218 (m, 1H), 1.98 (m, 2H), 1.22 (d, J=7.1 Hz), 1.05 (d, J=7.1 Hz), 0.98 (s, 3H), 0.88 (s, 3H).

Example 321

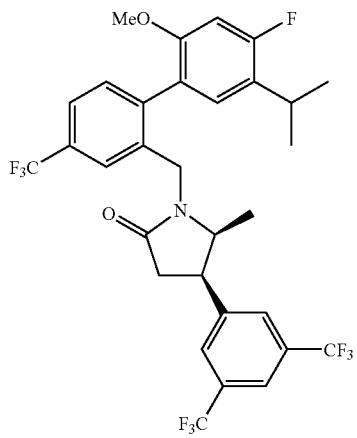 [SMILES: COc1cc(F)c(C(C)C)cc1-c1ccc(C(F)(F)F)cc1CN1C(=O)C[C@H](c2cc(C(F)(F)F)cc(C(F)(F)F)c2)[C@@H]1C]

(4R,5S)-4-[3,5-bis(trifluoromethyl)phenyl]-1-{[4'-fluoro-5'-isopropyl]-2'-methoxy-4-(trifluoromethyl)biphenyl-2-yl]methyl}-5-methyl-pyrrolidin-2-one

Step A: ethyl 3-[3,5-bis(trifluoromethyl)phenyl]acrylate

To a suspension of NaH (60% suspension in oil, 168 mg, 4.96 mmol) in THF (3 mL) was added a solution of triethyl phosphonoacetate (0.5 mL, 2.52 mmol) at 0° C., under an atmosphere of nitrogen. The reaction was allowed to stir for 30 min at 0° C. and 3,5-bis(trifluoromethyl)benzaldehyde (609 mg, 2.52 mmol) was added. The reaction was allowed to warm to ambient temperature, stirred for an additional 2 h and then concentrated in vacuo. The residue was diluted with EtOAc (20 mL), washed with $H_2O$, brine, dried over $MgSO_4$, concentrated and purified by flash chromatography with 10% EtOAc/hexanes to afford the title compound as a white solid. LCMS 313 (M+1)$^+$.

Step B. methyl 3-[3,5-bis(trifluoromethyl)phenyl]-4-nitropentanoate

Ethyl 3-[3,5-bis(trifluoromethyl)phenyl]acrylate (170 mg, 0.54 mmol) and nitromethane (736 uL, 10.29 mmol) were treated with a solution of tetrabutylammonium hydroxide (1.0 M solution in MeOH, 1.5 mL) and the mixture heated to reflux for 3 h, diluted with 10% aqueous ammonium chloride (10 mL) and extracted with EtOAC (4×30 mL). The combined organic extracts were washed with 10% ammonium chloride (20 mL), dried over $MgSO_4$, concentrated in vacuo to give the crude product. This was purified by flash chromatography using 10% EtOAC/hexanes to afford methyl 3-[3,5-bis(trifluoro methyl)phenyl]-4-nitropentanoate as a colorless oil. $^1$H NMR (CDCl$_3$, 500 MHz) δ 7.82 (br s 1H), 7.64 (br s, 2H), 4.91 (m, 1H), 3.91 (m, 1H), 3.61 (s, 3H), 2.82 (m, 2H), 1.42 (d, J=6.7 Hz, 3H).

Step C: 4-[3,5-bis(trifluoromethyl)phenyl]-5-methylpyrrolidin-2-one

A suspension of Raney Nickel (50% w/v slurry in $H_2O$, 200 mg) was added to a solution of methyl 3-[3,5-bis(trifluoromethyl)phenyl]-4-nitropentanoate in absolute EtOH (5 mL) and the resultant mixture was stirred at room temperature overnight under a balloon atmosphere of $H_2$. The reaction mixture was filtered through a pad of Celite and the filtrate was concentrated in vacuo to remove the EtOH. The residue was purified by flash chromatography using 75% EtOAC/hexanes to afford threo-4-[3,5-bis(trifluoromethyl)phenyl]-5-methylpyrrolidin-2-one and erythro-4-[3,5-bis(trifluoromethyl)phenyl]-5-methylpyrrolidin-2-one as white solids. erythro-diastereomer: LCMS 353 (M+1)$^+$. $^1$H NMR (CDCl$_3$, 500 MHz) δ 7.82 (br s 1H), 7.64 (br s, 2H), 5.72 (br s, 1H), 3.85 (m, 1H), 3.31 (dd, J=8.9, 8.2 Hz, 1H), 2.61 (dd, J=8.9, 8.2 Hz, 1H), 1.34 (d, J=6.1 Hz, 3H). erythro-diastereomer: LCMS 353 (M+1)$^+$. $^1$H NMR (CDCl$_3$, 500 MHz) δ 7.82 (br s 1H), 7.64 (br s, 2H), 5.76 (br s, 1H), 4.20 (m, 1H), 3.90 (m, 1H), 2.81 (dd, J=8.5, 8.2 Hz, 1H), 2.73 (dd, J=8.5, 8.2 Hz, 1H), 0.88 (d, J=6.7 Hz, 3H).

Step D: (4R,5S)-4-[3,5-bis(trifluoromethyl)phenyl]-1-{[4'-fluoro-5'-isopropyl]-2'-methoxy-4-(trifluoromethyl)biphenyl-2-yl]methyl}-5-methyl-pyrolidin-2-one To a stirred suspension of NaH (60% in oil, 4.4 mg, 0.11 mmol) in THF (3 mL), was added a solution of erythro-4-[3,5-bis(trifluoromethyl)phenyl]-5-methylpyrrolidin-2-one (16 mg, 0.051 mmol) in THF (1 mL) at 0° C. under an atmosphere of nitrogen. The resultant mixture was allowed to stir for 30 min at 0° C. before the addition of 2'-(bromomethyl)-4-fluoro-5-isopropyl-2-methoxy-4'-(trifluoromethyl)biphenyl (16 mg, 0.051 mmol). After 3 h, the reaction was diluted with 15 mL EtOAc and 5 mL $H_2O$. The phases were separated and the organic phase was washed with $H_2O$, brine, dried (MgSO$_4$), and concentrated. The residue was purified by flash chromatography using 10% EtOAC/hexanes to afford the title compound as a colorless oil. LCMS 636 (M+1)$^+$. $^1$H NMR (CDCl$_3$, 500 MHz) (atropisomers present) $^1$H NMR δ 7.82 (br s 1H), 7.80 (br s, 1H), 7.45-7.36 (m, 3H), 7.32-7.22 (m, 3H), 7.08 (d, J=10.1 Hz, 1H), 6.60 (m, 1H), 5.05 (m, 1H), 4.01 (d, J=15.5 Hz), 3.78 (s, 3H), 3.71-3.52 (m, 2H), 3.24 (m, 1H), 1.32-1.20 (m, 6H), 0.56 (d, J=6.4 Hz, 3H). This compound was separated into its two enantiomers (4R,5S)-4-[3,5-bis(trifluoromethyl)phenyl]-1-{[4'-fluoro-5'-isopropyl]-2'-methoxy-4-(trifluoromethyl)biphenyl-2-yl]methyl}-5-methyl-pyrrolidin-2-one and (4S,5R)-4-[3,5-bis(trifluoromethyl)phenyl]-1-{[4'-fluoro-5'-isopropyl]-2'-methoxy-4-(trifluoromethyl)biphenyl-2-yl]methyl}-5-methyl-pyrrolidin-2-one using chiral HPLC (IA column, 20×250 mm, 3% i-PrOH in heptane).

Following the general procedures outlined above, the compounds in Table 17 were prepared:

TABLE 17

[Structure: biphenyl with MeO, F, isopropyl, CF3, and CH2-R substituents]

| Example | R | LCMS (M + 1)⁺ |
|---|---|---|
| 322 | [pyrrolidinone with 3-chlorophenyl, R group] | 534.2 |
| 323 | [methyl pyrrolidinone with 3-chlorophenyl] | 534.2 |
| 324 | [methyl pyrrolidinone with 3-OCF3-phenyl] racemic | 584.2 |
| 325 | [methyl pyrrolidinone with 3,4-dichlorophenyl] racemic | 568.1 |
| 326 | [methyl pyrrolidinone with 3,5-dichlorophenyl] | 568.1 |

Example 327

[Structure of final compound]

(4S,5R)-5-[3,5-bis(trifluoromethyl)phenyl]-3-{[4'-fluoro-5'-isopropyl-2'-methoxy-6-methyl-4-(trifluoromethyl)biphenyl-2-yl]-methyl}-4-methyl-1,3-oxazolidin-2-one

Step A: [2,6-dimethyl-4-(trifluoromethyl)phenyl]amine

A mixture of 2,6-dibromo-4-trifluoromethyl aniline (1.00 g, 3.14 mmol), trimethylboroxin (1.16 ml, 1.04 g, 8.33 mmol), potassium carbonate (1.15 g, 8.33 mmol) and catalytic amount (10%) Pd(PPh$_3$)$_4$ in DMF (5 ml) was heated to 90° C. for 14 h. Water (10 ml) was added. The mixture was extracted with ethyl acetate (3×20 ml). The combined EtOAc layers were washed with brine and dried over sodium sulfate. The titled compound was obtained as a colorless oil after a flash column using EtOAc:hexane (1:9) as the elute. $^1$H NMR (CDCl$_3$, 500 MHz): δ 7.28 (s, 1H), 7.22 (s, 1H), 3.88 (br s, 2H), 2.21 (s, 6H).

Step B: 2-iodo-1,3-dimethyl-5-(trifluoromethyl)benzene

A mixture of the titled compound from Step A (0.27 g, 1.43 mmol), n-pentyl nitrite (0.50 g, 2.86 mmol) and I$_2$ (0.72 g, 2.86 mmol) in chloroform (10 ml) was refluxed for 1 h. The mixture was diluted with methylene chloride (20 ml) and washed with saturated sodium thiosulfate solution, and brine. The organic layer was dried over sodium sulfate. The titled compound was obtained as a light yellow liquid after flash column using hexane as the elute. $^1$H NMR (CDCl$_3$, 500 MHz) δ 7.31 (s, 2H), 2.58 (s, 6H).

Step C: 1-(bromomethyl)-2-iodo-3-methyl-5-(trifluoromethyl)benzene

A mixture of the titled compound from Step B (0.26 g, 0.87 mmol), NBS (0.154 g, 0.87 mmol) and catalytic amount of AIBN in CCl$_4$ was refluxed for 6 h. TLC (hexane) showed a mixture of starting material and a new spot. Upon addition of more AIBN the reaction was allowed to reflux for another 2 h. No change was observed. The reaction mixture was cooled to room temperature and the solvent was removed. The titled compound was obtained as a white solid along with the starting material after preparative TLC purification using hexane as the elute. $^1$H NMR (CDCl$_3$, 500 MHz): δ 7.54 (s, 1H), 7.42 (s, 1H), 4.67 (s, 2H), 2.60 (s, 3H).

Step D. (4S,5R)-5-[3,5-bis(trifluoromethyl)phenyl]-3-[2-iodo-3-methyl-5-(trifluoromethyl)benzyl]-4-methyl-1,3-oxazolidin-2-one To a solution of oxazolidone from Example xx, step xx, (0.058 g, 0.186 mmol) in THF (5 ml) at 0° C., NaH was added. The mixture was stirred for 30 min at 0° C. A solution of benzyl bromide from Step C (0.064 g, 0.169 mmol) in THF (5 ml) was added via syringe. The mixture was then allowed to stirred at room temperature for 12 h. The reaction was quenched with saturated ammonium chloride solution. The mixture was extracted with ethyl acetate (3×15 ml). The combined EtOAc layers were washed with brine and dried over sodium sulfate. The titled compound was obtained after a preparative TLC plate using EtOAc:hexane=1:9 as the elute. $^1$H NMR (CDCl$_3$, 500 MHz): δ 7.92 (s, 1H), 7.82 (s, 2H), 7.49 (s, 1H), 7.38 (s, 1H), 5.77 (d, J=8 Hz, 1H), 4.93 (d, J=16 Hz, 1H), 4.45 (d, J=16 Hz, 1H), 4.05 (m, 1H), 2.60 (s, 3H), 0.81 (d, J=6.5 Hz, 3H).

Step E: (4S,5R)-5-[3,5-bis(trifluoromethyl)phenyl]-3-{[4'-fluoro-5'-isopropyl-2'-methoxy-6-methyl-4-(trifluoromethyl)biphenyl-2-yl]methyl}-4-methyl-1,3-oxazolidin-2-one A mixture of the titled compound from Step D (0.07 g, 0.11 mmol), 2-methoxy-4-fluoro-5-isopropyl phenyl boronic acid (0.036 g, 0.17 mmol), sodium carbonate (0.024 g, 0.23 mmol) and catalytic amount of Pd(PPh$_3$)$_4$ in a mixture of 2:1:4 EtOH/H$_2$O/toluene was heated to reflux for 3 h. The solvents were removed and the aqueous was extracted with methylene chloride (3×20 ml). The combined methylene chloride layers were washed with brine, and dried over sodium sulfate. The titled compound was obtained after a preparative TLC plate using EtOAc:hexane=1:9 as the elute. Two diastereomeric atropisomers of the titled compound were separated by a chiral OD column using EtOH/n-Heptane as the elute. Isomer A (faster elute): $^1$H NMR (CDCl$_3$, 500 MHz): δ 7.89 (s, 1H), 7.75 (s, 2H), 7.52 (s, 2H), 6.85 (d, J=8.5 Hz, 1H), 6.71 (d, J=12 Hz, 1H), 5.63 (d, J=8 Hz, 1H), 4.71 (d, J=16 Hz, 1H), 3.93 (m, 1H), 3.87 (d, J=16 Hz, 1H), 3.72 (s, 3H), 3.22 (m, 1H), 2.09 (s, 3H), 1.26 (m, 6H), 0.53 (d, J=6.5 Hz, 3H); LC-MS (M+1): 652.3. Isomer B (slower elute): $^1$H NMR (CDCl$_3$, 500 MHz): δ 7.89 (s, 1H), 7.73 (s, 2H), 7.53 (s, 2H), 6.90 (d, J=8.5 Hz, 1H), 6.73 (d, J=12 Hz, 1H), 5.60 (d, J=8 Hz, 1H), 4.69 (d, J=15.5 Hz, 1H), 3.88 (m, 1H), 3.86 (d, J=15.5 Hz, 1H), 3.76 (s, 3H), 3.22 (m, 1H), 2.11 (s, 3H), 1.23 (m, 6H), 0.48 (d, J=6.5 Hz, 3H); LC-MS (M+1): 652.3.

Example 328

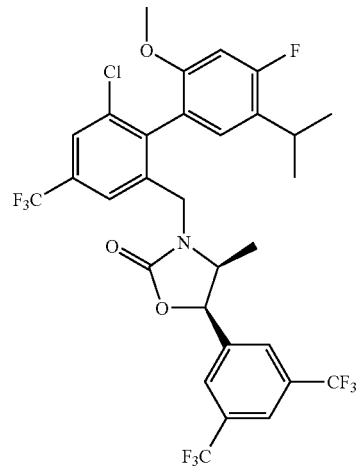 [SMILES: COc1cc(F)c(C(C)C)cc1-c1c(Cl)cc(C(F)(F)F)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-{[6-chloro-4'-fluoro-5'-isopropyl-2'-methoxy-4-(trifluoromethyl)biphenyl-2-yl]methyl}-4-methyl-1,3-oxazolidin-2-one Step A:
[2-chloro-6-methyl-4-(trifluoromethyl)phenyl]amine A mixture of 2-bromo-6-chloro-4-trifluoromethyl aniline (1.00 g, 3.64 mmol), trimethylboroxin (0.66 ml, 0.59 g, 4.47 mmol), potassium carbonate (1.00 g, 7.30 mmol) and catalytic amount (10%) Pd(PPh$_3$)$_4$ in DMF (5 ml) was heated to 90° C. for 14 h. Water (20 ml) was added. The mixture was extracted with ethyl acetate (3×50 ml). The combined EtOAc layers were washed with brine and dried over sodium sulfate. The titled compound was obtained as a colorless oil after a flash column using EtOAc:hexane (1:9) as the elute. $^1$H NMR (CDCl$_3$, 500 MHz): δ 7.43 (s, 1H), 7.24 (s, 1H), 4.38 (br s, 2H), 2.22 (s, 3H).

Step B [2-chloro-6-(iodomethyl)-4-(trifluoromethyl)phenyl]amine

A mixture of the titled compound from Step A (0.67 g, 3.20 mmol), n-pentyl nitrite (0.75 g, 6.41 mmol) and I$_2$ (1.05 g, 4.17 mmol) in chloroform (10 ml) was refluxed for 1 h. The mixture was diluted with methylene chloride (20 ml) and washed with saturated sodium thiosulfate solution, and brine. The organic layer was dried over sodium sulfate. 2-Iodo-3-chloro-4-trifluoromethyl benzyl iodide were obtained as after flash column using hexane as the elute. $^1$H NMR (CDCl$_3$, 500 MHz): δ 7.60 (s, 2H), 4.65 (s, 2H).

Step C. (4S,5R)-5-[3,5-bis(trifluoromethyl)phenyl]-3-[3-chloro-2-iodo-5-(trifluoromethyl)benzyl]-4-methyl-1,3-oxazolidin-2-one To a solution of oxazolidone from Example xx, step xx, (0.058 g, 0.186 mmol) in THF (5 ml) at 0° C., NaH was added.

The mixture was stirred for 30 min at 0° C. A solution of 2-iodo-3-chloro-4-trifluoromethyl benzyl iodide from Step B (0.226 g, 0.51 mmol) in THF (5 ml) was added via syringe. The mixture was then allowed to stir at room temperature for 3 h. The reaction was quenched with saturated ammonium chloride solution. The mixture was extracted with ethyl acetate (3×20 ml). The combined EtOAc layers were washed with brine and dried over sodium sulfate. The titled compound was obtained after a flash column using EtOAc:hexane=1:9 as the elute. LC-MS (M+1): 432.0.

Step D: (4S,5R)-5-[3,5-bis(trifluoromethyl)phenyl]-3-{[6-chloro-4'-fluoro-5'-isopropyl-2'-methoxy-4-(trifluoromethyl)biphenyl-2-yl]methyl}-4-methyl-1,3-oxazolidin-2-one A mixture of the titled compound from Step C (0.10 g, 0.16 mmol), 2-methoxy-4-fluoro-5-isopropyl phenyl boronic acid (0.067 g, 0.32 mmol), sodium carbonate (0.034 g, 0.32 mmol) and catalytic amount of Pd(PPh$_3$)$_4$ in a mixture of 2:1:4 EtOH/H2O/toluene was heated to reflux for 4 h. The solvents were removed and the aqueous was extracted with methylene chloride (3×15 ml). The combined methylene chloride layers were washed with brine, and dried over sodium sulfate. The titled compound was obtained after a preparative TLC plate using EtOAc:hexane=1:9 as the elute. Two diastereomeric atropisomers of the titled compound were separated by a chiral AD column using i-PrOH/n-Heptane as the elute. Isomer A (faster elute): $^1$H NMR (CDCl$_3$, 500 MHz): δ 7.91 (s, 1H), 7.75 (s, 3H), 7.61 (s, 1H), 6.92 (d, J=8.5 Hz, 1H), 6.73 (d, J=12 Hz, 1H), 5.64 (d, J=8 Hz, 1H), 4.72 (d, J=16 Hz, 1H), 3.95 (d, J=16 Hz, 1H), 3.93 (m, 1H), 3.78 (s, 3H), 3.22 (m, 1H), 1.23 (m, 6H), 0.55 (d, J=7 Hz, 3H); LC-MS (M+1): 672.1. Isomer B (slower elute): $^1$H NMR (CDCl$_3$, 500 MHz): δ 7.89 (s, 1H), 7.75 (s, 1H), 7.73 (s, 2H), 7.62 (s, 1H), 6.98 (d, J=8.5 Hz, 1H), 6.74 (d, J=12 Hz, 1H), 5.61 (d, J=8.5 Hz, 1H), 4.72 (d, J=16 Hz, 1H), 3.91 (d, J=16 Hz, 1H), 3.87 (m, 1H), 3.79 (s, 3H), 3.22 (m, 1H), 1.22 (m, 6H), 0.48 (d, J=6.5 Hz, 3H); LC-MS (M+1): 672.1.

INTERMEDIATE 22

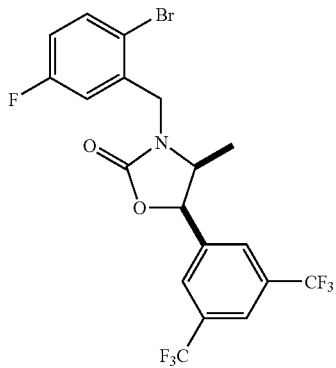

(4S,5R)-5-[3,5-bis(trifluoromethyl)phenyl]-3-(2-bromo-5-fluorobenzyl)-4-methyl-1,3-oxazolidin-2-one To a solution of (4S,5R)-5-[3,5-bis(trifluoromethyl)phenyl]-4-methyl-1,3-oxazolidin-2-one (2.0 g, 6.39 mmol) in THF (40 mL) at 0° C., NaH (285 mg, 60 w/w % in mineral oil, 7.13 mmol, 1.1 eq.) was added in one portion. The resulting foaming mixture was stirred in an ice bath. Additional THF (50 mL) was added into the reaction. The mixture was stirred at 0° C. for 30 min. A solution of 2-bromo-5-fluorobenzyl bromide (1.712 g, 6.39 mmol) in THF (20 mL) was added. The resulting mixture was stirred cold for 30 min and then allowed to warm to ambient. The reaction was completed in 3 h, monitored by LC-MS. The reaction was quenched with saturated aq. NH$_4$Cl (80 mL). Volatiles were removed in vacuo. Crude mixture was extracted with EtOAc, and dried over Na$_2$SO$_4$. The resulting clear gel was purified by SiO$_2$ (Biotage 40+M cartridge, EtOAc/hexane, gradient). The titled compound was obtained as a clear oil. LC-MS: 500.09 (M+1)$^+$. $^1$H NMR (CDCl$_3$, 500 MHz) δ 7.88 (s, 1H), 7.79 (s, 2H), 7.55 (dd, J=8.8, 5.2 Hz, 1H), 7.17 (dd, J=8.7, 4.5 Hz, 1H), 6.95 (m, 1H), 5.74 (d, J=8.0 Hz, 1H), 4.83 (d, J=15.8, 1H), 4.54 (d, J=16.0 Hz, 1H), 4.11 (m, 1H), 0.80 (d, J=6.6 Hz, 3H).

Example 329

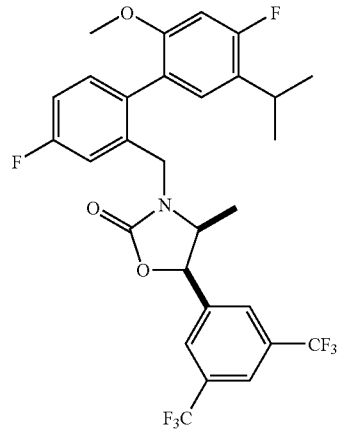 [SMILES: COc1cc(F)c(C(C)C)cc1-c1ccc(F)cc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-[(4,4'-difluoro-5'-isopropyl-2'-methoxybiphenyl-2-yl)methyl]-4-methyl-1,3-oxazolidin-2-one To a solution of (4S,5R)-5-[3,5-bis(trifluoromethyl)phenyl]-3-(2-bromo-5-fluorobenzyl)-4-methyl-1,3-oxazolidin-2-one (1.0 g, 2.0 mmol) in 1,4-dioxane (6 mL) was added (4-fluoro-5-isopropyl-2-methoxyphenyl)boronic acid (509 mg, 2.4 mmol), [1,1'-bis(diphenylphosphino) ferrocene] dichloropalladium (II) (82 mg, 5 mol %) and aq. potassium hydroxide (1.3 mL, 3M, 2 eq.). The reaction mixture was purged with nitrogen and then sealed in a microwave vessel. The reaction vessel was subject to microwave irradiation at 150° C. for 40 min. Crude mixture was worked up with water. Volatiles were evaporated. The resulting mixture was extracted with EtOAc. The combined extracts were dried over Na$_2$SO$_4$. The resulting purple residue was purified by SiO$_2$ (Biotage 40+M cartridge, eluted by EtOAc/hexane, gradient; 5% to 25%). The titled compound was obtained as clear solid. LC-MS: 588.23 (M+1)$^+$. $^1$H NMR (CDCl$_3$, 500 MHz) δ 6:4 mixture of rotamers δ 7.85 (s, 1 H), 7.69 (s, 2 H), 7.16-7.21 (m, 1.5 H), 7.04-7.13 (m, 1.5 H), 6.96 (dd, J=14.3, 8.80 Hz, 1 H), 6.65 (d, J=10.0 Hz, 1H), 5.59 (d, J=8.0 Hz, 0.6H), 5.43 (d, J=8.0 Hz, 0.4H), 4.85 (d, J=15.8 Hz, 0.6H), 4.82 (d, J=15.8 Hz, 0.4H), 4.02 (d, J=15.8 Hz, 0.6 H), 3.85 (m, 0.6 H), 3.76-3.81 (m, 0.8H), 3.75 (s, 1.8H), 3.73 (s, 1.2H), 3.19 (m, 1H), 1.14-1.26 (m, 6 H), 0.56 (d, J=6.6 Hz, 1.2 H), 0.38 (d, J=6.6 Hz, 1.8 H).

INTERMEDIATE 23

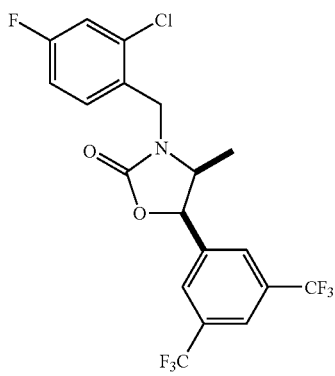

(4S,5R)-5-[3,5-bis(trifluoromethyl)phenyl]-3-(2-chloro-4-fluorobenzyl)-4-methyl-1,3-oxazolidin-2-one To a solution of (4S,5R)-5-[3,5-bis(trifluoromethyl)phenyl]-4-methyl-1,3-oxazolidin-2-one (1.0 g, 3.19 mmol)/THF (40 mL) at 0° C., was added NaH (153 mg, 60 w/w % in mineral oil, 3.83 mmol, 1.2 eq.) in one portion. The resulting foaming mixture was stirred in an ice bath for 30 min, followed by addition of 2-chloro-4-fluorobenzyl chloride (572 mg, 3.19 mmol). The resulting mixture was stirred at 0° C. for 30 min then warmed to ambient overnight. The reaction failed to proceed at room temperature and it was warmed in a 60° C. oil bath for 20 h. An aliquot indicated that the reaction was over. It was quenched with aq. $NH_4Cl$ (50 mL). Volatiles were evaporated. The resulting mixture was extracted with EtOAc. The combined extracts were dried over $Na_2SO_4$, filtered and concentrated in vacuo to a yellow oil. The oil was purified by $SiO_2$ (Biotage 40+M cartridge, eluted by EtOAc/hexanes, gradient; 5% to 40%). The titled compound was obtained as a colorless glassy material. LC-MS: 456.12 $(M+1)^+$. $^1H$ NMR ($CDCl_3$, 500 MHz) δ 7.89 (s, 1H), 7.77 (s, 2H), 7.46 (dd, J=8.7, 6.0 Hz, 1H), 7.17 (dd, J=8.4, 2.5 Hz, 1H), 7.03 (m, 1H), 5.68 (d, J=8.2 Hz, 1H), 4.83 (d, J=15.6, 1H), 4.36 (d, J=15.3 Hz, 1H), 4.06 (m, 1H), 0.79 (d, J=6.4 Hz, 3H).

Example 330

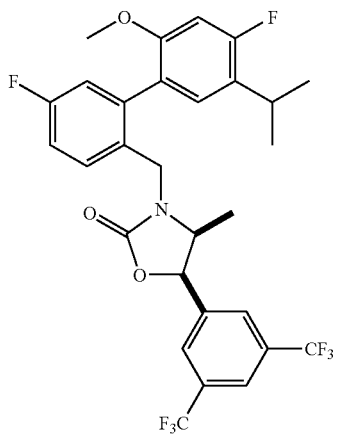

(4S,5R)-5-[3,5-bis(trifluoromethyl)phenyl]-3-[(4',5-difluoro-5'-isopropyl-2'-methoxybiphenyl-2-yl)methyl]-4-methyl-1,3-oxazolidin-2-one To a solution of (4S,5R)-5-[3,5-bis(trifluoromethyl)phenyl]-3-(2-chloro-4-fluorobenzyl)-4-methyl-1,3-oxazolidin-2-one (100 mg, 0.22 mmol) in 1,4-dioxane (1 mL) was added (4-fluoro-5-isopropyl-2-methoxyphenyl)boronic acid (55.8 mg, 0.26 mmol), palladium(II) acetate (10 mg, 20 mol %), potassium hydroxide aqueous solution (147 μL, 3M, 2 eq.) and tri-tert-butylphosphine (13.4 mg, 0.066 mmol, 30 mol % as a 10% w/w hexane solution). The resulting reaction mixture was $N_2$ purged and sealed in a microwave vessel. The vessel was subject to microwave irradiation at 140° C. for 40 min. LC-MS indicated the formation of desired product. It was quenched with water (50 mL). Volatiles were evaporated. The resulting mixture was extracted with EtOAc. The combined extracts were dried over $Na_2SO_4$, filtered and concentrated in vacuo to an oil. The titled compound was obtained after two purifications with silica gel and one reversed phase prep-HPLC. LC-MS: 588.25 $(M+1)^+$.

INTERMEDIATE 24

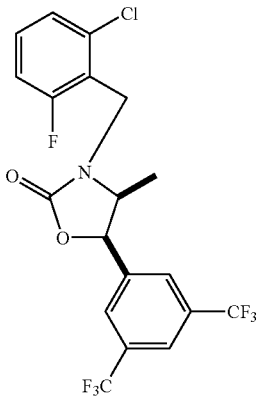

(4S,5R)-5-[3,5-bis(trifluoromethyl)phenyl]-3-(2-chloro-6-fluorobenzyl)-4-methyl-1,3-oxazolidin-2-one To a solution of (4S,5R)-5-[3,5-bis(trifluoromethyl)phenyl]-4-methyl-1,3-oxazolidin-2-one (1.0 g, 3.19 mmol) in THF (40 mL) at 0° C., was added NaH (153 mg, 60 w/w % in mineral oil, 3.83 mmol, 1.2 eq.) in one portion. The resulting foaming mixture was stirred in an ice bath for 30 min followed by addition of benzyl chloride (572 mg, 3.19 mmol). The resulting mixture was stirred at 0° C. for 30 min then warmed to 60° C. for 30 hr. An aliquot indicated about 10% of starting (4S,5R)-5-[3,5-bis(trifluoromethyl)phenyl]-4-methyl-1,3-oxazolidin-2-one left. The reaction was cooled and quenched with saturated $NH_4Cl$ (50 mL). Volatiles were evaporated. The resulting mixture was extracted with EtOAc. The combined extracts were dried over $Na_2SO_4$, filtered and concentrated in vacuo to a yellow oil. The titled compound was obtained as a colorless glassy material after purification by $SiO_2$ (Biotage 40+M, eluted by EtOAc/hex, gradient; 5% to 40%). LC-MS: 456.11 $(M+1)^+$. $^1H$ NMR ($CDCl_3$, 500 MHz) δ 7.87 (s, 1H), 7.77 (s, 2H), 7.22-7.34 (m, 2H), 7.01-7.09 (m, 1H), 5.62 (d, J=8.2 Hz, 1H), 5.01 (dd, J=14.8, 2.0 Hz, 1H), 4.45 (d, J=14.6 Hz, 1H), 3.91 (m, 1H), 0.81 (d, J=6.4 Hz, 3H).

Example 331

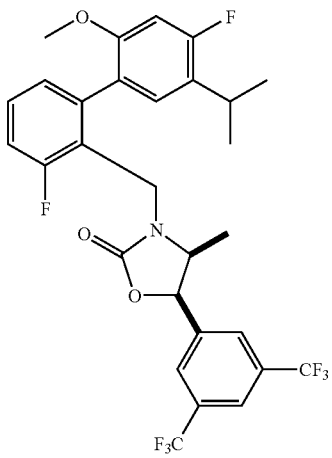

(4S,5R)-5-[3,5-bis(trifluoromethyl)phenyl]-3-[(3,4'-difluoro-5'-isopropyl-2'-methoxybiphenyl-2-yl)methyl]-4-methyl-1,3-oxazolidin-2-one To a solution of (4S,5R)-5-[3,5-bis(trifluoromethyl)phenyl]-3-(2-chloro-6-fluorobenzyl)-4-methyl-1,3-oxazolidin-2-one (327 mg, 0.72 mmol) in 1,4-dioxane (4 mL) was added (4-fluoro-5-isopropyl-2-methoxyphenyl)boronic acid (228 mg, 1.08 mmol), Palladium(II) acetate (33 mg, 20 mol %), potassium hydroxide (588 µL, 3M, 2.5 eq.) and tri-tert-butylphosphine (44 mg, 0.22 mmol, 30 mol % as a 10% w/w hexane solution). The resulting reaction mixture was purged with nitrogen and sealed in a microwave vessel. The vessel was subject to microwave irradiation at 135° C. for 50 min. LC-MS indicated the starting material/product ratio was about 55:45. The reaction mixture was re-submitted to reaction conditions (µw at 135° C. for 50 min). The LC-MS trace indicated that no progress was made from the $2^{nd}$ irradiation. More palladium(II) acetate (33 mg, 20 mol %) and tri-tert-butylphosphine (44 mg, 0.22 mmol, 30 mol % as a 10% w/w hexane solution) were added into reaction mixture. The mixture was resubmitted to reaction conditions (µw at 135° C., 1 hr). Again, the LC-MS indicated no significant progress. The reaction mixture was quenched with $H_2O$. The volatiles were removed under reduced pressure. The resulting mixture was extracted with EtOAc. The combined extracts were dried over $Na_2SO_4$, filtered and concentrated in vacuo to a yellow oil. The oil was dissolved in DMSO and purified twice by a reversed phase prep-HPLC (column: Kromasil, 100-5C18, 100×21.1 mm) eluted by 10% to 90% $H_2O$ (0.1% TFA, v/v)/MeCN (0.1% TFA, v/v). The resulting glassy material was then purified on a prep-TLC plate by 100% dichloromethane to afford the titled compound. LC-MS: 588.21 (M+1)$^+$. $^1$H NMR (CDCl$_3$, 500 MHz) δ 1:1 mixture of rotamers δ 7.83 (s, 1 H), 7.67 (s, 1 H) 7.65 (s, 1 H), 7.32-7.41 (m, 1H), 7.09-7.16 (m, 1H), 6.96-7.06 (m, 1H), 6.64-6.70 (m, 1H), 5.47 (d, J=8.0 Hz, 0.5 H), 5.19 (d, J=7.8 Hz, 0.5 H), 4.96 (d, J=14.9 Hz, 0.5 H), 4.80 (d, J=15.1 Hz, 0.5 H), 4.31 (d, J=15.1 Hz, 0.5 H), 3.91 (d, J=15.1 Hz, 0.5 H), 3.78 (s, 1.5 H), 3.75 (s, 1.5 H), 3.62-3.69 (m, 1 H), 3.15-3.26 (m, 1 H), 1.14-1.25 (m, 6 H), 0.54 (d, J=6.6 Hz, 1.5 H), 0.33 (d, J=6.4 Hz, 1.5 H).

Example 332

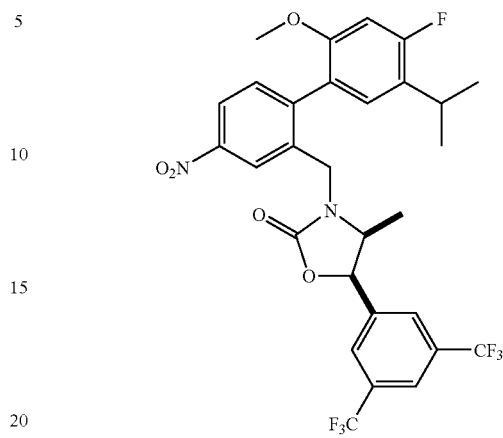

Step A: 2-bromo-5-nitrophenyl)methanol

Methyl 2-bromo-5-nitrobenzoate (10 g, 38.46 mmol) was dissolved in THF (100 mL) and cooled to internal temperature=−15~−10° C. To this mixture was added diisobutylaluminum hydride solution (1.0 M in toluene, 57 mL, 57 mmol) slowly while maintaining internal temperature <0° C. The resulting mixture was stirred at ambient for 1 hour then quenched with aq. $NH_4Cl$ (150 mL). The crude mixture was diluted with EtOAc (100 mL) and then filtered. Volatiles were removed under reduced pressure. The resulting residue was extracted with EtOAc (200 mL×2). The combined extracts were dried over $Na_2SO_4$, filtered and evaporated to an oil. The resulting oil was purified by $SiO_2$ (Biotage 65i, EtOAc/hexanes, gradient; 10% to 15%). The titled compound was obtained as a yellow crystalline solid. $^1$H NMR (CDCl$_3$, 500 MHz) δ 8.44 (d, J=2.74 Hz 1 H), 8.02 (dd, J=8.7, 2.8 Hz, 1 H), 7.72 (d, J=8.7, 1 H), 4.83 (s, 3 H).

Step B: 1-bromo-2-(bromomethyl)-4-nitrobenzene

To a solution of 2-bromo-5-nitrophenyl)methanol (4.746 g, 20.45 mmol) in anhydrous dichloromethane (150 mL), was added triphenylphosphine (6.43 g, 24.5 mmol) and carbon tetrabromide (8.15 g, 24.5 mmol). The mixture was stirred at 0° C. for 30 min then at 20° C. for 1 h. TLC showed complete consumption of starting material. Volatiles were removed under reduced pressure. The resulting oil was purified by $SiO_2$ (Biotage 40M, eluted by EtOAc/hexanes, gradient) to afford the titled compound as a colorless solid. $^1$H NMR (CDCl$_3$, 500 MHz) δ 8.33 (d, J=2.74 Hz 1H), 8.03 (dd, J=8.7, 2.5 Hz, 1 H), 7.78 (d, J=8.7, 1H), 4.63 (s, 3 H).

Step C: (4S,5R)-5-[3,5-bis(trifluoromethyl)phenyl]-3-(2-bromo-5-nitrobenzyl)-4-methyl-1,3-oxazolidin-2-one To a solution of (4S,5R)-5-[3,5-bis(trifluoromethyl)phenyl]-4-methyl-1,3-oxazolidin-2-one (5.3 g, 16.95 mmol) in THF (100 mL) at 0° C., NaH (746 mg, 60 w/w % in mineral oil, 18.65 mmol, 1.1 eq.) was added in one portion. The resulting foaming mixture was stirred in an ice bath. Additional THF (100 mL) was added into the reaction. The mixture was stirred at 0° C. for 30 min. A solution of 1-bromo- 2-(bromomethyl)-4-nitrobenzene (5.0 g, 16.95 mmol) in THF (25 mL) was added. The resulting mixture was stirred cold for 30 min and then allowed to warm to ambient. The reaction was completed in 1.5 h. The reaction was quenched with sat. aqueous NH$_4$Cl (100 mL). Crude mixture was extracted with EtOAc, and dried over Na$_2$SO$_4$. The resulting clear gel was purified by SiO$_2$ (Biotage 40M cartridge, EtOAc/hexane, gradient, 25% to 45%). The titled compound was obtained as a crystalline solid. LC-MS: 529.11 (M+1)$^+$. $^1$H NMR (CDCl$_3$, 500 MHz) δ 8.24 (d, J=2.5 Hz, 1H), 8.07 (dd, J=8.7, 2.8 Hz, 1H), 7.91 (s, 1H), 7.79-7.83 (m, 3H), 5.82 (d, J=7.8 Hz, 1H), 4.82 (d, J=16.2 Hz, 1H), 4.44 (d, J=16.3, 1H), 4.11-4.20 (m, 1H), 0.84 (d, J=6.6 Hz, 3H).

Step D: (4S,5R)-5-[3,5-bis(trifluoromethyl)phenyl]-3-[(4'-fluoro-5'-isopropyl-2'-methoxy-4-nitrobiphenyl-2-yl)methyl]-4-methyl-1,3-oxazolidin-2-one To a solution of (4S,5R)-5-[3,5-bis(trifluoromethyl)phenyl]-3-(2-bromo-5-nitrobenzyl)-4-methyl-1,3-oxazolidin-2-one (3.877 g, 7.35 mmol) in a toluene (24 mL): ethanol (12 mL): water (6 mL) mixture was added (4-fluoro-5-isopropyl-2-methoxyphenyl)boronic acid (2.337 g, 11.03 mmol), tetrakis (triphenylphosphine) palladium(0) (425 mg, 5 mol %) and sodium carbonate (1.56 g, 14.72 mmol). The resulting mixture was bubbled with nitrogen and then heated in a 90° C. oil bath for 10 h. An aliquot showed complete consumption of the starting material. The reaction was quenched with brine. The resulting mixture was extracted with EtOAc and dried over Na$_2$SO$_4$. The resulting glassy mixture was purified by SiO$_2$ (Biotage 40S cartridge, EtOAc/hexane, gradient). The titled compound was obtained as a crystalline solid. LC-MS: 615.26 (M+1)$^+$. $^1$H NMR (CDCl$_3$, 500 MHz) δ 1:1 mixture of rotamers δ 8.31 (s, 1 H), 8.20-8.26 (m, 1 H), 7.86 (s, 1 H), 7.70 (s, 2 H), 7.39-7.43 (m, 1 H), 6.96-7.01 (m, 1H), 6.67-6.72 (m, 1H), 5.64 (d, J=8.0 Hz, 0.5H), 5.48 (d, J=8.0 Hz, 0.5H), 4.90 (d, J=16.3 Hz, 0.5H), 4.86 (d, J=16.3 Hz, 0.5 H), 4.10-4.16 (m, 0.5 H), 3.84-3.94 (m, 1.5 H), 3.77 (s, 1.5H), 3.75 (s, 1.5H), 3.15-3.26 (m, 1H), 1.15-1.29 (m, 6 H), 0.57 (d, J=6.6 Hz, 1.5 H), 0.40 (d, J=6.6 Hz, 1.5 H).

Example 333

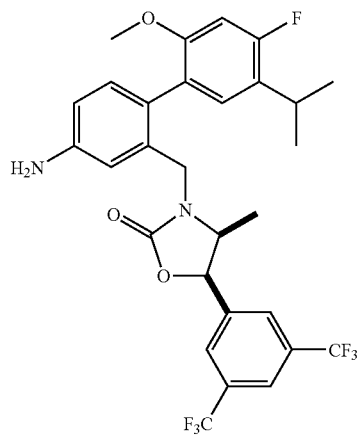

(4S,5R)-3-[(4-amino-4'-fluoro-5'-isopropyl-2'-methoxybiphenyl-2-yl)methyl]-5-[3,5-bis(trifluoromethyl)phenyl]-4-methyl-1,3-oxazolidin-2-one A solution of (4S,5R)-5-[3,5-bis(trifluoromethyl)phenyl]-3-[(4'-fluoro-5'-isopropyl-2'-methoxy-4-nitrobiphenyl-2-yl) methyl]-4-methyl-1,3-oxazolidin-2-one (1.94 g, 3.16 mmol) in methanol (20 mL) was subject to H$_2$ (40 psi., Parr shaker) at 20° C. for 1.5 h. LCMS indicated the presence of trace starting material. The crude mixture was filtered through a bed of Celite (521). The filtrate was evaporated in vacuo to afford a glass as the product. LC-MS: 585.32 (M+1)$^+$. $^1$H NMR (CDCl$_3$, 500 MHz) δ 1:1 mixture of rotamers δ 7.83 (s, 1 H), 7.67 (s, 2 H), 6.93-7.06 (m, 2 H), 6.87 (s, 0.5H), 6.72-6.82 (m, 1.5H), 5.57 (d, J=8.0 Hz, 0.5H), 5.36 (d, J=8.0 Hz, 0.5H), 4.77 (d, J=5.5 Hz, 0.51-1), 4.74 (d, J=6.5 Hz, 0.5 H), 3.95 (d, J=15.5 Hz, 0.5 H), 3.75-3.86 (m, 1.5 H), 3.73 (s, 3 H), 3.12-3.24 (m, 1H), 1.11-1.29 (m, 6 H), 0.47 (d, J=6.5 Hz, 1.5H), 0.29 (d, J=6 Hz, 1.5 H).

Example 334

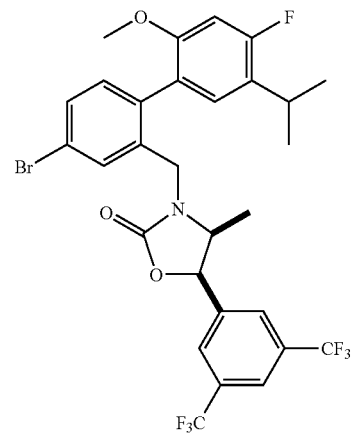

(4S,5R)-5-[3,5-bis(trifluoromethyl)phenyl]-3-[(4-bromo-4'-fluoro-5'-isopropyl-2'-methoxybiphenyl-2-yl)methyl]-4-methyl-1,3-oxazolidin-2-one To a solution (4S,5R)-3-[(4-amino-4'-fluoro-5'-isopropyl-2'-methoxybiphenyl-2-yl)methyl]-5-[3,5-bis(trifluoromethyl)phenyl]-4-methyl-1,3-oxazolidin-2-one (526 mg, 0.90 mmol) in bromoform (2.5 mL) was added tert-butyl nitrite (186 mg, 1.80 mmol). The resulting mixture was stirred at 80° C. for 20 min. An aliquot indicated completion of the reaction. The reaction crude was purified silica gel to afford the title compound as a yellow glass. LC-MS: 650.09 (M+1)$^+$. $^1$H NMR (CDCl$_3$, 500 MHz) δ 1:1 mixture of rotamers δ 7.85 (s, 1 H), 7.69 (s, 2 H), 7.60 (s, 0.5 H), 7.48-7.53 (m, 1.5H), 7.07-7.11 (m, 1 H), 6.93-6.99 (m, 1 H), 6.62-6.67 (m, 1H), 5.59 (d, J=8.0 Hz, 0.5H), 5.39 (d, J=7.0 Hz, 0.5H), 4.82 (d, J=6.5 Hz, 0.5H), 4.75 (d, J=6.5 Hz, 0.5 H), 3.98 (d, J=16.0 Hz, 0.5 H), 3.76-3.85 (m, 1.5 H), 3.75 (s, 1.5 H), 3.74 (s, 1.5 H), 3.13-3.23 (m, 1H), 1.13-1.29 (m, 6 H), 0.52 (d, J=6.5 Hz, 1.5H), 0.34 (d, J=7.0 Hz, 1.5 H).

Example 335

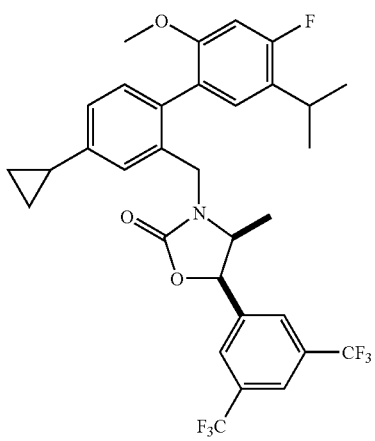

(4S,5R)-5-[3,5-bis(trifluoromethyl)phenyl]-3-[(4-cyclopropyl-4'-fluoro-5'-isopropyl-2'-methoxybiphenyl-2-yl)methyl]-4-methyl-1,3-oxazolidin-2-one To a solution of (4S,5R)-5-[3,5-bis(trifluoromethyl)phenyl]-3-[(4-bromo-4'-fluoro-5'-isopropyl-2'-methoxybiphenyl-2-yl)methyl]-4-methyl-1,3-oxazolidin-2-one (100 mg, 0.15 mmol) in 1,4-dioxane (0.5 mL) was added cyclopropylboronic acid (10 mg, 0.19 mmol), [1,1'-bis(diphenylphosphino)ferrocene]dichloropalladium (II) (82 mg, 8 mol %), bis(tri-tert-butylphosphine)palladium (0) (10 mg, 13 mol %) and aqueous potassium hydroxide (78 μL, 3M, 1.5 eq.). The reaction mixture was purged with nitrogen and then sealed in a microwave vessel. The reaction vessel was subject to microwave irradiation at 150° C. for 30 min. An aliquot indicated complete consumption of starting material. Reaction crude was worked up with water. The resulting mixture was extracted with EtOAc and dried over Na$_2$SO$_4$. The titled compound was obtained as a glassy material after two preparative TLC plates using respectively 20% EtOAc in hexanes and 5% EtOAc in dichloromethane as the eluent. LC-MS: 610.26 (M+1)$^+$. $^1$H NMR (CDCl$_3$, 500 MHz) δ 1:1 mixture of rotamers δ 7.84 (s, 1 H), 7.65-7.70 (m, 2 H), 7.21 (s, 0.5H), 7.08-7.14 (m, 1.5H), 6.95-7.04 (m, 2 H), 6.61-6.67 (m, 1 H), 5.52 (d, J=8.5 Hz, 0.5H), 5.27 (d, J=8.0 Hz, 0.5H), 4.85 (d, J=15.5 Hz, 0.5H), 4.81 (d, J=15.5 Hz, 0.5 H), 4.00 (d, J=15.5 Hz, 0.5 H), 3.69-3.81 (m, 4.5 H), 3.13-3.24 (m, 1H), 1.90-1.99 (m, 1 H), 1.12-1.30 (m, 6 H), 0.98-1.15 (m, 2 H), 0.71-0.77 (m, 2 H), 0.48 (d, J=6.5 Hz, 1.5 H), 0.29 (d, J=6.5 Hz, 1.5 H).

Example 336

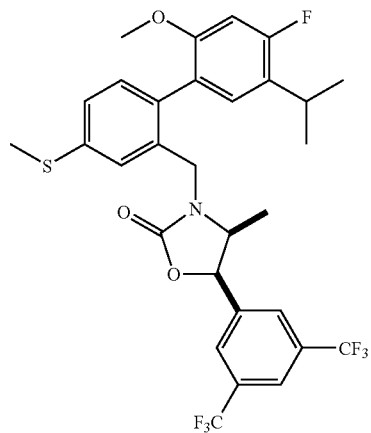

(4S,5R)-5-[3,5-bis(trifluoromethyl)phenyl]-3-{[4'-fluoro-5'-isopropyl-2'-methoxy-4-(methylthio)biphenyl-2-yl]methyl}-4-methyl-1,3-oxazolidin-2-one To a solution (4S,5R)-3-[(4-amino-4'-fluoro-5'-isopropyl-2'-methoxybiphenyl-2-yl)methyl]-5-[3,5-bis(trifluoromethyl)phenyl]-4-methyl-1,3-oxazolidin-2-one (200 mg, 0.34 mmol) in methyl disulfide (2 mL) was added tert-butyl nitrite (70 mg, 0.68 mmol). The resulting mixture was stirred at 80° C. for 30 min. An aliquot indicated completion of the reaction. The titled compound was obtained as a glassy material after two preparative TLC plates using respectively 20% EtOAc in hexanes and 10% EtOAc in dichloromethane as the eluent. LC-MS: 616.21 (M+1)$^+$. $^1$H NMR (CDCl$_3$, 500 MHz) δ 1:1 mixture of rotamers δ 7.84 (s, 1 H), 7.67 (s, 2 H), 7.35 (s, 0.5 H), 7.22-7.28 (m, 1.5 H), 7.12-7.19 (m, 1 H), 6.94-7.02 (m, 1 H), 6.61-6.68 (m, 1 H), 5.55 (d, J=8.0 Hz, 0.5H), 5.31 (d, J=9.5 Hz, 0.5H), 4.85 (d, J=16.0 Hz, 0.5H), 4.83 (d, J=15.5 Hz, 0.5 H), 3.99 (d, J=15.5 Hz, 0.5 H), 3.69-3.81 (m, 4.5 H), 3.12-3.24 (m, 1H), 2.54, (s, 1.5 H), 2.53 (s, 1.5 H), 1.11-1.27 (m, 6 H), 0.50 (d, J=6.5 Hz, 1.5 H), 0.31 (d, J=7.0 Hz, 1.5 H).

Example 337

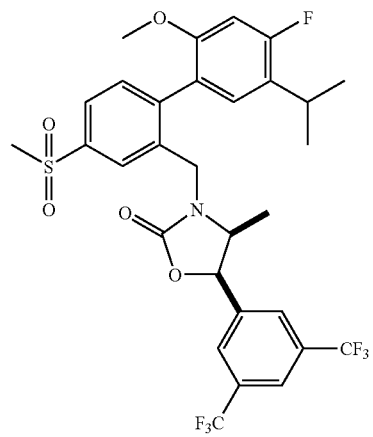

(4S,5R)-5-[3,5-bis(trifluoromethyl)phenyl]-3-{[4'-fluoro-5'-isopropyl-2'-methoxy-4-(methylsulfonyl)biphenyl-2-yl]methyl}-4-methyl-1,3-oxazolidin-2-one To a solution of (4S,5R)-5-[3,5-bis(trifluoromethyl)phenyl]-3-{[4'-fluoro-5'-isopropyl-2'-methoxy-4-(methylthio)biphenyl-2-yl]methyl}-4-methyl-1,3-oxazolidin-2-one (156 mg, 0.25 mmol) in dichloromethane (3 mL) was added 3-chloroperbenzoic acid (175 mg, 1.01 mmol). The resulting mixture was stirred at 20° C. for 1 h. An aliquot indicated completion of the reaction. Reaction crude was partitioned between water and dichloromethane. The organic layer was separated and dried over Na$_2$SO$_4$. The titled compound was obtained as a glassy material after three preparative TLC plates using respectively 50% EtOAc in hexanes, 20% EtOAc in dichloromethane and dichloromethane as the eluent. LC-MS: 648.29 (M+1)$^+$. $^1$H NMR (CDCl$_3$, 500 MHz) δ 1:1 mixture of rotamers δ 7.99 (s, 0.5 H), 7.92-7.96 (m, 1.5 H), 7.86 (s, 1H), 7.70 (s, 2 H), 7.42-7.46 (m, 1 H), 6.96-7.00 (m, 1 H), 6.69 (d, J=12 Hz, 1 H), 5.64 (d, J=8.0 Hz, 0.5H), 5.45 (d, J=8.0 Hz, 0.5H), 4.93 (d, J=6.0 Hz, 0.5H), 4.90 (d, J=6.5 Hz, 0.5H), 4.09 (d, J=16 Hz, 0.5 H), 3.88 (d, J=16 Hz, 0.5 H), 3.80-3.88 (m, 1 H), 3.78 (s, 1.5 H), 3.75 (s, 1.5 H), 3.16-3.25 (m, 1H), 3.14 (s, 1.5 H), 3.13 (s, 1.5H), 1.22-1.28 (m, 6H), 0.57 (d, J=6.5 Hz, 1.5 H), 0.38 (d, J=6.5 Hz, 1.5 H).

Example 338

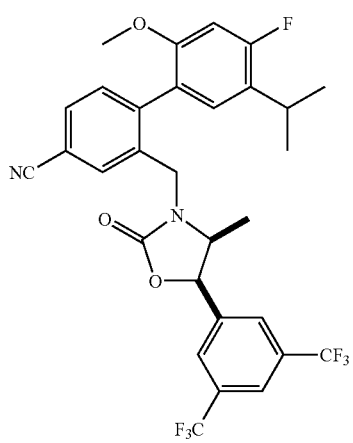

2-({(4S,5R)-5-[3,5-bis(trifluoromethyl)phenyl]-4-methyl-2-oxo-1,3-oxazolidin-3-yl}methyl)-4'-fluoro-5'-isopropyl-2'-methoxybiphenyl-4-carbonitrile To a solution of (4S,5R)-5-[3,5-bis(trifluoromethyl)phenyl]-3-[(4-bromo-4'-fluoro-5'-isopropyl-2'-methoxybiphenyl-2-yl)methyl]-4-methyl-1,3-oxazolidin-2-one (100 mg, 0.15 mmol) in N,N-dimethylformamide (1.5 mL) was added copper(I) cyanide (17 mg, 0.19 mmol). The resulting reaction mixture was $N_2$ purged and sealed in a microwave vessel. The vessel was subject to microwave irradiation at 150° C. for 30 min. LC-MS indicated only the starting bromide was present. Added tetrakis(triphenylphosphine)palladium(0) (10 mg, 6 mol %) into the reaction mixture. Repeated microwave irradiation at 150° C. for 30 min. An aliquot indicated the desired product was formed and all starting bromide was consumed. Reaction crude was partitioned between water and hexanes. The aqueous phase was back extracted with diethyl ether. The combined extracts were dried over $Na_2SO_4$. The titled compound was obtained as a glassy material after two preparative TLC plates developed respectively by 20% EtOAc in hexanes and 4% EtOAc in dichloromethane. LC-MS: 595.03 (M+1)$^+$. $^1$H NMR (CDCl$_3$, 500 MHz) δ 1:1 mixture of rotamers δ 7.86 (s, 1 H), 7.61 (S, 0.5 H), 7.67-7.71 (m, 2.5H), 7.64-7.68 (m, 1 H), 7.32-7.36 (m, 1 H), 6.98 (d, J=8.5 Hz, 0.5H), 6.95 (d, J=8.5 Hz, 0.5 H), 6.68 (d, J=12 Hz, 1H), 5.62 (d, J=8.0 Hz, 0.5H), 5.46 (d, J=8.0 Hz, 0.5H), 4.85 (d, J=16.0 Hz, 0.5H), 4.80 (d, J=16.0 Hz, 0.5 H), 4.06 (d, J=16 Hz, 0.5 H), 3.79-3.86 (m, 1 H), 3.70-3.78 (m, 3.5 H), 3.16-3.24 (m, 1H), 3.75 (s, 1.5 H), 3.16-3.25 (m, 1H), 3.14 (s, 1.5 H), 3.13 (s, 1.5 H), 1.15-1.27 (m, 6 H), 0.54 (d, J=7.0 Hz, 1.5 H), 0.37 (d, J=6.5 Hz, 1.5 H).

Example 339

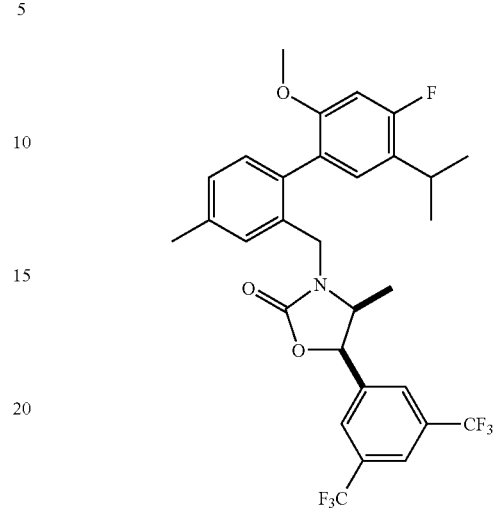

(4S,5R)-5-[3,5-bis(trifluoromethyl)phenyl]-3-[(4'-fluoro-5'-isopropyl-2'-methoxy-4-methylbiphenyl-2-yl)methyl]-4-methyl-1,3-oxazolidin-2-one To a solution of (4S,5R)-5-[3,5-bis(trifluoromethyl)phenyl]-3-[(4-bromo-4'-fluoro-5'-isopropyl-2'-methoxybiphenyl-2-yl)methyl]-4-methyl-1,3-oxazolidin-2-one (82.5 mg, 0.13 mmol) in 1,4-dioxane (1 mL) was added trimethylboroxin (39 mg, 0.31 mmol), Pd(PPh$_3$)$_4$ (15 mg, 10 mol %) and potassium carbonate (35 mg, 0.25 mmol). The resulting reaction mixture was purged with nitrogen and sealed in a microwave vessel. The vessel was subject to microwave irradiation at 130° C. for 15 min. The crude mixture was diluted with brine and extracted with EtOAc. The combined organic extracts were dried over $Na_2SO_4$. The titled compound was obtained as a glassy material after two preparative TLC plates developed respectively by 20% EtOAc in hexanes and dichloromethane. LC-MS: 584.08 (M+1)$^+$. $^1$H NMR (CDCl$_3$, 500 MHz) δ 1:1 mixture of rotamers δ 7.84 (s, 1 H), 7.65-7.70 (m, 2 H), 7.29 (s, 0.5), 7.18-7.22 (m, 1.5 H), 7.10-7.15 (m, 1 H), 7.01 (d, J=8.0 Hz, 0.5 H), 6.98 (d, J=8.5 Hz, 0.5 H), 6.66 (d, J=5.0 Hz, 0.5 H), 6.64 (d, J=5.5 Hz, 0.5 H), 5.54 (d, J=8.5 Hz, 0.5H), 5.31 (d, J=8.0 Hz, 0.5H), 4.82 (d, J=15.5 Hz, 1 H), 4.02 (d, J=15 Hz, 0.5 H), 3.71-3.82 (m, 5 H), 3.15-3.24 (m, 1 H), 2.42 (s, 1.5 H), 2.41 (s, 1.5 H), 1.13-1.27 (m, 6 H), 0.48 (d, J=6.5 Hz, 1.5 H), 0.31 (d, J=6.5 Hz, 1.5 H).

Example 340

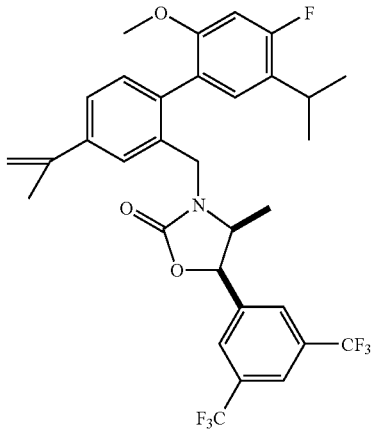

(4S,5R)-5-[3,5-bis(trifluoromethyl)phenyl]-3-[(4'-fluoro-4-isopropenyl-5'-isopropyl-2'-methoxybiphenyl-2-yl)methyl]-4-methyl-1,3-oxazolidin-2-one To a solution of (4S,5R)-5-[3,5-bis(trifluoromethyl)phenyl]-3-[(4-bromo-4'-fluoro-5'-isopropyl-2'-methoxybiphenyl-2-yl)methyl]-4-methyl-1,3-oxazolidin-2-one (38 mg, 0.059 mmol) in 1,4-dioxane (0.5 mL) was added (2-chloro-5-isopropylphenyl)boronic acid (10 mg, 0.12 mmol), [1,1'-bis(diphenylphosphino)ferrocene]dichloropalladium (II) (2.4 mg, 5 mol %) and aqueous potassium hydroxide (40 µL, 3M, 2 eq.). The reaction mixture was purged with nitrogen and then sealed in a microwave vessel. The reaction vessel was subject to microwave irradiation at 140° C. for 20 min. Crude mixture was worked up with water and EtOAc. The combined organic extracts were dried over $Na_2SO_4$ and concentrated in vacuo to give the crude product. This was purified by preparative TLC plate eluted by 20% EtOAc in hexanes to give the titled compound. LC-MS: 610.04 (M+1)$^+$. $^1$H NMR (CDCl$_3$, 500 MHz) δ 1:1 mixture of rotamers 7.84 (s, 1 H), 7.64-7.70 (m, 2 H), 7.56 (s, 0.5), 7.45-7.50 (m, 1.5 H), 7.18-7.23 (m, 1 H), 7.02 (d, J=9.0 Hz, 0.5 H), 6.99 (d, J=8.5 Hz, 0.5 H), 6.67 (d, J=7.0 Hz, 0.5 H), 6.64 (d, J=5.5 Hz, 0.5 H), 5.52 (d, J=8.0 Hz, 0.5H), 5.43 (d, J=8.5 Hz, 1 H), 5.26 (d, J=8.0 Hz, 0.5 H), 5.13-5.17 (m, 1H), 4.91 (d, J=15.0 Hz, 0.5 H), 4.86 (d, J=15.5 Hz, 0.5 H), 4.04 (d, J=15.5 Hz, 0.5 H), 3.83 (d, J=15.5, 0.5 H), 3.70-3.78 (m, 3 H), 3.14-3.25 (m, 1H), 2.18-2.22 (m, 3H), 1.14-1.29 (m, 6 H), 0.50 (d, J=6.5 Hz, 1.5 H), 0.31 (d, J=6.5 Hz, 1.5 H).

Example 341

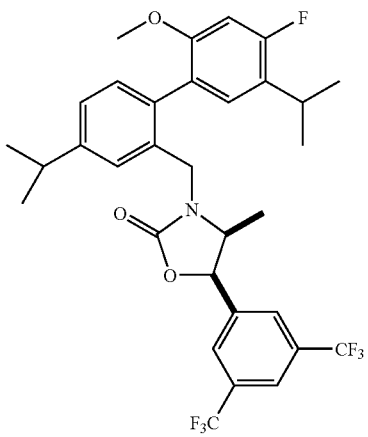

(4S,5R)-5-[3,5-bis(trifluoromethyl)phenyl]-3-[(4'-fluoro-4,5'-diisopropyl-2'-methoxybiphenyl-2-yl)methyl]-4-methyl-1,3-oxazolidin-2-one A solution of (4S,5R)-5-[3,5-bis(trifluoromethyl)phenyl]-3-[(4'-fluoro-4-isopropenyl-5'-isopropyl-2'-methoxybiphenyl-2-yl)methyl]-4-methyl-1,3-oxazolidin-2-one (15 mg, 0.025 mmol) in methanol (1 mL) was subject to $H_2$ (balloon atmosphere) at 20° C. overnight. The crude mixture was filtered through a syringe filter. The filtrate was evaporated in vacuo and purified by preparative TLC plates developed by 20% EtOAc in hexanes to give the titled compound. LC-MS: 612 (M+1)$^+$. $^1$H NMR (CDCl$_3$, 500 MHz) δ 1:1 mixture of rotamers δ 7.84 (s, 1 H), 7.64-7.68 (m, 2 H), 7.30 (s, 0.5), 7.20-7.27 (m, 1.5 H), 7.13-7.17 (m, 1 H), 7.02 (d, J=8.5 Hz, 0.5H), 6.99 (d, J=8.0 Hz, 0.5 H), 6.65 (d, J=6.0 Hz, 0.5 H), 6.63 (d, J=6.0 Hz, 0.5 H), 5.52 (d, J=8.0 Hz, 0.5H), 5.25 (d, J=8.0 Hz, 1 H), 4.87 (d, J=15.5 Hz, 0.5 H), 4.82 (d, J=15.5 Hz, 0.5H), 4.03 (d, J=15.0 Hz, 0.5 H), 3.81 (d, J=15.0 Hz, 0.5 H), 3.69-3.77 (m, 4 H), 3.14-3.24 (m, 1 H), 2.92-3.02 (m, 1 H), 1.14-1.33 (m, 12 H), 0.48 (d, J=6.5 Hz, 1.5 H), 0.30 (d, J=7.0 Hz, 1.5 H).

INTERMEDIATE 25

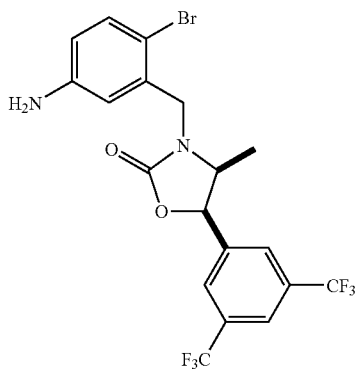

(4S,5R)-3-(5-amino-2-bromobenzyl)-5-[3,5-bis(trifluoromethyl)phenyl]-4-methyl-1,3-oxazolidin-2-one A mixture of (4S,5R)-5-[3,5-bis(trifluoromethyl)phenyl]-3-(2-bromo-5-nitrobenzyl)-4-methyl-1,3-oxazolidin-2-one (614 mg, 1.17 mmol), tin(II) chloride dehydrate (1.314 g, 5.823 mmol) and ethanol (3 mL) was stirred at 20° C. for 36 h. Reaction crude was worked up with water. The resulting mixture was extracted with EtOAc and dried over $Na_2SO_4$. The titled compound was obtained as a glassy material after $SiO_2$ purification (Biotage 40+M, gradient, 0% to 35% EtOAc in hexanes). LC-MS: 499.05 $(M+1)^+$. $^1H$ NMR ($CDCl_3$, 500 MHz) δ 7.88 (s, 1H), 7.77 (s, 2H), 7.31 (d, J=8.5, 1H), 6.77 (d, J=2.7, 1H), 6.54 (dd, J=8.5, 2.7 Hz, 1H), 5.69 (d, J=8.0 Hz, 1H), 4.77 (d, J=15.3, 1H), 4.29 (d, J=15.3 Hz, 1H), 4.05-4.12 (m, 1H), 0.79 (d, J=6.4 Hz, 3H).

INTERMEDIATE 26

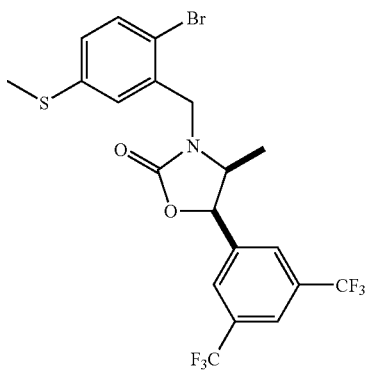

(4S,5R)-5-[3,5-bis(trifluoromethyl)phenyl]-3-[2-bromo-5-(methylthio)benzyl]-4-methyl-1,3-oxazolidin-2-one To a solution of (4S,5R)-3-(5-amino-2-bromobenzyl)-5-[3,5-bis(trifluoromethyl)phenyl]-4-methyl-1,3-oxazolidin-2-one (457 mg, 0.92 mmol) in methyl disulfide (4 mL) was added tert-butyl nitrite (182 μL, d=0.867, 1.38 mmol). The resulting mixture was stirred at 80° C. for 1 h. An aliquot indicated completion of the reaction. The titled compound was obtained as a glassy material after preparative TLC plates eluted by 25% EtOAc in hexanes. LC-MS: 529.71 $(M+1)^+$.

Example 342

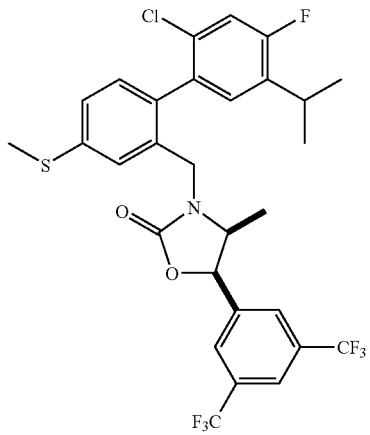 [SMILES: CSc1ccc(-c2cc(C(C)C)c(F)cc2Cl)c(CN2C(=O)O[C@H](c3cc(C(F)(F)F)cc(C(F)(F)F)c3)[C@@H]2C)c1]

(4S,5R)-5-[3,5-bis(trifluoromethyl)phenyl]-3-{[2'-chloro-4'-fluoro-5'-isopropyl-4-(methylthio)biphenyl-2-yl]methyl}-4-methyl-1,3-oxazolidin-2-one To a solution of (4S,5R)-5-[3,5-bis(trifluoromethyl)phenyl]-3-[2-bromo-5-(methylthio)benzyl]-4-methyl-1,3-oxazolidin-2-one (60 mg, 0.114 mmol) in 1,4-dioxane (1 mL) was added (2-chloro-4-fluoro-5-isopropylphenyl)boronic acid (10 mg, 0.12 mmol), [1,1'-bis(diphenylphosphino)ferrocene]dichloropalladium (II) (28 mg, 30 mol %) and aqueous potassium hydroxide (95 μL, 3M, 2 eq.). The reaction mixture was purged with nitrogen and then sealed in a microwave vessel. The reaction vessel was subject to microwave irradiation at 150° C. for 30 min. Crude mixture was worked up with water and EtOAc. The combined organic extracts were dried over $Na_2SO_4$ and concentrated in vacuo to give the crude product. This was purified by preparative TLC plate to afford the titled compound. LC-MS: 619.95 $(M+1)^+$. $^1H$ NMR ($CDCl_3$, 500 MHz) a 1:1 mixture of rotamers δ 7.83-7.88 (m, 1 H), 7.72 (s, 1 H) 7.68 (s, 1H), 7.30-7.35 (m, 1H), 7.24-7.29 (m, 1H), 7.11-7.19 (m, 2.5H), 7.04-7.07 (m, 0.5 H), 5.62 (d, J=8.2 Hz, 0.5H), 5.24 (d, J=8.0 Hz, 0.5 H), 4.87 (d, J=15.3 Hz, 0.5 H), 4.70 (d, J=15.8 Hz, 0.5 H), 3.79-3.98 (m, 2 H), 3.18 (m, 1 H), 2.55 (s, 1.5 H), 2.54 (s, 1.5 H), 1.20-1.29 (m, 6 H), 0.53 (d, J=6.4 Hz, 1.5 H), 0.47 (d, J=−6.6 Hz, 1.5 H).

Example 343

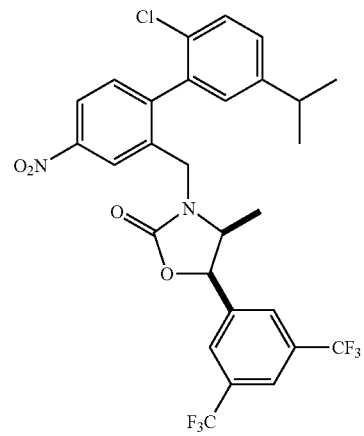

(4S,5R)-5-[3,5-bis(trifluoromethyl)phenyl]-3-[(2'-chloro-5'-isopropyl-4-nitrobiphenyl-2-yl)methyl]-4-methyl-1,3-oxazolidin-2-one To a solution of (4S,5R)-5-[3,5-bis(trifluoromethyl)phenyl]-3-(2-bromo-5-nitrobenzyl)-4-methyl-1,3-oxazolidin-2- one (950 mg, 1.80 mmol) in a toluene (5.2 mL): ethanol (2.6 mL): water (1.3 mL) mixture was added (2-chloro-5-isopropylphenyl)boronic acid (325 mg, 1.64 mmol), tetrakis(triphenylphosphine)palladium(0) (188 mg, 10 mol %) and sodium carbonate (346 mg, 3.26 mmol). The resulting mixture was heated in an 80° C. oil bath for 12 h. The reaction crude was evaporated into dryness. The resulting residue was taken up by a mixture of water and EtOAc. The combined organic extracts were dried over $Na_2SO_4$ and concentrated in vacuo to give the crude product, which was purified by $SiO_2$ (Biotage 40+S cartridge, EtOAc/hexane, gradient) to afford the titled compound. LC-MS: 601.19 $(M+1)^+$. $^1H$ NMR ($CDCl_3$, 500 MHz) a 1:1 mixture of rotamers δ 8.31-8.30 (m, 1 H), 8.24-8.28 (m, 1 H), 7.85-7.89 (m, 1 H), 7.68-7.76 (m, 2 H), 7.42-7.48 (m, 2 H), 7.26-7.30 (m, 1 H), 7.04-7.11 (m, 1 H), 5.74 (d, J=7.8 Hz, 0.5 H), 5.58 (d, J=8.0 Hz, 0.5 H), 4.92 (d, J=15.8 Hz, 0.5H), 4.76 (d, J=16.2 Hz, 0.5H), 3.97-4.04 (m, 1.5 H), 3.82 (dt, J=8.0, 6.6 Hz, 0.5H), 2.89-2.99 (m, 1H) 1.22-1.29 (m, 6 H), 0.60 (d, J=6.4 Hz, 1.5 H), 0.52 (d, J=6.6 Hz, 1.5 H).

Example 344

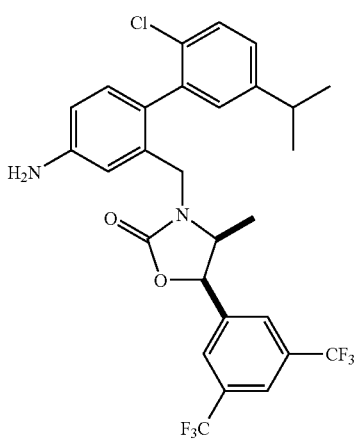 [SMILES: CC(C)c1ccc(Cl)c(-c2ccc([N+](=O)[O-])cc2CN2C(=O)O[C@H](c3cc(C(F)(F)F)cc(C(F)(F)F)c3)[C@@H]2C)c1]

(4S,5R)-3-[(4-amino-2'-chloro-5'-isopropylbiphenyl-2-yl)methyl]-5-[3,5-bis(trifluoromethyl)phenyl]-4-methyl-1,3-oxazolidin-2-one A solution of (4S,5R)-5-[3,5-bis(trifluoromethyl)phenyl]-3-[(2'-chloro-5'-isopropyl-4-nitrobiphenyl-2-yl)methyl]-4-methyl-1,3-oxazolidin-2-one (425 mg, 0.71 mmol) in methanol (10 mL) was subject to $H_2$ (40 psi., Parr shaker) at 20° C. for 6 h. The crude mixture was filtered through a bed of Celite (521). The filtrate was evaporated in vacuo to afford a glass. The titled compound was obtained after a preparative TLC plate developed by 20% EtOAc in hexanes. LC-MS: 571.22 $(M+1)^+$. $^1H$ NMR ($CDCl_3$, 500 MHz) a 6:4 mixture of rotamers δ 7.82-7.86 (m, 1 H), 7.65-7.71 (m, 2 H), 7.34-7.38 (m, 1 H), 7.11-7.17 (m, 2 H), 7.02-7.06 (m, 1 H), 6.76-6.82 (m, 1 H), 6.68-6.74 (m, 1 H), 5.58 (d, J=8.0 Hz, 0.4 H), 5.51 (d, J=8.2 Hz, 0.6H), 4.82 (d, J=15.3 Hz, 0.6H), 4.70 (d, J=15.6 Hz, 0.4H), 3.69-4.00 (m, 4 H), 2.84-2.94 (m, 1 H), 1.19-1.28 (m, 6 H), 0.45 (d, J=6.6 Hz, 1.2 H), 0.40 (d, J=6.6 Hz, 1.8 H).

Example 345

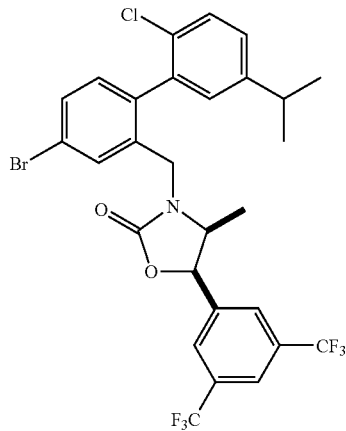 [SMILES: CC(C)c1ccc(Cl)c(-c2ccc(Br)cc2CN2C(=O)O[C@H](c3cc(C(F)(F)F)cc(C(F)(F)F)c3)[C@@H]2C)c1]

(4S,5R)-5-[3,5-bis(trifluoromethyl)phenyl]-3-[(4-bromo-2'-chloro-5'-isopropylbiphenyl-2-yl)methyl]-4-methyl-1,3-oxazolidin-2-one To a solution of (4S,5R)-3-[(4-amino-2'-chloro-5'-isopropylbiphenyl-2-yl)methyl]-5-[3,5-bis(trifluoromethyl)phenyl]-4-methyl-1,3-oxazolidin-2-one (100 mg, 0.175 mmol) in bromoform (0.5 mL) and dichloromethane (1 mL) was added t-butyl nitrite (23 μL, d=0.867, 90% pure, 0.193 mmol). The resulting mixture was stirred at 50° C. for 1 h. An aliquot indicated completion of the reaction. The reaction crude was deposited on 2 prep-TLC plates eluted by dichloromethane to afford the title compound. LC-MS: 635.80 $(M+1)^+$. $^1H$ NMR ($CDCl_3$, 500 MHz) a 6:4 mixture of rotamers δ 7.84-7.88 (m, 1H), 7.67-7.74 (m, 2 H), 7.60-7.63 (m, 1 H), 7.51-7.57 (m, 1 H), 7.38-7.42 (m, 1 H), 7.19-7.23 (m, 1 H), 7.11-7.16 (m, 1 H), 7.09 (d, J=2.3 Hz, 0.6 H), 7.03 (d, J=2.3 Hz, 0.4 H), 5.66 (d, J=8.0 Hz, 0.4 H), 5.55 (d, J=8.0 Hz, 0.6 H), 4.86 (d, J=15.6 Hz, 0.6H), 4.70 (d, J=15.6 Hz, 0.4H), 3.77-4.00 (m, 2 H), 2.87-2.95 (m, 1 H), 1.20-1.28 (m, 6 H), 0.53 (d, J=6.6 Hz, 1.2H), 0.45 (d, J=6.4 Hz, 1.8 H).

Example 346

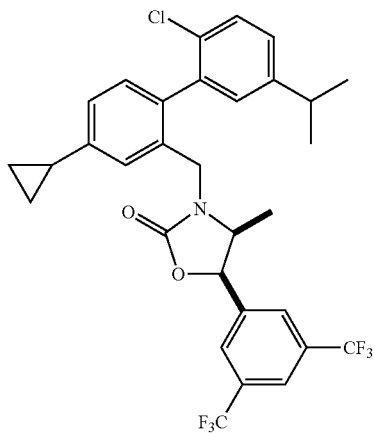 [SMILES: CC(C)c1ccc(Cl)c(-c2ccc(C3CC3)cc2CN2C(=O)O[C@H](c3cc(C(F)(F)F)cc(C(F)(F)F)c3)[C@@H]2C)c1]

(4S,5R)-5-[3,5-bis(trifluoromethyl)phenyl]-3-[(2'-chloro-4-cyclopropyl-5'-isopropylbiphenyl-2-yl) methyl]-4-methyl-1,3-oxazolidin-2-one To a solution of (4S,5R)-5-[3,5-bis(trifluoromethyl)phenyl]-3-[(4-bromo-2'-chloro-5'-isopropylbiphenyl-2-yl)methyl]-4-methyl-1,3-oxazolidin-2-one (27 mg, 0.043 mmol) in 1,4-dioxane (1 mL) was added cyclopropylboronic acid (9 mg, 0.10 mmol), [1,1'-bis(diphenylphosphino)ferrocene]dichloropalladium (II) (10.4 mg, 30 mol %) and aqueous potassium hydroxide (42 μL, 3M, 3 eq.). The reaction mixture was purged with nitrogen and then sealed in a microwave vessel. The reaction vessel was subject to microwave irradiation at 120° C. for 20 min. Crude mixture was worked up with water and EtOAc. The combined organic extracts were dried over Na$_2$SO$_4$ and concentrated in vacuo to give the crude product. This was purified by preparative TLC plate eluted by 20% EtOAc in hexanes to afford the titled compound. LC-MS: 595.99 (M+1)$^+$. $^1$H NMR (CDCl$_3$, 500 MHz) a 6:4 mixture of rotamers δ 7.82-7.86 (m, 1 H), 7.66-7.72 (m, 2 H), 7.36-7.40 (m, 1 H), 7.21-7.23 (m, 0.5 H), 7.11-7.19 (m, 3 H), 7.01-7.08 (m, 1.5 H), 5.58 (d, J=8.0 Hz, 0.4 H), 5.50 (d, J=8.0 Hz, 0.6 H), 4.88 (d, J=15.1 Hz, 0.6H), 4.71 (d, J=15.6 Hz, 0.4H), 3.76-3.95 (m, 2 H), 2.84-2.95 (m, 1H), 1.92-2.00 (m, 1 H), 1.18-1.29 (m, 6 H), 1.00-1.07 (m, 2 H), 0.71-0.82 (m, 2 H), 0.47 (d, J=6.6 Hz, 1.2 H), 0.42 (d, J=6.6 Hz, 1.8 H).

Following the procedures outlined in EXAMPLE 96 the compounds listed in Table 18 were prepared from (4R,5R)-5-[4'-fluoro-5'-isopropyl-2'-methoxy-4-(trifluoromethyl)-biphenyl-2-yl]-4-methyl-1,3-oxazolidin-2-one:

TABLE 18

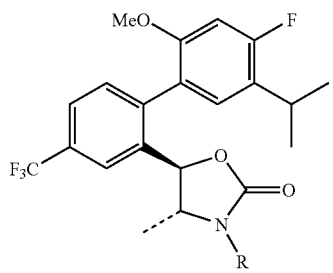

| EXAMPLE | R | LC/MS Data (M + 1) |
|---|---|---|
| 347 | 3,5-dichlorobenzyl | 570.3 |
| 348 | 3,5-difluorobenzyl | 538.4 |
| 349 | (tetrahydro-2H-pyran-4-yl)methyl | 511.4 |
| 350 | 3-methoxybenzyl | 532.4 |
| 351 | cyclohexylmethyl | 508.4 |
| 352 | 3,5-dimethoxybenzyl | 562.4 |
| 353 | (1-Cbz-piperidin-4-yl)methyl | 643.5 |
| 354 | 3-(trifluoromethyl)benzyl | 570.4 |
| 355 | 4-(trifluoromethyl)benzyl | 586.4 |
| 356 | (pyridin-2-yl)methyl | 503.4 |
| 357 | (pyridin-3-yl)methyl | 503.4 |
| 358 | (2-BocNH-pyridin-4-yl)methyl | 618.5 |

TABLE 18-continued

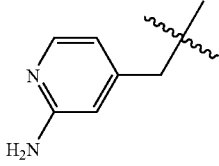

| EXAMPLE | R | LC/MS Data (M + 1) |
|---------|---|---------------------|
| 359 | 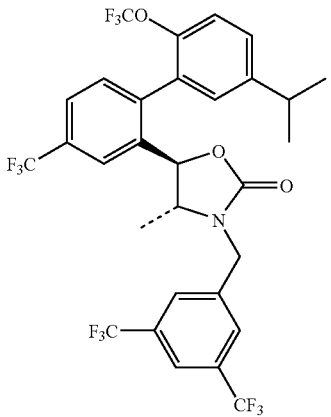 | 518.4 |

Example 360

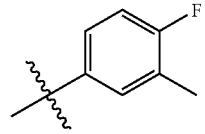 [SMILES: *c1ccc(F)c(C)c1]

(4R,5R)-3-[3,5-bis(trifluoromethyl)benzyl]-5-[5'-isopropyl-2'-(trifluoromethoxy)-4-(trifluoromethyl)biphenyl-2-yl]-4-methyl-1,3-oxazolidin-2-one To a solution of 80 mg of (4R,5R)-3-[3,5-bis(trifluoromethyl)benzyl]-5-[2-iodo-5-(trifluoromethyl)phenyl]-4-methyl-1,3-oxazolidin-2-one in 2 mL of benzene, 1 mL of water, and 0.5 mL ethanol was added 100 mg of 5-isopropyl-2-(trifluoromethoxy)phenyl boronic acid, 0.15 mL of 2M aqueous sodium carbonate, and 21 mg of Pd(PPh$_3$)$_4$. A reflux condenser was attached, and the mixture was heated to 100° C. The mixture was stirred at 100° C. for 24 hours, and then was diluted with 10 mL of EtOAc and 10 mL of water. The phases were separated and the aqueous phase was extracted with 10 mL of EtOAc. The combined organic phases were washed with 10 mL of brine, dried over Na$_2$SO$_4$, and concentrated. The residue was purified by flash chromatography on a Biotage Horizon, 25M column, eluting with 1 CV of 2% EtOAc in hexanes, followed by a linear gradient of EtOAc in hexanes from 2 to 100% over 10 CV. The product was repurified using the same conditions to provide the title compound. Mass spectrum (ESI) 674.4 (M+1).

Following the general procedures described above the compounds listed in Table 19 were prepared.

TABLE 19

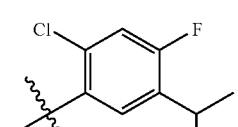

| EXAMPLE | A³ | LC/MS Data (M + 1) |
|---------|----|---------------------|
| 361 | 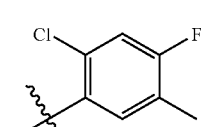 | 580.3 |
| 362 | 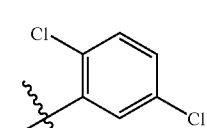 | 642.4 |
| 363 | 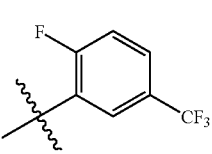 [SMILES: *c1cc(C(F)(F)F)ccc1F] | 614.3 |
| 364 | 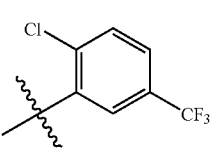 | 616.3 |
| 365 | 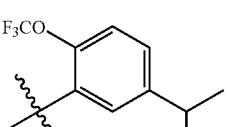 | 634.4 |
| 366 | | 650.3 |
| 367 | | 674.4 |

TABLE 19-continued

[Structure shown: oxazolidinone with A3 group, CF3-phenyl, and 3,5-bis(trifluoromethyl)benzyl substituent]

| EXAMPLE | A³ | LC/MS Data (M + 1) |
|---|---|---|
| 368 | [2-chloro-5-isopropylphenyl] | 623.9 |

INTERMEDIATE 27

[Structure of (4R,5R)-4-ethyl-5-[2-iodo-5-(trifluoromethyl)phenyl]-1,3-oxazolidin-2-one]

(4R,5R)-4-ethyl-5-[2-iodo-5-(trifluoromethyl)phenyl]-1,3-oxazolidin-2-one

Step A:
(4S)-4-benzyl-3-butyryl-1,3-oxazolidin-2-one

To a −78° C. solution of S-benzyl-oxazolidinone in 15 mL of THF was added n-BuLi over ca. 1 min, and then butyryl chloride. The mixture was stirred for 30 min at −78° C., and then allowed to warm to r.t. over ca. 30 min. Excess acid chloride was quenched by addition of 3 mL of saturated aqueous $NH_4Cl$, and then the bulk of the solvent was removed by rotary evaporation. The residue was diluted with 17 mL of saturated aqueous $NH_4Cl$ and 30 mL of $CH_2Cl_2$. The phases were separated and the aqueous phase was extracted with 20 mL of $CH_2Cl_2$. The combined organic extracts were washed with 20 mL of 1 N NaOH solution and 20 mL of brine, dried ($Na_2SO_4$), and concentrated. The residue was purified by flash chromatography on a Biotage Horizon, 40M column, eluting with 1 CV of 2% EtOAc in hexanes followed by a linear gradient of 2→100% EtOAc in hexanes over 10 CV. The residue was stored in the freezer overnight, where it crystallized. The resulting solid was triturated with hexanes, filtered, and dried under high vacuum. Mass spectrum (ESI) 178.2 (M−$C_3H_7CO$).

Step B: (4S)-4-benzyl-3-((2R)-2-{(S)-hydroxy-[2-iodo-5-trifluoromethyl)phenyl]methyl}butanoyl)-1,3-oxazolidin-2-one Following the procedure described in EXAMPLE 95, Step A, the title compound was prepared from 5'-isopropyl-2'-methoxy-4-(trifluoromethyl)biphenyl-2-carbaldehyde (EXAMPLE 80, Step A) and (4S)-4-benzyl-3-butyryl-1,3-oxazolidin-2-one. Mass spectrum (ESI) 530.1 (M−OH).

Step C: (4R,5R)-4-ethyl-5-[2-iodo-5-(trifluoromethyl)phenyl]-1,3-oxazolidin-2-one Following the procedure described in EXAMPLE 95, Step B, the title compound was prepared from (4S)-4-benzyl-3-((2R)-2-{(S)-hydroxy [2-iodo-5-(trifluoromethyl)phenyl]methyl}butanoyl)-1,3-oxazolidin-2-one. Mass spectrum (ESI) 386.2 (M+1).

INTERMEDIATE 28

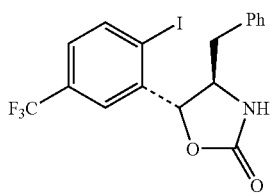

(4R,5R)-4-benzyl-5-[2-iodo-5-(trifluoromethyl)phenyl]-1,3-oxazolidin-2-one

Step A: (4S)-4-benzyl-3-(3-phenylpropanoyl)-1,3-oxazolidin-2-one

Following the procedure described in INTERMEDIATE 27, Step A, the title compound was prepared from S-benzyl-oxazolidinone and hydrocinnamoyl chloride. Mass spectrum (ESI) 178.2 (M−$PhC_2H_4CO$).

Step B: (4S)-4-benzyl-3-{(2R,3S)-2-benzyl-3-hydroxy-3-[2-iodo-5-(trifluoromethyl)phenyl]propanoyl}-1,3-oxazolidin-2-one Following the procedure described in EXAMPLE 95, Step A, the title compound was prepared from 5'-isopropyl-2'-methoxy-4-(trifluoromethyl)biphenyl-2-carbaldehyde (EXAMPLE 80, Step A) and (4S)-4-benzyl-3-(3-phenylpropanoyl)-1,3-oxazolidin-2-one. Mass spectrum (ESI) 592.3 (M−OH).

Step C: (4R,5R)-4-benzyl-5-[2-iodo-5-(trifluoromethyl)phenyl]-1,3-oxazolidin-2-one Following the procedure described in EXAMPLE 95, Step B, the title compound was prepared from (4S)-4-benzyl-3-{(2R,3S)-2-benzyl-3-hydroxy-3-[2-iodo-5-(trifluoromethyl)phenyl]propanoyl}-1,3-oxazolidin-2-one. Mass spectrum (ESI) 448.2 (M+1).

Following the general procedures outlined above, the compounds in Table 20 were prepared:

TABLE 20

| EXAMPLE | A³ | R₂ | R₃ | LC/MS Data (M + 1) |
|---|---|---|---|---|
| 369 | MeO-/F/isopropyl phenyl | Et | 3,5-bis(CF₃)benzyl | 652.4 |
| 370 | MeO-/F/isopropyl phenyl | Et | 3,5-dichlorobenzyl | 584.4 |
| 371 | Cl-/isopropyl phenyl | Et | 3,5-bis(CF₃)benzyl | 639.2 |

Example 372

Alternate procedure for making (4S,5R)-5-[3,5-bis(trifluoromethyl)phenyl]-3-{[4'-fluoro-5'isopropyl-2'-methoxy-4-(trifluoromethyl)biphenyl-2-yl]methyl}-4-methyl-1,3-oxazolidin-2-one (Example 73)

The compound of Example 73 can be made by the procedure shown below:

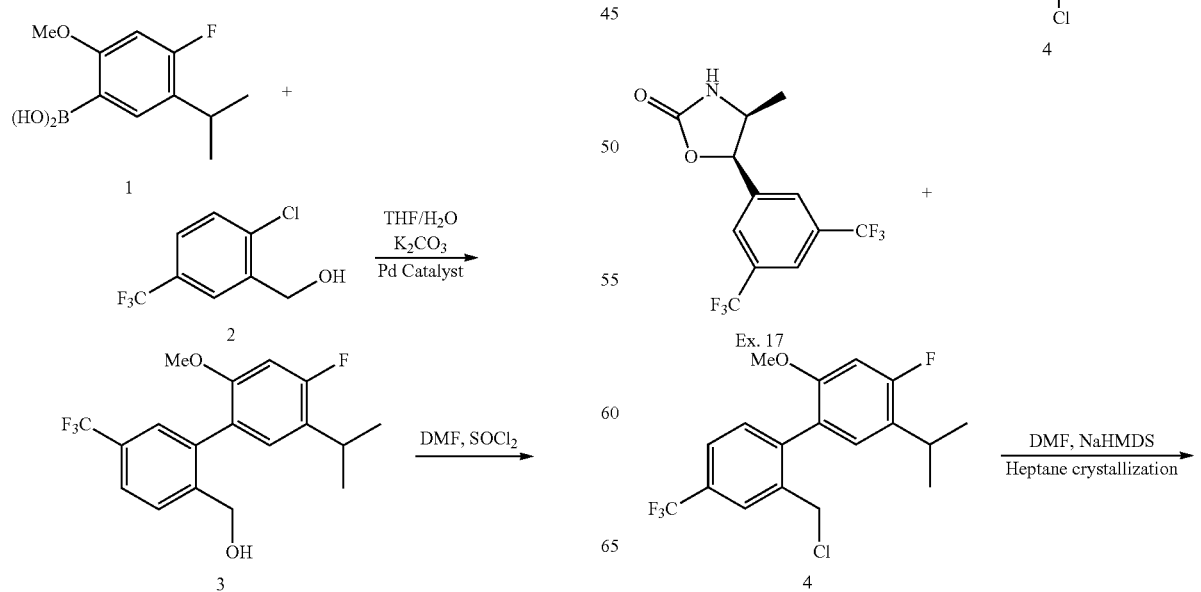

-continued

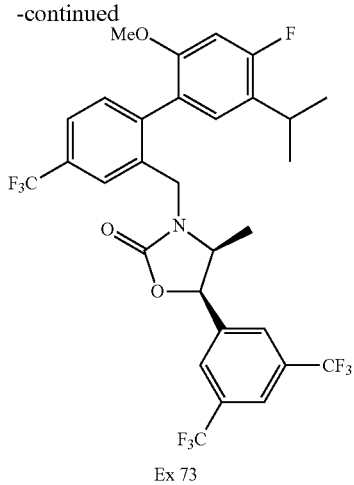

Ex 73

Step 1: Suzuki Coupling Reaction of Boronic Acid 1 and Aryl Chloride 2

A 3 M K$_2$CO$_3$ solution is prepared by adding 4.71 kg of solid K$_2$CO$_3$ to 10.3 L water. Cooling is applied to keep the solution at 20-25° C. THF (12 L), aryl chloride 2 (2.69 kg), and the boronic acid 1 that was made in Example 78 (2.74 kg) are added to the K$_2$CO$_3$ followed by a 1 L THF rinse. HPLC analysis is used to confirm the 1.00/1.00 ratio of 1/2. The solution is degassed by sparging with nitrogen gas for 70 min. The catalyst, 1,1 bis(di-tert-butylphosphino)ferrocene palladium dichloride (42 g) is added as a solid and is followed by a degassed THF rinse (1.5 L). The organic layer turns dark brown immediately. The biphasic mixture is aged at 36°-40° C. with vigorous stirring. After HPLC reveals complete conversion (15-18 h), the mixture is cooled to rt and the aqueous layer is removed. To the organic layer is added heptane (25.6 L) and water (25.6 L) and the layers are cut. The organic layer is washed with water (19 L). The organic layer is treated with 680 g Darco KB-B at rt for 60 min and filtered through solka-floc with a 10% THF/Heptane rinse (~15 L). The solvent is switched to heptane (~35 L) at ~45-50° C. until <0.5 v % of THF is left. More heptane is added to bring the total volume to ~45-50 L. The solution is seeded with crystals obtained from earlier runs if no seed bed forms. The slurry is slowly cooled to rt and then to −15° C. After aging at −15° C. for 1-2 h, after LC of the supernatant shows ~2 g/l loss of the product in the supernatant, the slurry is filtered and the product is washed with cold heptane (~25 L), providing compound 3.

Step 2: Chlorination of 3 to 4

To a solution of biaryl 3 (3.4 kg) in DMF (17 L) which was maintained at 10° C. was added thionyl chloride (940 ml), and then the mixture was warmed to room temperature. The mixture was aged until >99.8% conversion was measured by HPLC. Water (3.4 L) was then added. Seed crystals (1 wt %) were added, and the mixture was aged for 30 min more before slowly adding 5.1 L of additional water over ~1 hr. The solid was filtered and washed with first 20 L 1:1 DMF: water and then 3×20 L water. The solid product 4 was dried at 20° C. until <0.1 wt % water remained.

Step 3: Alkylation of the Product of Example 17 with Compound 4 to Yield the Product of Example 73

The chiral intermediate (4S,5R)-5-[3,5-Bis(trifluoromethyl)phenyl]-4-methyl-1,3-oxazolidin-2-one which was made in Example 17 is dissolved in DMF (2.8 kg in 32.7 L) and cooled to −15° C. 2.0 M NaHMDS (3.92 L, 1.05 eq) was then added over 1.5 hr, followed by addition of the biaryl chloride 4 (2.8 kg) in DMF. The mixture was warmed to +12° C. and was aged until complete conversion took place. Then 5N HCl (3.4 L) was added, followed by 16 L of 10% IPAC/Heptane and 34 L of water, keeping the temperature between 10° C. and 20° C. throughout. The layers were cut and the organic layer was washed twice with 14 L of 1:1 DMF:water followed by two 14 L water washes. The organic layer was assayed for yield and was then filtered through 2.4 kg of silica gel to remove the excess oxazolidinone to <0.5%. The silica was washed with 5% IPAC/Heptane. The combined organic solutions were distilled to remove IPAC to <1%. The warm heptane solution was then transferred slowly into a 20° C. heptane solution containing 10 wt % seed. The slurry was then cooled to −20° C. and filtered. The filter cake was washed with cold heptane and was then dried, yielding the compound that was originally made in Example 73.

INTERMEDIATE 29

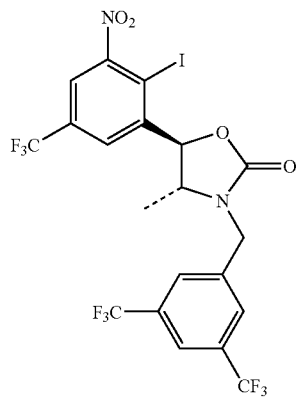

(4R,5R)-3-[3,5-bis(trifluoromethyl)benzyl]-5-[2-iodo-3-nitro-5-(trifluoromethyl)phenyl]-4-methyl-1,3-oxazolidin-2-one (4R,5R)-3-[3,5-Bis(trifluoromethyl)benzyl]-5-[2-iodo-5-(trifluoromethyl)phenyl]-4-methyl-1,3-oxazolidin-2-one was added in portions to 2 mL of fuming nitric acid at 0° C. The reaction mixture was stirred overnight at r.t., and then heated to 75° C. for 4 h. The reaction mixture was cooled and then added dropwise to a rapidly stirred mixture of 10 mL of water and 10 mL of EtOAc. The phases were separated and the organic phase was washed with 10 mL each of saturated NaHCO$_3$ and brine, dried (Na$_2$SO$_4$), and concentrated. The residue was purified by flash chromatography on a Biotage Horizon, 25S column, eluting with 1 CV of 5% EtOAc in hexanes followed by a linear gradient of 5→100% EtOAc in hexanes over 10 CV, to provide the title compound. Mass spectrum (ESI) 643 (M+1).

Example 373

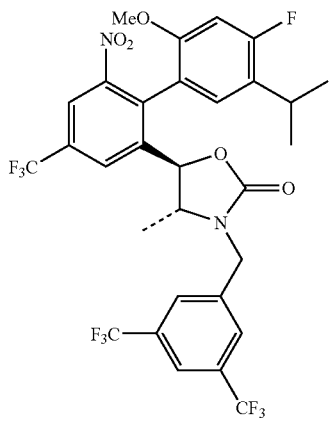 [SMILES: COc1cc(F)c(C(C)C)cc1-c1c([C@H]2OC(=O)N(Cc3cc(C(F)(F)F)cc(C(F)(F)F)c3)[C@@H]2C)cc(C(F)(F)F)cc1[N+](=O)[O-]]

(4R,5R)-3-[3,5-bis(trifluoromethyl)benzyl]-5-[4'-fluoro-5'-isopropyl-2'-methoxy-6-nitro-4-(trifluoromethyl)biphenyl-2-yl]-4-methyl-1,3-oxazolidin-2-one Following the procedure described in EXAMPLE 81, 48 mg of (4R,5R)-3-[3,5-bis(trifluoromethyl)benzyl]-5-[2-iodo-3-nitro-5-(trifluoromethyl)phenyl]-4-methyl-1,3-oxazolidin-2-one and 48 mg of (4-fluoro-5-isopropyl-2-methoxyphenyl)boronic acid (EXAMPLE 78) provided two atroposiomers, which were separable by flash chromatography on a Biotage Horizon, 25S column, eluting with 1 CV of 5% EtOAc in hexanes followed by a linear gradient of 5→100% EtOAc in hexanes over 10 CV, providing atropoisomer A [mass spectrum (ESI) 683.4 (M+1)] and atropoisomer B [mass spectrum (ESI) 683.3 (M+1)].

Example 374

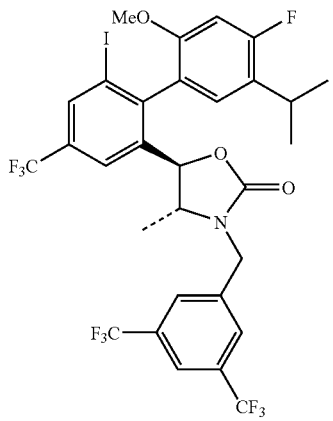 [SMILES: COc1cc(F)c(C(C)C)cc1-c1c(I)cc(C(F)(F)F)cc1[C@H]1OC(=O)N(Cc2cc(C(F)(F)F)cc(C(F)(F)F)c2)[C@@H]1C]

(4R,5R)-3-[3,5-bis(trifluoromethyl)benzyl]-5-[4'-fluoro-5'-isopropyl-2'-methoxy-6-iodo-4-(trifluoromethyl)biphenyl-2-yl]-4-methyl-1,3-oxazolidin-2-one (atropoisomer A)

To a solution of 17 mg of (4R,5R)-3-[3,5-bis(trifluoromethyl)benzyl]-5-[4'-fluoro-5'-isopropyl-2'-methoxy-6-nitro-4-(trifluoromethyl)biphenyl-2-yl]-4-methyl-1,3-oxazolidin-2-one, atropoisomer A (EXAMPLE 373), in 1 mL EtOAc was added 5 mg of $PtO_2$ (Adam's catalyst). The reaction mixture was flushed with $H_2$, and then stirred under an $H_2$ balloon for 2 h, at which point LC/MS analysis showed mostly the nitroso product. The reaction mixture was filtered through Celite, washing liberally with EtOAc, and the filtrate was concentrated and resubmitted to reaction conditions overnight. The reaction mixture was filtered through Celite, washing liberally with EtOAc, and the filtrate was concentrated. The residue was dissolved in 0.5 mL of $CH_2I_2$ and 6 μL of t-butyl nitrite was added. The reaction mixture was stirred for 1.5 h at 80° C. The reaction mixture was purified by preparative thin-layer chromatography on a 1000 μM plate, eluting with 20% EtOAc in hexanes, to provide the title compound. Mass spectrum (ESI) 764.3 (M+1).

Example 375

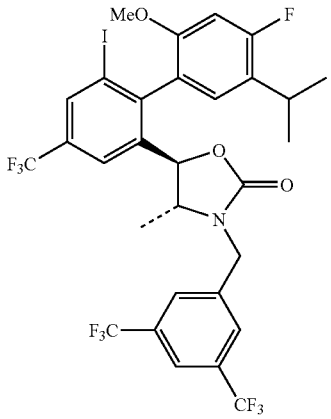

(4R,5R)-3-[3,5-bis(trifluoromethyl)benzyl]-5-[4'-fluoro-5'-isopropyl-2'-methoxy-6-iodo-4-(trifluoromethyl)biphenyl-2-yl]-4-methyl-1,3-oxazolidin-2-one (atropoisomer B)

To a solution of 70 mg of (4R,5R)-3-[3,5-bis(trifluoromethyl)benzyl]-5-[2-iodo-3-nitro-4-(trifluoromethyl)phenyl]-4-methyl-1,3-oxazolidin-2-one (intermediate 30) in 1 mL EtOH was added 124 mg of $SnCl_2$. The reaction mixture was stirred overnight at r.t; then another 60 mg of $SnCl_2$ was added and the mixture was heated to 80° C. and stirred overnight. The reaction mixture was concentrated and the residue was partitioned between 10 mL of $CH_2Cl_2$ and 10 mL of 1 N NaOH. The aqueous phase was extracted with 2×10 mL of $CH_2Cl_2$ and the combined organics were dried ($Na_2SO_4$), and concentrated. Following the procedure described in EXAMPLE 81, the residue from the reduction and 70 mg of (4-fluoro-5-isopropyl-2-methoxyphenyl)boronic acid (EXAMPLE 78) provided the corresponding biphenyl compound as a mixture of atropoisomers. This mixture was dissolved in 0.5 mL of $CH_2I_2$ and 14 μL of t-butyl nitrite was added. The reaction mixture was stirred for 1.5 h at 80° C. and then cooled and added directly to two 1000-μM thin-layer chromatography plates, eluting with 20% EtOAc in hexanes to provide approximately equal amounts of atropoisomer A and B of the title compound. Mass spectrum (ESI) 764.2 (M+1).

INTERMEDIATE 31

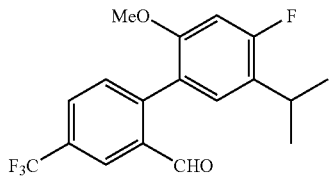

4'-fluoro-5-isopropyl-2'-methoxy-4-(trifluoromethyl)biphenyl-2-carbaldehyde

Following the procedure described in EXAMPLE 81, 200 mg of 2-iodo-5-(trifluoromethyl)benzaldehyde (EXAMPLE 80, Step A) and 170 mg of (4-fluoro-5-isopropyl-2-methoxyphenyl)boronic acid (EXAMPLE 78) gave the title compound. Mass spectrum (ESI) 341.3 (M+1).

INTERMEDIATE 32

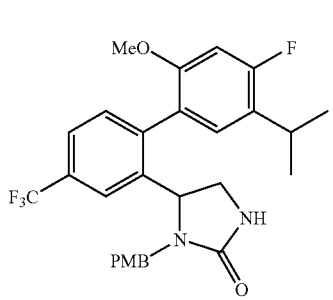

5-[4'-fluoro-5'-isopropyl-2'-methoxy-4-(trifluoromethyl)biphenyl-2-yl]-1-(4-methoxybenzyl)imidazolidin-2-one Step A: [4'-fluoro-5'-isopropyl-2'-methoxy-4-(trifluoromethyl)biphenyl-2-yl][(4-methoxybenzyl)amino]acetonitrile To a solution of 203 mg of 4'-fluoro-5'-isopropyl-2'-methoxy-4-(trifluoromethyl)biphenyl-2-carbaldehyde (INTERMEDIATE 31) in 2 mL of $CH_2Cl_2$ was added 100 µL of TMSCN, and then 1 mg of $ZnI_2$. The mixture was stirred for 30 min at r.t. p-Methoxybenzylamine (157 µL) in 2 mL of MeOH was added and the mixture was heated to reflux for 1.5 h. The reaction mixture was cooled and concentrated. The residue was purified by flash chromatography on a Biotage Horizon, 25M column, eluting with 1 CV of 2% EtOAc in hexanes followed by a linear gradient of 2→100% EtOAc in hexanes over 10 CV to provide the title compound. Mass spectrum (ESI) 487.2 (M+1).

Step B: 5-[4'-fluoro-5'-isopropyl-2'-methoxy-4-(trifluoromethyl)biphenyl-2-yl]-1-(4-methoxybenzyl)imidazolidin-2-one To a 0° C. solution of 100 mg of [4'-fluoro-5'-isopropyl-2'-methoxy-4-(trifluoromethyl)biphenyl-2-yl][(4-methoxybenzyl)amino]acetonitrile in 4 mL of THF was added 620 µL of a 1 M solution of $LiAlH_4$ in $Et_2O$. The cooling bath was removed and the mixture was stirred for 45 min at r.t. The mixture was recooled to 0° C. and carefully quenched by dropwise addition of 24 µL of water, 24 µL of 15% aqueous NaOH solution, and 60 µL of water. The solids were filtered, washing liberally with $Et_2O$, and the filtrate was concentrated. The residue was dissolved in 2 mL of $CH_2Cl_2$ and cooled to 0° C. Triethylamine (55 µL) and then triphosgene (32 mg) were added. The mixture was stirred for 45 min at 0° C. The reaction mixture was partitioned between 10 mL of EtOAc and 10 mL of water. The aqueous was extracted with 10 mL of EtOAc and the combined organics were washed with 10 mL of brine, dried ($Na_2SO_4$), and concentrated. The residue was purified by flash chromatography on a Biotage Horizon, 25S column, eluting with 1 CV of 15% EtOAc in hexanes followed by a linear gradient of 15→100% EtOAc in hexanes over 10 CV to provide the title compound. Mass spectrum (ESI) 517.3 (M+1).

Example 376

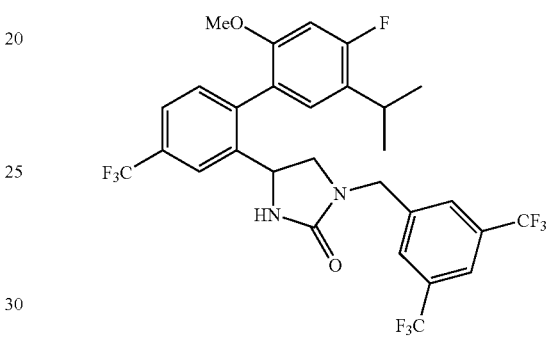

1-[3,5-bis(trifluoromethyl)benzyl]-4-[4'-fluoro-5'-isopropyl-2'-methoxy-4-(trifluoromethyl)biphenyl-2-yl]imidazolidin-2-one Step A: 1-[3,5-bis(rifluoromethyl)benzyl]-4-[4'-fluoro-5-isopropyl-2'-methoxy-4-(trifluoromethyl)biphenyl-2-yl]-3-(4-methoxybenzyl)imidazolidin-2-one To a 0° C. solution of 19 mg of 5-[4'-fluoro-5'-isopropyl-2'-methoxy-4-(trifluoromethyl)biphenyl-2-yl]-1-(4-methoxybenzyl)imidazolidin-2-one (INTERMEDIATE 32) in 1 mL of DMF was added 3 mg of NaH (60% dispersion in oil). The solution was stirred for 10 min at 0° C. and then 8 µL of 3,5-bistrifluoromethylbenzyl bromide was added and the mixture was stirred for 3 h at 0° C. The reaction mixture was quenched with a drop of water and then filtered and purified by reverse-phase HPLC [Waters XTerra C8 19×50 mm column, eluting at 20 mL/min with 90% water (0.1% TFA) to 100% acetonitrile (0.1% TFA) over 5.15 min, hold for 1.45 min, then back to 90% water over 0.5 min] to provide the title compound. Mass spectrum (ESI) 743.2 (M+1).

Step B: 1-[3,5-bis(trifluoromethyl)benzyl]-4-[4'-fluoro-5'-isopropyl-2'-methoxy-4-(trifluoromethyl)biphenyl-2-yl]imidazolidin-2-one A solution of 15 mg of 1-[3,5-bis(trifluoromethyl)benzyl]-4-[4'-fluoro-5'-isopropyl-2'-methoxy-4-(trifluoromethyl)biphenyl-2-yl]-3-(4-methoxybenzyl)imidazolidin-2-one in 0.5 mL of TFA was stirred overnight at r.t. The reaction mixture was concentrated and then purified by reverse-phase HPLC [Waters XTerra C8 19×25 mm column, eluting at 20 mL/min with 90% water (0.1% TFA) to 100% acetonitrile (0.1% TFA)

over 5.15 min, hold for 1.45 min, then back to 90% water over 0.5 min] to provide the title compound. Mass spectrum (ESI) 623.4 (M+1).

Example 377

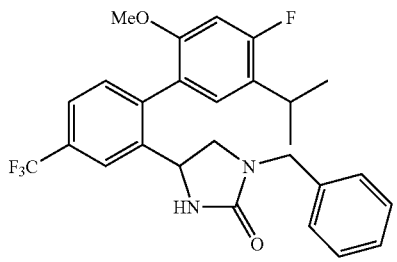 [SMILES: COc1cc(F)c(C(C)C)cc1-c1ccc(C(F)(F)F)cc1C1CN(Cc2ccccc2)C(=O)N1]

1-benzyl-4-[4'-fluoro-5'-isopropyl-2'-methoxy-4-(trifluoromethyl)biphenyl-2-yl]imidazolidin-2-one Step A: 1-benzyl-4-[4'-fluoro-5'-isopropyl-2'-methoxy-4-(trifluoromethyl)biphenyl-2-yl]-3-(4-methoxybenzyl)imidazolidin-2-one Following the procedure described in EXAMPLE 379, Step A, 31 mg of 5-[4'-fluoro-5'-isopropyl-2'-methoxy-4-(trifluoromethyl)biphenyl-2-yl]-1-(4-methoxybenzyl)imidazolidin-2-one (INTERMEDIATE 32) and 9 μL of benzyl bromide gave the title compound. Mass spectrum (ESI) 607.5 (M+1).

Step B: 1-benzyl-4-[4'-fluoro-5'-isopropyl-2'-methoxy-4-(trifluoromethyl)biphenyl-2-yl]imidazolidin-2-one Following the procedure described in EXAMPLE 379, Step B, 5 mg of 1-benzyl-4-[4'-fluoro-5'-isopropyl-2'-methoxy-4-(trifluoromethyl)biphenyl-2-yl]-3-(4-methoxybenzyl)imidazolidin-2-one gave the title compound. Mass spectrum (ESI) 487.4 (M+1).

What is claimed is:

1. A method of treating atherosclerosis in a patient in need of treatment comprising the administration of a therapeutically effective amount of a compound of Formula Ii, or a pharmaceutically acceptable salt thereof, wherein:

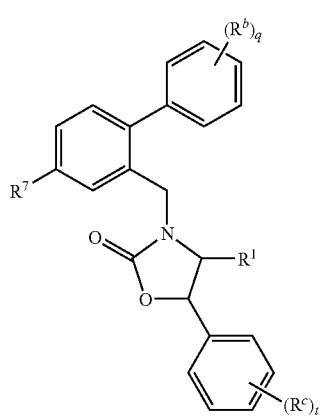

Ii $R^7$ is selected from the group consisting of Cl and —CF$_3$;
Each $R^b$ is independently selected from the group consisting of —C$_1$-C$_3$ alkyl, —OCH$_3$, and F;
$R^1$ is selected from the group consisting of H and —C$_1$-C$_2$ alkyl;
$R^c$ is selected from the group consisting of halogen, —CH$_3$, —CF$_3$, and —CN;
q is 2 or 3; and
t is an integer from 0-2.

2. The method of claim 1 wherein the compound is selected from the group consisting of the following compounds, or a pharmaceutically acceptable salt thereof:

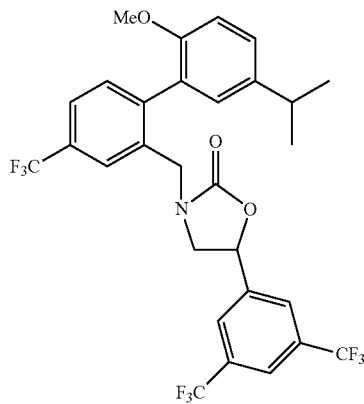

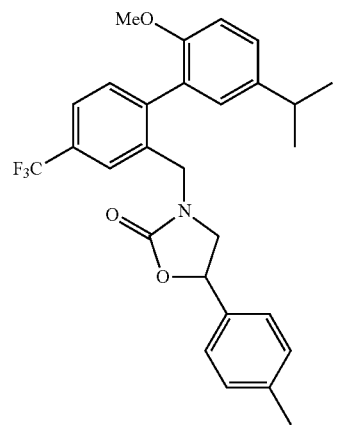

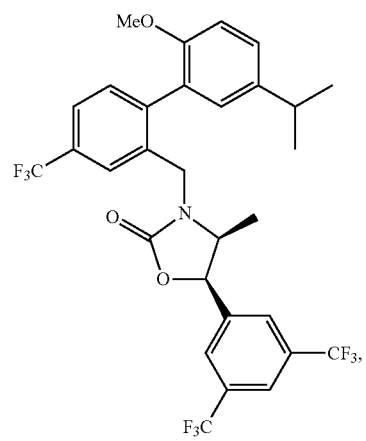

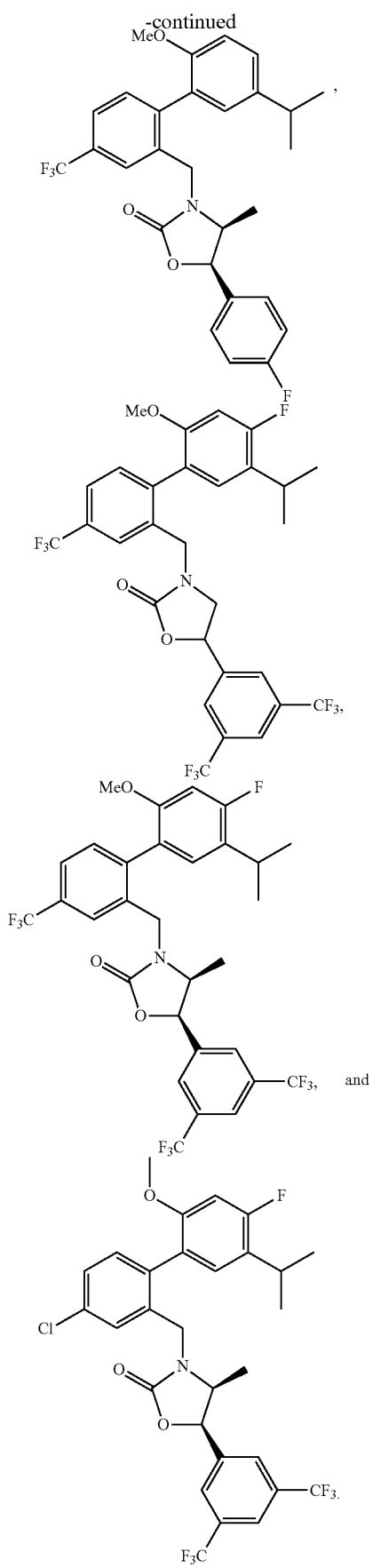
3. The method of claim 1 wherein the compound is selected from the group consisting of the following compounds, or a pharmaceutically acceptable salt thereof:
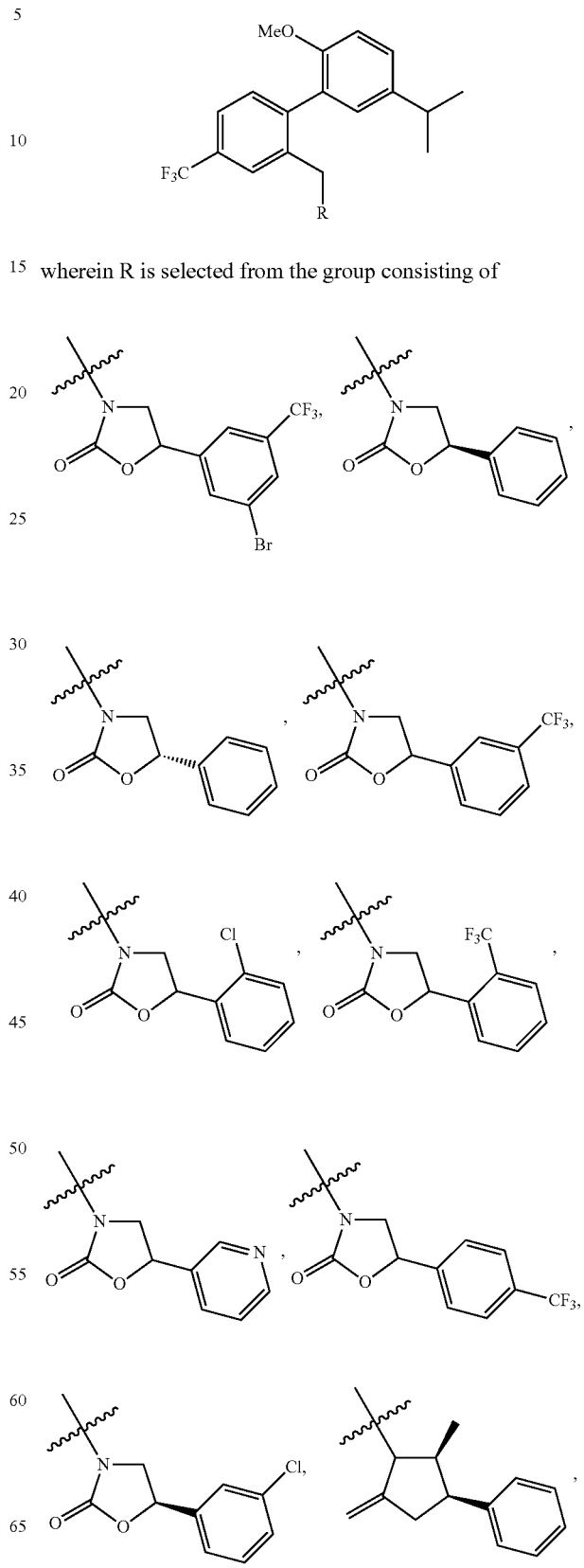
wherein R is selected from the group consisting of 237
-continued

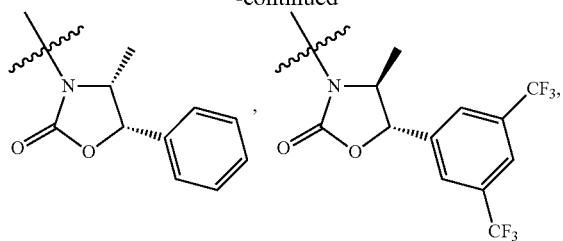
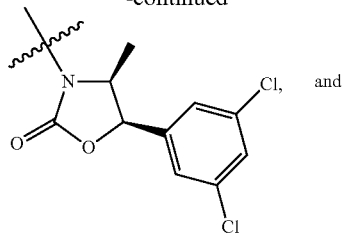

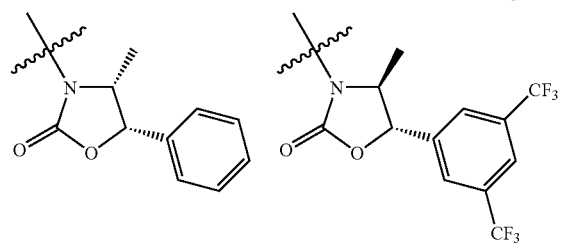
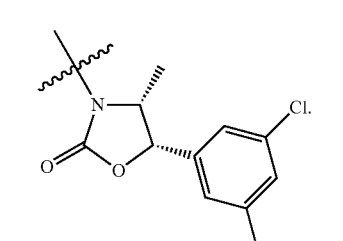

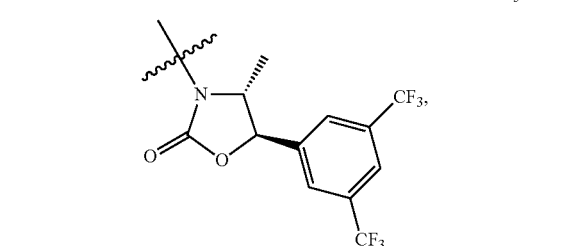

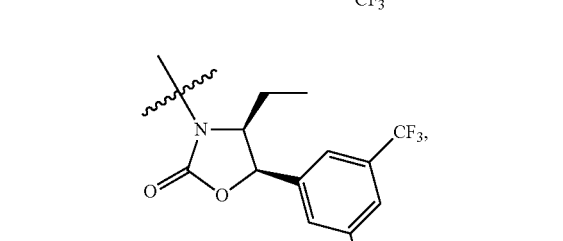

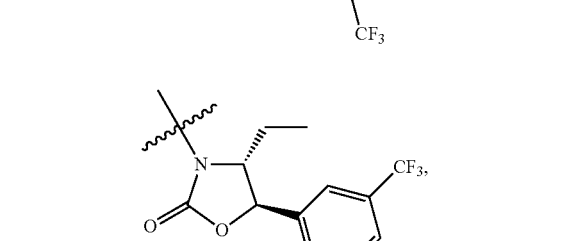

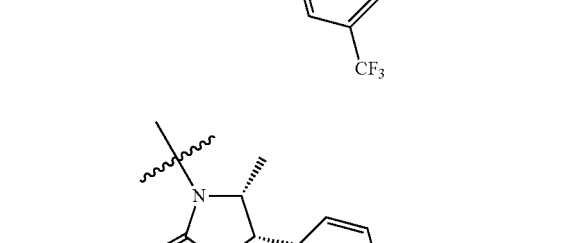

238
-continued

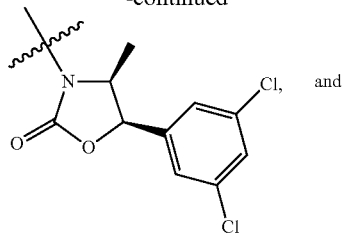

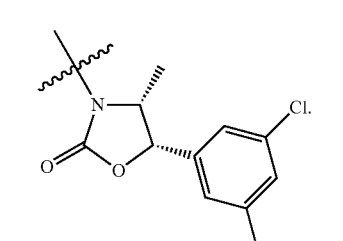

4. A method of treating atherosclerosis in a patient in need of treatment comprising the administration of a therapeutically effective amount of a compound having the structure:

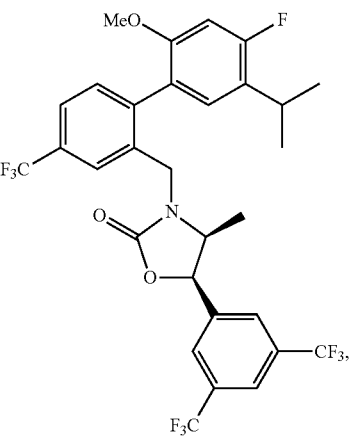 [SMILES: COc1cc(F)c(C(C)C)cc1-c1ccc(C(F)(F)F)cc1CN1C(=O)O[C@H](c2cc(C(F)(F)F)cc(C(F)(F)F)c2)[C@@H]1C]

or a pharmaceutically acceptable salt thereof.

5. A method of treating atherosclerosis in a patient in need of treatment comprising the administration of a therapeutically effective amount of a compound having the structure:

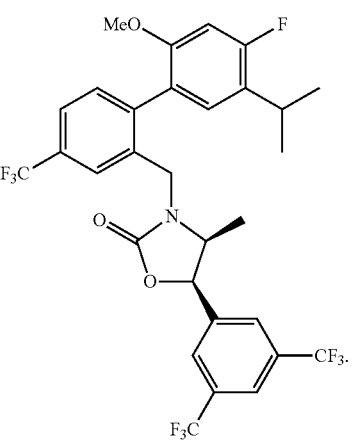 [SMILES: COc1cc(F)c(C(C)C)cc1-c1ccc(C(F)(F)F)cc1CN1C(=O)O[C@H](c2cc(C(F)(F)F)cc(C(F)(F)F)c2)[C@@H]1C]

6. The method of claim 5 comprising the administration of a therapeutically effective amount of the compound having the structure:

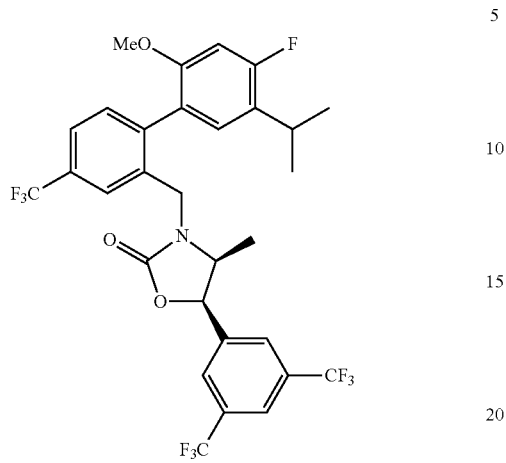

and an HMG-CoA reductase inhibitor.

7. The method of claim 6, wherein the HMG-CoA reductase inhibitor is a statin selected from the group consisting of simvastatin, lovastatin, rosuvastatin, pravastatin, fluvastatin, atorvastatin, rivastatin, and itavastatin.

8. The method of claim 7, further comprising a cholesterol absorption inhibitor.

9. The method of claim 8, wherein the cholesterol absorption inhibitor is ezetimibe.

* * * * *

UNITED STATES PATENT AND TRADEMARK OFFICE
CERTIFICATE OF CORRECTION

| | | |
|---|---|---|
| PATENT NO. | : 8,735,435 B2 | Page 1 of 1 |
| APPLICATION NO. | : 12/625783 | |
| DATED | : May 27, 2014 | |
| INVENTOR(S) | : Ali et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 804 days.

Signed and Sealed this
Seventeenth Day of November, 2015

Michelle K. Lee
*Director of the United States Patent and Trademark Office*